US009062315B2

United States Patent
Sakaguchi et al.

(10) Patent No.: US 9,062,315 B2
(45) Date of Patent: Jun. 23, 2015

(54) METHOD FOR TRANSFORMATION OF STRAMENOPILE

(75) Inventors: Keishi Sakaguchi, Fukuoka (JP); Rie Hamaguchi, Fukuoka (JP); Takanori Matsuda, Fukuoko (JP); Makoto Ito, Fukuoka (JP); Naoki Nagano, Miyazaki (JP); Masahiro Hayashi, Miyazaki (JP); Daisuke Honda, Kobe (JP); Yuji Okita, Tokyo (JP); Shinichi Sugimoto, Tokyo (JP)

(73) Assignees: KYUSHU UNIVERSITY, NATIONAL UNIVERSITY CORPORATION, Fukuoka-shi (JP); UNIVERISTY OF MIYAZAKI, Miyazaki-shi (JP); KONAN GAKUEN, Kobe-shi (JP); NIPPON SUISAN KAISHA, LTD., Tokyo (JP)

( * ) Notice: Subject to any disclaimer, the term of this patent is extended or adjusted under 35 U.S.C. 154(b) by 78 days.

(21) Appl. No.: 13/877,225

(22) PCT Filed: Sep. 30, 2011

(86) PCT No.: PCT/JP2011/072650
§ 371 (c)(1),
(2), (4) Date: Aug. 1, 2013

(87) PCT Pub. No.: WO2012/043826
PCT Pub. Date: Apr. 5, 2012

(65) Prior Publication Data
US 2013/0309772 A1 Nov. 21, 2013

(30) Foreign Application Priority Data

Oct. 1, 2010 (JP) ................................. 2010-224225
Aug. 18, 2011 (JP) ................................. 2011-179194

(51) Int. Cl.
| C12N 15/79 | (2006.01) |
| C12N 15/89 | (2006.01) |
| C12N 9/02 | (2006.01) |
| C12N 9/10 | (2006.01) |
| C12P 7/64 | (2006.01) |
| C12N 15/52 | (2006.01) |

(52) U.S. Cl.
CPC .............. *C12N 15/79* (2013.01); *C12N 9/0083* (2013.01); *C12N 9/1029* (2013.01); *C12P 7/6409* (2013.01); *C12P 7/6427* (2013.01); *C12P 7/6472* (2013.01); *C12N 15/895* (2013.01); *C12N 9/0071* (2013.01); *C12N 15/52* (2013.01)

(58) Field of Classification Search
CPC ........................................................ C12N 15/79
See application file for complete search history.

(56) References Cited

U.S. PATENT DOCUMENTS

| 6,172,188 | B1 | 1/2001 | Thastrup et al. |
| 7,217,856 | B2 | 5/2007 | Weaver et al. |
| 7,259,006 | B2 | 8/2007 | Komazawa et al. |
| 2002/0107362 | A1 | 8/2002 | Thastrup et al. |
| 2005/0014231 | A1 | 1/2005 | Mukerji et al. |
| 2005/0054050 | A1 | 3/2005 | Thastrup et al. |
| 2006/0275904 | A1 | 12/2006 | Ono et al. |
| 2006/0286650 | A1 | 12/2006 | Ono et al. |
| 2008/0009045 | A1 | 1/2008 | Komazawa et al. |
| 2009/0093033 | A1 | 4/2009 | Luy et al. |
| 2012/0322116 | A1 | 12/2012 | Sakaguchi et al. |

FOREIGN PATENT DOCUMENTS

| JP | 2005-102680 A | 4/2005 | |
| JP | 2006-304685 A | 11/2006 | |
| JP | 2006-304686 A | 11/2006 | |
| JP | 2007-143479 A | 6/2007 | |
| JP | 2007-532104 A | 11/2007 | |
| WO | 97/11094 A1 | 3/1997 | |
| WO | 2006/044646 A2 | 4/2006 | |
| WO | WO2006/044646 * | 4/2006 | ................ C12P 7/64 |
| WO | 2011/037207 A1 | 3/2011 | |

OTHER PUBLICATIONS

Poulos, Alf, "Very Long Chain Fatty Acids in Higher Animals—A Review", Lipids, 1995, vol. 30, No. 1, pp. 1-14, cited in Specification (14 pages).

Horrocks, Lloyd A. et al., "Health Benefits of Docosahexaenoic Acid (DHA)", Pharmacological Research, 1999, vol. 40, No. 3, pp. 211-225, cited in Specification (15 pages).

Yokoyama, Rinka et al., "Taxonomic rearrangement of the genus *Schizochytrium* sensu lato based on morphology, chemotaxonomic characteristics, and 18S rRNA gene phylogeny (Thraustochytriaceae, Labyrinthulomycetes): emendation for *Schizochytrium* and erection of *Aurantiochytrium* and *Oblongichytrium* gen. nov.", Mycoscience, 2007, vol. 48, pp. 199-211, cited in Specification (13 pages).

Iwasaka, Hiroaki et al., "Modification of lipid composition by genetic engineering in oleaginous microorganisms, Labyrinthulida", Lecture Summary for the 60th Conference of The Society for Biotechnology, Japan, 2008, p. 136, cited in ISR and Specification, w/ English abstract (2 pages).

(Continued)

*Primary Examiner* — Scott Long
(74) *Attorney, Agent, or Firm* — Westerman, Hattori, Daniels & Adrian, LLP

(57) ABSTRACT

To provide a transformation method for producing a stramenopile organism having an improved unsaturated fatty acid production capability by disrupting a gene of the stramenopile organism or inhibiting the expression of the gene in a genetically engineering manner. [Solution] A method for transforming a stramenopile organism, which comprises disrupting a gene of the stramenopile organism or inhibiting the expression of the gene in a genetically engineering manner, and which is characterized in that the stramenopile organism is selected from *Thraustochytrium aureum, Parietichytrium sarkarianum, Thraustochytrium roseum* and *Parietichytrium* sp. and the gene to be disrupted or of which the expression is to be inhibited is a gene associated with the biosynthesis of a fatty acid.

38 Claims, 65 Drawing Sheets

(56) References Cited

OTHER PUBLICATIONS

Lippmeier, J. Casey et al., "Characterization of Both Polyunsaturated Fatty Acid Biosynthetic Pathways in *Schizochytrium* sp.", Lipids, 2009, vol. 44, No. 7, pp. 621-630, cited in ISR and Specification (10 pages).

Tonon, Thierry et al., "Identification of a very long chain polyunsaturated fatty acid D4-desaturase from the microalga *Pavlova lutheri*", FEBS Letters, 2003, vol. 553, pp. 440-444, cited in Specification (5 pages).

Thompson, Julie D. et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680, cited in Specification (8 pages).

Yazawa, Kazunaga, "Production of Eicosapentaenoic Acid from Marine Bacteria", Lipids, vol. 31, Supplement, 1996, pp. 197-300, cited in Specification (4 pages).

Jiang, X. et al., "Cloning and expression of two elongase genes involved in the biosynthesis of docosahexaenoic acid in *Thraustochytrium* sp. FJN-10", Wei Sheng Wu Xue Bao, 2008, vol. 48, No. 2, pp. 176-183, cited in Specification, w/ English abstract (9 pages).

Pereira, Suzette L. et al., "A novel w3-fatty acid desaturase involved in the biosynthesis of eicosapentaenoic acid", Biochem. J., 2004, vol. 378, pp. 665-671, cited in Specification (7 pages).

Prasher, Douglas C. et al., "Primary structure of the Aequorea victoria green-fluorescent protein", Gene, 1992, vol. 111, pp. 229-233, cited in Specification (5 pages).

Chalfie, Martin et al., "Green Fluorescent Protein as a Marker for Gene Expression", Science, 1994, vol. 263, pp. 802-805, cited in Specification (4 pages).

Southern, P. J. et al., "Transformation of Mammalian Cells to Antibiotic Resistance with a Bacterial Gene Under Control of the SV40 Early Region Promoter", Journal of Molecular and Applied Genetics, 1982, vol. 1, pp. 327-341, cited in Specification (15 pages).

Saitou, Naruya et al., "The Neighbor-joining Method: A New Method for Reconstructing Phylogenetic Trees", Mol. Biol. Evol., 1987, vol. 4, No. 4, pp. 406-425, cited in Specification (20 pages).

Schiestl, Robert H. et al., "High efficiency transformation of intact yeast cells using single stranded nucleic acids as a carrier", Current Genetics, 1989, vol. 16, pp. 339-346 (8 pages).

Abe, Eriko et al., "A Novel Phosphatidylcholine Which Contains Pentadecanoic Acid at sn-1 and Docosahexaenoic Acid at sn-2 in *Schizochytrium* sp. F26-b", J. Biochem, 2006, vol. 140, pp. 247-253 (7 pages).

Bio-Experiment Illustrated, vol. 2, Fundamentals of Gene Analysis, 1995, Shujunsha, pp. 117-128, cited in Specification, w/ English translation (29 pages).

"Gene Knockout Construct Producing Method by PCR", Japan Society for Bioscience, Biotechnology, and Agrochemistry, 2003, vol. 77, No. 2, pp. 150-153, cited in Specification, w/ English translation (11 pages).

Bio-Experiment Illustrated, vol. 2, Fundamentals of Gene Analysis, 1995, Shujunsha, pp. 63-68, cited in Specification, w/ English translation (12 pages).

Sanger, F. et al., "DNA sequencing with chain-terminating inhibitors", Proc. Natl. Acad. Sci. USA, 1977, vol. 74, No. 12, pp. 5463-5467, cited in Specification (5 pages).

Meyer, Astrid et al., "Novel fatty acid elongases and their use for the reconstitution of docosahexaenoic acid biosynthesis", Journal of Lipid Research, 2004, vol. 45, pp. 1899-1909, cited in Specification (11 pages).

Cigan, A. Mark et al., "Sequence and structural features associated with translational initiator regions in yeast—a review", Gene, 1987, vol. 59, pp. 1-18, cited in Specification (18 pages).

Romanos, Michael A. et al., "Foreign Gene Expression in Yeast: a Review", Yeast, 1992, vol. 8, pp. 423-488, cited in Specification (66 pages).

Qiu, Xiao et al., "Identification of a D4 Fatty Acid Desaturase from *Thraustochytrium* sp. Involved in the Biosynthesis of Docosahexanoic Acid by Heterologous Expression in *Saccharomyces cerevisiae* and *Brassica juncea*", Journal of Biol. Chem., 2001, vol. 276, No. 34, pp. 31561-31566, cited in Specification (6 pages).

"PCR DIG Probe Synthesis Kit", DIG Application Manual 8th, Roche Applied Science, pp. 1-6, cited in Specification (6 pages).

Kobayashi, Takumi et al., "Expression of a delta-5 desaturase gene results in the alternation of fatty acid composition of *Aurantiochytrium* sp. mh0186", Japanese Biochemical Society, 2009, 2P-200, cited in ISR, w/ English translation (3 pages).

Matsuda, Takanori et al., "Isolation of a delta-12 desaturase from *Pinguiochrysis pyriformis* MBIC 10872 and its expression in thraustochytrids", Japanese Biochemical Society, 2009, 2P-199, cited in ISR, w/ English translation (3 pages).

Kang, Dong Hoon et al., "Identification and Characterization of a Novel Enzyme Related to the Synthesis of PUFAs Derived from *Thraustochytrium aureum* ATCC 34304", Biotechnology and Bioprocess Engineering, 2010, vol. 15, pp. 261-272, cited in ISR (12 pages).

Kang, Dong-Hoon et al., "Coexpression of Elo-like Enzyme and D5, D4-Desaturases Derived from *Thraustochytrium aureum* ATCC 34304 and the Production of DHA and DPA in *Pichia pastoris*", Biotechnology and Bioprocess Engineering, 2008, vol. 13, pp. 483-490, cited in ISR (8 pages).

International Search Report dated Nov. 26, 2011, issued in corresponding application No. PCT/JP2011/072650 (2 pages).

* cited by examiner

Fig.3
(A)
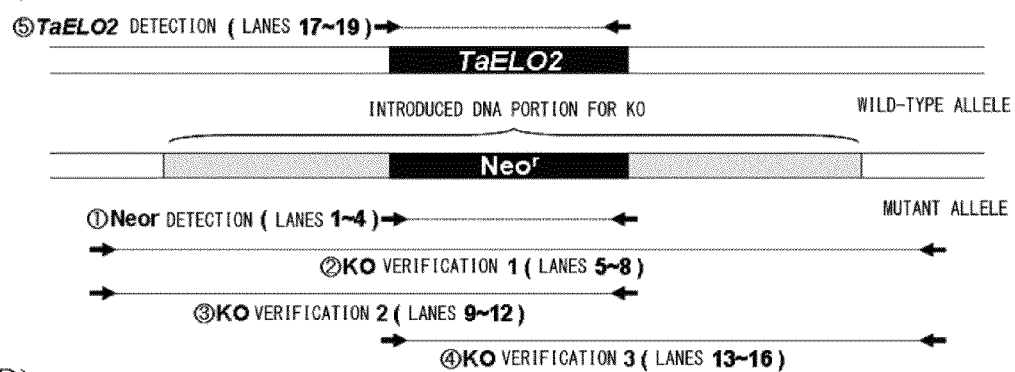
(B)
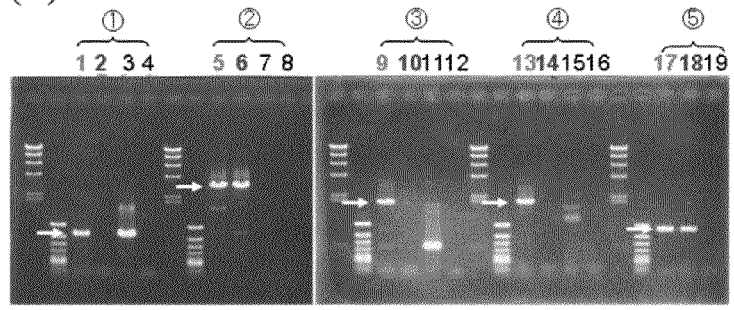
Fig.4
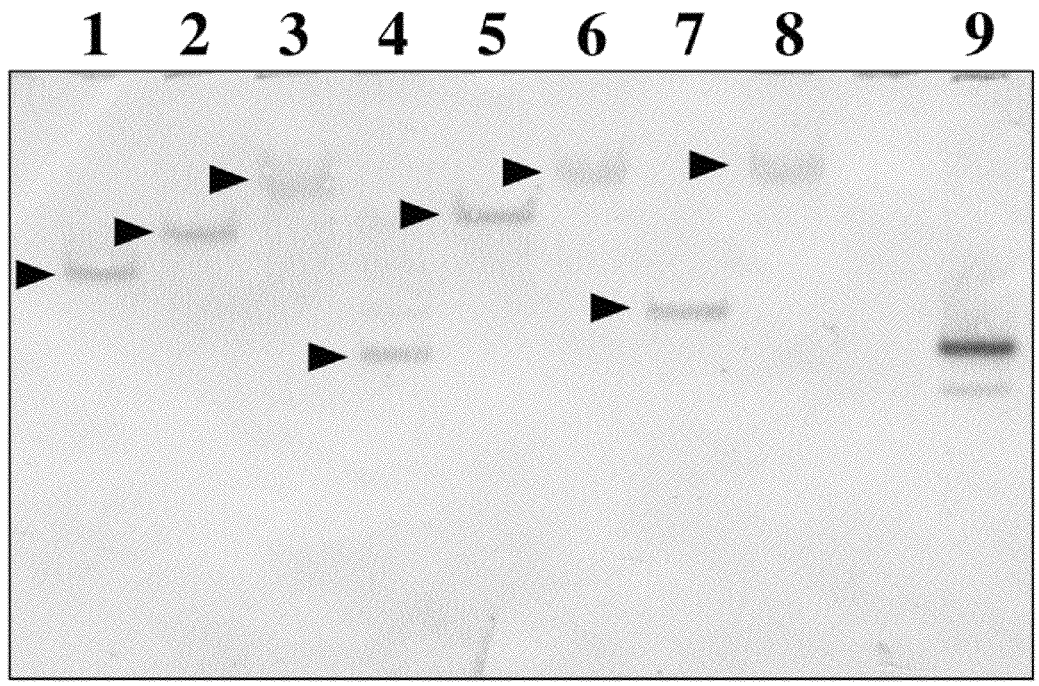

Fig.6
(A)
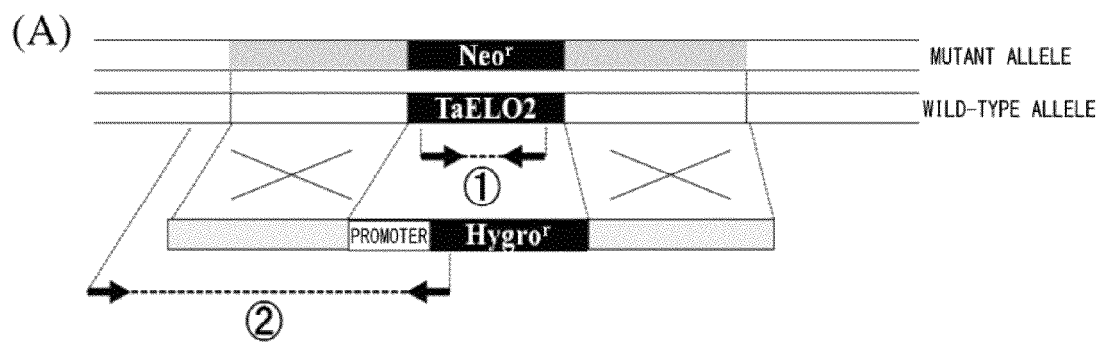
(B)
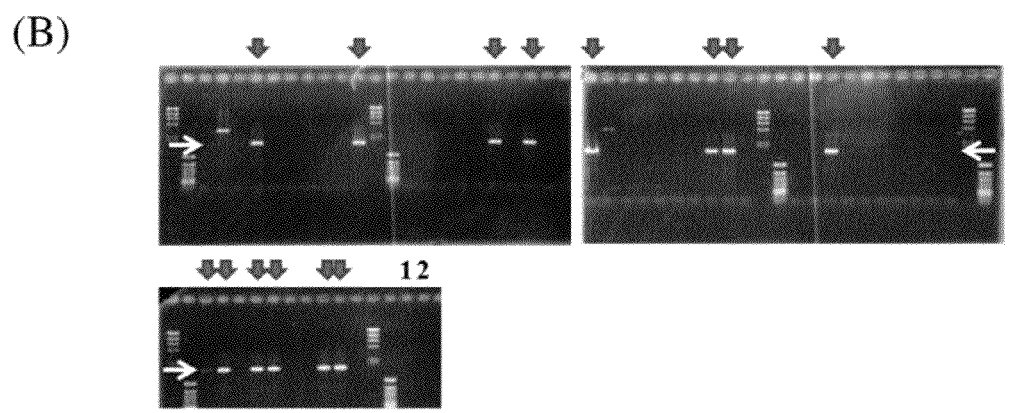
(C)
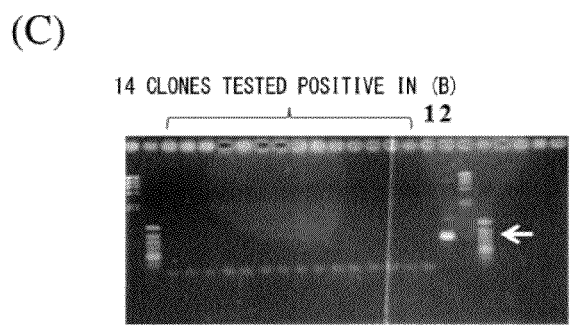

(A)

Fig.9
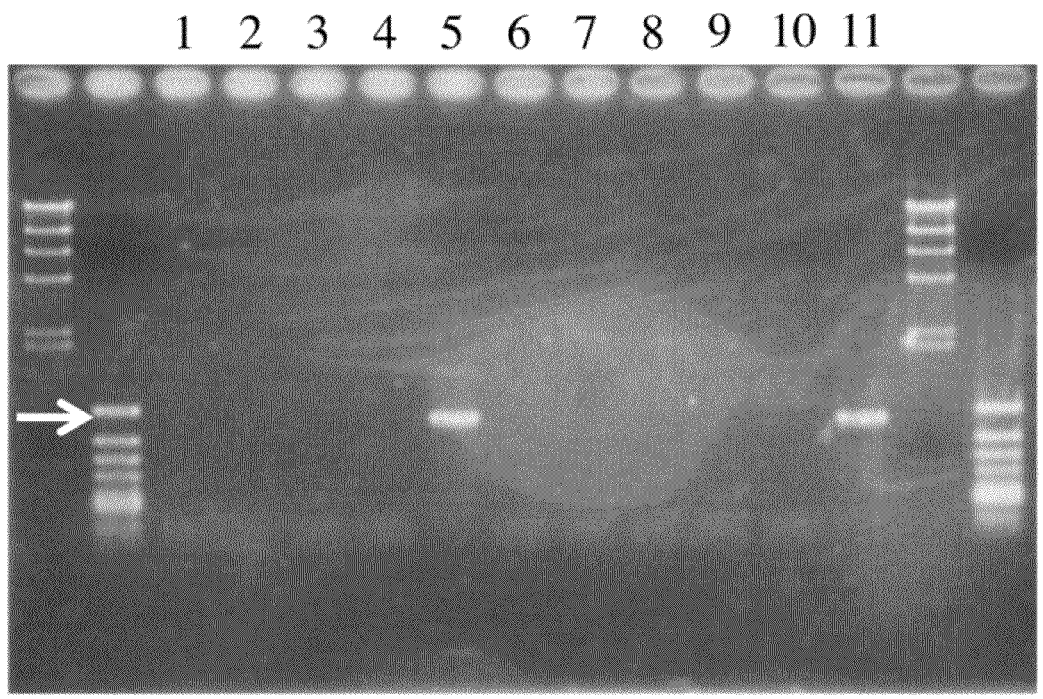
[Fig.10]
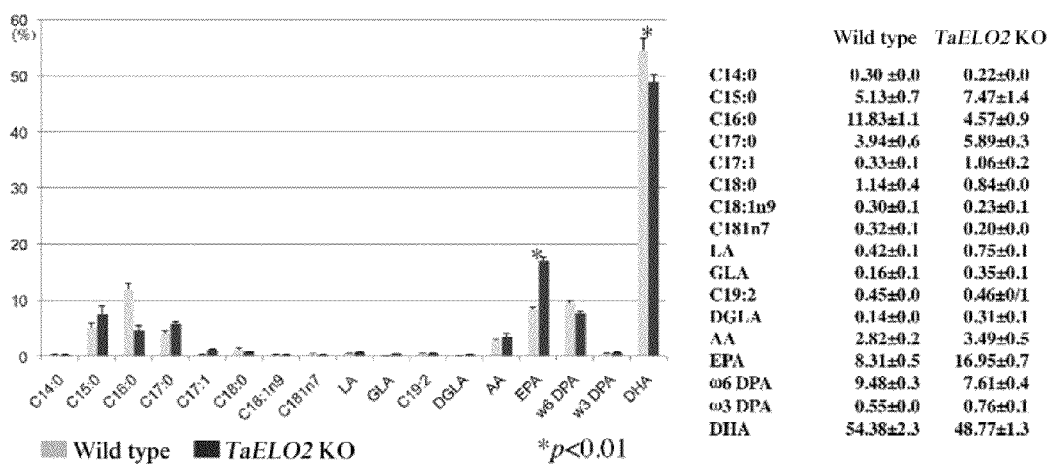

Fig.18
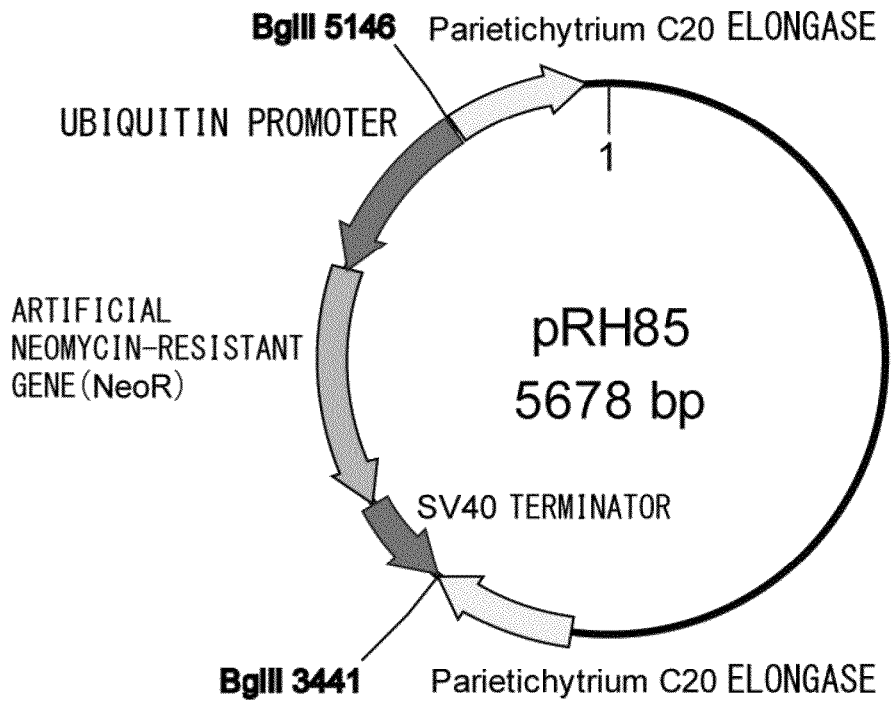
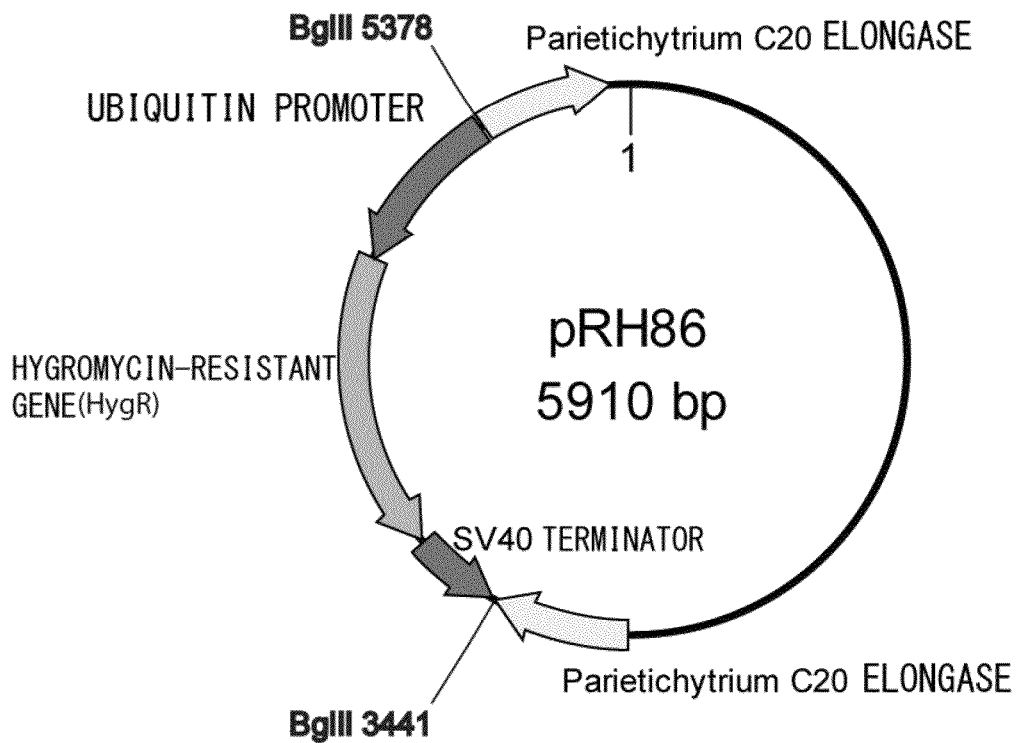

Fig.19
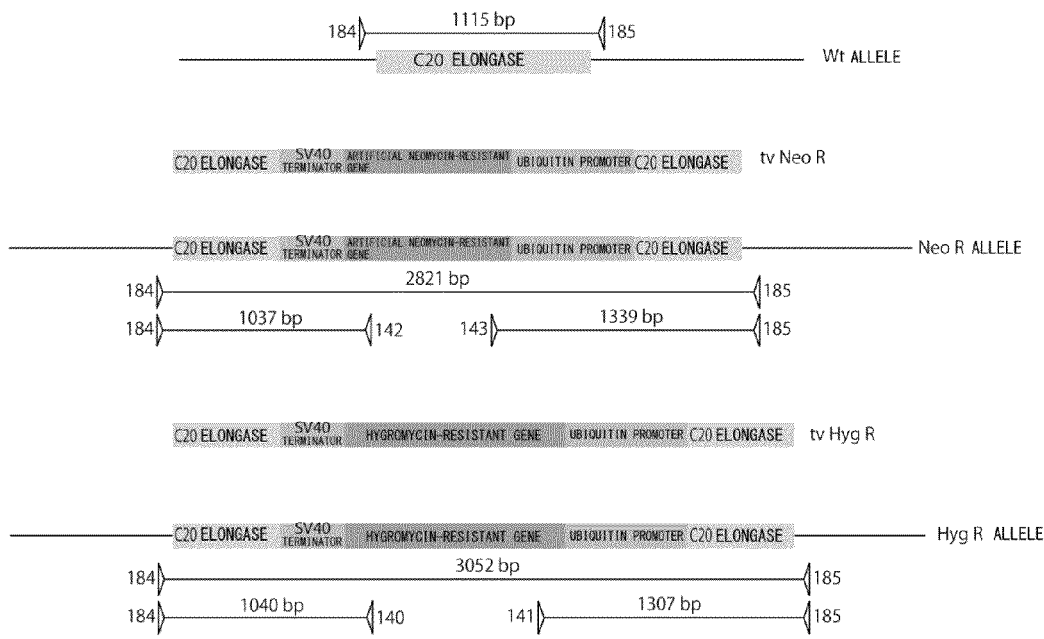
[Fig.20]
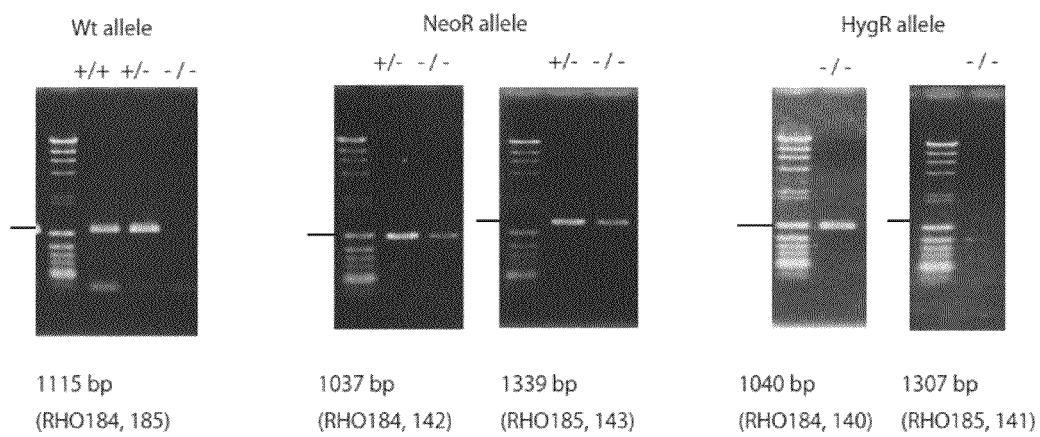

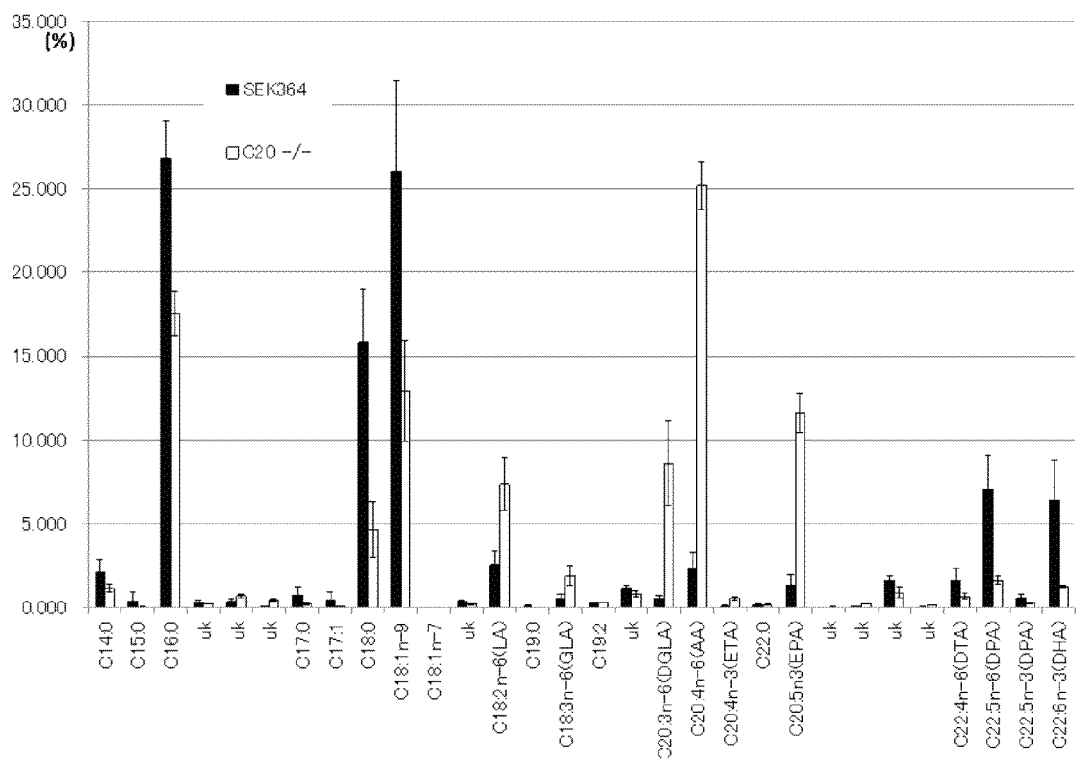

Fig.22

| COMPARISON WITH WILD-TYPE STRAIN | C20 -/- | SEK364 | FA |
|---|---|---|---|
| 54.4% | 1.16 | 2.13 | C14:0 |
| 6.5% | 0.02 | 0.38 | C15:0 |
| 65.4% | 17.55 | 26.83 | C16:0 |
| 31.6% | 0.24 | 0.76 | C17:0 |
| 12.0% | 0.05 | 0.42 | C17:1 |
| 29.4% | 4.66 | 15.84 | C18:0 |
| 49.5% | 12.91 | 26.08 | C18:1n-9 |
| - | 0.00 | 0.00 | C18:1n-7 |
| 289.4% | 7.38 | 2.55 | C18:2n-6(LA) |
| 35.3% | 0.02 | 0.05 | C19:0 |
| 366.7% | 1.91 | 0.52 | C18:3n-6(GLA) |
| 99.5% | 0.31 | 0.31 | C19:2 |
| 1673.7% | 8.62 | 0.51 | C20:3n-6(DGLA) |
| 1079.4% | 25.22 | 2.34 | C20:4n-6(AA) |
| 722.8% | 0.56 | 0.08 | C20:4n-3(ETA) |
| 105.7% | 0.18 | 0.17 | C22:0 |
| 851.2% | 11.58 | 1.36 | C20:5n3(EPA) |
| 42.2% | 0.67 | 1.59 | C22:4n-6(DTA) |
| 23.1% | 1.64 | 7.07 | C22:5n-6(DPA) |
| 45.4% | 0.26 | 0.56 | C22:5n-3(DPA) |
| 20.0% | 1.28 | 6.38 | C22:6n-3(DHA) |

Fig.31

| PKS(OrfA)KO | | T.aureum | FA |
|---|---|---|---|
| 121.2% | 0.33 | 0.27 | C14:0 |
| 60.9% | 7.07 | 11.61 | C15:0 |
| 151.2% | 13.21 | 8.74 | C16:0 |
| 82.8% | 11.97 | 14.46 | C17:0 |
| 83.4% | 2.30 | 2.76 | C17:1 |
| 153.7% | 2.77 | 1.80 | C18:0 |
| 172.6% | 1.21 | 0.70 | C18:1n-9 |
| 339.0% | 3.03 | 0.89 | C18:1n-7 |
| 130.6% | 1.07 | 0.82 | C18:2n-6(LA) |
| 101.5% | 1.02 | 1.01 | C19:0 |
| 105.2% | 0.77 | 0.73 | C18:3n-6(GLA) |
| 131.6% | 0.65 | 0.49 | C19:2 |
| 125.9% | 0.23 | 0.18 | C20:3n-6(DGLA) |
| 141.2% | 3.10 | 2.19 | C20:4n-6(AA) |
| 184.6% | 0.04 | 0.02 | C20:4n-3(ETA) |
| 126.9% | 6.82 | 5.38 | C20:5n3(EPA) |
| 169.6% | 2.00 | 1.18 | C22:4n-6(DTA) |
| 196.3% | 10.66 | 5.43 | C22:5n-6(DPA) |
| 93.6% | 1.13 | 1.20 | C22:5n-3(DPA) |
| 66.5% | 22.58 | 33.97 | C22:6n-3(DHA) |

Fig.40
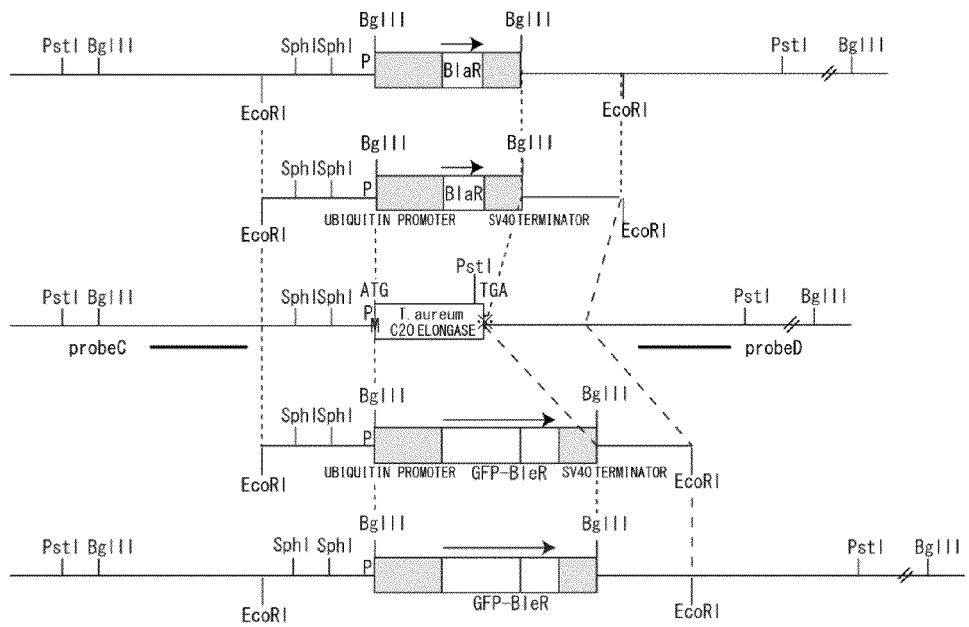
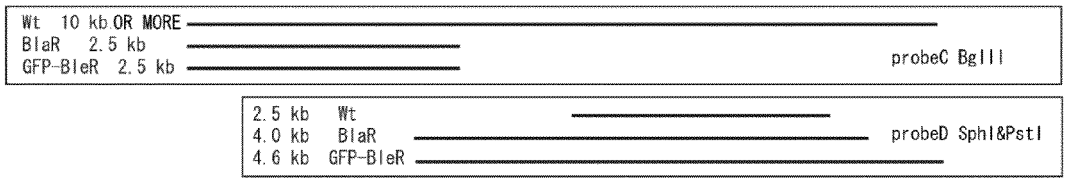
Fig.41
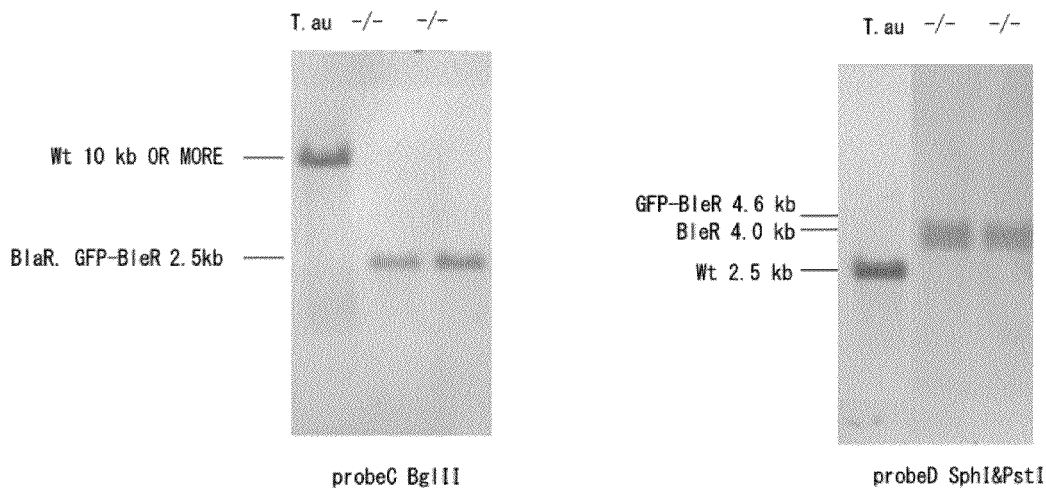

Fig.43

| PKS AND C20KO | T.aureum | | FA |
|---|---|---|---|
| 113.0% | 0.31 | 0.27 | C14:0 |
| 23.3% | 2.71 | 11.61 | C15:0 |
| 176.4% | 15.41 | 8.74 | C16:0 |
| 23.8% | 3.44 | 14.46 | C17:0 |
| 37.0% | 1.02 | 2.76 | C17:1 |
| 125.2% | 2.26 | 1.80 | C18:0 |
| 279.4% | 1.96 | 0.70 | C18:1n-9 |
| 443.0% | 3.96 | 0.89 | C18:1n-7 |
| 208.2% | 1.71 | 0.82 | C18:2n-6(LA) |
| 26.0% | 0.26 | 1.01 | C19:0 |
| 60.9% | 0.45 | 0.73 | C18:3n-6(GLA) |
| 163.7% | 0.81 | 0.49 | C19:2 |
| 996.6% | 1.81 | 0.18 | C20:3n-6(DGLA) |
| 889.0% | 19.50 | 2.19 | C20:4n-6(AA) |
| 1550.6% | 0.31 | 0.02 | C20:4n-3(ETA) |
| 463.3% | 24.92 | 5.38 | C20:5n3(EPA) |
| 40.3% | 0.47 | 1.18 | C22:4n-6(DTA) |
| 108.6% | 5.90 | 5.43 | C22:5n-6(DPA) |
| 47.9% | 0.58 | 1.20 | C22:5n-3(DPA) |
| 20.0% | 6.78 | 33.97 | C22:6n-3(DHA) |

Fig.50

| COMPARISON WITH WILD-TYPE STRAIN | PKS(OrfA)KO Sdic w3 | PKS(OrfA)KO mock | FA |
|---|---|---|---|
| 106.1% | 0.52 | 0.49 | C14:0 |
| 105.7% | 0.63 | 0.59 | C15:0 |
| 118.1% | 23.39 | 19.81 | C16:0 |
| 109.6% | 0.56 | 0.51 | C17:0 |
| 147.4% | 0.13 | 0.09 | C17:1 |
| 86.7% | 9.43 | 10.87 | C18:0 |
| 84.2% | 8.50 | 10.09 | C18:1n-9 |
| 120.5% | 3.09 | 2.56 | C18:1n-7 |
| 98.4% | 5.18 | 5.26 | C18:2n-6(LA) |
| 94.4% | 0.17 | 0.18 | C19:0 |
| 124.3% | 0.59 | 0.47 | C18:3n-6(GLA) |
| 99.4% | 0.70 | 0.70 | C19:2 |
| 83.7% | 1.77 | 2.12 | C20:3n-6(DGLA) |
| 13.8% | 1.53 | 11.13 | C20:4n-6(AA) |
| 5398.4% | 0.54 | 0.01 | C20:4n-3(ETA) |
| 375.8% | 11.36 | 3.02 | C20:5n3(EPA) |
| 40.0% | 2.04 | 5.11 | C22:4n-6(DTA) |
| 7.0% | 1.16 | 16.55 | C22:5n-6(DPA) |
| 669.3% | 3.85 | 0.58 | C22:5n-3(DPA) |
| 314.1% | 22.04 | 7.02 | C22:6n-3(DHA) |

Fig.57

| COMPARISON WITH WILD-TYPE STRAIN | C20elo KO | T. roseum | FA |
|---|---|---|---|
| 14.5% | 1.11 | 7.65 | C14:0 |
| 23.9% | 1.81 | 7.57 | C15:0 |
| 78.2% | 21.89 | 27.99 | C16:0 |
| 28.8% | 0.48 | 1.68 | C18:0 |
| 59.9% | 1.42 | 2.37 | C18:1n9 |
| 8.4% | 0.08 | 0.99 | C18:1n7 |
| 79.9% | 2.47 | 3.09 | C19:2 |
| 121.8% | 5.50 | 4.51 | C20:4n-6(ARA) |
| 163.8% | 8.45 | 5.16 | C20:5n-3(EPA) |
| 124.8% | 13.17 | 10.55 | DPA(n-6) |
| 154.5% | 43.94 | 28.44 | DHA |
|  | 100 | 100 | total |

Fig.60
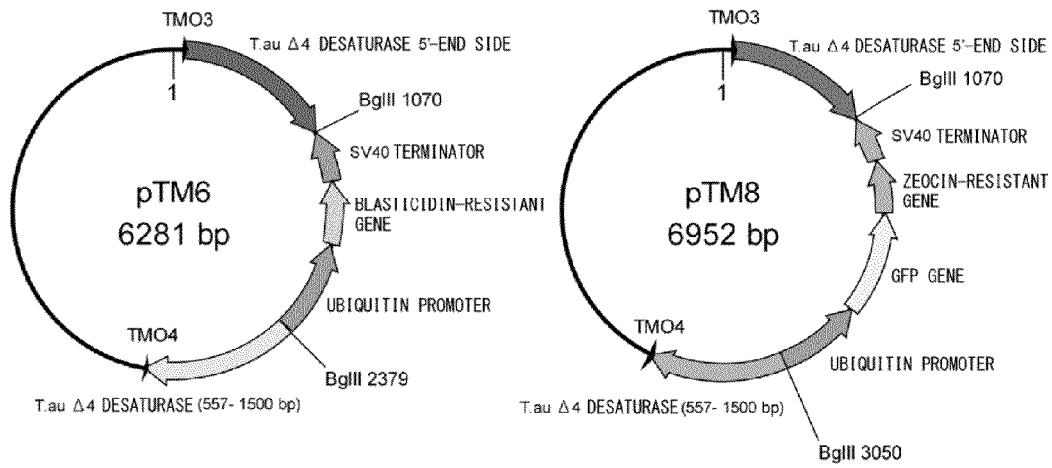
Fig.61
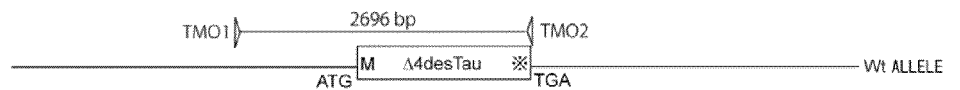
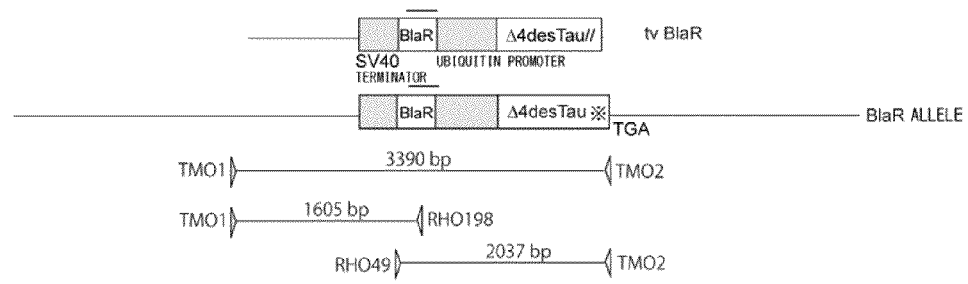
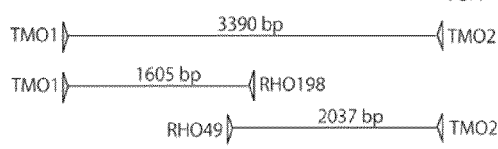
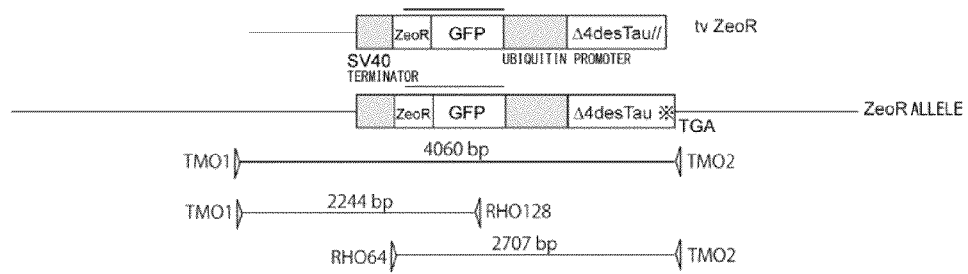

Fig.64

| PKS AND ⊿4des KO | T.aureum | FA |
|---|---|---|
| 92.6% | 0.58 | 0.62 | C14:0 |
| 101.0% | 4.48 | 4.43 | C15:0 |
| 53.7% | 7.28 | 13.56 | C16:0 |
| 176.1% | 5.84 | 3.32 | C17:0 |
| 128.4% | 2.05 | 1.60 | C18:0 |
| 304.9% | 4.83 | 1.58 | C18:1n-9 |
| 250.1% | 4.49 | 1.80 | C18:1n-7 |
| 450.5% | 4.47 | 0.99 | C18:2n-6(LA) |
| 310.7% | 0.81 | 0.26 | C19:0 |
| 784.5% | 2.67 | 0.34 | C18:3n-6(GLA) |
| 229.0% | 0.59 | 0.26 | C19:2 |
| 353.7% | 0.90 | 0.25 | C20:3n-6(DGLA) |
| 164.2% | 6.35 | 3.87 | C20:4n-6(AA) |
| 182.8% | 0.28 | 0.15 | C20:4n-3(ETA) |
| 78.1% | 6.22 | 7.96 | C20:5n3(EPA) |
| 2008.9% | 11.01 | 0.55 | C22:4n-6(DTA) |
| 2.4% | 0.21 | 8.79 | C22:5n-6(DPA) |
| 2695.8% | 15.78 | 0.59 | C22:5n-3(DPA) |
| 1.2% | 0.51 | 41.71 | C22:6n-3(DHA) |

Fig.67

| C20 elongase KO | SEK358 | FA |
|---|---|---|
| 101.0% | 1.41 | 1.40 | C14:0 |
| 32.0% | 2.44 | 7.63 | C15:0 |
| 62.1% | 13.49 | 21.73 | C16:0 |
| 26.6% | 1.96 | 7.34 | C17:0 |
| 39.6% | 2.95 | 7.46 | C18:0 |
| 22.0% | 3.19 | 14.47 | C18:1n-9 |
| 84.5% | 0.19 | 0.23 | C18:1n-7 |
| 269.4% | 4.28 | 1.59 | C18:2n-6(LA) |
| 247.0% | 2.61 | 1.06 | C18:3n-6(GLA) |
| 201.5% | 0.34 | 0.17 | C19:2 |
| 499.9% | 8.64 | 1.73 | C20:3n-6(DGLA) |
| 654.8% | 21.35 | 3.26 | C20:4n-6(AA) |
|  | 2.14 | 0.00 | C20:4n-3(ETA) |
|  | 0.30 | 0.00 | C22:0 |
| 1069.6% | 23.83 | 2.23 | C20:5n3(EPA) |
| 8.0% | 0.26 | 3.28 | C22:4n-6(DTA) |
| 6.4% | 0.46 | 7.10 | C22:5n-6(DPA) |
| 21.6% | 0.23 | 1.06 | C22:5n-3(DPA) |
| 12.3% | 0.94 | 7.61 | C22:6n-3(DHA) |

Fig.70

| C20 elongase KO | SEK571 | FA | |
|---|---|---|---|
| 43.8% | 0.98 | 2.23 | C14:0 |
| 197.0% | 4.86 | 2.47 | C15:0 |
| 40.6% | 14.13 | 34.78 | C16:0 |
| 152.7% | 4.80 | 3.14 | C17:0 |
| 43.4% | 4.71 | 10.86 | C18:0 |
| 85.5% | 3.66 | 4.28 | C18:1n-9 |
| 234.8% | 0.37 | 0.16 | C18:1n-7 |
| 251.6% | 1.70 | 0.67 | C18:2n-6(LA) |
| 228.8% | 1.07 | 0.47 | C18:3n-6(GLA) |
| 156.9% | 0.24 | 0.16 | C19:2 |
| 450.2% | 1.93 | 0.43 | C20:3n-6(DGLA) |
| 388.5% | 13.24 | 3.41 | C20:4n-6(AA) |
| 1048.9% | 1.14 | 0.11 | C20:4n-3(ETA) |
| 182.8% | 0.43 | 0.24 | C22:0 |
| 796.8% | 29.58 | 3.71 | C20:5n3(EPA) |
| 9.0% | 0.15 | 1.61 | C22:4n-6(DTA) |
| 8.2% | 0.96 | 11.69 | C22:5n-6(DPA) |
| 34.0% | 0.25 | 0.75 | C22:5n-3(DPA) |
| 8.6% | 1.17 | 13.62 | C22:6n-3(DHA) |

Fig. 71

```
Thalassiosira    1  PLAKDAP------------ELPSKGEIKAVIPKECFERSYLHSMYFVLRDTVMAVACA
Phaeodactylum    1  PLAKDAP------------ELPTKGQIKAVIPKECFQRSAFWSTFYLMRDLAMAAAFC
TD12d            1  ------------KLPTIGELRKAVPAHCFEKSTLKSLFTVARDLAFCSAIG
Micromonas       1  ATQDIPHSGLEGQALRFPTKDLFPTRAEVLTSIPEDCFEKDTVKSLFYAALSAAMTLSCG
consensus        1  .......              ..*........*.**......*........

Thalassiosira   47  YIAHSTLSTDIPSLLSVDALKWFLGWNTYAFWMGCILTGHWVLAHECGHGAFSPSQTFN
Phaeodactylum   47  YGTSQVLSTDLPQDATLI--LPWALGWGVYAFWMGTILTGPWVLAHECGHGAYSDSQTFN
TD12d           40  YAAWEYIPVEWSIKAIAL----WTLYAIVQGTVATGVWLCHEGGHGGISSYSIVN
Micromonas      61  LLAFAYVPMKLAYLPTWL----AYAALTGTIGTGCWVIAHECGHNAFSKNRFIQ
consensus       61  .. .. .... ...        **...*... ** **. **.**...*  ....

Thalassiosira  107  DFWGFIMHQAVLVPYFAWQYSHAKHHRRTNNIMDGESHVPNIAKEMGLNEKNERSGGYAA
Phaeodactylum  105  DVVGFIVHQALLVPYFAWQYTHAKHHRRTNHLVDGESHVPSTAKDNGLGPHNERNSFYAA
TD12d           92  DTVGYVYLHSILLVPYFSWQDSHRRHHARCNHLLDGESHNPDLKR---------KVYKMYEK
Micromonas     111  DAVGYLLHSLLLVPYFSWQRSHAVHHSRTNHLTEGETHVPYVKG---------EVKGSLNLE
consensus      121  *..*...*...*****.**..*.**.*.*...** *.*......      ...

Thalassiosira  167  IHEAIGDGPFAMFQIFAHLVIGWPIYLMGFASTGRLCQDGKELQAG-EIIDHYRPWSKMF
Phaeodactylum  165  WHEAMGDGAFAVFQVWSHLFVGWPLYLAGLASTGKLAHEGWWLEERNAIADHTRPSSPMF
TD12d          144  ILDTVGEDAFVIMQIVLHLVLGWPMYLLMHATGSRRSPVTGQKYTLKPNHFNWGASNEQY
Micromonas     164  LHKRLGEGPFAILQLVAHLVFGWPAYLLTGATGGSARGVTNHFIPS----INTGP-IELF
consensus      181  .....*...*..*...**. ***.*....*....                .....

Thalassiosira  226  PTKLRFKIALSTLGVIAAWVGLYFAAQEYGVLPVVLWYIGPLWWNQAWLVLYTWLQHNDP
Phaeodactylum  225  PAKIRAKIALSSATELAVLAGLLVVGTQVGHLPVLLWYWGPYTFVNAWLVLYTWLQHTDP
TD12d          204  PAKLRFKIFLSSLGVIATLAGIIAVLANKLGAAKVSLMYFGPYLVVNAWLVGYTWLQHTDQ
Micromonas     219  PCSWKKKVWLSDVGVVGFVAILAHWAYNSGLATVAALYFGPYLFVNIWLVLYTWLQHTDT
consensus      241  *.....*..**.........*....*..*.***..**.******.*

Thalassiosira  286  SVPQYGSDEWTWVKGALSTIDRPYG-IFDFFHHKIGSTHVAHHLFHEMPFYKADVATASI
Phaeodactylum  285  SIPHYGEGEWTWVKGALSTIDRDYG-IFDFFHHTIGSTHVVHHLFHEMPWYNAGIATQKV
TD12d          264  DAPHYGEDEWTWIKGAMTTIDRPYPWIVDELHHHIGTTHVCHHLFSDMPHYKAQEATEAL
Micromonas     279  DVPHLAASEWSYIKGAFLTIDRPYGAIFDFLHHRIGSTHVAHHVECAIPHYNALKATDAL
consensus      301  .*...**...***..****.*. *.*..**.***.**....*.***.**...

Thalassiosira  345  KGFLEPKGLYNYDPTPWYVAMWRVAKTCHYIEDVDGVQYKSLEDVPLKKDAKKSD-
Phaeodactylum  344  KEFLEPQGLYNYDPTPWYKAMWRIARTCHYVESNEGVQYIKSMENVPLTKDVRSKAA
TD12d          324  KPVLGKII---YRTDPTPLAQAMWNTARDCHYVEGLDGVQYPQSII--IAEKRAAKKL---
Micromonas     339  KQKYPDL---YLYDPTPINAALWRVASKCVAVEP--RCQGKDLIWTFTTKKQPAVERS
consensus      361  * .......*.****.. *.*.*..*...*....*.......
```

| FA LEVEL (μg) DRAY CELL WEIGHT 1mg | | | | |
|---|---|---|---|---|
| | mock ave. | mock std. | TΔ12d ave. | TΔ12d std. |
| C14:0 | 0.483883 | 0.118188 | 0.5181282 | 0.05081 |
| C16:0 | 7.127198 | 1.223085 | 7.451359 | 0.579578 |
| C16:1n7 | 19.16444 | 2.936704 | 17.042456 | 2.69802 |
| C18:0 | 1.910871 | 0.255276 | 1.9670849 | 0.22879 |
| C18:1n9 | 11.05722 | 0.945736 | 6.1005013 | 0.498143 |
| C18:2n6 | 0 | 0 | 3.5566365 | 0.98697 |
| Total | 40.45796 | 5.459088 | 37.350518 | 4.913859 | n=3

Fig.75
Hygr INHERITANCE
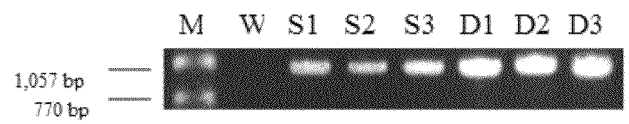
Blar GENE
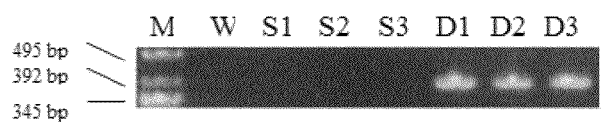
Δ12 desaturase GENE
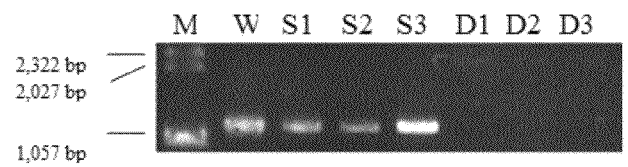
[Fig.76]
Hygr INHERITANCE
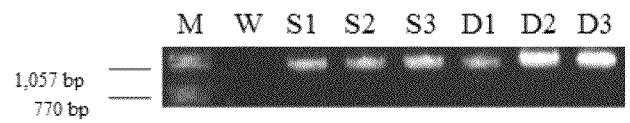
Blar GENE
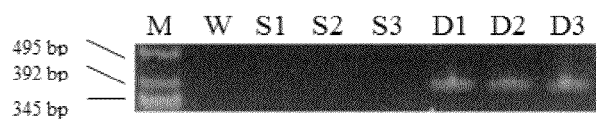
Δ12 desaturase GENE
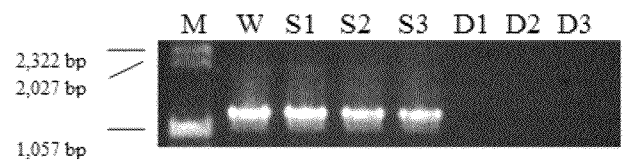

Fig.77
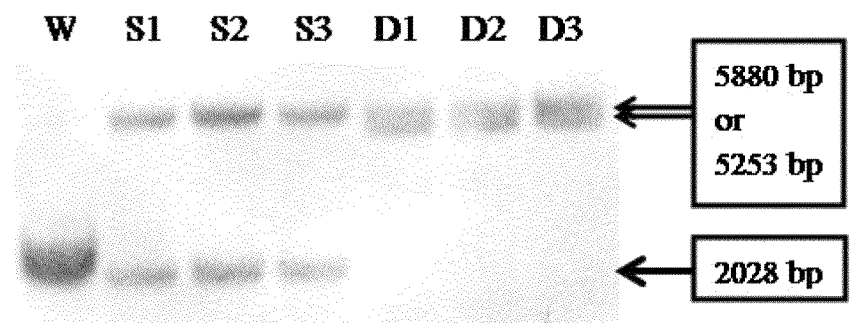
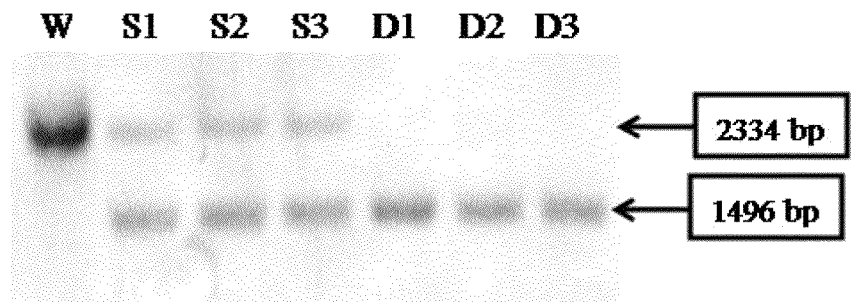

Fig.87

| PKS, AND C20 ELONGASE KO AND ω3 DESATURASE EXPRESSION | T.aureum | FA | |
|---|---|---|---|
| 106.7% | 0.89 | 0.83 | C14:0 |
| 162.2% | 0.84 | 0.52 | C15:0 |
| 87.1% | 25.22 | 28.96 | C16:0 |
| 86.7% | 0.36 | 0.42 | C17:0 |
| 101.1% | 11.75 | 11.62 | C18:0 |
| 281.5% | 6.55 | 2.33 | C18:1n-9 |
| 795.0% | 2.01 | 0.25 | C18:1n-7 |
| 372.7% | 2.55 | 0.69 | C18:2n-6(LA) |
| 0.0% | 0.00 | 0.06 | C19:0 |
| 333.5% | 0.37 | 0.11 | C18:3n-6(GLA) |
| 300.4% | 0.59 | 0.20 | C19:2 |
| 576.4% | 2.19 | 0.38 | C20:3n-6(DGLA) |
| 601.0% | 15.95 | 2.65 | C20:4n-6(AA) |
| 235.5% | 0.31 | 0.13 | C20:4n-3(ETA) |
| 1075.4% | 21.58 | 2.01 | C20:5n3(EPA) |
| 60.2% | 0.22 | 0.36 | C22:4n-6(DTA) |
| 43.9% | 2.10 | 4.77 | C22:5n-6(DPA) |
| 40.4% | 0.21 | 0.52 | C22:5n-3(DPA) |
| 5.9% | 2.17 | 36.59 | C22:6n-3(DHA) |

Fig. 90
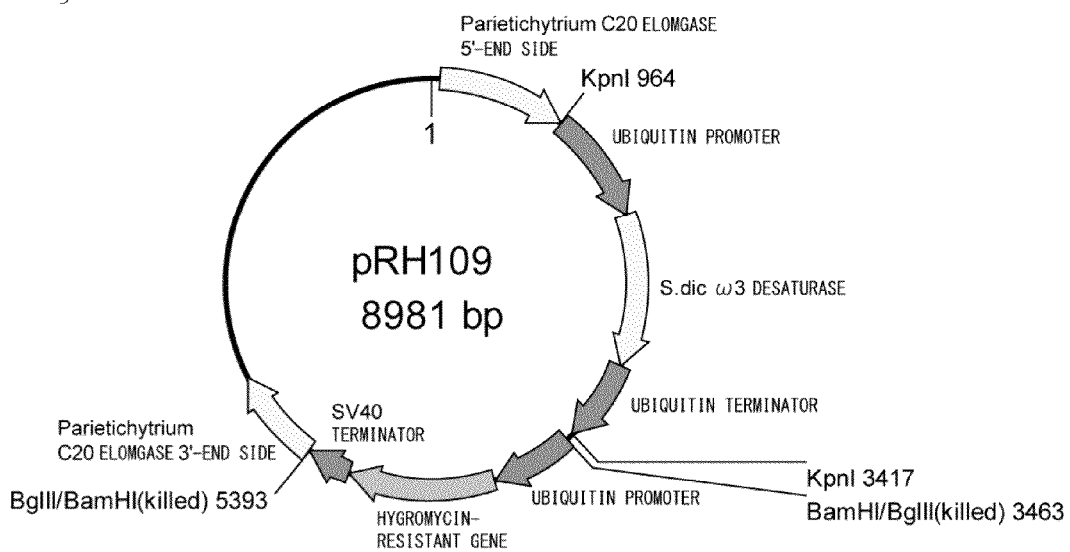
[Fig. 91]
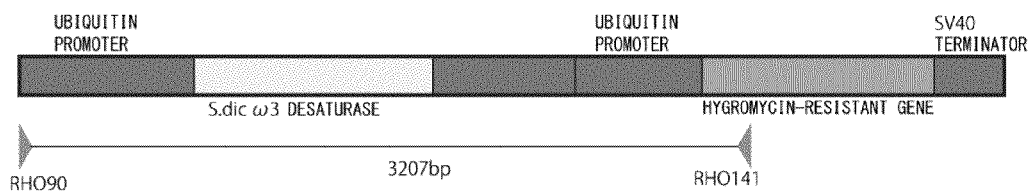

Fig.94

| C20 ELONGASE KO AND ω3 DESATURASE EXPRESSION | SEK571 | FA | |
|---|---|---|---|
| 154.8% | 3.45 | 2.23 | C14:0 |
| 0.0% | 0.00 | 2.47 | C15:0 |
| 45.6% | 15.86 | 34.78 | C16:0 |
| 4.7% | 0.15 | 3.14 | C17:0 |
| 182.1% | 19.77 | 10.86 | C18:0 |
| 925.2% | 39.58 | 4.28 | C18:1n-9 |
| 0.0% | 0.00 | 0.16 | C18:1n-7 |
| 265.2% | 1.79 | 0.67 | C18:2n-6(LA) |
| 0.0% | 0.00 | 0.47 | C18:3n-6(GLA) |
| 141.0% | 0.22 | 0.16 | C19:2 |
| 57.1% | 0.24 | 0.43 | C20:3n-6(DGLA) |
| 42.9% | 1.46 | 3.41 | C20:4n-6(AA) |
| 449.2% | 0.49 | 0.11 | C20:4n-3(ETA) |
| 108.3% | 0.26 | 0.24 | C22:0 |
| 139.6% | 5.18 | 3.71 | C20:5n3(EPA) |
| 0.0% | 0.00 | 1.61 | C22:4n-6(DTA) |
| 1.8% | 0.21 | 11.69 | C22:5n-6(DPA) |
| 28.5% | 0.21 | 0.75 | C22:5n-3(DPA) |
| 3.2% | 0.44 | 13.62 | C22:6n-3(DHA) |

| COMPARISON WITH WILD-TYPE STRAIN | C20elo KO | S. sp. TY12Ab | FA |
|---|---|---|---|
| 150.0% | 3.0±0.06 | 2.0 | C14:0 |
| 59.8% | 26.4±1.97 | 43.5 | C16:0 |
| 160.0% | 8.0±1.52 | 5.0 | C18:0 |
| 197.0% | 6.5±1.32 | 3.3 | C18:1 |
| 127.3% | 2.8±0.12 | 2.2 | C18:2 |
| 166.7% | 17.2±1.45 | 10.2 | C20:4n-6 |
| 132.0% | 3.3±0.64 | 2.5 | C20:5n-3 |
| 114.0% | 13.7±2.19 | 11.4 | C22:5n-6 |
| 66.7% | 0.4±0.10 | 0.6 | C22:5n-3 |
| 87.7% | 15.6±1.81 | 17.1 | C22:6n-3 |
| 139.1% | 3.2±1.08 | 2.3 | other |
|  | 100 | 100 | total |

METHOD FOR TRANSFORMATION OF STRAMENOPILE

TECHNICAL FIELD

The present invention relates to a method for transforming stramenopile whereby genes of stramenopile are disrupted and/or expression thereof is inhibited by genetic engineering. Particularly, the invention relates to a transformation method for disrupting genes associated with fatty acid biosynthesis and/or inhibiting expression thereof, a method for modifying the fatty acid composition of a stramenopile, a method for highly accumulating fatty acids in a stramenopile, a stramenopile having an enhanced unsaturated fatty acid content, and a method for producing unsaturated fatty acid from the unsaturated fatty acid content-enhanced stramenopile, among others.

BACKGROUND ART

Polyunsaturated fatty acids (PUFA) represent an important component of animal and human nutrition. ω3 polyunsaturated fatty acids (also called n-3 polyunsaturated fatty acids) such as eicosapentaenoic acid (EPA) and docosahexaenoic acid (DHA) have a wide range of roles in many aspects of health, including brain development in children, eye functions, syntheses of hormones and other signaling substances, and prevention of cardiovascular disease, cancer, and diabetes mellitus (Non-Patent Documents 1 and 2). These fatty acids therefore represent an important component of human nutrition. Accordingly, there is a need for polyunsaturated fatty acid production.

Meanwhile, microorganisms of the class Labyrinthulomycetes are known to produce polyunsaturated fatty acids. Concerning microorganisms of the family *Thraustochytrium*, there are reports of, for example, a polyunsaturated fatty acid-containing phospholipid producing method using *Schizochytrium* microorganisms (Patent Document 1), and *Thraustochytrium* microorganisms having a docosahexaenoic acid producing ability (Patent Document 2). For enhancement of food and/or feed by the unsaturated fatty acids, there is a strong demand for a simple economical process for producing these unsaturated fatty acids, particularly in the eukaryotic system.

With regard to the class Labyrinthulomycetes, there have been reported foreign gene introducing methods for specific strains of the genus *Schizochytrium* (the genus *Auranthiochytrium* (Non-Patent Document 4) in the current classification scheme (Non-Patent Document 3)) (Patent Documents 3 and 4). Further, a method that causes a change in fatty acid composition by means of transformation is known in which a polyketide synthase (PKS) gene is destroyed to change the resulting fatty acid composition (Non-Patent Document 5). However, there is no report directed to changing a fatty acid composition by manipulating the enzymes of the elongase/desaturase pathway. Under these circumstances, the present inventors found ways to change fatty acid compositions through introduction of elongase/desaturase genes into various species of Labyrinthulomycetes, and have filed a patent application therefor (Patent Document 5).

CITATION LIST

Patent Documents

Patent Document 1: JP-A-2007-143479
Patent Document 2: JP-A-2005-102680
Patent Document 3: JP-A-2006-304685
Patent Document 4: JP-A-2006-304686
Patent Document 5: WO2011/037207
Patent Document 6: WO1997/011094
Patent Document 7: US Patent Application US2005/0014231
Patent Document 8: JP-T-2007-532104 (the term "JP-T" as used herein means a published Japanese translation of a PCT patent application)

Non-Patent Documents

Non-Patent Document 1: Poulos A., Lipids, 30, 1-14 (1995)
Non-Patent Document 2: Horrocks L. A. and Yeo Y. K., Pharmacol Res., 40, 211-225 (1999)
Non-Patent Document 3: Yokoyama R., Honda D., Mycoscience, 48, 199-211 (2007)
Non-Patent Document 4: Lecture Summary for the 60th Conference of The Society for Biotechnology, Japan, p 136 (2008)
Non-Patent Document 5: Lippmeier J. C. et al., Lipids, 44(7), 621-630 (2009)
Non-Patent Document 6: Tonon T. et al., FEBS Lett., 553, 440-444 (2003).
Non-Patent Document 7: Thompson J. D. et al., Nucleic Acids Res., 22, 4673-4680 (1994)
Non-Patent Document 8: Yazawa K., Lipids, 31, Supple. 297-300 (1996)
Non-Patent Document 9: Jiang X. et al., Wei Sheng Wu Xue Bao., 48(2), 176-183 (2008)
Non-Patent Document 10: PEREIRA S. L. et al., Biochem. J., 378, 665-671 (2004)
Non-Patent Document 11: Prasher D. C. et al., Gene, 111(2), 229-233 (1992)
Non-Patent Document 12: Chalfie M. et al., Science, 263, 802-805 (1994)
Non-Patent Document 13: Southern P. J., and Berg, P., J. Molec. Appl. Gen., 1, 327-339 (1982)
Non-Patent Document 14: Saitou N. et al., Mol. Biol. Evol., 4, 406-425 (1987)
Non-Patent Document 15: Ausubel F. M. et al., Current Protocols in Molecular Biology, Unit 13 (1994)
Non-Patent Document 16: Guthrie C., Fink G. et al., Methods in Enzymology: Guide to Yeast Genetics and Molecular Biology, Volume 194 (1991)
Non-Patent Document 17: Abe E., et al., J. Biochem, 142, 31561-31566 (2006)
Non-Patent Document 18: Bio-Experiment Illustrated 2, Fundamentals of Gene Analysis, p 117-128, Shujunsha, 1995
Non-Patent Document 19: Japan Society for Bioscience, Biotechnology, and Agrochemistry, 77, 2, 150-153 (2003)
Non-Patent Document 20: Bio-Experiment Illustrated 2, Fundamentals of Gene Analysis, p 63-68, Shujunsha, 1995
Non-Patent Document 21: Sanger, F. et al., Proc. Natl. Acad. Sci, 74, 5463 (1977)
Non-Patent Document 22: Meyer, A., et al. J. Lipid Res., 45, 1899-1909 (2004)
Non-Patent Document 23: Cigan and Donahue, 1987; Romanos et al., 1992
Non-Patent Document 24: Qiu, X., et al. J. Biol. Chem., 276, 31561-6 (2001)
Non-Patent Document 25: DIG Application Manual [Japanese version] 8th, Roche Applied Science

SUMMARY OF THE INVENTION

Problems that the Invention is to Solve

The present invention is directed to improving the ability of a stramenopile to produce useful substances byway of transformation through disruption of stramenopile genes and/or inhibition of expression thereof by genetic engineering. By modifying the ability to produce useful substances through disruption of stramenopile genes associated with production of useful substances and/or inhibition of expression thereof by genetic engineering, the invention provides a modification method of a fatty acid composition produced by a stramenopile, a method for highly accumulating fatty acids in a stramenopile, an unsaturated fatty acid producing method, a stramenopile having an enhanced unsaturated fatty acid content, and production of unsaturated fatty acid from the unsaturated fatty acid content-enhanced stramenopile. With the modification of a fatty acid composition produced by a stramenopile, and the method for highly accumulating fatty acids in a stramenopile, the present invention enables more efficient production of polyunsaturated fatty acids.

Means for Solving the Problems

The present inventors conducted intensive studies under the foregoing circumstances of the conventional techniques, and succeeded in transforming a stramenopile by way of disrupting stramenopile genes and/or inhibiting expression thereof by genetic engineering to greatly improve the ability of the stramenopile to produce an unsaturated fatty acid. The present inventors also found a method for modifying the fatty acid composition produced by a stramenopile through disruption of stramenopile genes or inhibition of expression thereof by genetic engineering, and a method for highly accumulating unsaturated fatty acids in the transformed stramenopile. The present invention was completed after further studies and development for practical applications.

The gist of the present invention includes the following stramenopile transformation methods (1) to (12).

(1) A method for transforming stramenopile, the method including disrupting a stramenopile gene and/or inhibiting expression thereof by genetic engineering.

(2) The method according to (1), wherein the stramenopile belongs to the class Labyrinthulomycetes.

(3) The method according to (2), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium,* or *Sicyoidochytrium.*

(4) The method according to (3), wherein the microorganisms are *Thraustochytrium aureum, Parietichytrium sarkarianum, Thraustochytrium roseum, Parietichytrium* sp., or *Schizochytrium* sp.

(5) The method according to (4), wherein the microorganisms are *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(6) The method according to any one of (1) to (5), wherein the stramenopile gene is a gene associated with fatty acid biosynthesis.

(7) The method according to (6), wherein the gene associated with fatty acid biosynthesis is a gene associated with polyketide synthase, fatty acid chain elongase, and/or fatty acid desaturase.

(8) The method according to (7), wherein the fatty acid chain elongase is a C20 elongase.

(9) The method according to (7), wherein the fatty acid desaturase is a Δ12 desaturase.

(10) The method according to any one of (1) to (9), wherein the method used to disrupt the stramenopile gene by genetic engineering is electroporation or a gene-gun technique introducing a loss-of-function gene or a DNA fragment from which a coding region of the gene is deleted.

(11) The method according to any one of (1) to (10), wherein the method used to inhibit expression of the stramenopile gene by genetic engineering is an antisense technique or RNA interference.

(12) The method according to any one of (1) to (11), further including introducing a gene associated with fatty acid desaturase.

(13) The method according to (12), wherein the gene associated with fatty acid desaturase is an ω3 desaturase.

Further, the gist of the present invention includes the following methods (14) to (26) for modifying the fatty acid composition of a stramenopile.

(14) A method for modifying the fatty acid composition of a stramenopile, the method including disrupting a stramenopile gene and/or inhibiting expression thereof by genetic engineering.

(15) The method according to (14), wherein the stramenopile belongs to the class Labyrinthulomycetes.

(16) The method according to (15), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium,* or *Sicyoidochytrium.*

(17) The method according to (16), wherein the microorganisms are *Thraustochytrium aureum, Parietichytrium sarkarianum, Thraustochytrium roseum, Parietichytrium* sp., or *Schizochytrium* sp.

(18) The method according to (17), wherein the microorganisms are *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(19) The method according to any one of (14) to (18), wherein the stramenopile gene is a gene associated with fatty acid biosynthesis.

(20) The method according to (19), wherein the gene associated with fatty acid biosynthesis is a gene associated with polyketide synthase, fatty acid chain elongase, and/or fatty acid desaturase.

(21) The method according to (20), wherein the fatty acid chain elongase is a C20 elongase.

(22) The method according to (21), wherein the fatty acid desaturase is a Δ12 desaturase.

(23) The method according to any one of (14) to (22), wherein the method used to disrupt the stramenopile gene by genetic engineering is electroporation or a gene-gun technique introducing a loss-of-function gene or a DNA fragment from which a coding region of the gene is deleted.

(24) The method according to any one of (14) to (23), wherein the method used to inhibit expression of the stramenopile gene by genetic engineering is an antisense technique or RNA interference.

(25) The method according to any one of (14) to (24), further including introducing a gene associated with fatty acid desaturase.

(26) The method according to (25), wherein the gene associated with fatty acid desaturase is an ω3 desaturase.

Further, the gist of the present invention includes the following methods (27) to (29) for highly accumulating fatty acids in a stramenopile.

(27) A method for highly accumulating a fatty acid in a stramenopile, wherein the method uses the method of any one of (14) to (26).

(28) The method according to (27), wherein the fatty acid is an unsaturated fatty acid.

(29) The method according to (28), wherein the unsaturated fatty acid is an unsaturated fatty acid of 18 to 22 carbon atoms.

Further, the gist of the present invention includes the following fatty acid (30).

(30) A fatty acid obtained from the stramenopile in which the fatty acid is highly accumulated by using the method of any one of (27) to (29).

Further, the gist of the present invention includes the following transformed stramenopiles (31) to (43).

(31) A stramenopile transformed for the modification of the fatty acid composition through disruption of its gene and/or inhibition of expression thereof by genetic engineering.

(32) The stramenopile according to (31), wherein the stramenopile belongs to the class Labyrinthulomycetes.

(33) The stramenopile according to (32), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium*, or *Sicyoidochytrium*.

(34) The stramenopile according to (33), wherein the microorganisms are *Thraustochytrium aureum, Parietichytrium sarkarianum, Thraustochytrium roseum, Parietichytrium* sp., or *Schizochytrium* sp.

(35) The stramenopile according to (34), wherein the microorganisms are *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), *Parietichytrium* sp. SEK571 (FERM BP-11406), or *Schizochytrium* sp. TY12Ab (FERM BP-11421).

(36) The stramenopile according to any one of (31) to (35), wherein the stramenopile gene is a gene associated with fatty acid biosynthesis.

(37) The stramenopile according to (36), wherein the gene associated with fatty acid biosynthesis is a gene associated with polyketide synthase, fatty acid chain elongase, and/or fatty acid desaturase.

(38) The stramenopile according to (36), wherein the fatty acid chain elongase is a C20 elongase.

(39) The stramenopile according to (37), wherein the fatty acid desaturase is a Δ12 desaturase.

(40) The stramenopile according to any one of (31) to (39), wherein the method used to disrupt the stramenopile gene by genetic engineering is electroporation or a gene-gun technique introducing a loss-of-function gene or a DNA fragment from which a coding region of the gene is deleted.

(41) The stramenopile according to any one of (31) to (40), wherein the method used to inhibit expression of the stramenopile gene by genetic engineering is an antisense technique or RNA interference.

(42) The stramenopile according to any one of (31) to (41), further comprising introducing a gene associated with fatty acid desaturase is introduced.

(43) The stramenopile according to (42), wherein the gene associated with fatty acid desaturase is an ω3 desaturase.

Advantage of the Invention

The present invention improves the ability of a stramenopile to produce useful substances by way of transformation through disruption of stramenopile genes and/or inhibition of expression thereof by genetic engineering. By modifying the stramenopiles' ability to produce useful substances through disruption of stramenopile genes associated with production of useful substances and/or inhibition of expression thereof by genetic engineering, the invention provides a modification method of a fatty acid composition produced by a stramenopile, a method for highly accumulating fatty acids in a stramenopile, an unsaturated fatty acid producing method, a stramenopile having an enhanced unsaturated fatty acid content, and production of unsaturated fatty acid from the unsaturated fatty acid content-enhanced stramenopile. With the modification of the fatty acid composition produced by a stramenopile, and the method for highly accumulating fatty acids in a stramenopile, the present invention enables more efficient production of polyunsaturated fatty acids.

BRIEF DESCRIPTION OF THE DRAWINGS

FIG. 3 represents the evaluation of transfectants with the introduced KONeor in Example 2-8. (A), an oligonucleotide primer set used for the evaluation of the transfectants by a PCR performed with template genomic DNA. [Brief Description of Reference Numerals] (1) Neor detection primers (SNeoF and SNeoR), (2) KO verification 1 (KO Pro F SmaI and KO Term R SmaI), (3) KO verification 2 (E2 KO ProF EcoRV and SNeoR), (4) KO verification 3 (SNeoF and E2 KO Term R EcoRV), (5) TaELO2 detection (E2 HindIII and E2 XbaI); (B), the result of agarose electrophoresis in the evaluation of the transfectants by a PCR performed with template genomic DNA. [Brief Description of Reference Numerals] 1, 5, 9, 13, 17: transfectants; 2, 6, 10, 14, 18: wild-type strains; 3, 7, 11, 15, 19: samples using KONeor as a template; 4, 8, 12, 16: no template. The numbers (1) to (5) above the lane numbers represent the oligonucleotide primer sets used.

FIG. 4 represents the result of confirming the copy numbers of TaELO2 by southern blotting in Example 2-9. [Brief Description of Reference Numerals] 1: genomic DNA (2.5 µg), BamHI treatment; 2: BglII treatment; 3: EcoRI treatment; 4: EcoRV treatment; 5: HindIII treatment; 6: KpnI treatment; 7: SmaI treatment; 8: XbaI treatment; 9: positive control (a PCR product amplified with 1-ng E2 KO ProF EcoRV and E2 KO Term R EcoRV, containing TaELO2).

FIG. 6 represents the PCR evaluation performed in Example 2-12 by using as a template the genomic DNA of the transfectant obtained by KOub600Hygr reintroduction. (A), the oligonucleotide primer set used. [Brief Description of Reference Numerals] (1) TaELO2 ORF detection (SNeoF and SNeoR), (2) KO verification (E2 KO Pro F EcoRV and ubi-hygro R); (B), the result of agarose electrophoresis in a PCR using the oligonucleotide primer set (1) for KO verification (arrows indicate transfectants for which amplification of a specific product was confirmed, and that were assumed to be TaELO2-deficient homozygotes); (C) the result of agarose electrophoresis in a PCR performed for the transfectants identified as TaELO2-deficient homozygotes using the oligonucleotide primer set (2) for TaELO2 ORF detection. [Brief Description of Reference Numerals] 1: sample using KOub600Hygr as a template; 2: wild-type strain.

FIG. 9 represents the result of the RT-PCR agarose gel electrophoresis performed for the detection of TaELO2 mRNA in Example 2-12. [Brief Description of Reference Numerals] 1-4 TaELO2-deficient homozygotes; 5: wild-type strain; 6-9: TaELO2-deficient homozygotes, using total RNA as a template (negative control); 10: wild-type strain, using total RNA as a template (negative control); 11: sample using wild-type strain genomic DNA as a template (positive control).

FIG. 10 represents the result of the comparison of the fatty acid compositions of the wild-type strain and a TaELO2-deficient homozygote in Example 2-13.

FIG. 18 represents produced *Parietichytrium* C20 elongase gene targeting vectors (two vectors). The vectors have a neomycin-resistant gene (pRH85) or a hygromycin-resistant gene (pRH86) as a drug-resistance marker.

FIG. 19 is a schematic view representing the positions of the PCR primers used for the identification of the C20 elongase gene disrupted strain of *Parietichytrium sarkarianum* SEK364, and the expected products.

FIG. 20 represents the C20 elongase gene disruption evaluation performed by a PCR using the *Parietichytrium sarkarianum* SEK364 genomic DNA as a template. [Description of Reference Numerals]+/+: *Parietichytrium sarkarianum* SEK364 wild-type strain; +/−: *Parietichytrium sarkarianum* SEK364-derived C20 elongase gene first allele homologous recombinant; −/−: *Parietichytrium sarkarianum* SEK364-derived C20 elongase gene disrupted strain.

FIG. 21 represents the result of the comparison of the fatty acid compositions of the *Parietichytrium sarkarianum* SEK364 wild-type strain and the C20 elongase gene disrupted strain. Blank bar and solid bar indicate the fatty acid compositions of the wild-type strain and the gene disrupted strain, respectively. All values are given as mean value±standard deviation.

FIG. 22 represents the proportions of the fatty acids of the C20 elongase gene disrupted strain relative to the *Parietichytrium sarkarianum* SEK364 wild-type strain taken as 100%.

*Thraustochytrium aureum* ATCC 34304 wild-type strain; +/−: *Thraustochytrium aureum* ATCC 34304-derived PKS pathway-associated gene orfA first allele homologous recombinant; −/−: *Thraustochytrium aureum* ATCC 34304-derived PKS pathway-associated gene orfA disrupted strain.

Figure 30:
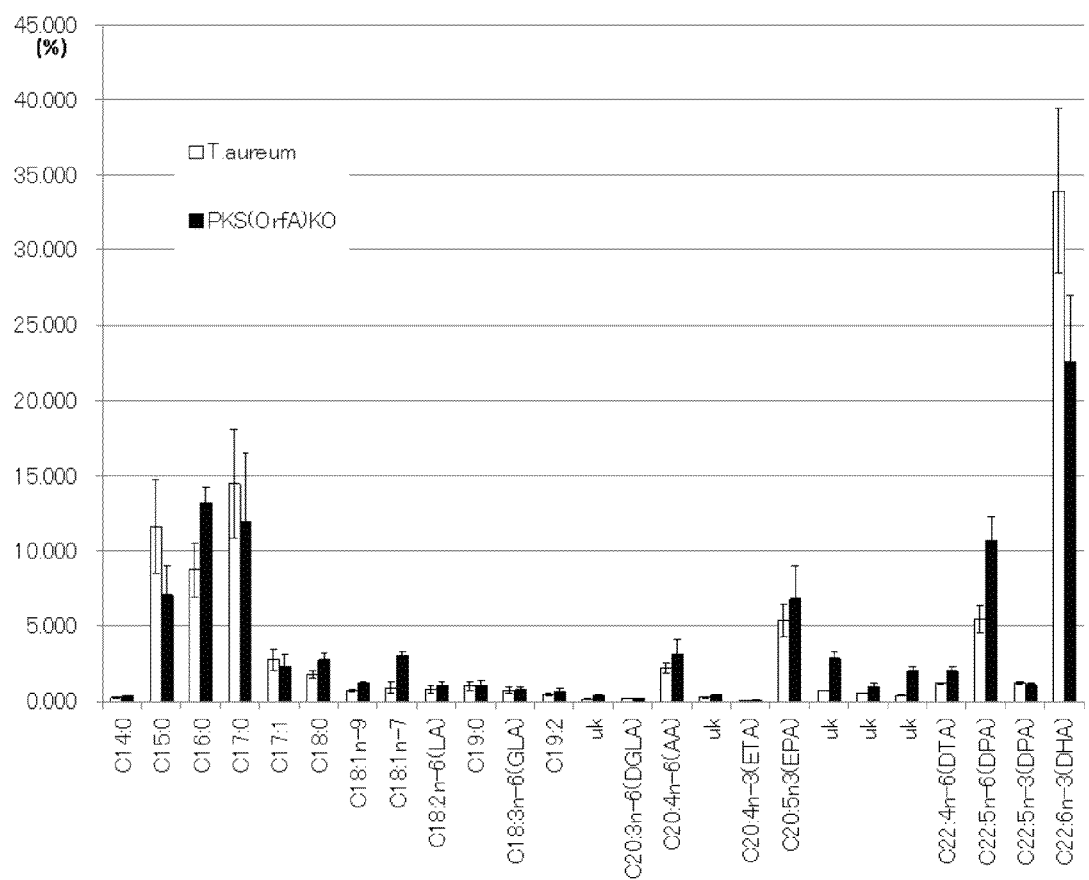

FIG. 30 represents the result of the comparison of the fatty acid compositions of the *Thraustochytrium aureum* ATCC 34304 wild-type strain and the PKS pathway-associated gene orfA disrupted strain. Blank bar and solid bar indicate the fatty acid compositions of the wild-type strain and the gene disrupted strain, respectively. All values are given as mean value±standard deviation.

FIG. 31 represents the proportions of the fatty acids of the PKS pathway-associated gene orfA disrupted strain relative to the *Thraustochytrium aureum* ATCC 34304 wild-type strain taken as 100%.

Figure 32:
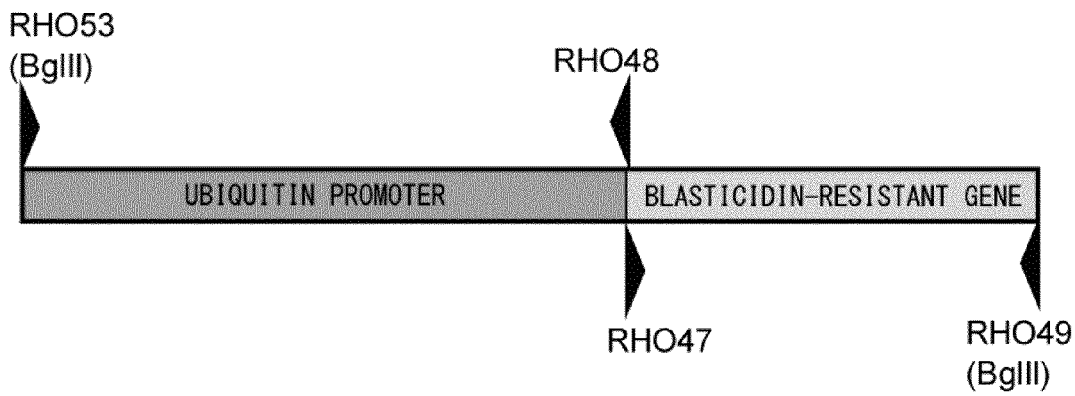

FIG. 32 is a schematic view representing the primers used for fusion PCR, and the product. The end product is the fused sequence of *Thraustochytrium aureum* ATCC 34304-derived ubiquitin promoter and pTracer-CMV/Bsd/lacZ-derived blasticidin-resistant gene.

Figure 33:
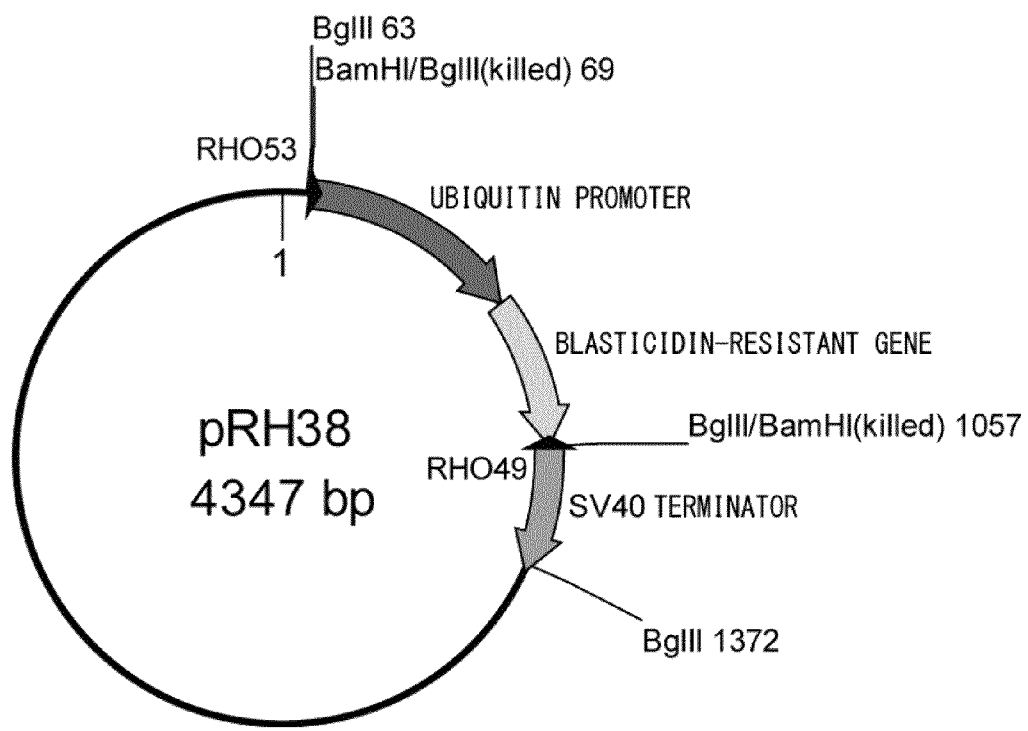

FIG. 33 represents a pTracer-CMV/Bsd/lacZ-derived blasticidin-resistant gene BglII cassette.

Figure 34:
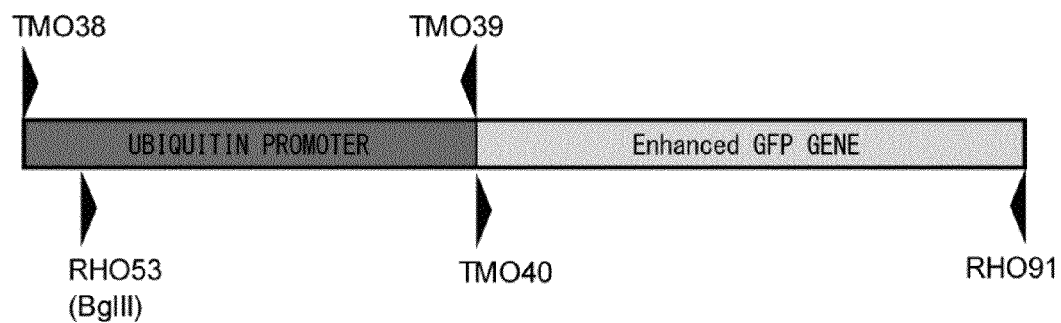

FIG. 34 is a schematic view representing the primers used for fusion PCR, and the product. The end product is the fused sequence of *Thraustochytrium aureum* ATCC 34304-derived ubiquitin promoter and enhanced GFP gene (clontech).

Figure 35:
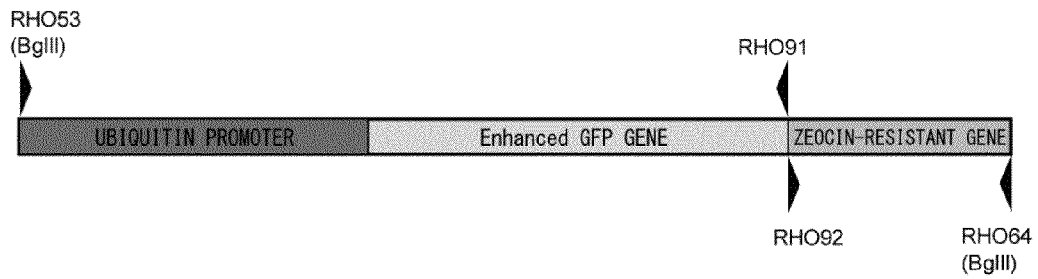

FIG. 35 is a schematic view representing the primers used for fusion PCR, and the product. The end product is the fused sequence of *Thraustochytrium aureum* ATCC 34304-derived ubiquitin promoter, enhanced GFP gene (clontech), and pcDNA3.1 Zeo(+)-derived zeocin-resistant gene.

Figure 36:
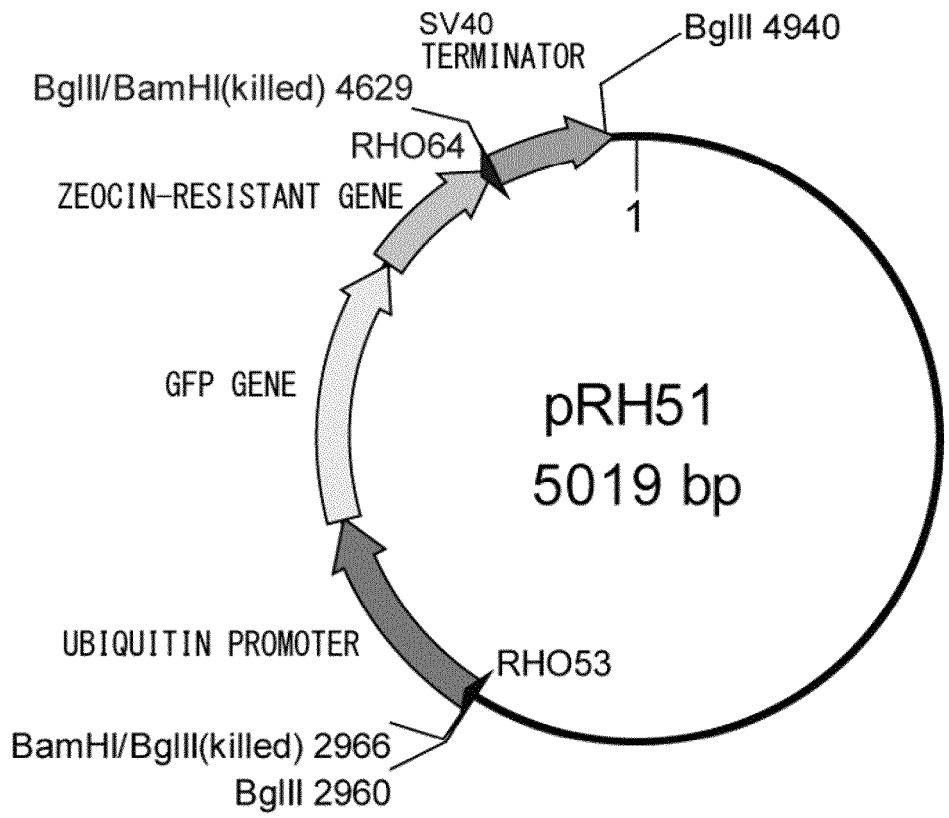

FIG. 36 represents a produced enhanced GFP-zeocin-resistant fused gene BglII cassette.

Figure 37:
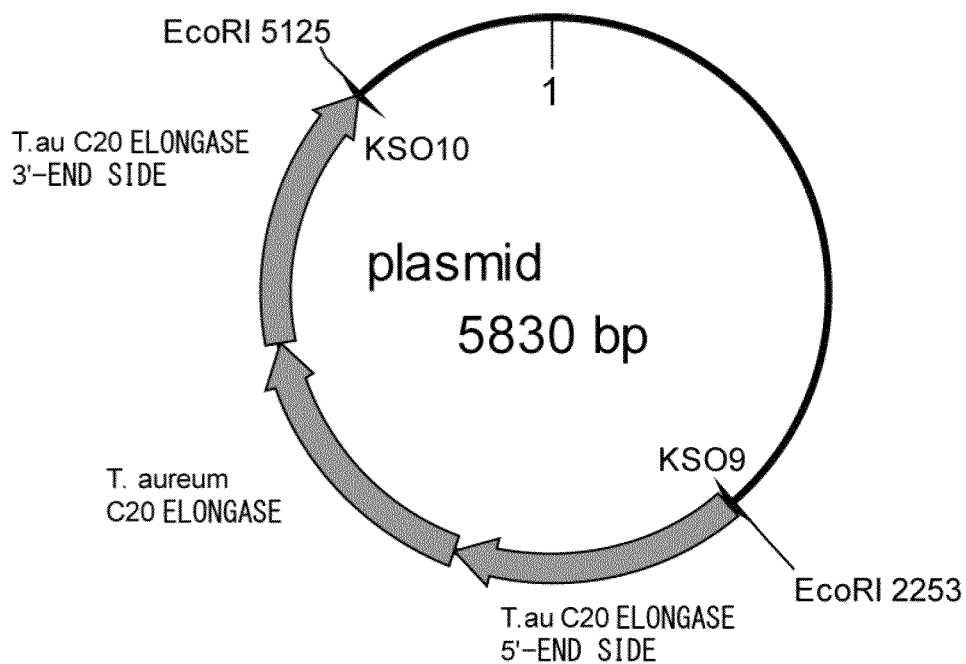

FIG. 37 represents a plasmid containing a cloned *Thraustochytrium aureum* ATCC 34304 C20 elongase sequence and nearby sequences.

Figure 38:
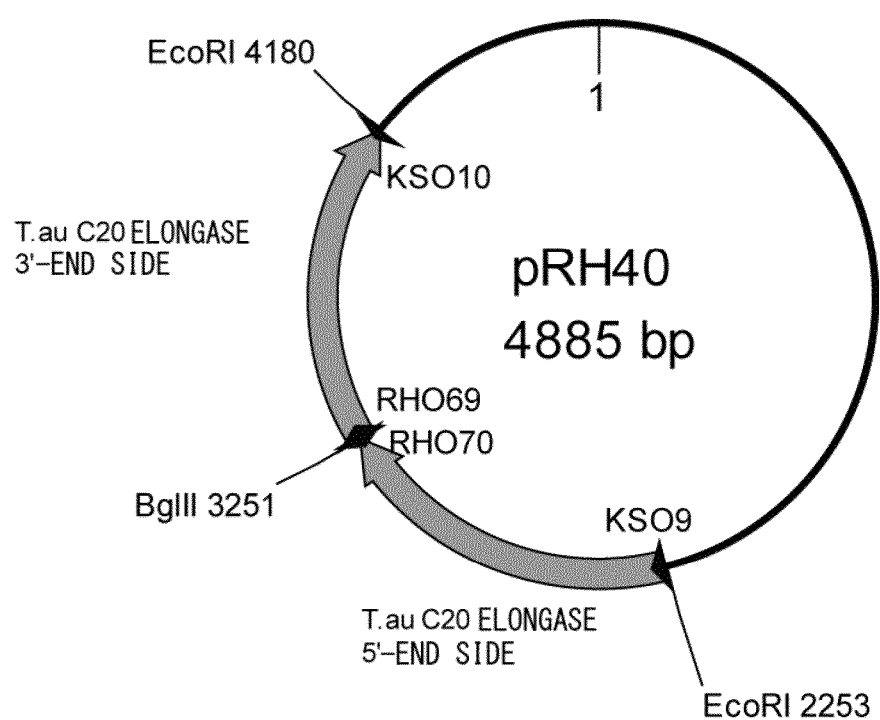

FIG. 38 represents a plasmid with the inserted BglII site after the complete deletion of the *Thraustochytrium aureum* ATCC 34304 C20 elongase sequence from the plasmid of FIG. 37.

Figure 39:
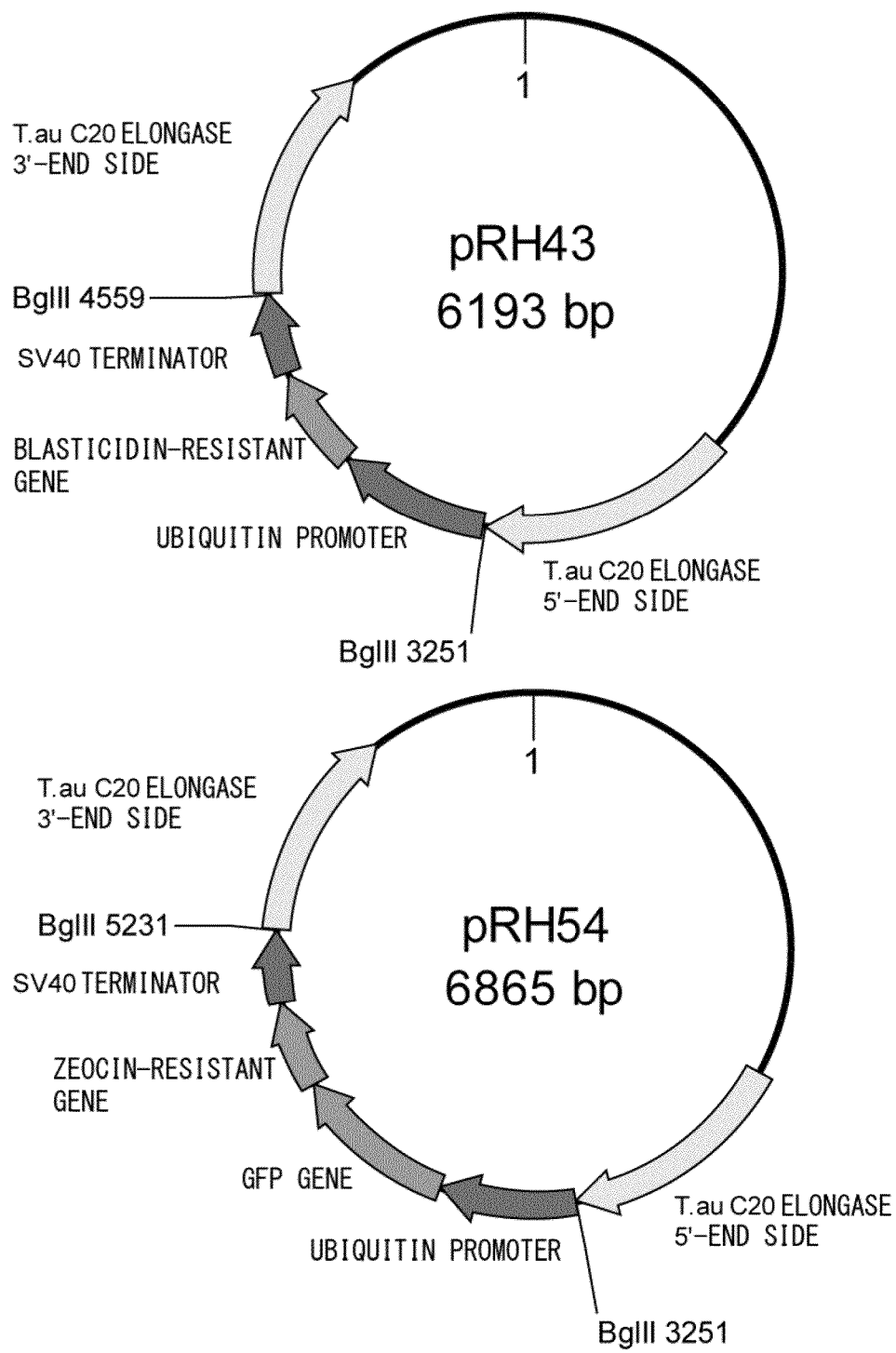

FIG. 39 represents produced *Thraustochytrium aureum* ATCC 34304 C20 elongase gene targeting vectors (two vectors). The vectors have a blasticidin-resistant gene (pRH43) or an enhanced GFP-zeocin-resistant fused gene (pRH54) as a drug-resistance marker.

FIG. 40 is a schematic view representing the positions of the southern hybridization analysis probes used for the identification of the C20 elongase gene disrupted strain of the *Thraustochytrium aureum* ATCC 34304 PKS pathway (orfA gene) disrupted strain, and the expected gene fragment sizes.

FIG. 41 represents the evaluation of C20 elongase gene disruption performed by southern hybridization using the *Thraustochytrium aureum* ATCC 34304 genomic DNA. [Description of Reference Numerals] T. au: *Thraustochytrium aureum* ATCC 34304 wild-type strain; −/−: *Thraustochytrium aureum* ATCC 34304-derived PKS pathway (orfA gene) and C20 elongase gene double disrupted strain.

Figure 42:
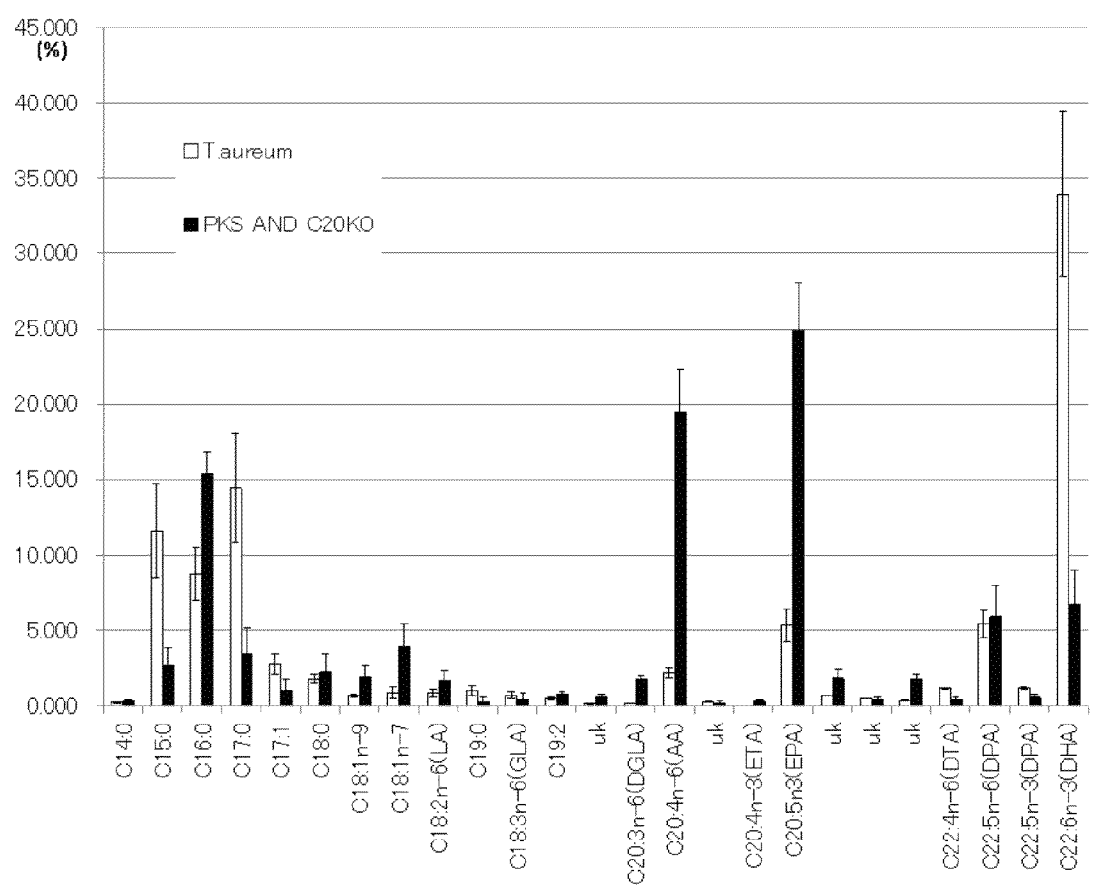

FIG. 42 represents the result of the comparison of the fatty acid compositions of the *Thraustochytrium aureum* ATCC 34304 wild-type strain and the PKS pathway (orfA gene) and C20 elongase gene double disrupted strain. Blank bar and solid bar indicate the fatty acid compositions of the wild-type strain and the gene disrupted strain, respectively. All values are given as mean value±standard deviation.

FIG. 43 represents the proportions of the fatty acids of the PKS pathway (orfA gene) and C20 elongase gene double disrupted strain relative to the *Thraustochytrium aureum* ATCC 34304 wild-type strain taken as 100%.

Figure 44:

FIG. 44 is a schematic view representing the primers used for fusion PCR, and the product. The end product is the fused sequence of *Thraustochytrium aureum* ATCC 34304-derived ubiquitin promoter, *Saprolegnia diclina*-derived? ω3 desaturase gene sequence, and *Thraustochytrium aureum* ATCC 34304-derived ubiquitin terminator.

Figure 45:
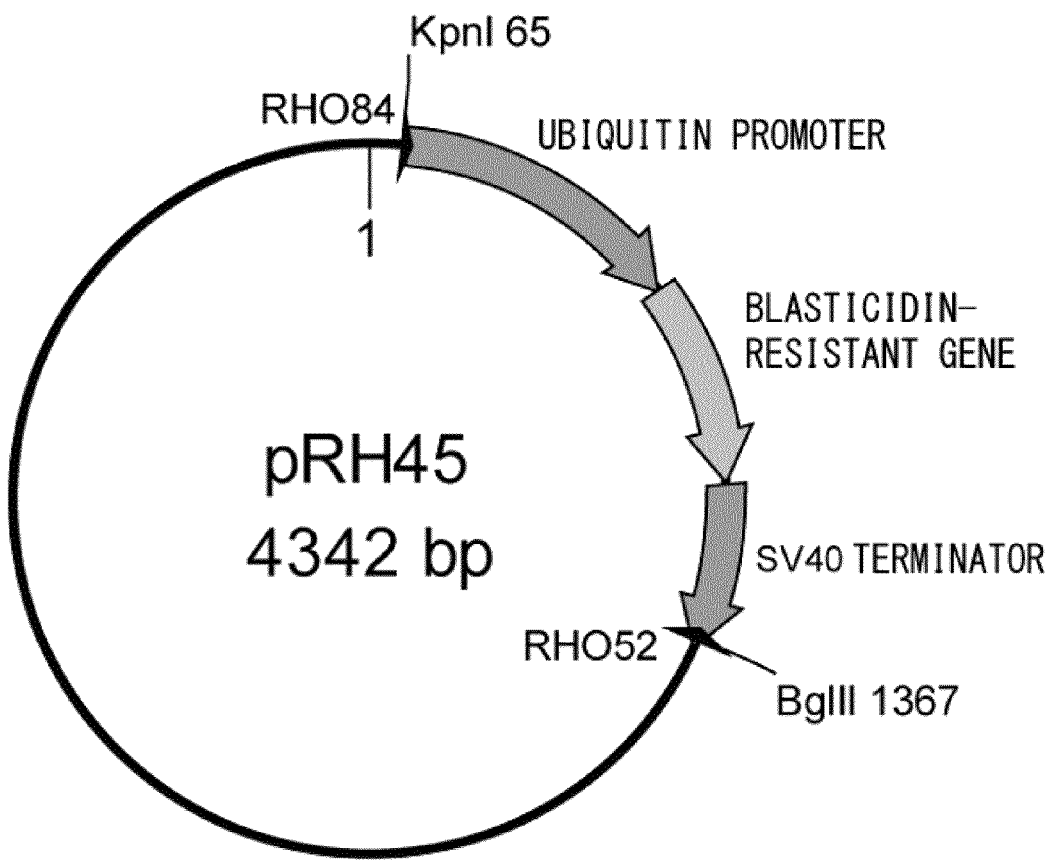

FIG. 45 represents the plasmid containing a KpnI site replacing one of the BglII sites in the blasticidin-resistant gene BglII cassette of FIG. 33.

Figure 46:
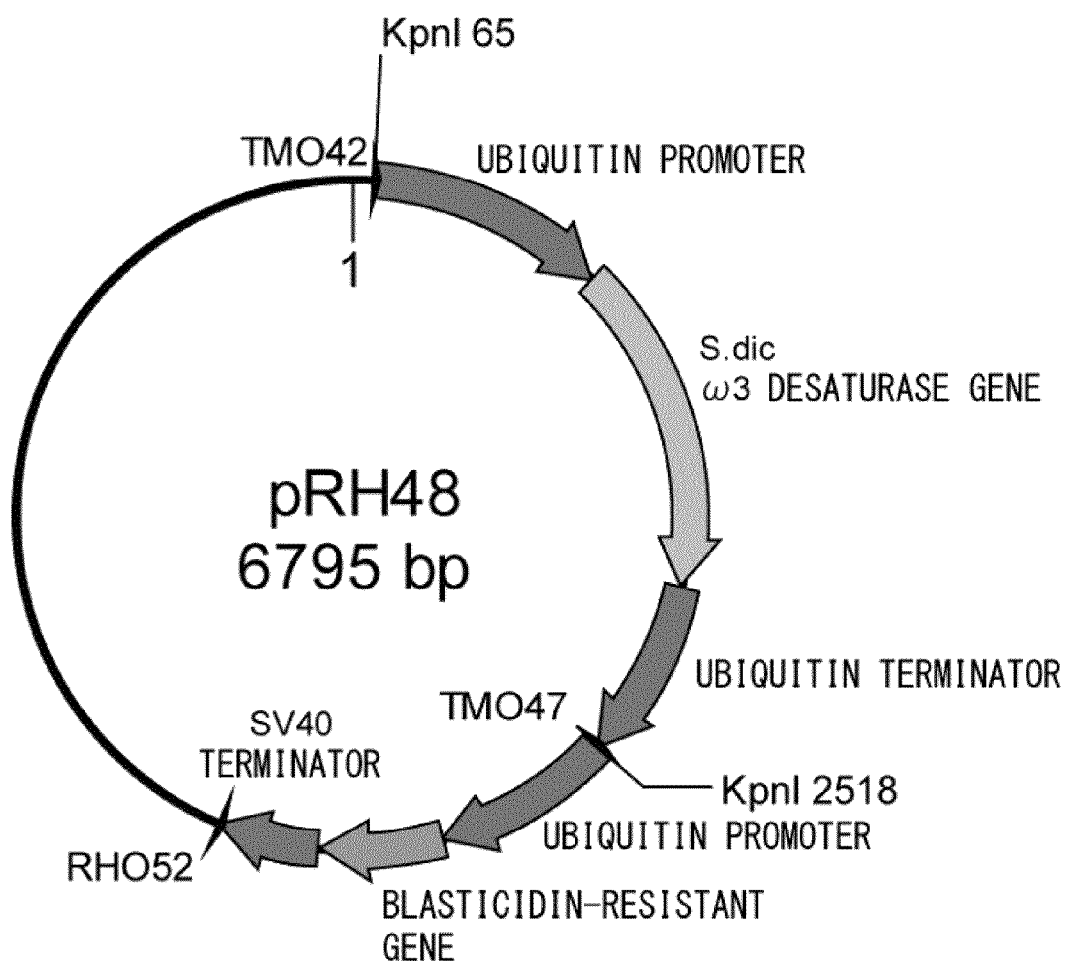

FIG. 46 represents a produced *Saprolegnia diclina*-derived ω3 desaturase gene expression plasmid. The plasmid has a blasticidin-resistant gene as a drug-resistance marker.

Figure 47:
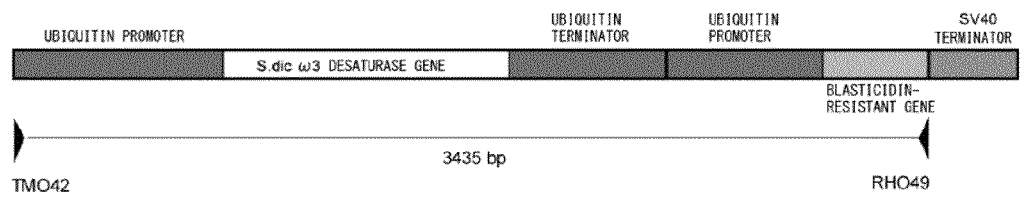

FIG. 47 is a schematic view representing the positions of the PCR primers used for the confirmation of the genome insertion of the *Saprolegnia diclina*-derived ω3 desaturase gene.

Figure 48:
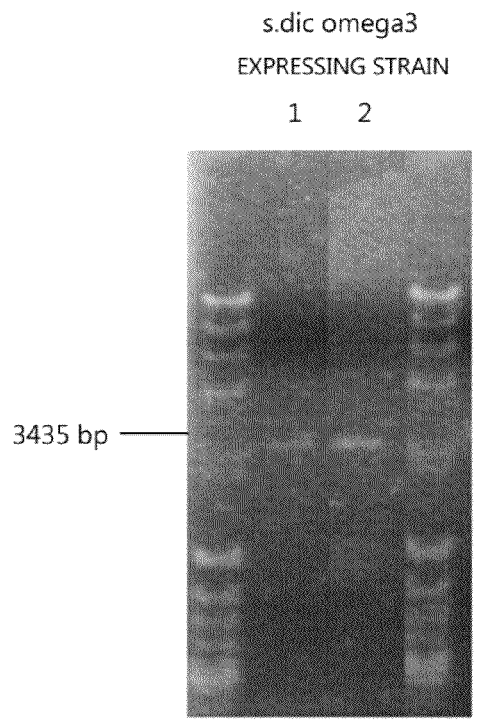

FIG. 48 represents the evaluation of the transfectant strain derived from the *Thraustochytrium aureum* ATCC 34304 PKS pathway (orfA gene) disrupted strain. [Description of Reference Numerals] lanes 1 to 2: transfectants.

Figure 49:
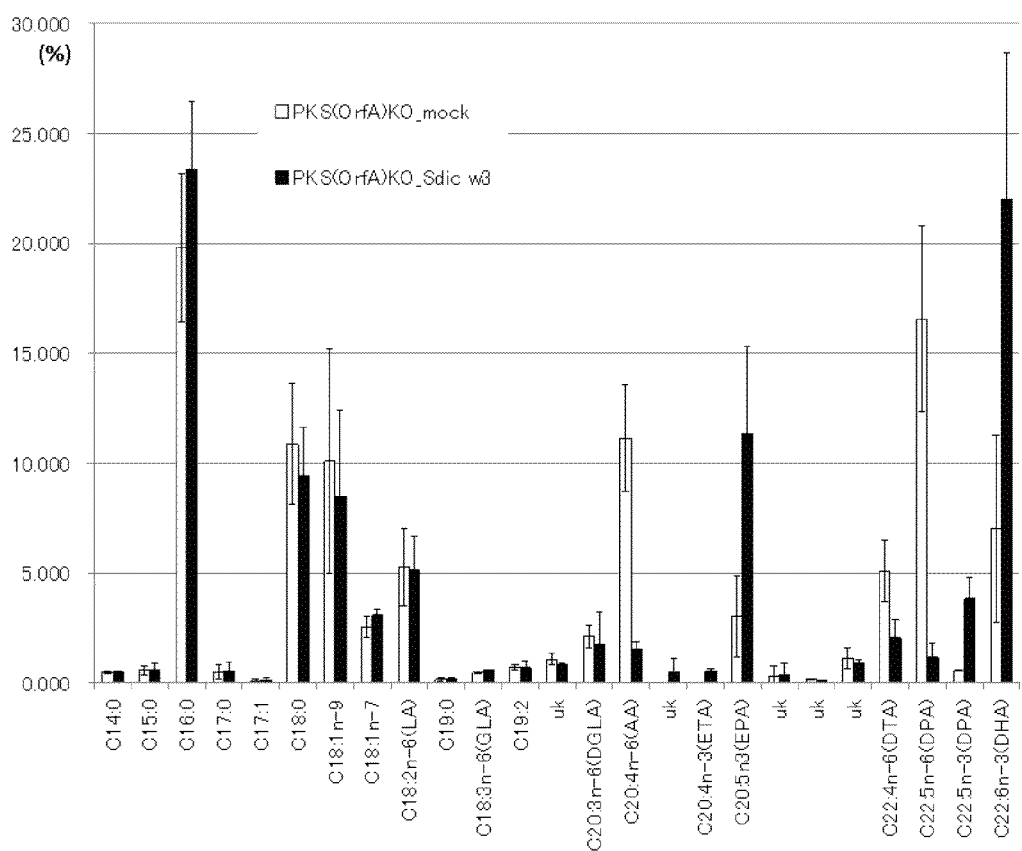

FIG. 49 represents the results of the comparison of the fatty acid compositions of the control *Thraustochytrium aureum* ATCC 34304 PKS pathway (orfA gene) disrupted strain and the ω3 desaturase gene introduced strain. Blank bar and solid bar indicate the fatty acid compositions of the control strain and the ω3 desaturase gene introduced strain, respectively. All values are given as mean value±standard deviation.

FIG. 50 represents the proportions of the fatty acids of the ω3 desaturase gene introduced strain relative to the *Thraustochytrium aureum* ATCC 34304 PKS pathway (orfA gene) disrupted strain taken as 100%.

Figure 51:
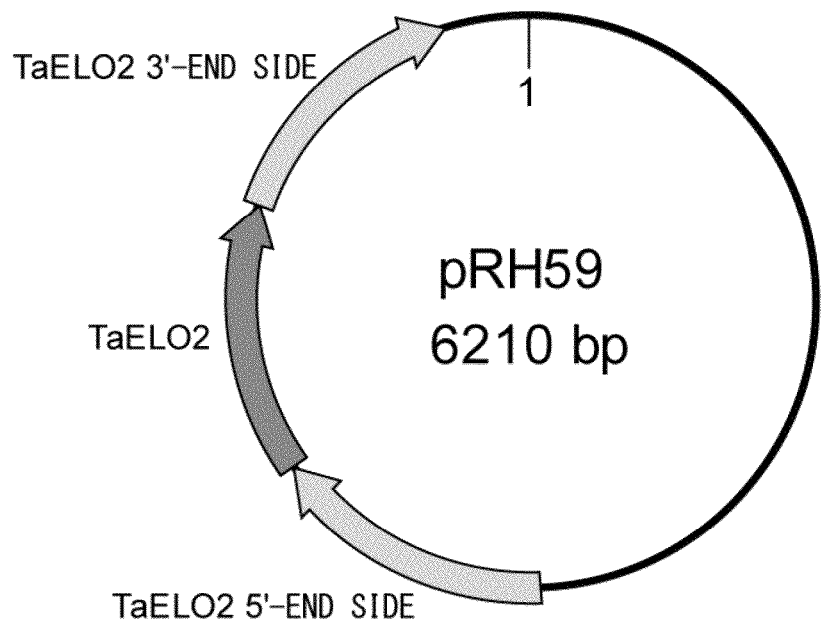

FIG. 51 is a diagram representing a pRH59 cloning the sequence containing the *Thraustochytrium aureum* ATCC 34304-derived C20 elongase.

Figure 52:
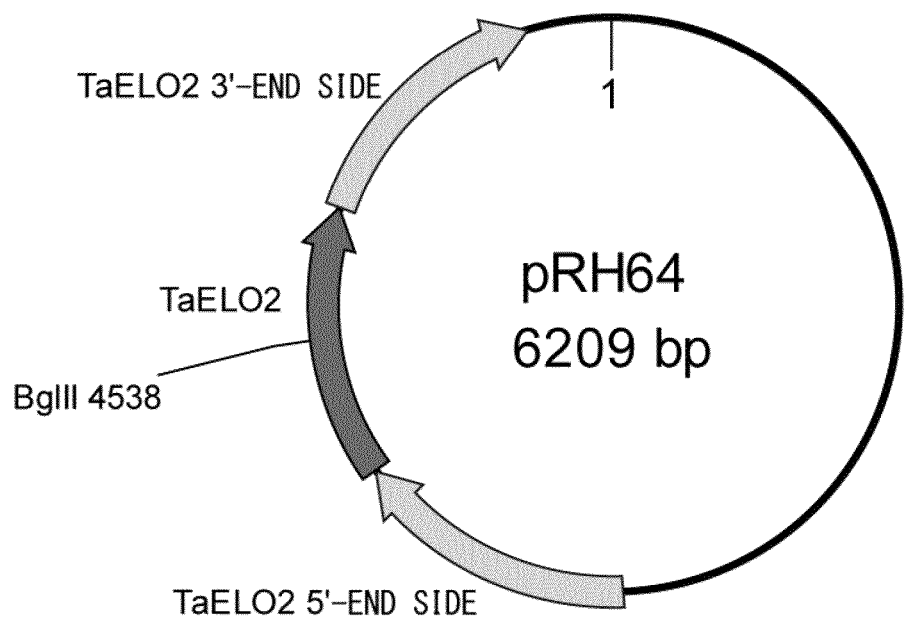

FIG. 52 is a diagram representing a pRH64 cloning the sequence containing a BglII site in the *Thraustochytrium aureum* ATCC 34304-derived C20 elongase.

Figure 53:
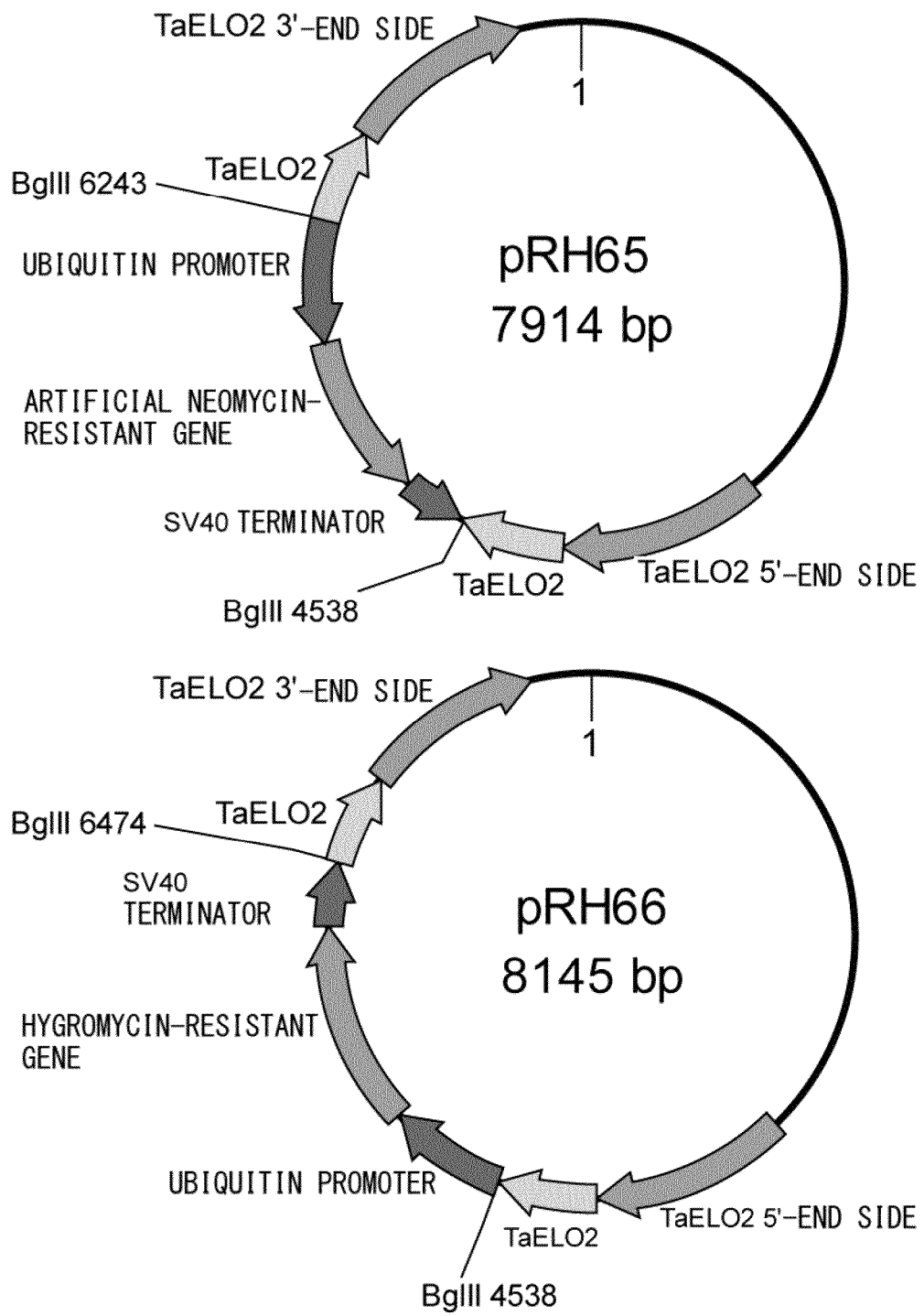

FIG. 53 is a diagram representing a pRH65 containing a ubiquitin promoter-, neomycin-resistant gene-, and SV40 terminator-containing sequence cloned into the *Thraustochytrium aureum* ATCC 34304-derived C20 elongase, and a pRH66 containing a ubiquitin promoter-, hygromycin-resistant gene-, and SV 40 terminator-containing sequence cloned into the *Thraustochytrium aureum* ATCC 34304-derived C20 elongase.

Figure 54:
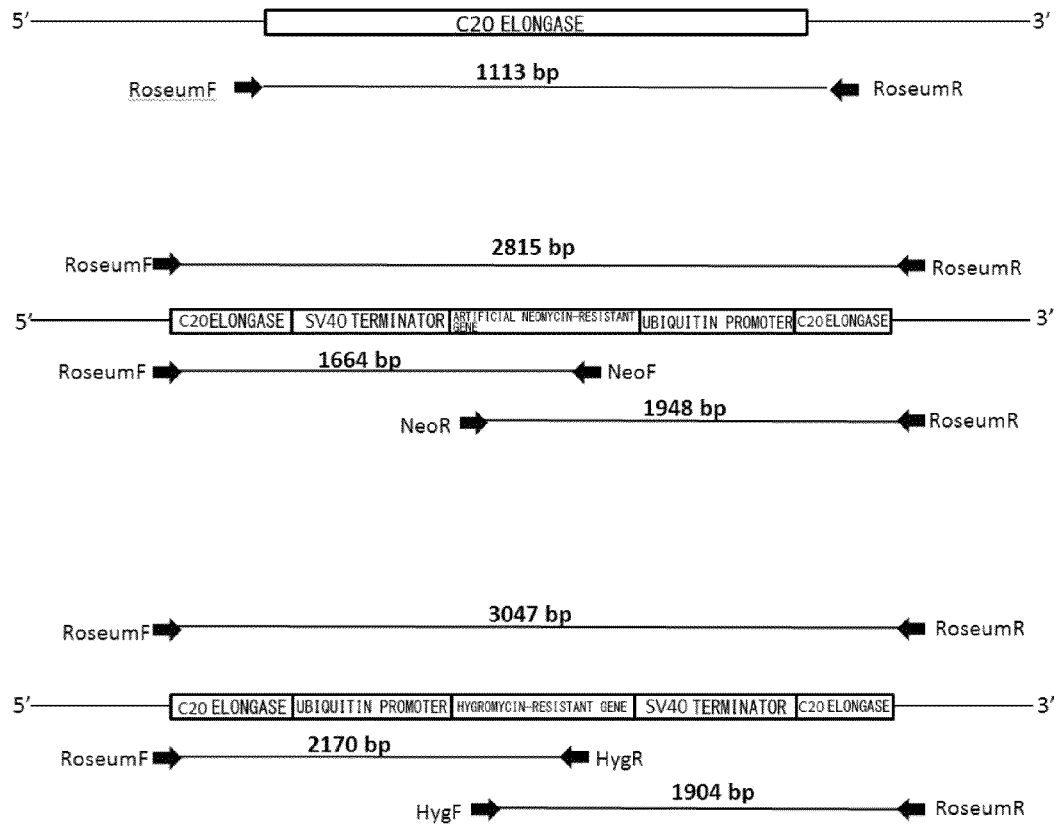

FIG. 54 represents the expected fragment sizes of the wild-type strain allele and knockout strains in a PCR.

Figure 55:
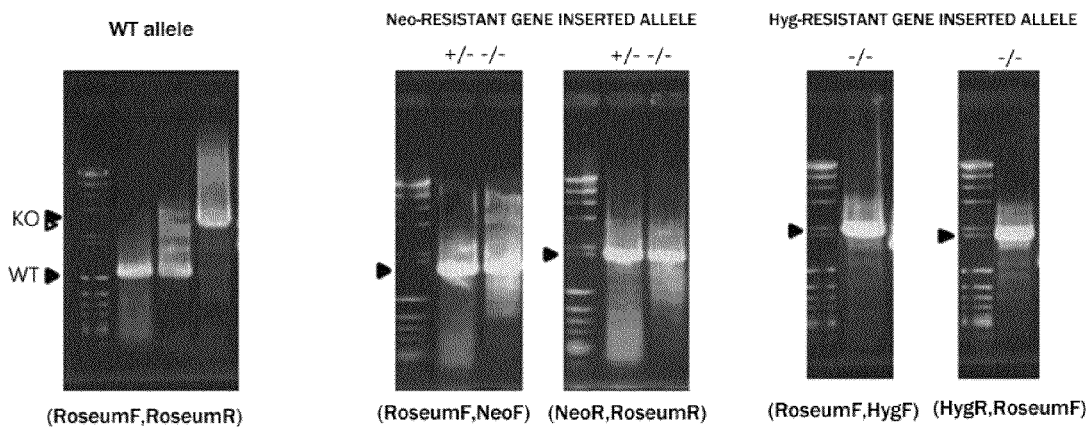

FIG. 55 represents the detection results for the wild-type strain allele and knockout strains in a PCR.

Figure 56:
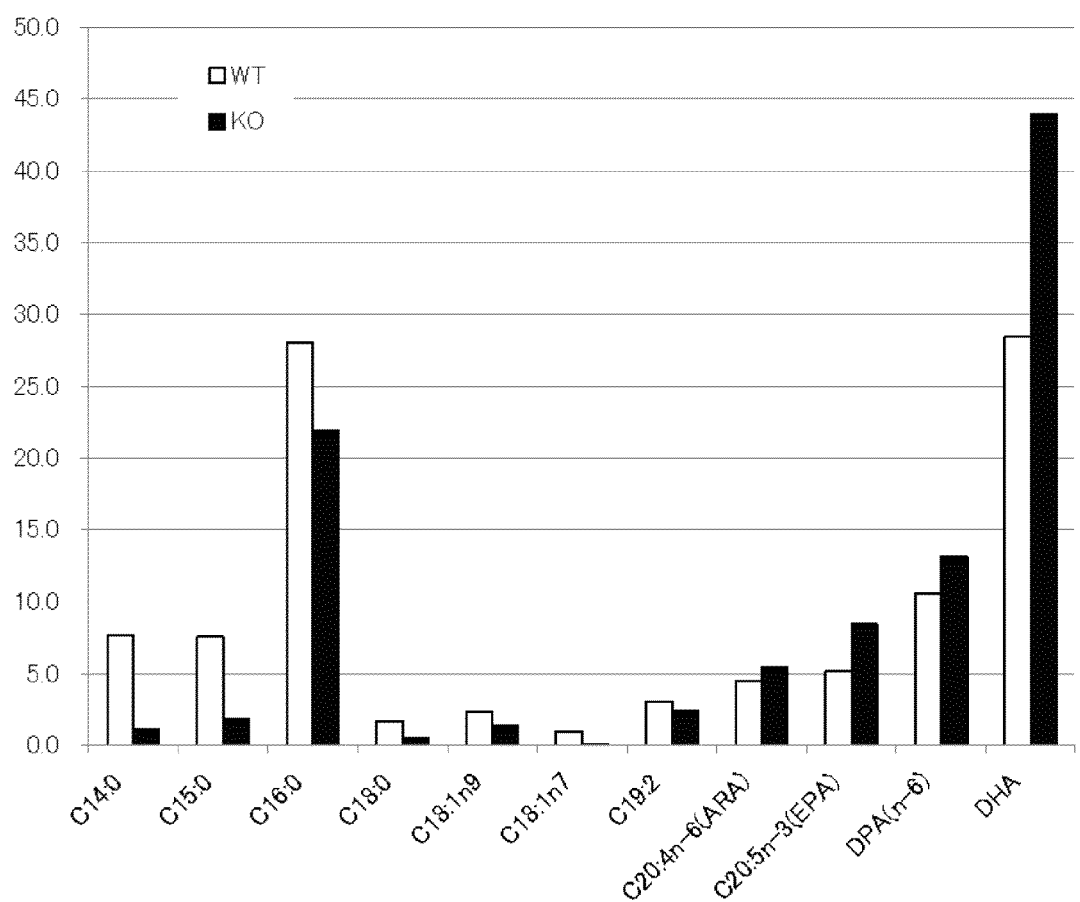

FIG. 56 represents the fatty acid compositions of the wild-type strain and the C20 elongase knockout strain. Blank bar and solid bar indicate the fatty acid compositions of the wild-type strain and the strain, respectively.

FIG. 57 represents the result of the comparison of the fatty acid compositions of the wild-type strain and the knockout strain.

Figure 58:
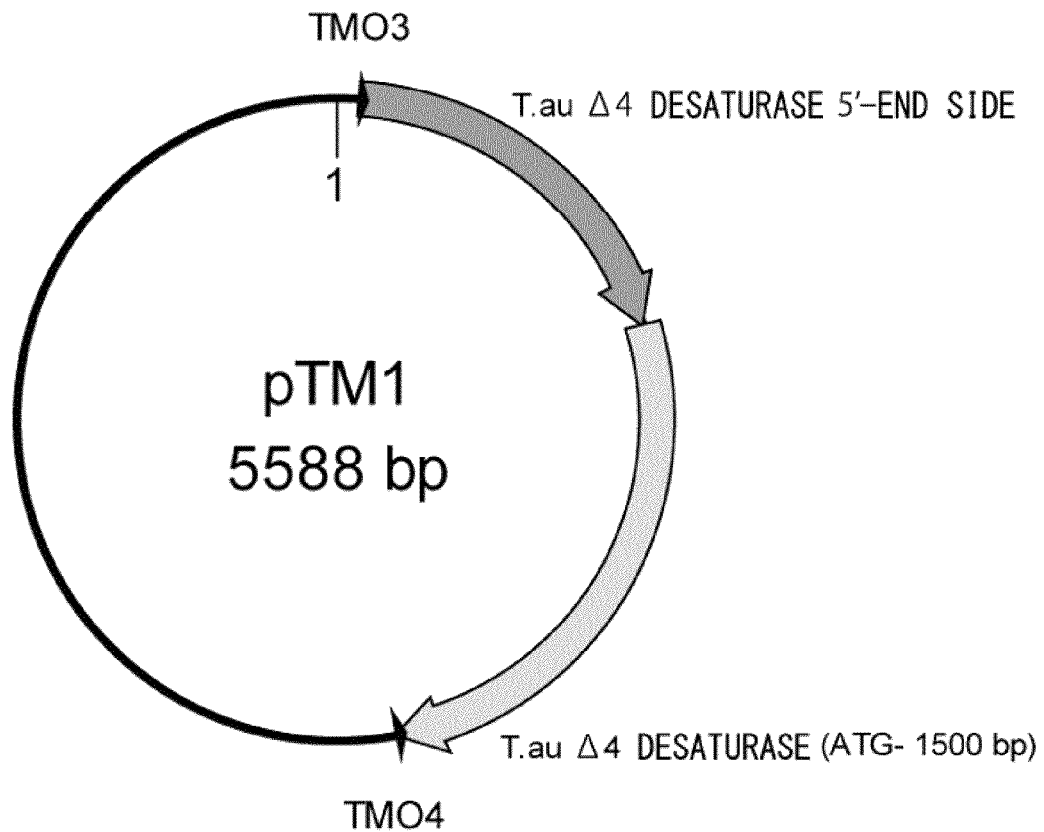

FIG. 58 represents a plasmid containing a sequence from 1,071 bp upstream of the Δ4 desaturase gene to 1,500 bp within the Δ4 desaturase gene of the cloned *Thraustochytrium aureum* ATCC 34304 strain.

Figure 59:
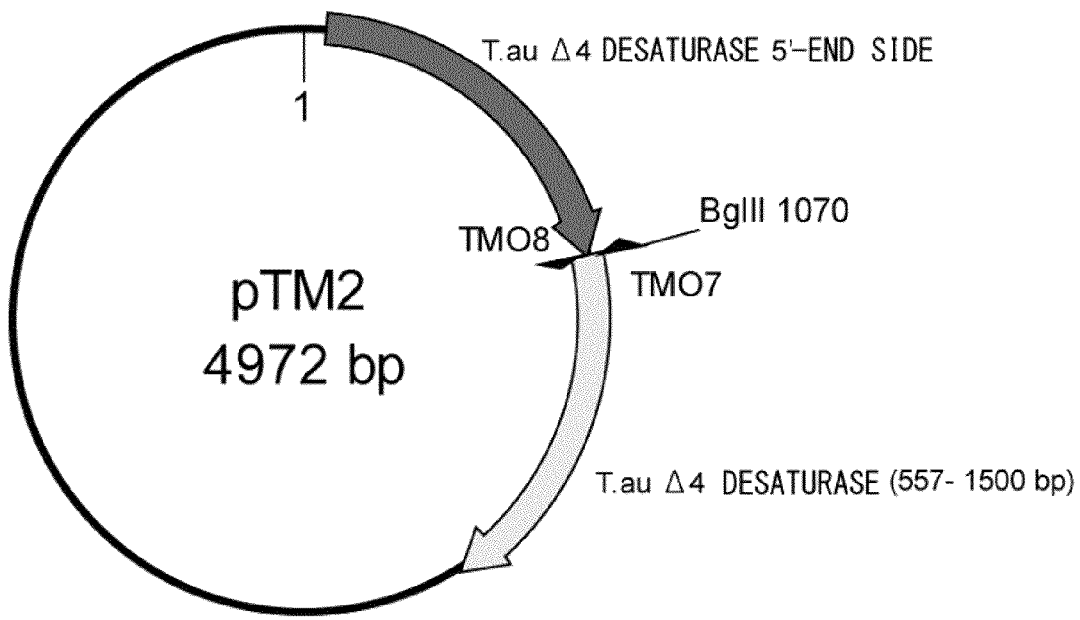

FIG. 59 represents a plasmid containing a BglII site inserted into the deleted portion of the plasmid of FIG. 58 containing the 60 bp upstream of the Δ4 desaturase gene and the 556-bp sequence containing the start codon within the Δ4 desaturase gene (616 bp, SEQ ID NO: 205).

FIG. 60 represents produced *Thraustochytrium aureum* ATCC 34304 strain Δ4 desaturase gene targeting vectors (two vectors). The vectors have a blasticidin resistant gene (pTM6) or an enhanced GFP-zeocin-resistant fused gene (pTM8) as a drug-resistance marker.

FIG. 61 is a schematic view representing the positions of the PCR primers used for the identification of the Δ4 desaturase gene disrupted strain of the *Thraustochytrium aureum* ATCC 34304 PKS pathway (orfA gene) disrupted strain, and the expected product.

Figure 62:
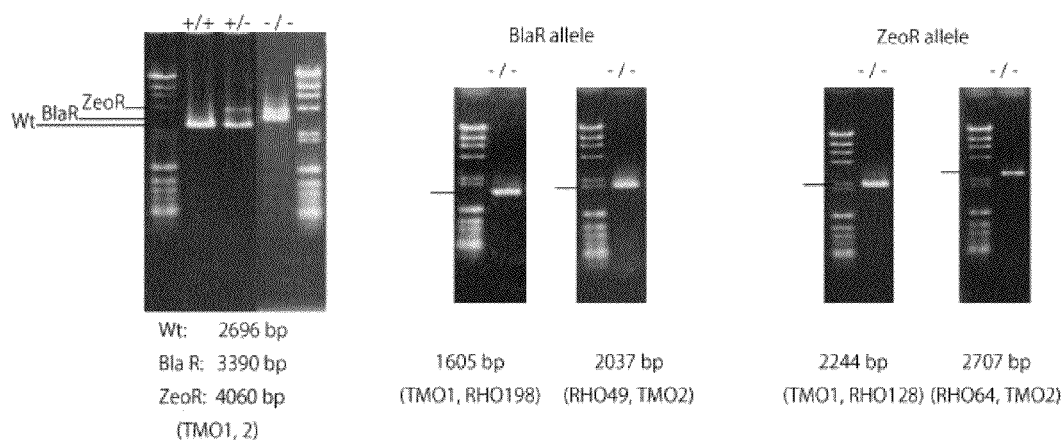

FIG. 62 represents the evaluation of Δ4 desaturase gene disruption performed by a PCR using the genomic DNA of the *Thraustochytrium aureum* ATCC 34304 strain as a template. [Description of Reference Numerals]+/+: *Thraustochytrium aureum* ATCC 34304-derived PKS pathway (orfA gene) disrupted strain; +/−: Δ4 desaturase gene first allele homologous recombinant derived from *Thraustochytrium aureum* ATCC 34304-derived PKS pathway (orfA gene) disrupted strain; −/−: *Thraustochytrium aureum* ATCC 34304-derived PKS pathway (orfA gene) and Δ4 desaturase gene double disrupted strain.

Figure 63:
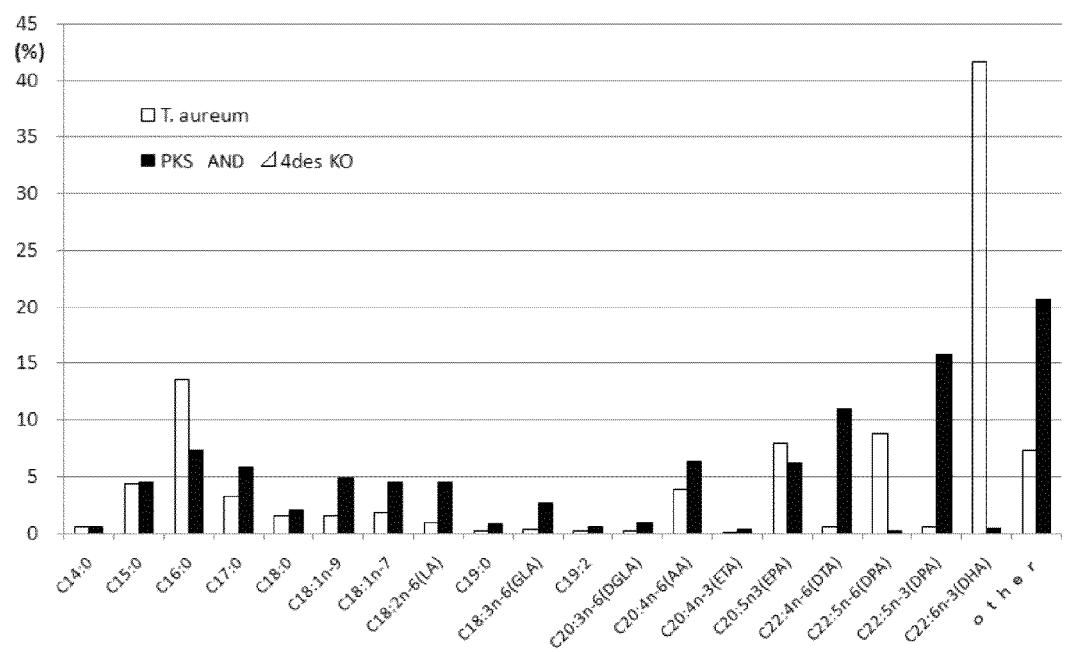

FIG. 63 represents the result of the comparison of the fatty acid compositions of the *Thraustochytrium aureum* ATCC 34304 wild-type strain, and the PKS pathway (orfA gene) and Δ4 desaturase gene double disrupted strain. Blank bar and solid bar indicate the fatty acid compositions of the wild-type strain and the gene disrupted strain, respectively.

FIG. 64 represents the proportions of the fatty acids of the PKS pathway (orfA gene) and Δ4 desaturase gene double disrupted strain relative to the *Thraustochytrium aureum* ATCC 34304 wild-type strain taken as 100%.

Figure 65:
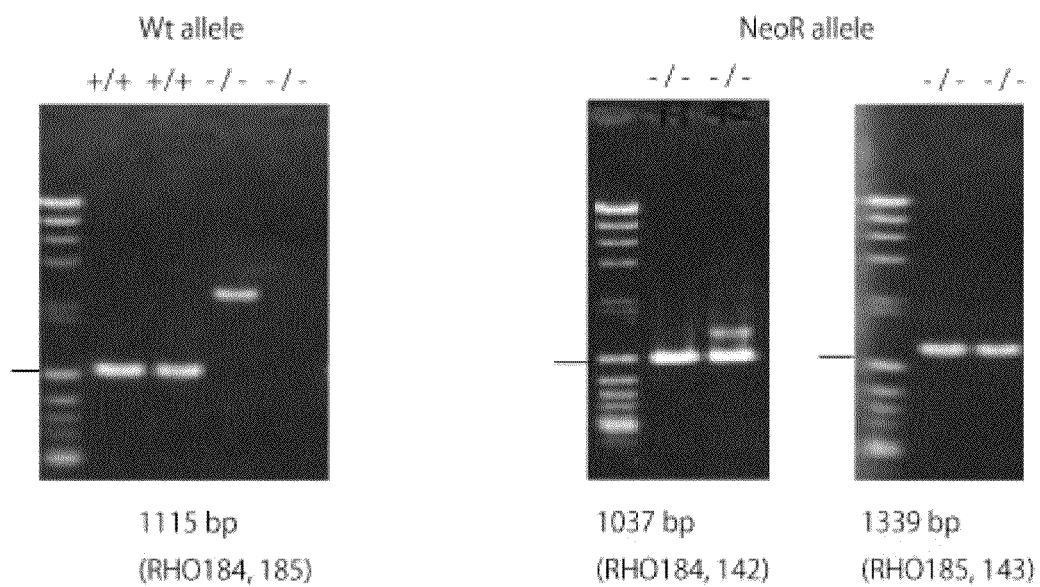

FIG. 65 represents the evaluation of C20 elongase gene disruption performed by a PCR using the genomic DNA of the *Parietichytrium* sp. SEK358 strain as a template. [Description of Reference Numerals]+/+: *Parietichytrium* sp. SEK358 wild-type strain; −/−: *Parietichytrium* sp. SEK358 strain-derived C20 elongase gene disrupted strain.

Figure 66:
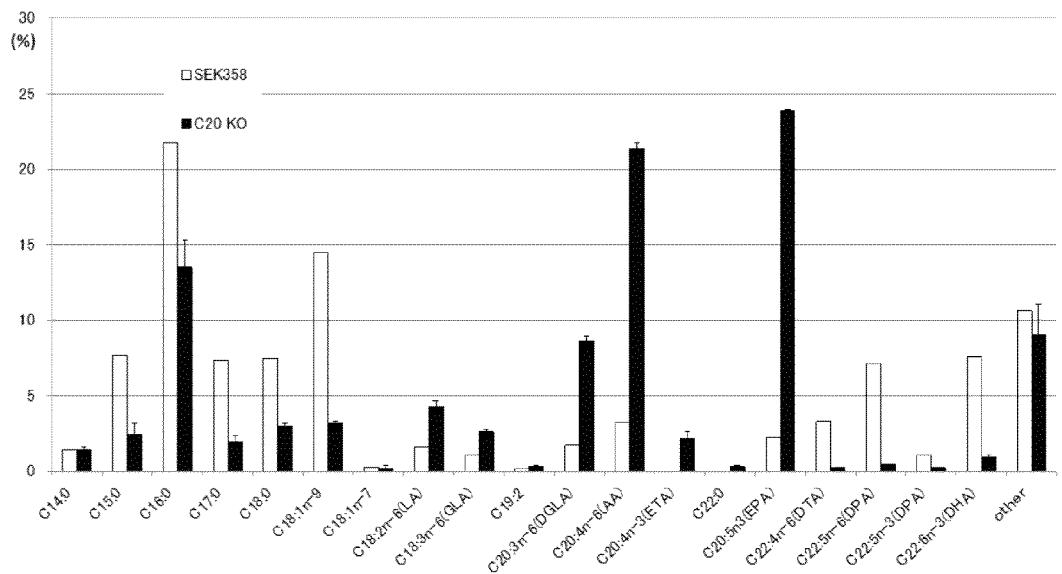

FIG. 66 represents the result of the comparison of the fatty acid compositions of the *Parietichytrium* sp. SEK358 wild-type strain, and the *Parietichytrium* sp. SEK358 strain-derived C20 elongase gene disrupted strain. Blank bar and solid bar indicate the fatty acid compositions of the wild-type strain and the gene disrupted strain, respectively.

FIG. 67 represents the proportions of the fatty acid compositions of the *Parietichytrium* sp. SEK358 strain-derived C20 elongase gene disrupted strain relative to the *Parietichytrium* sp. SEK358 wild-type strain taken as 100%. The diagonal line indicates that the fatty acid produced by the *Parietichytrium* sp. SEK358 wild-type strain is below the detection limit.

Figure 68:
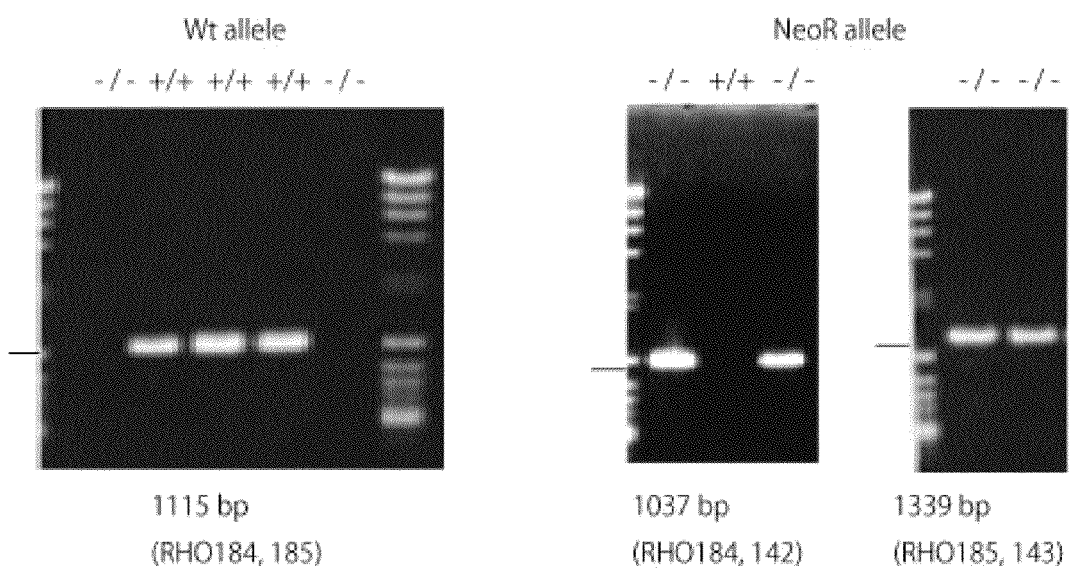

FIG. 68 represents the evaluation of C20 elongase gene disruption performed by a PCR using the genomic DNA of the *Parietichytrium* sp. SEK571 strain as a template. [Description of Reference Numerals]+/+: *Parietichytrium* sp. SEK571 wild-type strain; −/−: *Parietichytrium* sp. SEK571 strain-derived C20 elongase gene disrupted strain.

Figure 69:
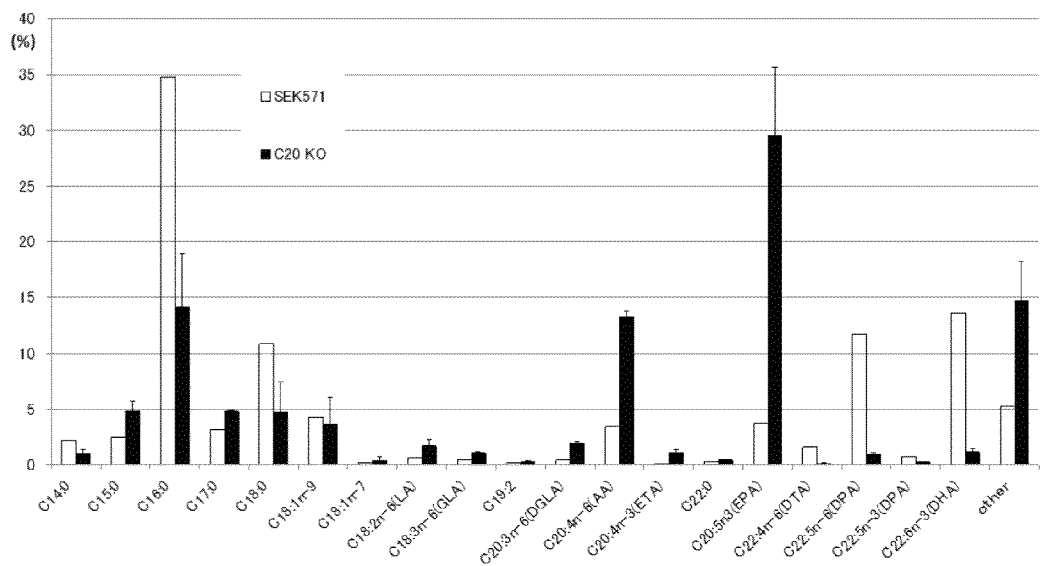

FIG. 69 represents the result of the comparison of the fatty acid compositions of the *Parietichytrium* sp. SEK571wild-type strain, and the *Parietichytrium* sp. SEK571 strain-derived C20 elongase gene disrupted strain. Blank bar and solid bar indicate the fatty acid compositions of the wild-type strain and the gene disrupted strain, respectively.

FIG. 70 represents the proportions of the fatty acids of the *Parietichytrium* sp. SEK571 strain-derived C20 elongase gene disrupted strain relative to the *Parietichytrium* sp. SEK571 wild-type strain taken as 100%.

FIG. 71 represents the multiple alignment of TΔ12d with the putative amino acid sequences of the Δ12 desaturase genes derived from *Thalassiosira pseudonana*, *Micromonas* sp, and *Phaeodactylum tricornutum*. [Description of Reference Numerals] Underlined portion: histidine box.

Figure 72:
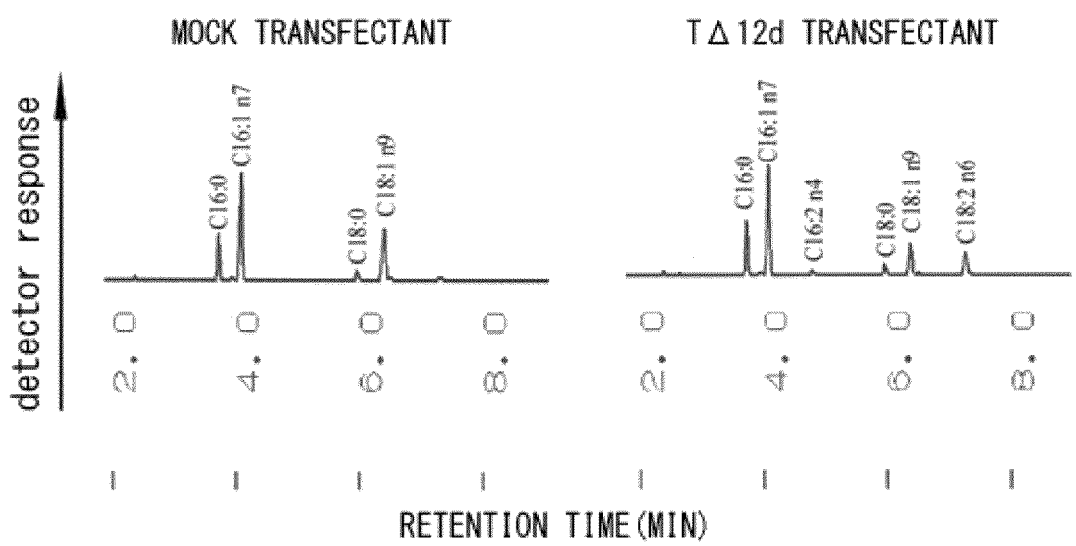

FIG. 72 represents a GC analysis chart for the TΔ12d overexpressing strain of the budding yeast *Sacchromyces cerevisiae*, and the proportions of fatty acid compositions.

Figure 73:
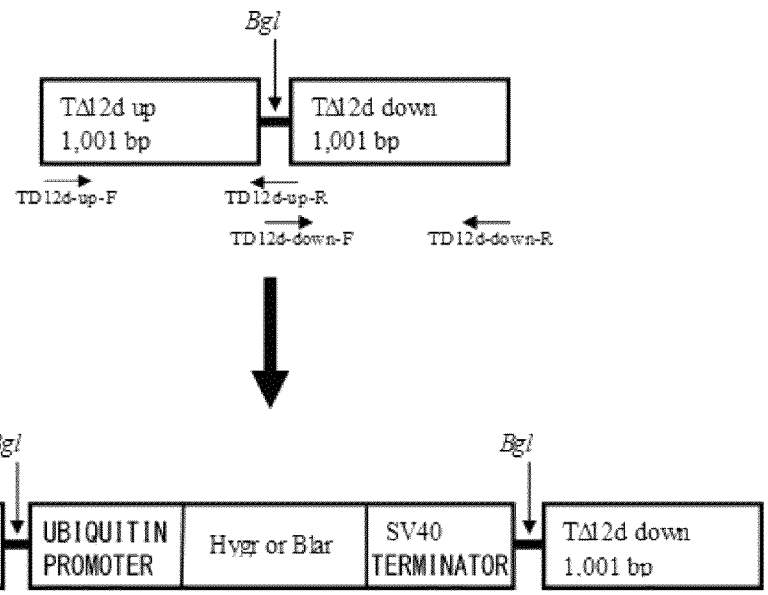

FIG. 73 is a diagram representing a TΔ12d KO targeting vector construction scheme.

Figure 74:
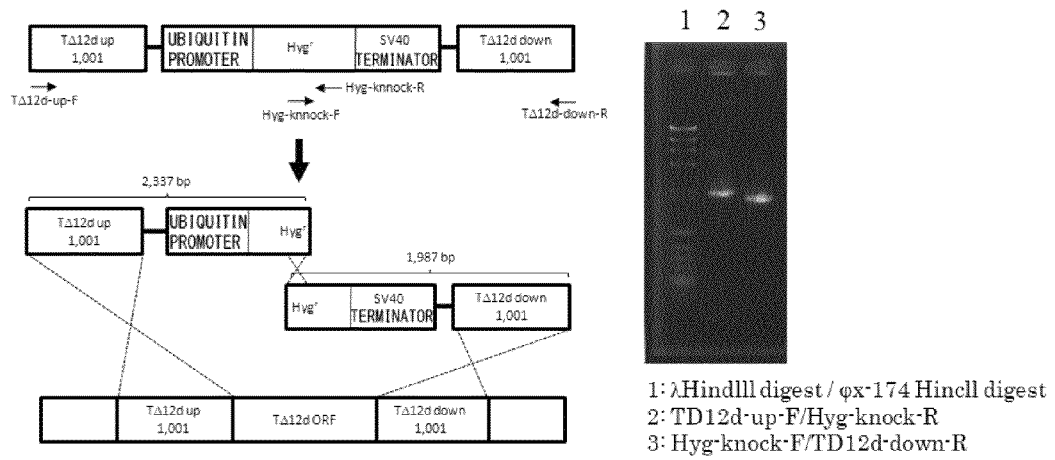

FIG. 74 represents a scheme for the preparation of a homologous recombination fragment for efficiently obtaining a homologous recombinant by a split marker method.

FIG. 75 represents the result of the amplification of the hygromycin-resistant gene, blasticidin-resistant gene, and TΔ12d gene by a PCR performed by using the genomic DNAs of the wild-type strain, the TΔ12d first allele disrupted strain, and the TΔ12d disrupted strain (two alleles are disrupted). [Description of Reference Numerals] M: λHindIII digest/ (φX174 HincII digest; W: wild-type; S1 to S3: 1st allele knock-out strain; D1 to D3: 2nd allele knock-out strain.

FIG. 76 represents the result of the mRNA detection of the hygromycin-resistant gene, blasticidin-resistant gene, and TΔ12d gene by a RT-PCR for the wild-type strain, the TΔ12d first allele disrupted strain, and the TΔ12d disrupted strain. [Description of Reference Numerals] M: λHindIII digest/ φX174 HincII digest; W: wild-type; S1 to S3: 1st allele knock-out strain; D1 to D3: 2nd allele knock-out strain.

FIG. 77 represents the result of the southern blotting performed for the wild-type strain, the TΔ12d first allele disrupted strain, and the TΔ12d disrupted strain.

Figure 78:
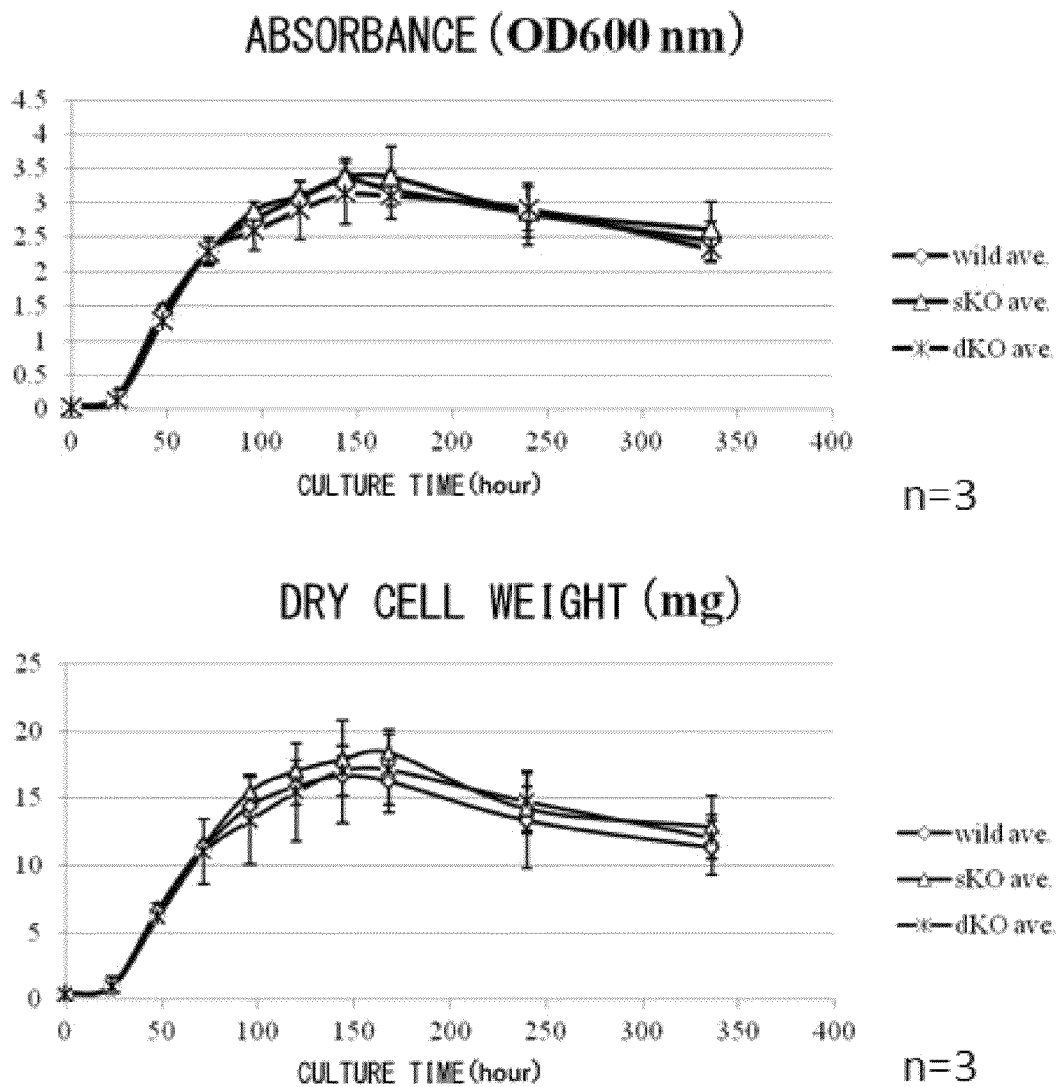

FIG. 78 represents the result of the growth rate comparison by the measurements of OD600 and dry cell weight for the wild-type strain, the TΔ12d first allele disrupted strain, and the TΔ12d disrupted strain.

Figure 79:
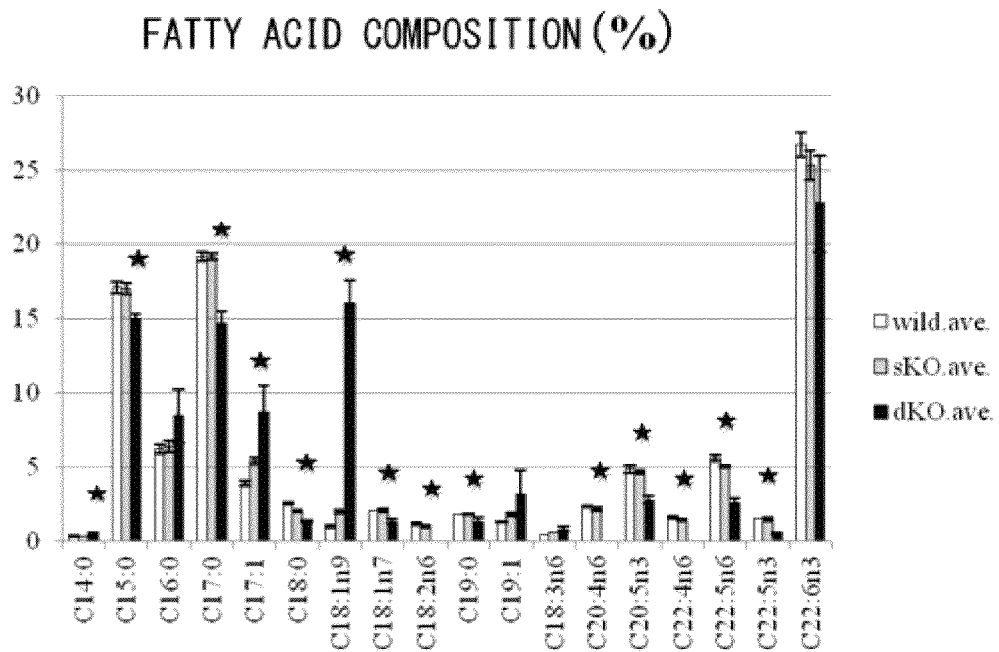

FIG. 79 represents the proportions of the fatty acid compositions of the wild-type strain, the TΔ12d first allele disrupted strain, and the TΔ12d disrupted strain. [Description of Reference Numerals] Asterisk: significant difference at $p<0.01$ (n=3).

Figure 80:
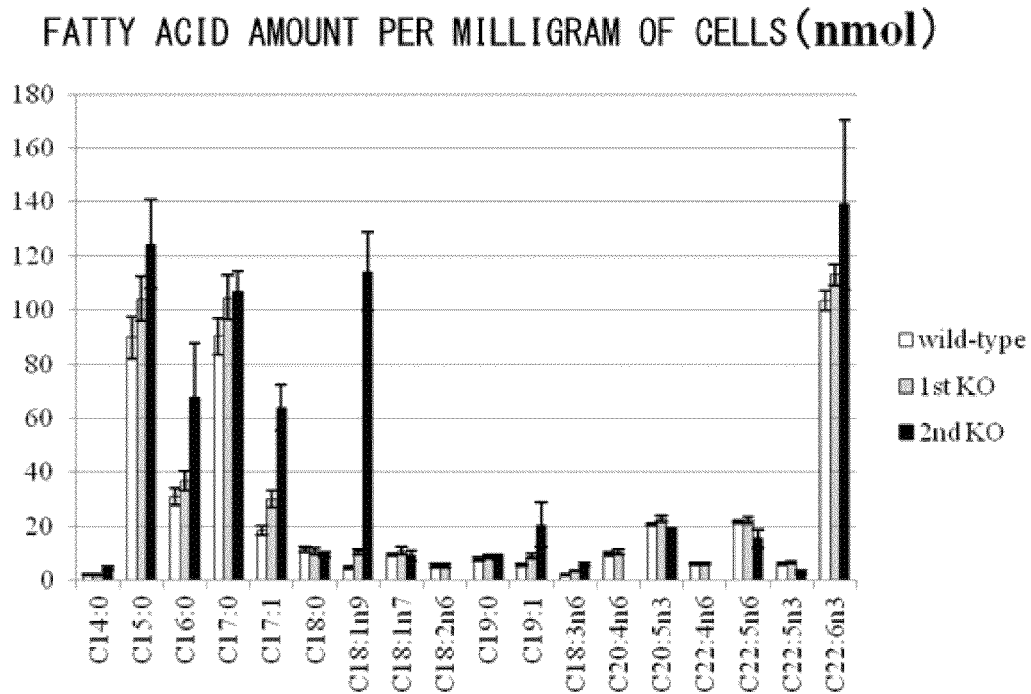

FIG. 80 represents the fatty acid level per dry cell in the wild-type strain, the TΔ12d first allele disrupted strain, and the TΔ12d disrupted strain. [Description of Reference Numerals] Asterisk: significant difference at $p<0.01$ (n=3).

Figure 81:
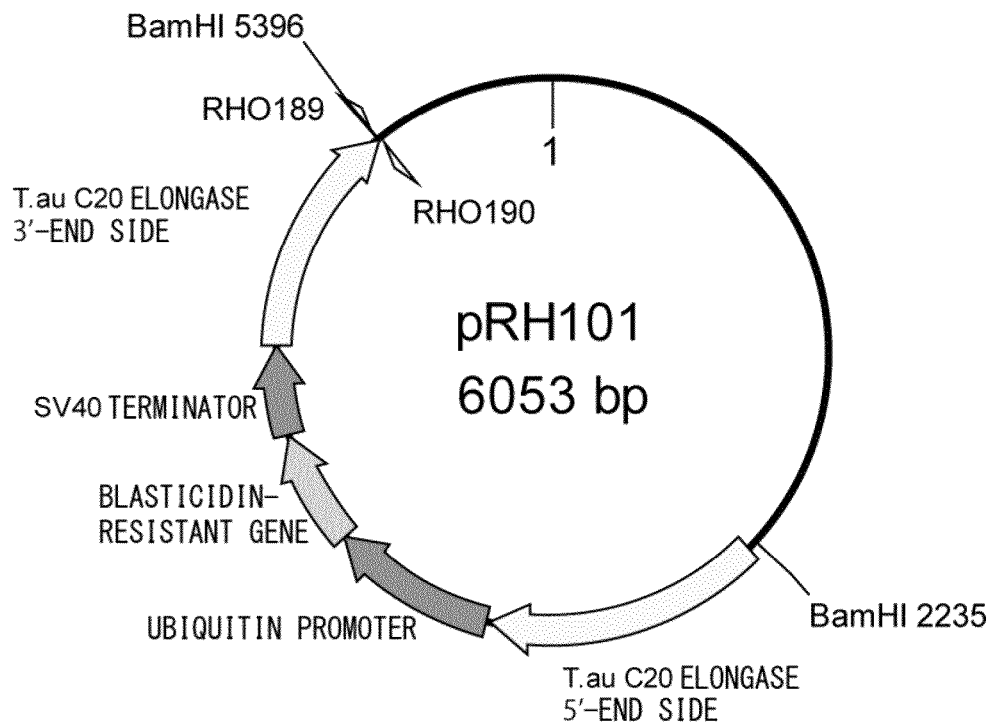

FIG. 81 represents a plasmid containing a BamHI site inserted through modification of the *Thraustochytrium aureum* C20 elongase gene targeting vector (pRH43) of FIG. 39 with a blasticidin-resistant gene.

Figure 82:
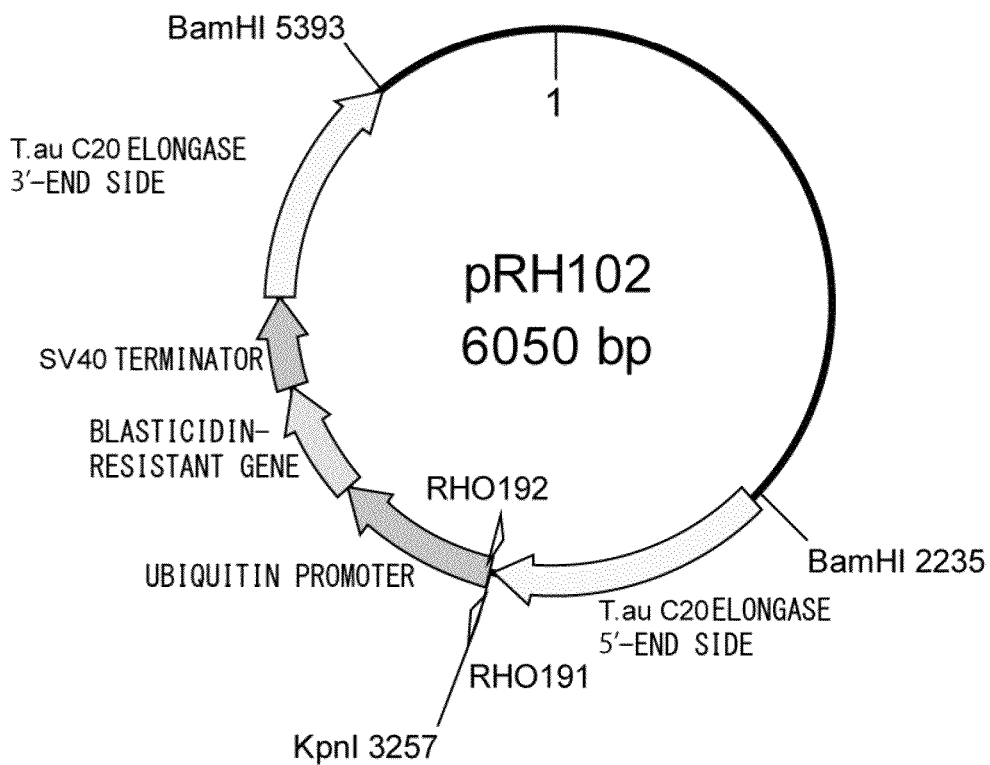

FIG. 82 represents a plasmid containing a KpnI site inserted through modification of the plasmid of FIG. 81.

Figure 83:
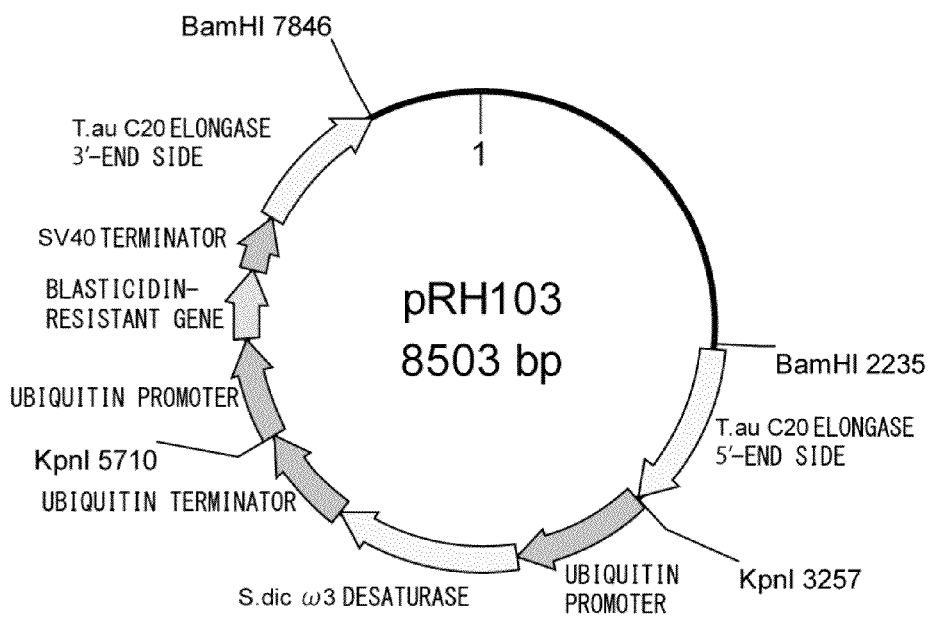

FIG. 83 represents a produced *Thraustochytrium aureum* C20 elongase gene targeting and *Saprolegnia diclina*-derived ω3 desaturase expression vector. The vector has a blasticidin-resistant gene as a drug-resistance marker.

Figure 84:
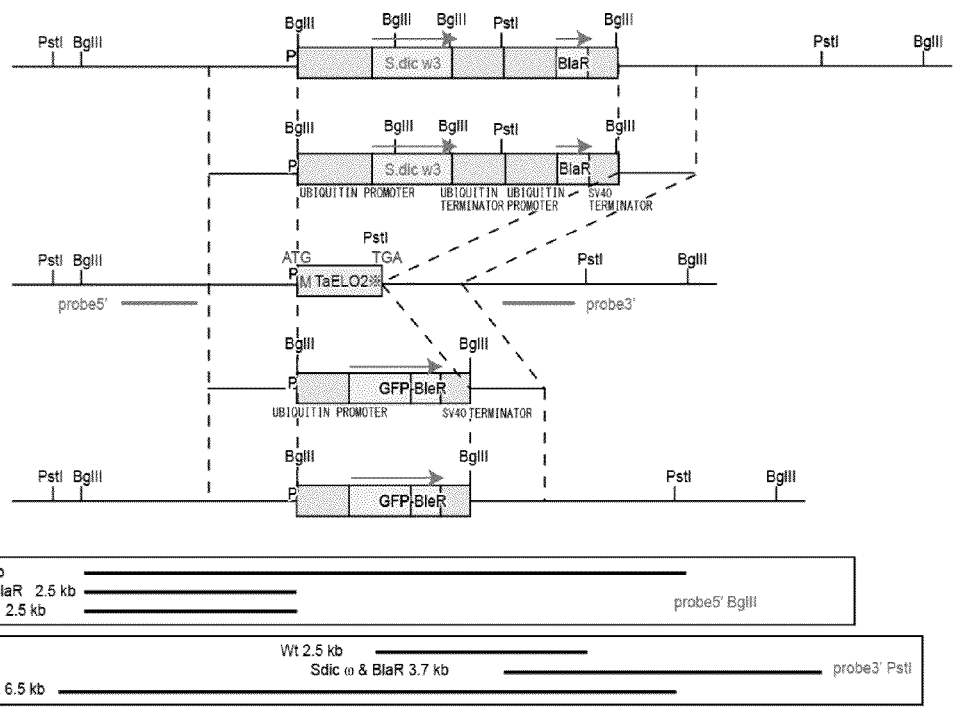

FIG. 84 is a schematic view representing the positions of the southern hybridization analysis probes used for the identification of the C20 elongase gene disrupted and *Saprolegnia diclina*-derived ω3 desaturase expressing strain of the *Thraustochytrium aureum* PKS pathway (orfA gene) disrupted strain, and the expected gene fragment sizes.

Figure 85:
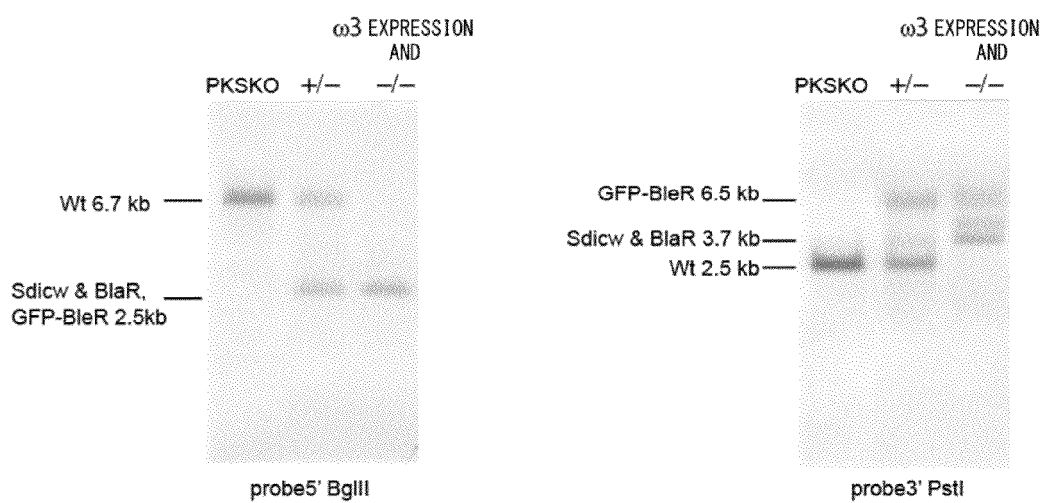

FIG. 85 represents the evaluation of the C20 elongase gene disrupted and *Saprolegnia diclina*-derived ω3 desaturase expressing strain by southern hybridization using the *Thraustochytrium aureum* ATCC 34304 genomic DNA. [Description of Reference Numerals] PKSKO: *Thraustochytrium aureum* ATCC 34304-derived PKS pathway (orfA gene) disrupted strain; +/−: C20 elongase gene first allele homologous recombinant of the *Thraustochytrium aureum* ATCC 34304-derived PKS pathway (orfA gene) disrupted strain; −/−: *Thraustochytrium aureum*-derived PKS pathway (orfA gene) and C20 elongase gene double disrupted and *Saprolegnia diclina*-derived ω3 desaturase expressing strain.

Figure 86:
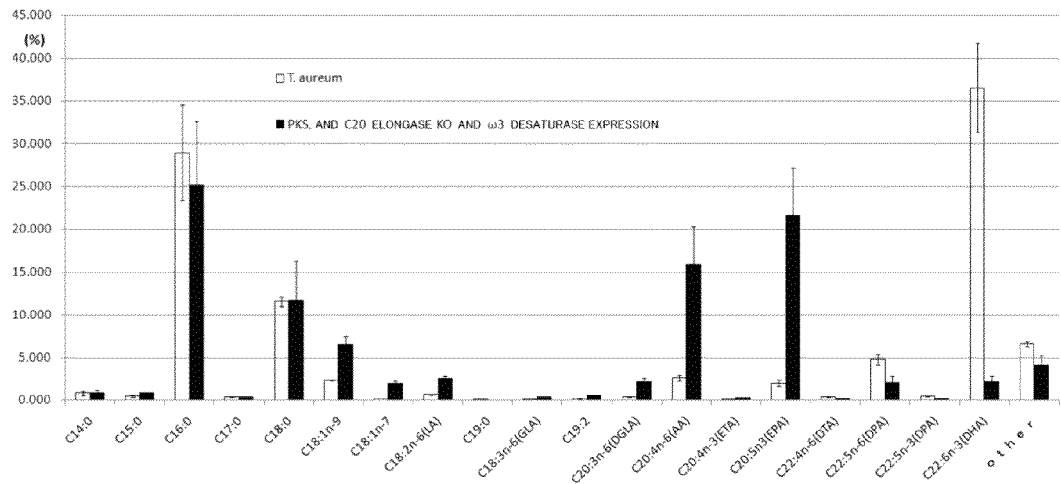

FIG. 86 represents the result of the comparison of the fatty acid compositions of the *Thraustochytrium aureum* ATCC 34304 wild-type strain, and the PKS pathway (orfA gene) and C20 elongase gene double disrupted and *Saprolegnia diclina*-derived ω3 desaturase expressing strain. Blank bar and solid bar indicate the fatty acid compositions of the wild-type strain and the gene disrupted strain, respectively.

FIG. 87 represents the proportions of the fatty acids of the PKS pathway (orfA gene) and C20 elongase gene double disrupted and *Saprolegnia diclina*-derived ω3 desaturase expressing strain relative to the *Thraustochytrium aureum* ATCC 34304 wild-type strain taken as 100%.

Figure 88:
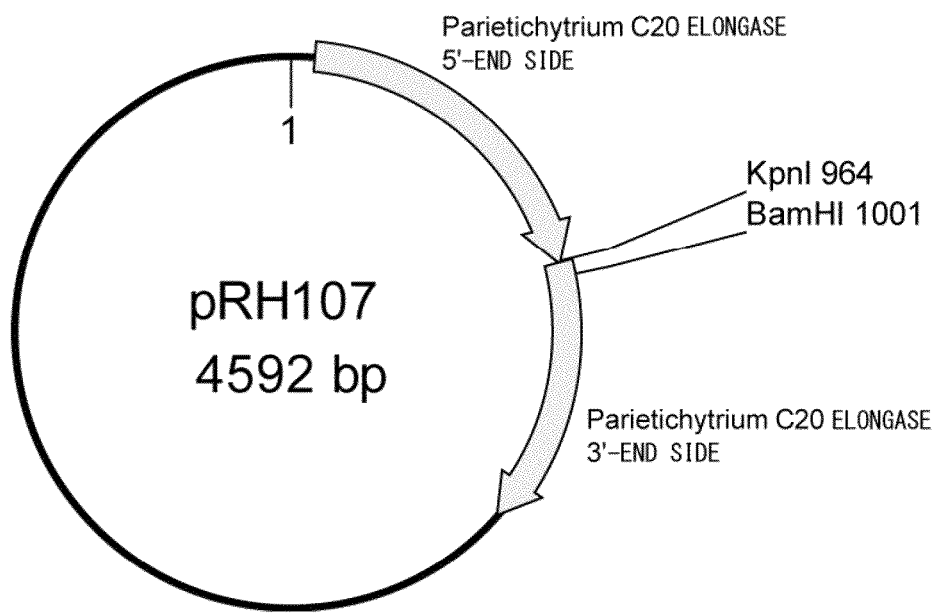

FIG. 88 represents a base plasmid used for *Saprolegnia diclina*-derived ω3 desaturase expression vector production.

Figure 89:
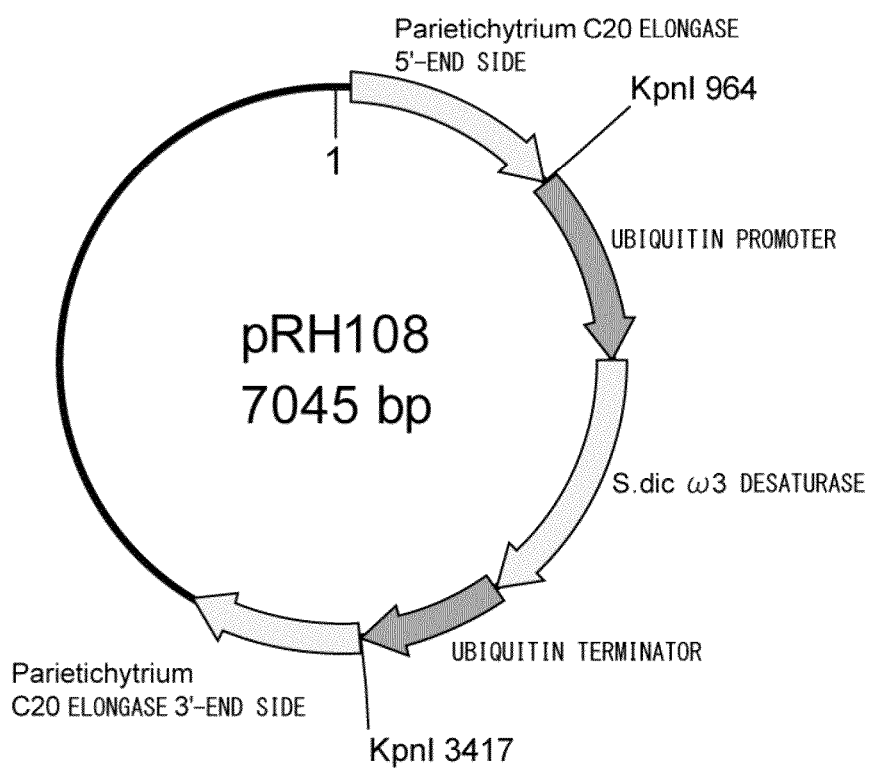

FIG. 89 represents a plasmid containing a *Saprolegnia diclina*-derived ω3 desaturase expression KpnI cassette inserted into the plasmid of FIG. 88.

FIG. 90 represents a *Saprolegnia diclina*-derived ω3 desaturase expression vector produced by inserting a hygromycin-resistant gene as a drug-resistance marker into the plasmid of FIG. 89.

FIG. 91 is a schematic view representing the positions of the PCR primers used for the confirmation of the genome insertion of the *Saprolegnia diclina*-derived ω3 desaturase gene.

Figure 92:
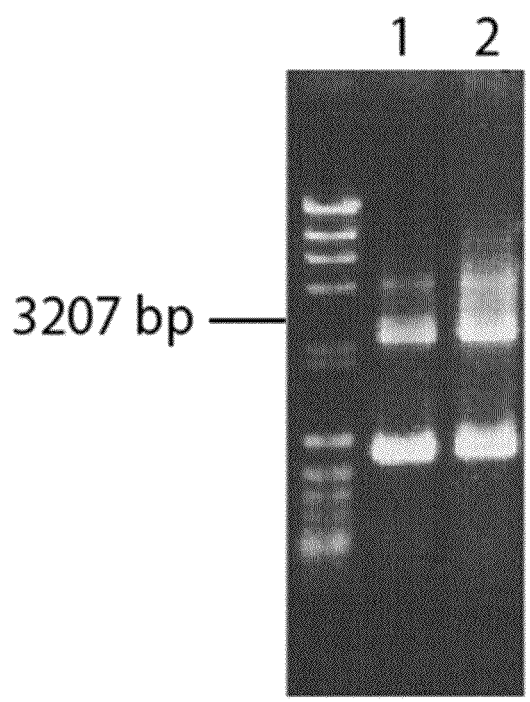
Figure 93:
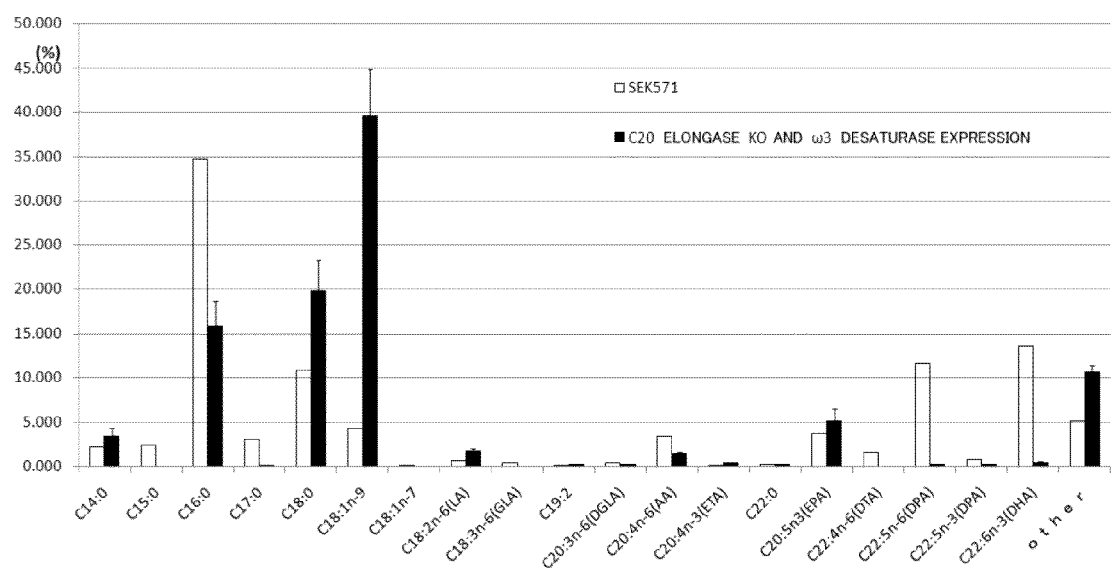

FIG. 92 represents the evaluation of the *Parietichytrium* sp. SEK571 C20 elongase gene disrupted strain-derived transfectant strain. [Description of Reference Numerals] Lanes 1 to 2: transfectants FIG. 93 represents the result of the comparison of the fatty acid compositions of the *Parietichytrium* sp. SEK571 wild-type strain, and the C20 elongase gene disrupted and *Saprolegnia diclina*-derived ω3 desaturase expressing strain. Blank bar and solid bar indicate the fatty acid compositions of the wild-type strain and the transfectant strain, respectively.

FIG. 94 represents the proportions of the fatty acids of the C20 elongase gene disrupted and *Saprolegnia diclina*-derived ω3 desaturase expressing strain relative to the *Parietichytrium* sp. SEK571wild-type strain taken as 100%.

Figure 95:
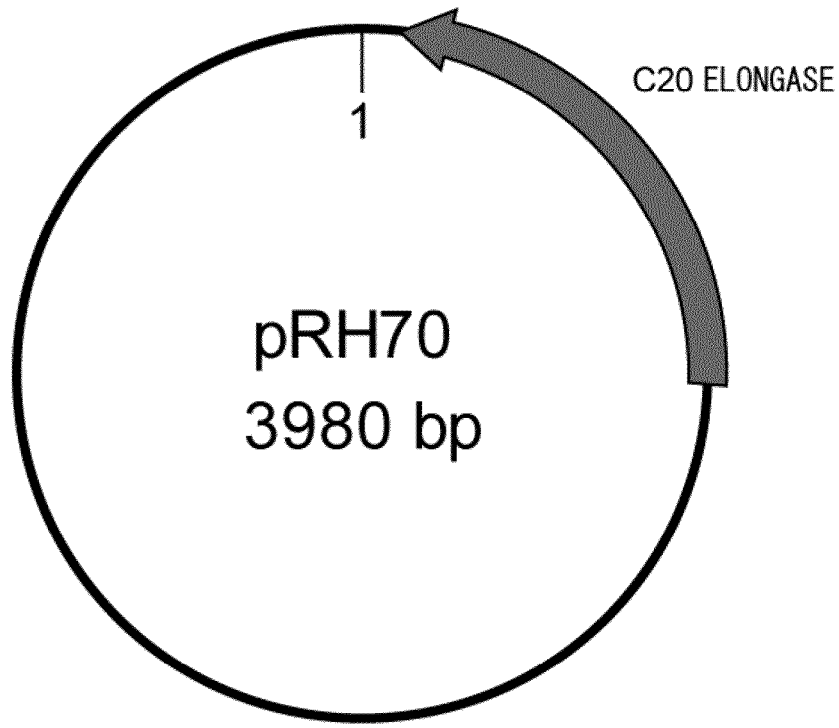

FIG. 95 is a diagram representing a pRH70 cloning a sequence containing a *Schizochytrium*-derived C20 elongase gene.

Figure 96:
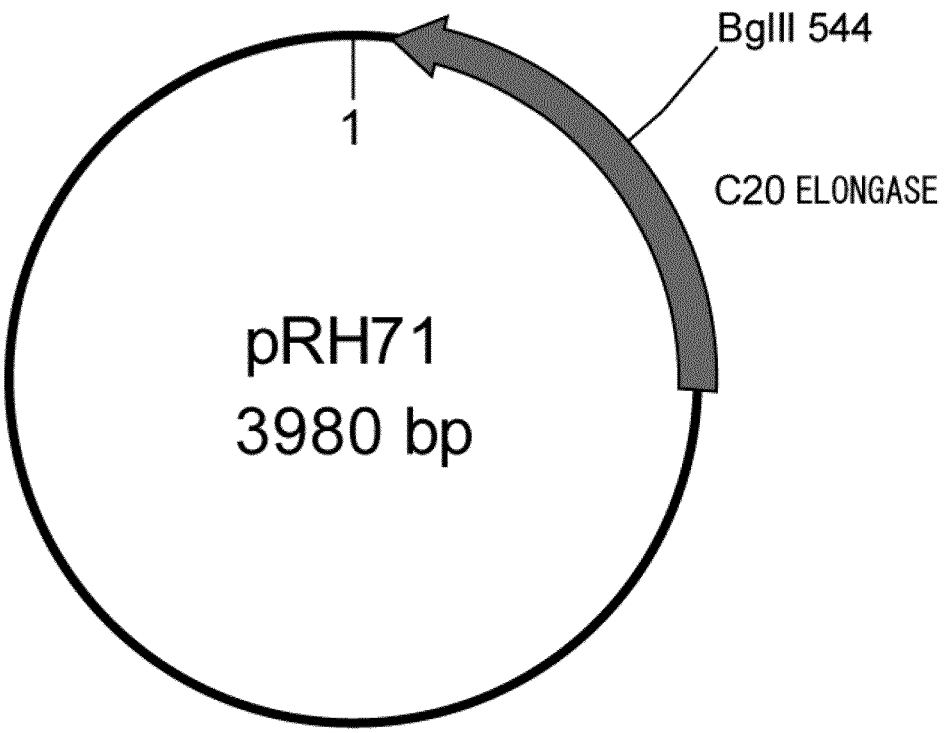

FIG. 96 is a diagram representing a pRH71 cloning a sequence containing a BglII site within the *Schizochytrium*-derived C20 elongase.

Figure 97:
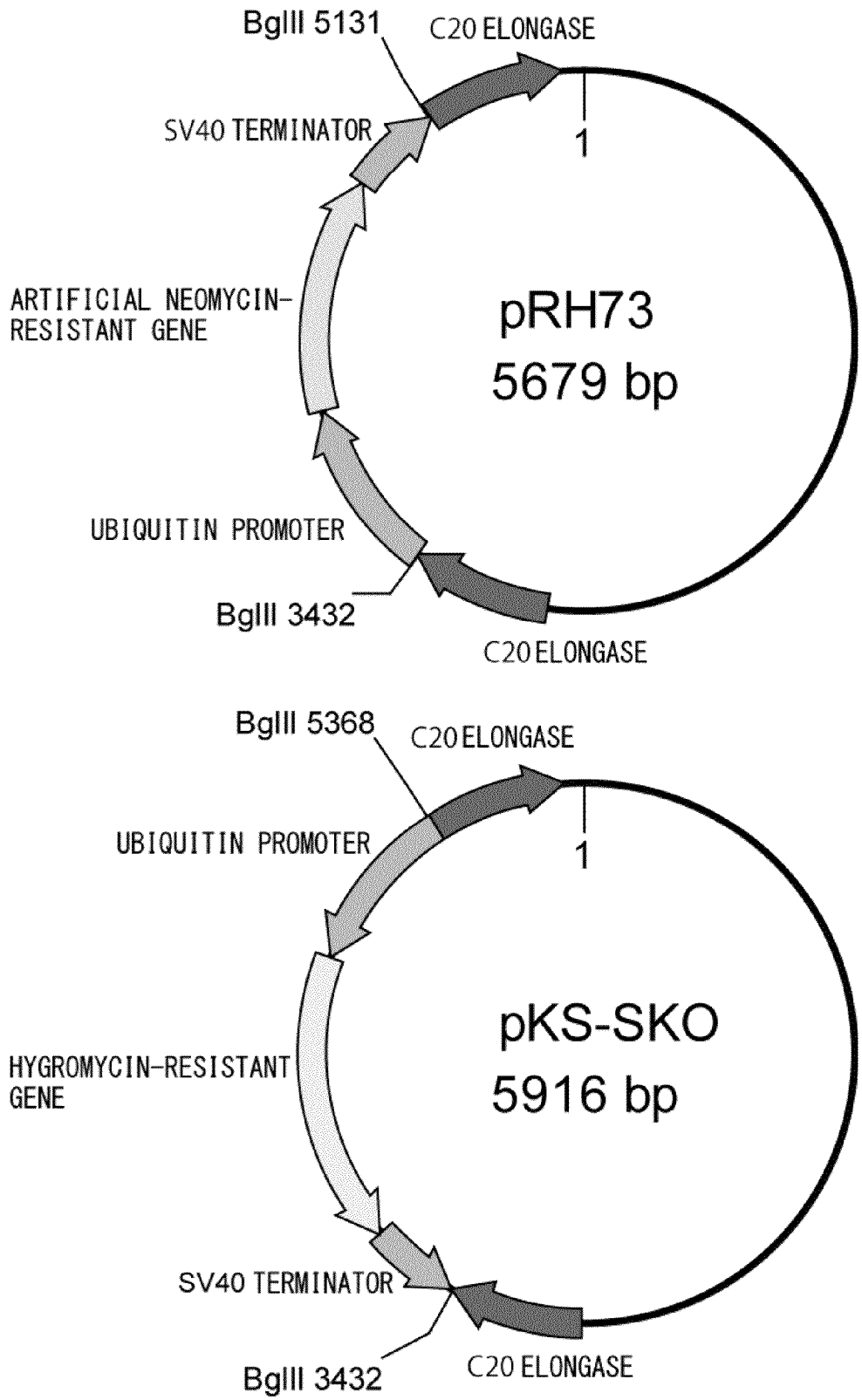

FIG. 97 is a diagram representing a pRH73 cloning a sequence containing a ubiquitin promoter, a neomycin-resistant gene, and an SV40 terminator within the *Schizochytrium*-derived C20 elongase, and a pKS-SKO cloning a sequence containing a ubiquitin promoter, a hygromycin-resistant gene, and an SV40 terminator within the *Schizochytrium*-derived C20 elongase.

Figure 98:
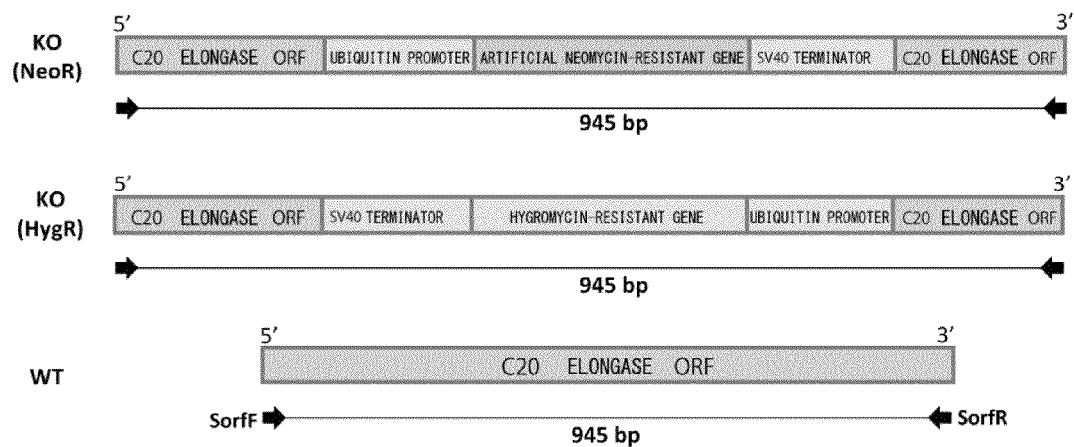

FIG. 98 represents the expected fragment sizes of the wild-type strain allele and the knockout strains in a PCR.

Figure 99:
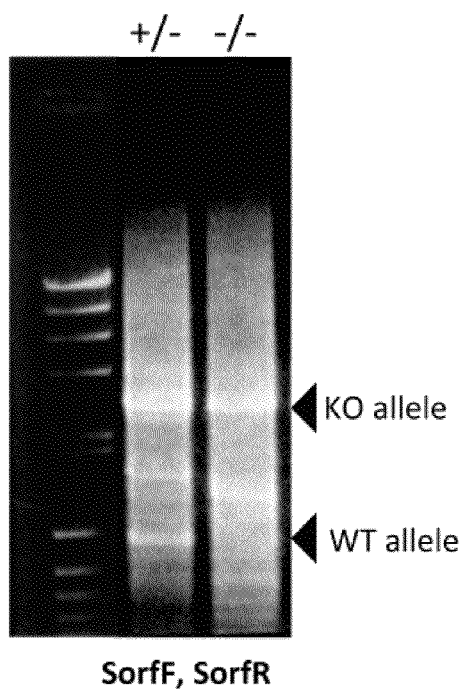

FIG. 99 represents the PCR detection result for the wild-type strain allele and the knockout strain.

Figures 100, 101:
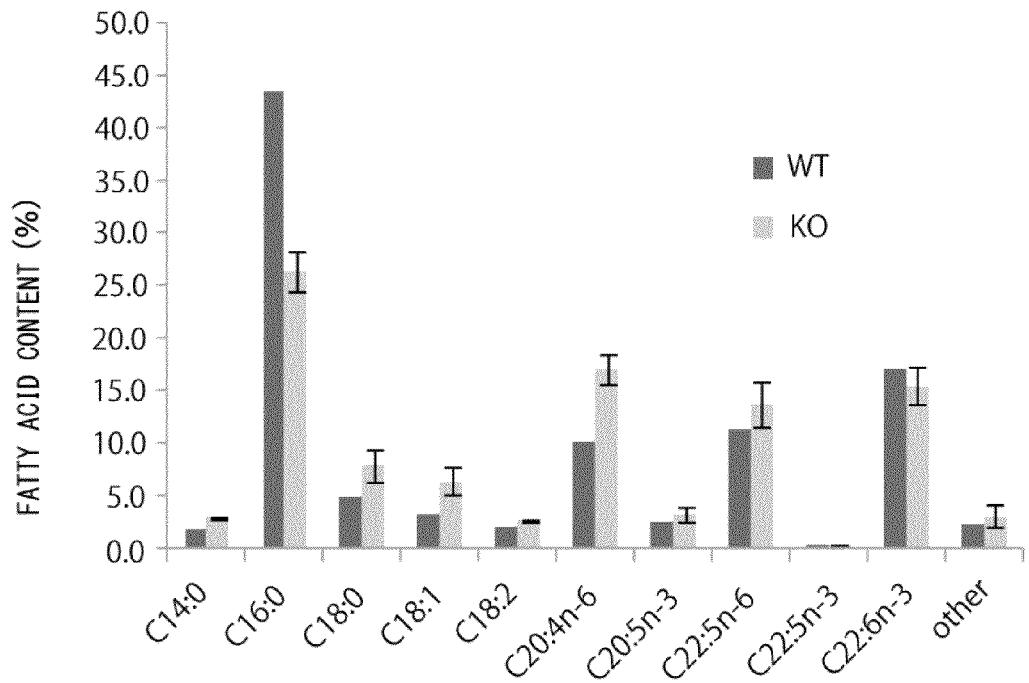

FIG. 100 represents the fatty acid compositions of the wild-type strain and the C20 elongase knockout strain. Blank bar and solid bar indicate the fatty acid compositions of the wild-type strain and the strain, respectively.

FIG. 101 represents the result of the comparison of the fatty acid compositions of the wild-type strain and the knockout strain.

MODE FOR CARRYING OUT THE INVENTION

The recent studies of the physiological activity and the pharmacological effects of lipids have elucidated the conversion of unsaturated fatty acids into various chemical substances, and the roles of unsaturated fatty acids in the unsaturated fatty acid metabolism. Particularly considered important in relation to disease is the nutritionally preferred proportions of saturated fatty acids, monounsaturated fatty acids, and unsaturated fatty acids, and the proportions of fish oil-derived ω3 series (also known as the n-3 series) fatty acids such as eicosapentaenoic acid and docosahexaenoic acid, and plant-derived ω6 series (also known as the n-6 series) fatty acids as represented by linoleic acid. Because animals are deficient in fatty acid desaturases (desaturases) or have low levels of fatty acid desaturases, some unsaturated fatty acids need to be ingested with food. Such fatty acids are called essential fatty acids (or vitamin F), which include linoleic acid (LA), γ-linolenic acid (GLA), and arachidonic acid (AA or ARA).

Unsaturated fatty acid production involves enzymes called fatty acid desaturases (desaturases). The fatty acid desaturases (desaturases) are classified into two types: (1) those creating a double bond (also called an unsaturated bond) at a fixed position from the carbonyl group of a fatty acid (for example, Δ9 desaturase creates a double bond at the 9th position as counted from the carbonyl side), and (2) those creating a double bond at a specific position from the methyl end of a fatty acid (for example, ω3 desaturase creates a double bond at the 3rd position as counted from the methyl end). It is known that the biosynthesis of unsaturated fatty acid involves the creation of a double bond by the desaturase (unsaturation), and the repeated elongation of the chain length by several different elongases. For example, Δ9 desaturase synthesizes oleic acid (OA) by unsaturating the stearic acid either synthesized in the body from palmitic acid or ingested directly from the outside of the body. Δ6, Δ5, and Δ4 desaturases are fatty acid desaturases (desaturases) essential for the syntheses of polyunsaturated fatty acids such as arachidonic acid (AA), eicosapentaenoic acid (EPA), and docosahexaenoic acid (DHA).

The Labyrinthulomycetes, a member of stramenopile, has two families: *Thraustochytrium* (Thraustochytriaceae) and Labyrinthulaceae. These microorganisms are known to accumulate polyunsaturated fatty acids such as arachidonic acid, EPA, DTA, DPA, and DHA.

The present invention is concerned with a stramenopile transformation method whereby stramenopile genes are disrupted and/or expression thereof is inhibited by genetic engineering. Specifically, the present invention developed and provides a transformation method for disrupting genes associated with fatty acid biosynthesis and/or inhibiting expression thereof, a method for modifying the fatty acid composition of a stramenopile with the use of the transformation method, a method for highly accumulating fatty acids in a stramenopile, a stramenopile having an enhanced unsaturated fatty acid content, and a method for producing unsaturated fatty acid from the unsaturated fatty acid content-enhanced stramenopile.

The present invention includes manipulating the enzymes of the stramenopile elongase/desaturase pathway to change the fatty acid composition produced by a stramenopile. Specifically, the present invention enables modification of the fatty acid composition produced by stramenopile through (1) disruption of a fatty acid chain elongase gene and/or inhibition of expression thereof, (2) disruption of a polyketide synthase gene and/or inhibition of expression thereof, (3) disruption of a fatty acid desaturase and/or inhibition of expression thereof, (3) disruption of two of or all of a polyketide synthase gene, a fatty acid chain elongase gene, and a fatty acid desaturase and/or inhibition of expression thereof, (4) disruption of a fatty acid chain elongase gene and/or inhibition of expression thereof, and introduction of a fatty acid desaturase gene, (5) disruption of a polyketide synthase gene and/or inhibition of expression thereof, and introduction of a fatty acid desaturase gene, (6) disruption of a fatty acid desaturase and/or inhibition of expression thereof, and introduction of a fatty acid desaturase gene, (6) disruption of two of or all of a polyketide synthase gene, a fatty acid chain elongase gene, and a fatty acid desaturase and/or inhibition of expression thereof, and introduction of a fatty acid desaturase gene.

The present invention is described below in more detail.

[Microorganism]

The microorganisms used in the fatty acid modification method of the present invention are not particularly limited, as long as the microorganisms are stramenopiles considered to undergo modification of the fatty acid composition through disruption of genes associated with fatty acid biosynthesis and/or inhibition of expression thereof. Particularly preferred microorganisms are those belonging to the class Labyrinthulomycetes. Examples of the Labyrinthulomycetes include those of the genus *Labyrinthula, Althornia, Aplanochytrium, Japonochytrium, Labyrinthuloides, Schizochytrium, Thraustochytrium, Ulkenia, Aurantiochytrium, Oblongichytrium, Botryochytrium, Parietichytrium*, and *Sicyoidochytrium*.

Of note, *Labyrinthuloides* and *Aplanochytrium* are regarded as being synonymous among some scholars (Leander, Celeste A. & David Porter, Mycotaxon, vol. 76, 439-444 (2000)).

The Labyrinthulomycetes used in the present invention are preferably microorganisms belonging to the genus *Thraustochytrium* and the genus *Parietichytrium*, particularly preferably *Thraustochytrium aureum, Parietichytrium sarkarianum*, and *Thraustochytrium roseum*. Specific examples include strains of *Thraustochytrium aureum* ATCC 34304, *Parietichytrium sarkarianum* SEK 364 (FERM BP-11298), *Thraustochytrium roseum* ATCC 28210, *Parietichytrium* sp. SEK358 (FERM BP-11405), and *Parietichytrium* sp. SEK571 (FERM BP-11406). *Thraustochytrium aureum* ATCC 34304 and *Thraustochytrium roseum* ATCC 28210 are deposited at the ATCC, and are commonly available. The *Parietichytrium* sarkarianum SEK364 strain was obtained from the surface water collected at the mouth of fukidougawa on Ishigakijima. The water (10 ml) was placed in a test tube, and left unattended at room temperature after adding pine pollens. After 7 days, the pine pollens were applied to a sterile agar medium (2 g glucose, 1 g peptone, 0.5 g yeast extract, 0.2 g chloramphenicol, 15 g agar, distilled water 100 mL, sea water 900 mL). Colonies appearing after 5 days were isolated and cultured. This was repeated several times to isolate the cells. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11298; Sep. 24, 2010). The *Parietichytrium* sp. SEK358 strain was isolated from the cells cultured as above from the sea water sample collected at the mouth of Miyaragawa on Ishigakijima. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11405; Aug. 11, 2011). The *Parietichytrium* sp. SEK571 strain was isolated from the cells cultured as above from the sea water sample collected at the mouth of Shiiragawa on Iriomotejima. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM BP-11406; Aug. 11, 2011). The *Schizochytrium* sp. TY12Ab strain was isolated from the cells cultured as above from the dead leaves collected on the coast of *Tanegashima*. This strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM ABP-11421; Sep. 29, 2011). Then, the RECEIPT IN THE CASE OF AN ORIGINAL DEPOSIT (FERM BP-11421) was issued by International Patent Organism Depositary on Nov. 30, 2011.

[Genes Associated with Fatty Acid Biosynthesis]

In the present invention, the genes associated with fatty acid biosynthesis are not particularly limited, as long as the genes are genes of enzymes associated with the fatty acid biosynthesis in stramenopile, particularly the Labyrinthulomycetes. Examples of such genes include polyketide synthase gene, fatty acid chain elongase gene, and fatty acid desaturase gene. In the present invention, one of or both of these genes are subject to the disruption or inhibition of expression by genetic engineering. Here, the target of the gene disruption and/or inhibition of expression is, for example, the open reading frame, when, for example, the fatty acid produced by the polyketide synthase in a stramenopile is not the desired fatty acid. In the case of the fatty acid chain elongase, the target is the gene associated with an enzyme that converts the desired fatty acid into an other fatty acid. For example, when eicosapentaenoic acid (EPA) is the desired product, the gene of the fatty acid chain elongase associated with the conversion of eicosapentaenoic acid into docosapentaenoic acid (DPA), specifically C20 elongase gene may be disrupted and/or expression thereof may be inhibited. In the case of the fatty acid desaturase, the target is the gene associated with the enzyme that converts the desired fatty acid into an other fatty acid. For example, when oleic acid is the desired product, the gene of the fatty acid desaturase associated with the conversion of oleic acid into linoleic acid, specifically Δ12 desaturase gene may be disrupted and/or expression thereof may be inhibited. Further, two of or all of the polyketide synthase gene, the fatty acid chain elongase gene, and the fatty acid desaturase may be disrupted and/or expression thereof may be inhibited according to the desired fatty acid.

Further, a gene associated with fatty acid biosynthesis may be introduced into a transfectant strain produced by disrupting a gene and/or inhibiting expression thereof by genetic engineering as above. Here, the introduced gene is a gene associated with the enzyme that performs biosynthesis of the desired fatty acid. For example, when eicosapentaenoic acid is the desired product, a gene of the fatty acid desaturase that converts arachidonic acid (AA) into eicosapentaenoic acid, specifically ω3 desaturase gene may be introduced.

[Polyketide Synthase and Fatty Acid Chain Elongase]

Polyketide synthase (PKS) is an enzyme that catalyzes the multiple condensation reactions of a starter substrate (acetyl-CoA, fatty acid CoA ester, benzoyl CoA, coumaroyl CoA)

with an extender substrate (such as malonyl CoA), and the enzyme is generally known to be involved in the biosyntheses of secondary metabolites in organisms such as plants and fungi. Involvement in the biosynthesis of polyunsaturated fatty acid is also reported in some species of organisms. For example, the marine bacteria *Shewanella* produce eicosapentaenoic acid (EPA) with this enzyme (Non-Patent Document 8). In some species of stramenopile, the polyketide synthase is known to be involved in the biosynthesis of polyunsaturated fatty acid, and the gene sequence has been elucidated in the Labyrinthulomycetes. For example, as described in Patent Document 7, the polyketide synthase gene of the genus *Schizochytrium* of *Labyrinthula* has three open reading frames, OrfA, OrfB, and OrfC. Further, as described in Patent Document 8, the polyketide synthase gene of the genus *Ulkenia* of *Labyrinthula* is considered to have three open reading frames.

The fatty acid chain elongase of the present invention is not particularly limited, as long as it extends the chain length of a fatty acid. Preferred examples include C18 elongase gene, and C20 elongase gene. The C18 elongase gene and the C20 elongase gene extend fatty acids of 18 and 20 carbon atoms, respectively, in two-carbon units to produce fatty acids of 20 and 22 carbon atoms. These fatty acid chain elongases are found in a wide range of organisms, including stramenopiles, and in, for example, the genus *Thraustochytrium* of Labyrinthulomycetes, as reported in Non-Patent Document 9. The C18 elongase catalyzes the conversion of γ-linolenic acid (GLA) to dihomo-γ-linolenic acid (DGLA), and the conversion of stearidonic acid (STA) into eicosatetraenoic acid (ETA). The C20 elongase catalyzes the conversion of arachidonic acid (AA) into docosatetraenoic acid (DTA), and the conversion of eicosapentaenoic acid (EPA) into n-3 docosapentaenoic acid (DPA, 22:5n-3).

It follows from this that when the desired product is, for example, stearidonic acid (STA), a gene of the fatty acid chain elongase associated with the conversion of stearidonic acid into eicosatetraenoic acid (ETA), specifically C18 elongase gene may be disrupted and/or expression thereof may be inhibited. When the desired product is, for example, eicosapentaenoic acid (EPA), a gene of the fatty acid chain elongase associated with the conversion of the eicosapentaenoic acid into docosapentaenoic acid (DPA), specifically C20 elongase gene may be disrupted and/or expression thereof may be inhibited. Further, when the fatty acid biosynthesized with the polyketide synthase in a stramenopile is not the desired fatty acid, the polyketide synthase gene may be disrupted and/or expression thereof may be inhibited. As reported in Non-Patent Document 5, a strain of the genus *Schizochytrium* of *Labyrinthula* loses the ability to biosynthesize docosahexaenoic acid after the disruption of the polyketide synthase gene, and cannot grow in media unless supplemented with polyunsaturated fatty acid. In the present invention, however, some species of *Labyrinthula*, even with the disrupted polyketide synthase gene, are able to grow in media without adding polyunsaturated fatty acid, and the desired polyunsaturated fatty acid can thus be obtained by disrupting the gene or inhibiting gene expression in the manner described above.

[Fatty Acid Desaturase]

The fatty acid desaturase (desaturase) of the present invention is not particularly limited, as long as it functions as a fatty acid desaturase. The origin of the fatty acid desaturase gene is not particularly limited, and may be, for example, animals and plants. Examples of the preferred fatty acid desaturase genes include Δ4 desaturase gene, Δ5 desaturase gene, Δ6 desaturase gene, Δ12 desaturase gene, and ω3 desaturase gene, and these may be used either alone or in combination. The Δ4 desaturase gene, Δ5 desaturase gene, Δ6 desaturase gene, and Δ12 desaturase gene form an unsaturated bond at carbon 4, 5, 6, and 12, respectively, as counted from the carbon atom of the terminal carboxyl group (delta end) of the fatty acid. A specific example of these fatty acid desaturase genes is the microalgae-derived Δ4 desaturase gene (Non-Patent Document 6). Specific examples of Δ5 desaturase include *T. aureum*-derived Δ5 desaturase, and Δ5 desaturases derived from *Thraustochytrium* sp. ATCC 26185, *Dictyostelium discoideum*, *Rattus norvegicus*, *Mus musculus*, *Homo sapiens*, *Caenorhabditis elegans*, and *Leishmania major*. Examples of Δ12 desaturase include *Pinguiochrysis pyriformis*-derived Δ12 desaturase, and fungus- and protozoa-derived Δ12 desaturases. The ω3 desaturase forms a double bond at the third position as counted from the methyl terminal of the fatty acid carbon chain. Examples include *Saprolegnia*-derived ω3 desaturase (Non-Patent Document 10). The Δ5 desaturase catalyzes, for example, the conversion of dihomo-γ-linolenic acid (DGLA) to arachidonic acid (AA), and the conversion of eicosatetraenoic acid (ETA) to eicosapentaenoic acid (EPA). Δ6 desaturase catalyzes, for example, the conversion of linoleic acid (LA) to γ-linolenic acid (GLA), and the conversion of α-linolenic acid (ALA) to stearidonic acid (STA). The ω3 desaturase catalyzes the conversion of arachidonic acid to eicosapentaenoic acid. Linoleic acid (LA) is produced from oleic acid (OA) by the action of Δ12 desaturase.

[Product Unsaturated Fatty Acid]

The unsaturated fatty acid produced by the fatty acid desaturase expressed in a stramenopile is, for example, an unsaturated fatty acid of 18 to 22 carbon atoms. Preferred examples include docosahexaenoic acid (DHA) and eicosapentaenoic acid (EPA), though the preferred unsaturated fatty acids vary depending on the types of the fatty acid desaturase and the fatty acid substrate used. Other examples include α-linolenic acid (ALA), octadecatetraenoic acid (OTA, 18:4n-3), eicosatetraenoic acid (ETA, 20:4n-3), n-3 docosapentaenoic acid (DPA, 22:5n-3), tetracosapentaenoic acid (TPA, 24:5n-3), tetracosahexaenoic acid (THA, 24:6n-3), linoleic acid (LA), γ-linolenic acid (GLA), eicosatrienoic acid (20:3n-6), arachidonic acid (AA), and n-6 docosapentaenoic acid (DPA, 22:5n-6).

[Gene Source of Enzyme Associated with Fatty Acid Biosynthesis]

The organisms that can be used as the gene sources of the polyketide synthase, fatty acid chain elongase, and/or fatty acid desaturase in the present invention are not limited to particular genuses, species, or strains, and may be any organisms having an ability to produce polyunsaturated fatty acids. For example, in the case of microorganisms, such organisms are readily available from microorganism depositary authorities. Examples of such microorganisms include the bacteria *Moritella marina* MP-1 strain (ATCC15381) of the genus *Moritella*. The following describes a method using this strain as an example of desaturase and elongase gene sources. The method, however, is also applicable to the isolation of the constituent desaturase and elongase genes from all biological species having the desaturase/elongase pathway.

Isolation of the desaturase and/or elongase gene from the MP-1 strain requires estimation of a conserved region in the amino acid sequence of the target enzyme gene. For example, in desaturase, it is known that a single cytochrome b5 domain and three histidine boxes are conserved across biological species, and that elongase has two conserved histidine boxes across biological species. More specifically, the conserved region of the target enzyme can be estimated by the multiple alignment comparison of the known amino acid sequences of the desaturase or elongase genes derived from various biological species using the clustal w program (Non-Patent Document 7). It is also possible to estimate conserved regions specific to desaturase and/or elongase having the same substrate specificity by the multiple alignment comparison of the amino acid sequences of desaturase or elongase genes having the same substrate specificity in the desaturase and/or elongase derived from known other organisms. Various degenerate oligonucleotide primers are then produced based on the estimated conserved regions, and the partial sequence of the target gene derived from the MP-1 strain is amplified using an MP-1 strain-derived cDNA library as a template, by using methods such as PCR and RACE. The resulting amplification product is cloned into a plasmid vector, and the base sequence is determined using an ordinary method. The sequence is then compared with a known enzyme gene to confirm isolation of a part of the target enzyme gene from the MP-1 strain. The full-length target enzyme gene can be obtained by hybridization screening using the obtained partial sequence as a probe, or by the RACE technique using the oligonucleotide primers produced from the partial sequence of the target gene.

The polyketide synthase can be cloned by using an ordinary method, using the PUFA PKS sequence of Patent Document 7 as a reference.

[Other Gene Sources]

Reference should be made to Non-Patent Document 11 or 12 for GFP (Green Fluorescent Protein), Patent Document 6 for EGFP (enhanced GFP), and Non-Patent Document 13 for neomycin-resistant gene.

[Disruption of Gene Associated with Fatty Acid Biosynthesis in Stramenopile]

The stramenopile gene associated with fatty acid biosynthesis may be disrupted by using conventional gene disruption methods used for microorganisms. An example of such a method is the transformation introducing a recombinant expression vector into a cell.

For example, for the disruption of a *Thraustochytrium aureum* gene, genomic DNA is extracted from a *Thraustochytrium aureum* by using an ordinary method, and a genome library is created. Then, genome walking primers are set using the DNA sequence of the target gene to be disrupted, and a PCR is run using the produced genome library as a template to obtain the upstream and downstream sequences of the target gene of *Thraustochytrium aureum*. These sequences are flanked on both sides to provide homologous recombination regions for gene disruption, and a drug marker gene is inserted therebetween for selection. The DNA is then linearized, and introduced into a *Thraustochytrium aureum* using a gene-gun technique, and the cells are cultured for about 1 week on a drug-containing plate. By using an ordinary method, genomic DNA is extracted from cells that have acquired drug resistance, and strains that underwent homologous recombination are identified by PCR or southern hybridization. Because the *Thraustochytrium aureum* is a diploid, the procedures from the introduction of the linearized DNA into the cells using a gene-gun technique to the identification of homologous recombinant strains are repeated twice. In this way, a *Thraustochytrium aureum* with the disrupted target gene can be obtained. When two or more target genes are present, a strain with the disrupted multiple target genes can be obtained by repeating the foregoing procedures. Here, because the *Thraustochytrium aureum* is a diploid, two selection markers need to be prepared for each gene.

For the disruption of, for example, the C20 elongase of *Parietichytrium sarkarianum*, genomic DNA is extracted from a *Parietichytrium* species by using an ordinary method, and the genome is decoded. Then, a search is made for a gene sequence highly homologous to a known C20 elongase gene, and the gene sequence is amplified by PCR from the start codon to the stop codon. This is followed by insertion of a restriction enzyme site at substantially the center of the gene sequence by using a mutagenesis method, and insertion of a drug marker gene cassette to the restriction enzyme site for selection. The DNA is linearized, and introduced into a *Parietichytrium sarkarianum* SEK364 using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Parietichytrium sarkarianum* SEK364 is a diploid, the procedures from the introduction of the linearized DNA into the cells using a gene-gun technique to the identification of the homologous recombinant strains are repeated twice. In this way, a *Parietichytrium sarkarianum* SEK364 with the disrupted C20 elongase gene can be obtained. Here, because the *Parietichytrium sarkarianum* SEK364 is a diploid, two selection markers need to be prepared. For the disruption of, for example, the Δ4 desaturase of a *Thraustochytrium aureum* ATCC 34304-derived OrfA disrupted strain, genomic DNA is extracted from a *Thraustochytrium aureum* ATCC 34304 by using an ordinary method, and the genome is decoded. Then, a search is made for a gene sequence highly homologous to a known Δ4 desaturase, and the gene sequence is amplified by PCR from the upstream region to a region in the vicinity of the stop codon. By using a mutagenesis method, a restriction enzyme site is inserted at the same time as deleting a part of the ORF containing the start codon, and a drug marker gene cassette is inserted to the restriction enzyme site for selection. The DNA is linearized, and introduced into a *Thraustochytrium aureum* ATCC 34304-derived OrfA disrupted strain by using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Thraustochytrium aureum* ATCC 34304 is a diploid, the procedures from the introduction of the linearized DNA using a gene-gun technique to the identification of homologous recombinant strains are repeated twice. In this way, a *Thraustochytrium aureum* ATCC 34304-derived OrfA disrupted strain with the disrupted Δ4 desaturase gene can be obtained. Here, because the *Thraustochytrium aureum* ATCC 34304 is a diploid, two selection markers need to be prepared.

The C20 elongase gene sequence of *Thraustochytrium aureum* was used for disrupting the C20 elongase of *Thraustochytrium roseum*. Genomic DNA is extracted from a *Thraustochytrium aureum* by using an ordinary method, and the C20 elongase gene is amplified from the start codon to the stop codon by PCR. A restriction enzyme site is inserted to substantially the center of the gene sequence by using a mutagenesis method, and a drug marker gene cassette is inserted to the restriction enzyme site for selection. The DNA is linearized, and introduced into a *Thraustochytrium roseum* by using a gene-gun technique. The cells are then cultured for about 1 week on a drug-containing plate. By using an ordinary method, genomic DNA is extracted from cells that have acquired drug resistance, and strains that underwent homologous recombination are identified by PCR. Because the *Thraustochytrium roseum* is a diploid, the procedures from the introduction of the linearized DNA using a gene-gun technique to the identification of the homologous recombinant strain are repeated twice. In this way, a *Thraustochytrium roseum with the disrupted C20 elongase gene can be obtained. Here, because the *Thraustochytrium roseum* is a diploid, two selection markers need to be prepared.

Details of the disruption of stramenopile genes associated with fatty acid biosynthesis according to the present invention will be specifically described later in Examples. The stramenopile subject to transformation is not particularly limited, and those belonging to the class Labyrinthulomycetes can preferably be used, as described above.

For example, for the disruption of the C20 elongase of the *Parietichytrium* sp. SEK358 strain, the *Parietichytrium* C20 elongase gene targeting vector produced in Example 3-6 was used. The DNA is linearized, and introduced into a *Parietichytrium* sp. SEK358 strain by using a gene-gun technique. The cells are then cultured for about 1 week on a drug-containing plate. By using an ordinary method, genomic DNA is extracted from cells that have acquired drug resistance, and strains that underwent homologous recombination were identified by PCR (see Example 9). For the disruption of, for example, the C20 elongase of the *Parietichytrium* sp. SEK571 strain, the *Parietichytrium* C20 elongase gene targeting vector produced in Example 3-6 was used. The DNA is linearized, and introduced into a *Parietichytrium* sp. SEK571 strain by using a gene-gun technique. The cells are then cultured for about 1 week on a drug-containing plate. By using an ordinary method, genomic DNA was extracted from cells that had acquired drug resistance, and the homologous recombinant strain was identified by PCR (see Example 10).

The expression vector is not particularly limited, and a recombinant expression vector with an inserted gene may be used. The vehicle used to produce the recombinant expression vector is not particularly limited, and, for example, a plasmid, a phage, and a cosmid may be used. A known method may be used for the production of the recombinant expression vector. The vector is not limited to specific types, and may be appropriately selected from vectors expressible in a host cell. Specifically, the expression vector may be one that is produced by incorporating the gene of the present invention into a plasmid or other vehicles with a promoter sequence appropriately selected according to the type of the host cell for reliable expression of the gene. The vector may be a cyclic or a linear vector. The expression vector preferably includes at least one selection marker. Examples of such selection markers include auxotrophic markers, drug-resistance markers, fluorescent protein markers, and fused markers of these. Examples of the auxotrophic markers include dihydrofolate reductase genes. Examples of the drug-resistance markers include neomycin-resistant genes, hygromycin-resistant genes, blasticidin-resistant genes, and zeocin-resistant genes. Examples of the fluorescent protein markers include GFPs, and enhanced GFPs (EGFPs). Examples of the fused markers include fused markers of fluorescent protein markers and drug-resistance markers, specifically, for example, GFP-fused zeocin-resistant genes. These selection markers allow for confirmation of whether the polynucleotide according to the present invention has been introduced into a host cell, or whether the polynucleotide is reliably expressed in the host cell. Alternatively, the fatty acid desaturase according to the present invention may be expressed as a fused polypeptide. For example, the fatty acid desaturase according to the present invention may be expressed as a GFP-fused polypeptide, using GFP as a marker.

Preferably, electroporation or a gene gun is used as the method of gene introduction for the gene disruption. In the present invention, the disruption of the gene associated with fatty acid biosynthesis changes the fatty acid composition of the cell from that before the gene disruption. Specifically, the fatty acid composition is modified by the disruption of the gene associated with fatty acid biosynthesis. A stramenopile with the disrupted fatty acid biosynthesis-related enzyme gene can produce the desired fatty acid in greater amounts when further introduced with a fatty acid desaturase gene. Preferably, an ω3 desaturase gene is introduced as the fatty acid desaturase gene.

The stramenopile transformation produces a stramenopile (microorganism) in which the composition of the fatty acid it produces is modified. The stramenopile with the disrupted gene associated with fatty acid biosynthesis can be used for, for example, the production of unsaturated fatty acids. Unsaturated fatty acid production is possible with the stramenopile that has been modified to change its produced fatty acid composition as above, and other conditions, including steps, equipment, and instruments are not particularly limited. The unsaturated fatty acid production includes the step of culturing a microorganism that has been modified to change its produced fatty acid composition by the foregoing modification method, and the microorganism is used with its medium to produce unsaturated fatty acids.

The cell culture conditions (including medium, culture temperature, and aeration conditions) may be appropriately set according to such factors as the type of the cell, and the type and amount of the unsaturated fatty acid to be produced. As used herein, the term "unsaturated fatty acids" encompasses substances containing unsaturated fatty acids, and attributes such as the content, purity, shape, and composition are not particularly limited. Specifically, in the present invention, the cell or its medium itself having a modified fatty acid composition may be regarded as unsaturated fatty acids. Further, a step of purifying the unsaturated fatty acids from such cells or media also may be included. A known method of purifying unsaturated fatty acids and other lipids (including conjugate lipids) may be used for the purification of the unsaturated fatty acids.

[Method of Highly Accumulating Unsaturated Fatty Acid in Stramenopile]

Accumulation of unsaturated fatty acids in stramenopile is realized by culturing the transformed stramenopile of the present invention. For example, the culture is performed using a common solid or liquid medium. The type of medium used is not particularly limited, as long as it is one commonly used for culturing Labyrinthulomycetes, and that contains, for example, a carbon source (such as glucose, fructose, saccharose, starch, and glycerine), a nitrogen source (such as a yeast extract, a corn steep liquor, polypeptone, sodium glutamate, urea, ammonium acetate, ammonium sulfate, ammonium nitrate, ammonium chloride, and sodium nitrate), and an inorganic salt (such as potassium phosphate) appropriately combined with other necessary components. Particularly preferably, a yeast extract/glucose medium (GY medium) is used. The prepared medium is adjusted to a pH of 3.0 to 8.0, and used after being sterilized with an autoclave or the like. The culture may be performed by aerated stirred culture, shake culture, or static culture at 10 to 40° C., preferably 15 to 35° C., for 1 to 14 days.

For the collection of the produced unsaturated fatty acids, the stramenopile is grown in a medium, and the intracellular lipids (oil and fat contents with the polyunsaturated fatty acids, or the polyunsaturated fatty acids) are released by processing the microorganism cells obtained from the medium. The lipids are then collected from the medium containing the released intracellular lipids. Specifically, the cultured stramenopile is collected by using a method such as centrifugation. The cells are then disrupted, and the intracellular fatty acids are extracted using a suitable organic solvent according to an ordinary method. Oil and fat with the enhanced polyunsaturated fatty acid content can be obtained in this manner.

In the present invention, the composition of the fatty acids produced by a stramenopile is modified by culturing a stramenopile transformed through disruption of genes associated with fatty acid biosynthesis, and/or inhibition of expression thereof, specifically disruption of the polyketide synthase, the fatty acid chain elongase, and/or the fatty acid desaturase gene, and/or inhibition of expression of these genes. Because the genes associated with fatty acid biosynthesis are disrupted and/or expression thereof is inhibited, the desired fatty acid can be accumulated in the stramenopile without being converted into other fatty acids. Further, by introducing the gene associated with fatty acid desaturase into a stramenopile transformed through gene disruption and/or inhibition of gene expression, the ability to convert the precursor fatty acid of the desired fatty acid into the desired fatty acid can be enhanced, and the desired fatty acid is accumulated.

The unsaturated fatty acids of the present invention encompass various drugs, foods, and industrial products, and the applicable areas of the unsaturated fatty acids are not particularly limited. Examples of the food containing oil and fat that contain the unsaturated fatty acids of the present invention include foods with health claims such as supplements, and food additives. Examples of the industrial products include feeds for non-human organisms, films, biodegradable plastics, functional fibers, lubricants, and detergents.

The present invention is described below in more detail based on examples. Note, however, that the present invention is in no way limited by the following examples.

Example 1

Labyrinthulomycetes, Culture Method, and Preservation Method (1) Strains Used in the Present Invention

*Thraustochytrium aureum* ATCC 34304 and *Thraustochytrium roseum* ATCC 28210 were obtained from ATCC. *Parietichytrium sarkarianum* SEK364 (FERM BP-11298), *Parietichytrium* sp. SEK358 (FERM BP-11405), and *Parietichytrium* sp. SEK571 (FERM BP-11406) were obtained from Konan University, Faculty of Science and Engineering. *Schizochytrium* sp. TY12Ab (FERM BP-11421) was obtained from University of Miyazaki, Faculty of Agriculture.

(2) Medium Composition
i. Agar Plate Medium Composition
PDA Agar Plate Medium

A 0.78% (w/v) potato dextrose agar medium (Nissui Pharmaceutical Co., Ltd.), 1.75% (w/v) Sea Life (Marine Tech), and 1.21% (w/v) agar powder (nacalai tesque) were mixed, and sterilized with an autoclave at 121° C. for 20 min. After sufficient cooling, ampicillin sodium (nacalai tesque) was added in a final concentration of 100 µg/ml to prevent bacterial contamination. The medium was dispensed onto a petri dish, and allowed to stand on a flat surface to solidify.
ii. Liquid Medium Composition
GY Liquid Medium 3.18% (w/v) glucose (nacalai tesque), 1.06% (w/v) dry yeast extract (nacalai tesque), and 1.75% (w/v) Sea Life (Marine Tech) were mixed, and sterilized with an autoclave at 121° C. for 20 min. Then, 100 µg/ml ampicillin sodium (nacalai tesque) was added.

PD Liquid Medium 0.48% (w/v) potato dextrose (Difco), and 1.75% (w/v) Sea Life (Marine Tech) were mixed, and sterilized with an autoclave at 121° C. for 20 min. Then, 100 µg/ml ampicillin sodium (nacalai tesque) was added.
(3) Culture Method
i. Agar Plate Culture

*Labyrinthula* cells were inoculated using a platinum loop or a spreader, and static culture was performed at 25° C. to produce colonies. Subcultures were produced by collecting the colonies with a platinum loop, suspending the collected colonies in a sterilized physiological saline, and applying the suspension using a platinum loop or a spreader. As required, the cells on the plate were inoculated in a liquid medium for conversion into a liquid culture.
ii. Liquid Culture

*Labyrinthula* cells were inoculated, and suspension culture was performed by stirring at 25° C., 150 rpm in an Erlenmeyer flask or in a test tube. Subcultures were produced by adding a culture fluid to a new GY or PD liquid medium in a 1/200 to 1/10 volume after confirming proliferation from the logarithmic growth phase to the stationary phase. As required, the cell culture fluid was applied onto a PDA agar plate medium for conversion into an agar plate culture.
(4) Maintenance and Preservation Method of Labyrinthulomycetes In addition to the subculture, cryopreservation was performed by producing a glycerol stock. Specifically, glycerol (nacalai tesque) was added in a final concentration of 15% (v/v) to the logarithmic growth phase to stationary phase of a cell suspension in a GY liquid medium, and the cells were conserved in a −80° C. deep freezer.

Example 2

Disruption of *Thraustochytrium aureum* C20 Elongase Gene

Example 2-1

Extraction of *T. aureum* ATCC 34304-Derived Total RNA, and mRNA Purification

A *T. aureum* ATCC 34304 culture fluid grown for 3 days using a GY liquid medium was centrifuged at 3,500×g for 15 min, and the cells were collected. After being suspended in sterilized physiological saline, the cells were washed by being recentrifuged. The cells were then rapidly frozen with liquid nitrogen, and ground into a powdery form with a mortar. Total RNA was extracted from the resulting cell disruption liquid, using Sepasol-RNA I Super (nacalai tesque). This was followed by purification of mRNA from the total RNA using the Oligotex™-dT30 <Super> mRNA Purification Kit (Takara Bio) according to the manufacturer's protocol. The resulting total RNA and the mRNA were dissolved in a suitable amount of TE, and electrophoresed with a formalin-denatured gel (1% agarose/MOPS buffer). The result confirmed successful extraction of the total RNA, and purification of mRNA from the total RNA. It was also confirmed that the RNA was not degraded by the RNase. In order to minimize RNA degradation, all experimental procedures were performed with sanitary equipment such as rubber gloves and a mask. All instruments were RNase free, or were used after a diethylpyrocarbonate (nacalai tesque) treatment to deactivate the RNase. The solution used to dissolve the RNA was prepared by adding the recombinant RNase inhibitor RNaseOUT™ (invitrogen) to sterilized Milli Q water treated with diethylpyrocarbonate.

Example 2-2

Isolation of *T. aureum* ATCC 34304-Derived Elongase Gene by RACE

Figure 1:
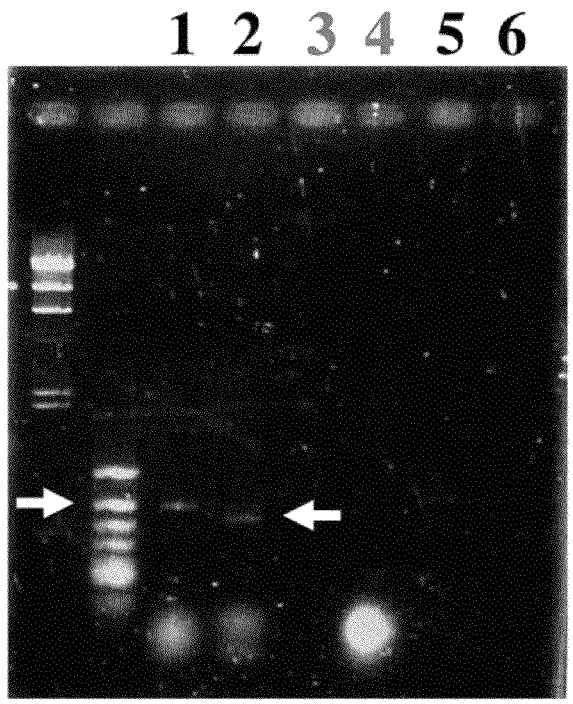
FIG. 1 represents the result of RACE performed to amplify a *T. aureum* ATCC 34304-derived elongase gene in Example 2-2. [Brief Description of Reference Numerals] 1: 5'-RACE using a synthetic adapter-specific oligonucleotide and a denatured oligonucleotide elo-R; 2: 3'-RACE using a synthetic adapter-specific oligonucleotide and a denatured oligonucleotide elo-F; 3: 5'-RACE using only elo-R (negative control); 4: 3'-RACE using only elo-F (negative control); 5: 5'-RACE using only a synthetic adapter-specific oligonucleotide (negative control); 6: 3'-RACE using only a synthetic adapter-specific oligonucleotide (negative control).

Forward (elo-F; 5'-TTY YTN CAY GTN TAY CAY CAY-3') (SEQ ID NO: 1), and reverse (elo-R; 5'-GCR TGR TGR TAN ACR TGN ARR AA-3') (SEQ ID NO: 2) denatured oligonucleotides were synthesized, targeting the histidine box (His box) highly conserved in elongase genes. The oligonucleotides were synthesized with a DNA synthesizer (Applied Biosystems). Then, by addition of synthetic adapters to the 3'- and 5'-ends, 3'- and 5'-RACE cDNA libraries were produced by using the SMART™ RACE cDNA Amplification Kit (clontech) according to the manufacturer's protocol, respectively. By using these as templates, 3'- and 5'-RACE were performed using the synthetic adapter-specific oligonucleotides, and the denatured oligonucleotides elo-F and elo-R [PCR cycles: 94° C. 1 min/94° C. 30 sec, 60° C. 30 sec, 72° C. 3 min, 30 cycles/72° C. 10 min/4° C. ∞]. The result confirmed bands for the specifically amplified 3'- and 5'-RACE products (FIG. 1). The total RACE product amounts were subjected to electrophoresis with 1% agarose gel, and the isolated DNA fragments were cut out with a clean cutter or the like and extracted from the agarose gel according to the method described in Non-Patent Document 20. The DNA fragments were then TA cloned with a pGEM-T easy Vector (Promega), and the base sequences were determined by the method of Sanger et al. (Non-Patent Document 21). Specifically, the base sequences were determined by using a dye terminator method, using a BigDyeR Terminator v3.1 Cycle Sequencing Kit and a 3130 genetic analyzer (Applied Biosystems) according to the manufacturers' protocols.

As a result, two sequences, 190 bp and 210 bp, named elo1 (SEQ ID NO: 3) and elo2 (SEQ ID NO: 4) were successfully identified for the 3'-RACE product, and one sequence, 200 bp, named elo3 (SEQ ID NO: 5) was successfully identified for the 5'-RACE product. Because the elo1, elo2, and elo3 sequences had significant homology to the sequences of various elongase genes, the results suggested that these sequences were partial sequences of the *T. aureum* ATCC 34304-derived elongase gene. In an attempt to obtain cDNA sequences by RACE, oligonucleotide primers were redesigned for the elo1, elo2, and elo3. The oligonucleotide primers produced are as follows.

elo1 forward oligonucleotide primer (elo1-F1; 5'-TAT GAT CGC CAA GTA CGC CCC-3') (SEQ ID NO: 6) and reverse oligonucleotide primer (elo1-R1; 5'-GAA CTG CGT CAT CTG CAG CGA-3') (SEQ ID NO: 7)

elo2 forward oligonucleotide primer (elo2-F1; 5'-TCT CGC CCT CGA CCA CCA AC-3') (SEQ ID NO: 8) and reverse oligonucleotide primer (elo2-R1; 5'-CGG TGA CCG AGT TGA GGT AGC C-3') (SEQ ID NO: 9)

elo3 forward oligonucleotide primer (elo3-F1; 5'-CAA CCC TTT CGG CCT CAA CAA G-3') (SEQ ID NO: 10) and reverse oligonucleotide primer (elo3-R1; 5'-TTC TTG AGG ATC ATC ATG AAC GTG TC-3') (SEQ ID NO: 11)

By using these forward and reverse oligonucleotide primers, RACE and base sequence analysis of the amplification products were performed as above. As a result, specifically amplified 3'- and 5'-RACE products were obtained for elo1, and there was a complete match in the overlapping portion, identifying the sequence as a 1,139-bp elo1 cDNA sequence (SEQ ID NO: 12). Similarly, specifically amplified 3'- and 5'-RACE products were obtained for elo3, and there was a complete match in the overlapping portion, identifying the sequence as a 1,261-bp elo3 cDNA sequence (SEQ ID NO: 13).

It was found from the sequence analysis result that elo1 consisted of an 825-bp translated region (SEQ ID NO: 15) coding for 275 amino acid residues (SEQ ID NO: 14). It was also found from the result of a BLAST search that the sequence had significant homology to various elongase genes, and completely coincided with the sequence of a known *T. aureum*-derived putative Δ5 elongase gene (NCBI accession No. CS486301). On the other hand, it was assumed that the elo3 consisted of a 951-bp translated region (SEQ ID NO: 17) coding for 317 amino acid residues (SEQ ID NO: 16). It was also found from the result of a BLAST search that the sequence had significant homology to various elongase genes, and thus represented a *T. aureum* ATCC 34304-derived putative elongase gene. Note that the putative amino acid sequences of these genes contained His boxes highly conserved in elongase genes. From these results, elo1 and elo3 genes were identified as *T. aureum* ATCC 34304-derived putative elongase genes, and were named TaELO1 and TaELO2, respectively, Example 2-3

TaELO1 and TaELO2 Phylogenetic Analysis

Elongases are broadly classified into three groups on the basis of substrate specificity.
1. SFA/MUFA elongases (act on saturated fatty acids or monovalent unsaturated fatty acids)
2. PUFA-elongases (single-step) (act on polyvalent unsaturated fatty acids of certain chain lengths)
3. PUFA elongases (multi-step) (act on polyvalent unsaturated fatty acids of various chain lengths)

According to the elongase phylogenetic analysis conducted by Meyer et al. (Non-Patent Document 22), there is a good correlation between the substrate specificity and the phylogenetic relationships.

Figure 2:
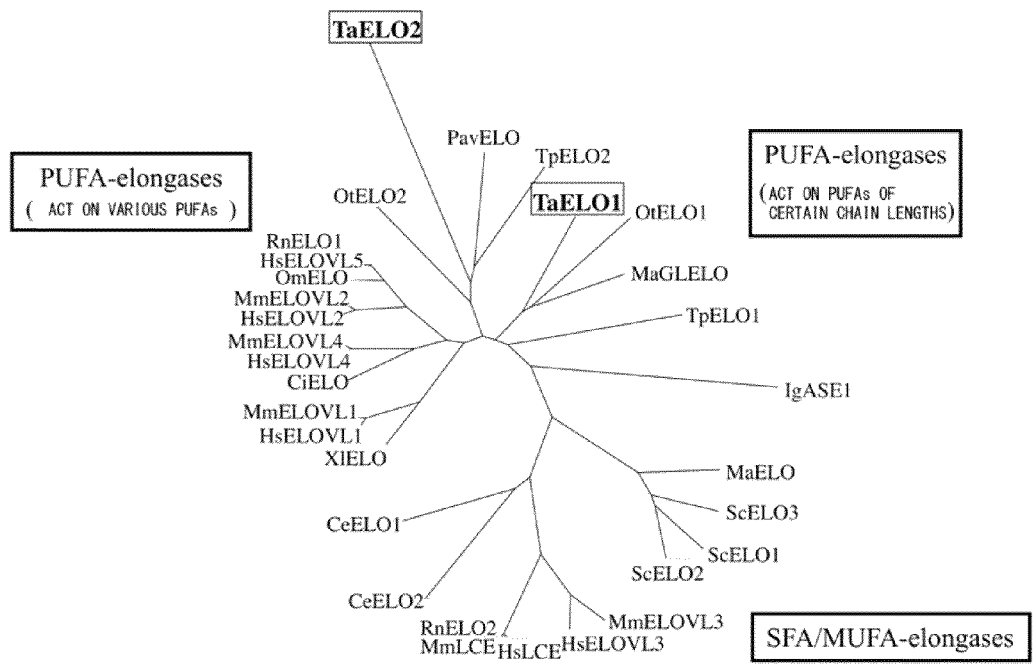
FIG. 2 represents a molecular phylogenetic tree of *T. aureum* ATCC 34304-derived Δ6/Δ9 elongase and Δ5/Δ6 elongase (TaELO1 and TaELO2) of Example 2-3.

Accordingly, a phylogenetic analysis was performed for TaELO1, TaELO2, and various other elongase genes derived from other organisms, using the method of Meyer et al. Specifically, a molecular phylogenetic tree was created according to the neighbor-joining method (Non-Patent Document 14), using the CLUSTAL W program (Non-Patent Document 7). It was found as a result that the TaELO1 and TaELO2 were classified into the PUFA-elongases (single-step) group, suggesting that these elongases act on polyvalent unsaturated fatty acids of certain chain lengths (FIG. 2).

Example 2-4

TaELO1 and TaELO2 Expression in Budding Yeast *Saccharomyces cerevisiae* Host, and Fatty Acid Composition Analysis of Gene Introduced Strain Expression vectors were constructed for TaELO1 and TaELO2 for their expression in budding yeast *S. cerevisiae* used as a host, as briefly described below. A set of oligonucleotide primer (E1 HindIII; 5'-ATA AGC TTA AAA TGT CTA GCA ACA TGA GCG CGT GGG GC-3') (SEQ ID NO: 18) and E1 XbaI; 5'-TGT CTA GAA CGC GCG GAC GGT CGC GAA A-3') (SEQ ID NO: 19) was produced using the sequence of the TaELO1 translated region. The E1 HindIII is a forward oligonucleotide primer, and has a restriction enzyme HindIII site (AAGCTT) at the 5'-end. The sequence in the vicinity of the TaELO1 start codon is modified by referring to a yeast consensus sequence ((A/Y) A (A/U) A AUG UCU; the start codon is underlined) (Non-Patent Document 23). The E1 XbaI is a reverse oligonucleotide primer, and has an XbaI site (TCTAGA) at the 5'-end.

In the same manner, a set of oligonucleotide primer (E2 HindIII; 5'-TAA AGC TTA AAA TGT CTA CGC GCA CCT CGA AGA GCG CTC C-3') (SEQ ID NO: 20) and E2 XbaI; 5'-CAT CTA GAC TCG GAC TTG GTG GGG GCG CTT G-3') (SEQ ID NO: 21) was produced using the sequence of the TaELO2 translated region. The E2 HindIII is a forward oligonucleotide primer, and has a restriction enzyme HindIII site at the 5'-end. The sequence in the vicinity of the TaELO2 start codon is modified by referring to a yeast consensus sequence. The E2 XbaI is a reverse oligonucleotide primer, and has an XbaI site at the 5'-end.

By using the two oligonucleotide primer sets, a PCR was performed using the 5'-RACE cDNA library of Example 2-2 as a template. The PCR amplified a 949-bp TaELO1 translated region (SEQ ID NO: 22) and a 967-bp TaELO2 translated region (SEQ ID NO: 23) having the restriction enzyme HindIII and the restriction enzyme XbaI site at the 5'-end and the 3'-end, and modified to the yeast consensus sequence in the vicinity of the start codon. Note that a PrimeSTARR DNA polymerase (Takara Bio) of high proofreading activity was used as the PCR enzyme to avoid extension errors [PCR cycles: 98° C. 2 min/98° C. 5 sec, 60° C. 5 sec, 72° C. 1.5 min, 30 cycles/72° C. 7 min/4° C. ∞].

After isolating the amplified PCR products with a 1% agarose gel, the DNA fragments were cut and extracted from the agarose gel. After treatment with restriction enzymes HindIII and XbaI, the product was purified again with an agarose gel. To construct a cyclic vector, the product was joined to a budding yeast expression vector pYES2/CT (invitrogen) with a DNA Ligation Kit <Mighty Mix> (Takara Bio) after linearizing the pYES2/CT vector with restriction enzymes HindIII and XbaI. This was followed by a base sequence analysis, which confirmed that no PCR extension error occurred and no mutation was introduced to the TaELO1 and TaELO2 translated region sequences introduced into the pYES2/CT. In this manner, a TaELO1 expression vector pYEELO1, and a TaELO2 expression vector pYEELO2 were successfully constructed.

The two expression vectors constructed above, and the pYES2/CT were introduced into the budding yeast S. cerevisiae by using the lithium acetate technique according to the methods described in Non-Patent Documents 15 and 16, and the transfectants were screened for. The resulting transfectants (pYEELO1 introduced strain, pYEELO2 introduced strain, and mock introduced strain) were cultured according to the method of Qiu et al. (Non-Patent Document 24), and the cell-derived fatty acids were extracted and methylesterificated. Note that each culture was performed in a medium supplemented with α-linolenic acid (ALA, C18:3Δ9, 12, 15) and linoleic acid (LA, C18:2Δ9, 12) added as Δ49 elongase substrates, stearidonic acid (STA, C18:4Δ6, 9, 12, 15) and γ-linolenic acid (GLA, C18:3Δ6, 9, 12) added as Δ6 elongase substrates, and eicosapentaenoic acid (EPA, C20:5Δ5, 8, 11, 14, 17) and arachidonic acid (AA, C20:4Δ5, 8, 11, 14) added as Δ5 elongase substrates. Here, each supplement was added in a final concentration of 0.2 mM. This was followed by the gas chromatography (GC) analysis of the methylesterificated fatty acids according to the method of Abe et al. (Non-Patent Document 17). The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

It was found as a result that, the pYEELO1 introduced strain had the Δ6 elongase activity not found in the host (mock introduced strain), converting the stearidonic acid (STA) into eicosatetraenoic acid (ETA, C20:4Δ8, 11, 14, 17), and the γ-linolenic acid (GLA) into dihomo-γ-linolenic acid (DGLA, C20:3Δ8, 11, 14). The pYEELO1 introduced strain also had the Δ9 elongase activity of converting the α-linolenic acid (ALA) into eicosatrienoic acid (ETrA, C20:3Δ11, 14, 17), and the linoleic acid (LA) into eicosadienoic acid (EDA, C20:3Δ11, 14), and the Δ5 elongase activity of converting the eicosapentaenoic acid (EPA) into ω3 docosapentaenoic acid (ω3 DPA, C22:5Δ7, 10, 13, 16, 19), and the arachidonic acid (AA) into docosatetraenoic acid (DTA, C22:4Δ7, 10, 13, 16) (Table 1).

As for the pYEELO2 introduced strain, it was found that this strain had the Δ5 elongase activity not found in the host, converting EPA to ω3 DPA (C22:5Δ7, 10, 13, 16, 19), and AA to DTA. The pYEELO2 introduced strain also had a weak Δ6 elongase activity, converting STA to ETA, and GLA to DGLA (Table 1). These results confirmed that the TaELO1 was a Δ6/Δ9/Δ5 elongase, and the TaELO2 was a Δ5/Δ6elongase, contrary to the results expected from the TaELO1 and TaELO2 substrate specificity in the phylogenetic analysis described in Example 2-3 and FIG. 2.

TABLE 1

| | mock | TaELO1 | TaELO2 |
|---|---|---|---|
| LA addition (0.2 mM) | | | |
| LA | 30.5 | 23.5 | 36.3 |
| EDA | 0.2 | 8.9 | 0.2 |
| Conversion efficiency (%) | | 27.4 | |
| GLA addition (0.2 mM) | | | |
| GLA | 44.0 | 7.6 | 43.6 |
| DGLA | 0.2 | 29.0 | 0.8 |
| Conversion efficiency (%) | | 79.3 | 1.9 |
| ARA addition (0.2 mM) | | | |
| ARA | 30.9 | 23.2 | 8.9 |
| ADA | — | 5.8 | 13.6 |
| Conversion efficiency (%) | | 20.1 | 60.3 |
| ALA addition (0.2 mM) | | | |
| ALA | 49.1 | 25.8 | 47.1 |
| ETrA | 0.2 | 17.9 | 0.3 |
| Conversion efficiency (%) | | 41 | |
| STA addition (0.2 mM) | | | |
| STA | 46.2 | 8.3 | 40.5 |
| ETA | 0.3 | 28.1 | 1.7 |
| Conversion efficiency (%) | | 77.2 | 4.0 |
| EPA addition (0.2 mM) | | | |
| EPA | 42.0 | 31.2 | 13.1 |
| DPA | 0.1 | 19.6 | 24.5 |
| Conversion efficiency (%) | | 25.3 | 65.1 |

Conversion efficiency (%) = 100 × product (area)/substrate (area) + product (area) (n = 1)

Example 2-5

Obtaining TaELO2 ORF Upstream and Downstream Regions by PCR Genome Walking

The TaELO2 ORF upstream and downstream regions as the homologous recombination sites in a targeting vector for disrupting TaELO2 were obtained by using the PCR genome walking technique, as briefly described below.

*T. aureum* ATCC 34304 cell grown for 3 days using a GY liquid medium was rapidly frozen with liquid nitrogen, and ground into a powdery form with a mortar. Then, genomic DNA was extracted according to the method described in Non-Patent Document 18, and dissolved in a suitable amount of TE. Genomic DNA levels and purity were assayed by O.D.260 and O.D.280 measurements. This was followed by construction of a genomic DNA library by adding a cassette sequence with restriction enzyme sites to the genomic DNA cut with various restriction enzymes, using a TaKaRa LA PCR™ in vitro Cloning Kit (Takara Bio) according to the manufacturer's protocol. Then, by using the genomic DNA library as a template, a nested PCR was performed according to the manufacturer's protocol, using the forward oligonucleotide primers E2 XbaI (Example 2-4; SEQ ID NO: 21) and elo3-F1 (Example 2-2; SEQ ID NO: 10) or the reverse oligonucleotide primers E2 HindIII (Example 2-4; SEQ ID NO: 20) and elo3-R1 (Example 2-2; SEQ ID NO: 11) produced from the TaELO2 sequence, and the oligonucleotide primers complementary to the cassette sequence (attached to the kit). As a result, a 1,122-bp TaELO2 ORF upstream sequence (SEQ ID NO: 24), and a 1,204-bp TaELO2 ORF downstream sequence (SEQ ID NO: 25) were successfully obtained.

Example 2-6

Construction of TaELO2 Targeting Vector Using Selection Marker Neor

A DNA fragment joining TaELO2 ORF upstream sequence/artificial Neor/TaELO2 ORF downstream sequence was produced by fusion PCR. The following oligonucleotide primers were used.

KO Pro F SmaI (31 mer: 5'-CTC CCG GGT GGA CCT AGC GCG TGT GTC ACC T-3') (SEQ ID NO: 26)
Pro R (25 mer: 5'-GGT CGC GTT TAC AAA GCA GCG CAG C-3') (SEQ ID NO: 27)
SNeo F (52 mer; 5'-GCT GCG CTG CTT TGT AAA CGC GAC CAT GAT TGA ACA GGA CGG CCT TCA CGC T-3') (SEQ ID NO: 28)
SNeoR (52 mer; 5'-TCG GGA GCC AGC CGG AAA CAG GTT CAA AAG AAC TCG TCC AGG AGG CGG TAG A-3') (SEQ ID NO: 29)
Term F (23 mer: 5'-ACC TGT TTC CGG CTG GCT CCC GA-3') (SEQ ID NO: 30)
KO Term R SmaI (27 mer: 5'-ATC CCG GGG CCG AGA ACG GGG TCG CCC-3') (SEQ ID NO: 31)

The oligonucleotide primers KO Pro F SmaI/Pro R were used for the amplification of the TaELO2 ORF upstream sequence using the *T. aureum* ATCC 34304 genomic DNA of Example 2-5 as a template. The oligonucleotide primers SNeo F/SNeo R were used for the amplification of the artificial Neor using artificial Neor as a template. The oligonucleotide primers Term F/KO Term R SmaI were used for the amplification of the TaELO2 ORF downstream sequence using the *T. aureum* ATCC 34304 genomic DNA of Example 2-5 as a template. The PCR reaction was performed at a denature temperature of 98° C. for 10 seconds, and the annealing and the extension reaction were performed while appropriately adjusted according to the primer Tm and the amplification product length.

As a result, a 2,696-bp sequence (SEQ ID NO: 32) joining TaELO2 ORF upstream sequence/artificial Neor/TaELO2 ORF downstream sequence was successfully obtained, and the sequence after TA cloning with a pGEM-T easy Vector (Promega) was used as a knockout vector, named pTKONeor.

Example 2-7

**Introduction of TKONeor into *T. aureum* ATCC 34304**

The TaELO2 targeting vector pTKONeor using artificial Neor as a selection marker (Example 2-6) was used as a template, and the TaELO2 ORF upstream sequence/artificial Neor/TaELO2 ORF downstream sequence was amplified using a set of oligonucleotide primers KO Pro F SmaI (Example 2-6, SEQ ID NO: 26)/KO Term R SmaI (Example 2-6, SEQ ID NO: 31), and PrimeSTAR HS DNA polymerase (Takara Bio) [PCR cycles: 98° C. 2 min/98° C. 10 sec, 68° C. 3 min, 30 cycles/68° C. 10 min/4° C. $\infty$]. The DNA fragments were extracted after electrophoresis using a 1% agarose gel, and dissolved in a suitable amount of TE after ethanol precipitation. The DNA fragment levels and the purity were assayed by O.D.260 and O.D.280 measurements. In the following, the DNA fragment will be referred to as TKONeor.

This was followed by DNA penetration using the gene-gun technique. Specifically, *T. aureum* ATCC 34304 was cultured in a GY liquid medium from the middle to late stage of the logarithmic growth phase at 25° C., 150 rpm, and the supernatant was removed by centrifugation at 3,500×g, 4° C. for 10 min. The resulting cells were resuspended in a GY liquid medium in 100 times the concentration of the original culture fluid, and a 20-μl portion of the cell suspension was evenly applied as a thin layer of about a 3-cm diameter on a 5-cm diameter PDA agar plate medium containing 1 mg/ml G418 (nacalai tesque). After drying, penetration was performed using a PDS-1000/He system (BioRad) under the following conditions.

Target distance: 6 cm
Vacuum: 26 inches Hg
Micro carrier size: 0.6 μm
Rupture disk (penetration pressure): 1,100 psi Thereafter, a PD liquid medium (100 μl) was dropped onto the PDA agar plate medium, and the cells were spread and statically cultured. As a result, transfectants with the conferred G418 resistance were obtained at the efficiency of $4.7 \times 10^1$ cfu/μg DNA.

Example 2-8

PCR Using TKONeor-Introduced Transfectant Genomic DNA as a Template

Seven colonies of transfectants were collected with a toothpick, and inoculated in a GY liquid medium containing 0.5 mg/ml G418 (nacalai tesque). After multiple subculturing, genomic DNA was extracted from the cells using the method of Example 2-5, and dissolved in a suitable amount of TE after ethanol precipitation. The levels of extracted genomic DNA and the purity were assayed by O.D.260 and O.D.280 measurements. By using the genomic DNAs of the transfectants and the wild-type strain as templates, a PCR was performed with various oligonucleotide primer sets. The following oligonucleotide primer sets were used.

(1) Neor detection: SNeoF (Example 2-6; SEQ ID NO: 28) and SNeoR (Example 2-6; SEQ ID NO: 29)

(2) KO verification 1: KO Pro F SmaI (Example 2-6; SEQ ID NO: 26) and KO Term R SmaI (Example 2-6; SEQ ID NO: 31)

(3) KO verification 2: E2 KO ProF EcoRV (30 mer: 5'-GGA TAT CCC CCG CGA GGC GAT GGC TGC TCC-3') (SEQ ID NO: 33) and SNeoR (4) KO verification 3: SNeoF and E2 KO Term R EcoRV (30 mer: 5'-TGA TAT CGG GCC GCG CCC TGG GCC GTA GAT-3') (SEQ ID NO: 34)

(5) TaELO2 amplification: E2 HindIII (Example 2-4; SEQ ID NO: 20) and E2 XbaI (Example 2-4; SEQ ID NO:21) (FIG. 3A)

Six out of the seven clones analyzed were transfectants by random integration, and the homologous recombination replacement of TaELO2 ORF with Neor was confirmed in the remaining clone (FIG. 3B, lanes 9 and 13). It was also found that this was accompanied by the simultaneous TaELO2 ORF amplification (FIG. 3B, lane 17). These results suggested the possibility that the *T. aureum* ATCC 34304 was a diploid or higher ploidy, or the TaELO2 was a multicopy gene.

Example 2-9

Confirmation of TaELO2 Copy Number by Southern Blotting

The following experiments were conducted according to the methods described in DIG Application Manual [Japanese version] 8th, Roche Applied Science (Non-Patent Document 25). Specifically, the genomic DNA of the wild-type strain was cut with various restriction enzymes, and electrophoresed in 2.5 μg per lane using a 0.7% SeaKemR GTGR agarose (Takara Bio). This was transferred to a nylon membrane (Hybond™-N+, GE Healthcare), and hybridized at 48° C. for 16 hours with DIG-labeled probes produced by using a PCR DIG Probe Synthesis Kit (Roche Applied Science). The following oligonucleotide primer set was used for the production of the DIG-labeled probes.

TaELO2 det F (25 mer: 5'-GTA CGT GCT CGG TGT GAT GCT GCT C-3') (SEQ ID NO: 35)

TaELO2 det R (24 mer: 5'-GCG GCG TCC GAA CAG GTA GAG CAT-3') (SEQ ID NO: 36)

[PCR cycles: 98° C. 2 min/98° C. 30 sec, 65° C. 30 sec, 72° C. 1 min, 30 cycles/72° C. 7 min/4° C. ∞]

Detection of the hybridized probes was made by using a chromogenic method (NBT/BCIP solution).

As a result, a single band was detected in all lanes treated with the various restriction enzymes (FIG. 4), suggesting that the TaELO2 was a single copy gene. The result thus suggested that the *T. aureum* ATCC 34304 was a diploid or higher ploidy.

Example 2-10

Evaluation of TKONeor-Introduced Transfectants by Southern Blotting

Figure 5:
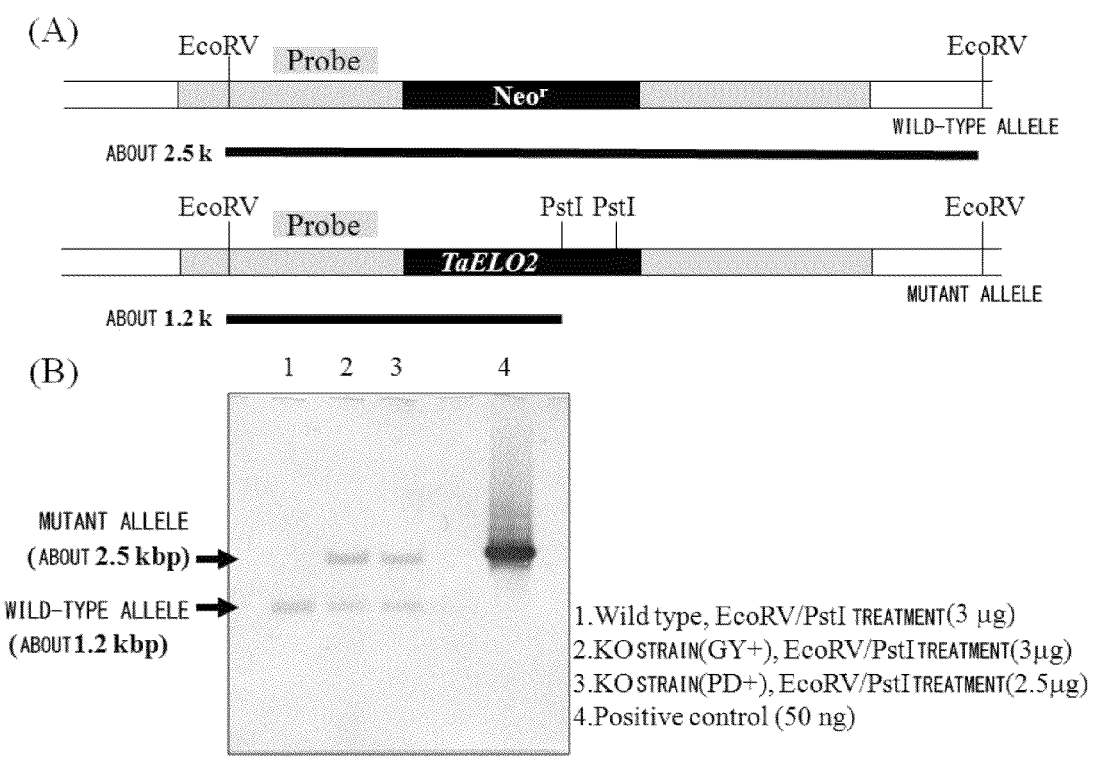
FIG. 5 represents the evaluation of TKONeor-introduced transfectants by southern blotting in Example 2-10. (A), a schematic view representing the southern blotting performed for the detection of a wild-type allele or a TKONeor-introduced mutant allele; (B), the result of southern blotting. [Brief Description of Reference Numerals] 1: *T. aureum* wild-type strain (2.5-μg genomic DNA); 2, 3: TKONeor-introduced transfectants (2.5-μg genomic DNA); 4: positive control (a PCR product amplified with 50-ng E2 KO ProF EcoRV and E2 KO Term R EcoRV, containing TaELO2).

Southern blotting was performed by using the method of Example 2-9. Specifically, the genomic DNAs of the wild-type strain and the transfectants digested with EcoRV and PstI were subjected to southern blotting using a chromogenic method (NBT/BCIP solution), using DIG-labeled probes PCR amplified with a set of oligonucleotide primers uprobe F (35 mer: 5'-ATC CGC GTA TAT ATC CGT AAA CAA CGG AAC ATT CT-3') (SEQ ID NO: 37) and uprobe R (26 mer: 5'-CTT CGG GTG GAT CAG CGA GCG ACA GC-3') (SEQ ID NO: 38) [PCR cycles: 98° C. 2 min/98° C. 30 sec, 65° C. 30 sec, 72° C. 1 min, 30 cycles/72° C. 7 min/4° C. ∞]. Here, in contrast to about a 1.2-kbp DNA fragment detected for the wild-type allele, about a 2.5-kbp DNA fragment was detected for the mutant allele that underwent the homologous recombination replacement of TaELO2 ORF with Neor (FIG. 5A).

Because the wild-type allele band was simultaneously detected with the mutant allele band in the transfectants (FIG. 5B), the analysis result suggested that the *T. aureum* ATCC 34304 was a diploid or higher ploidy.

Example 2-11

Construction of TaELO2 Targeting Vector using Selection Marker Hygr

A TaELO2 targeting vector was constructed with a selection marker Hygr to disrupt the remaining wild-type allele.

First, a fusion PCR was performed to join Hygr to a *T. aureum* ATCC 34304-derived ubiquitin promoter sequence. The following oligonucleotide primers were used.

ubi-600p F (27 mer: 5'-GCC GCA GCG CCT GGT GCA CCC GCC GGG-3') (SEQ ID NO: 39)

ubi-hygro R (59 mer: 5'-TCG CGGG TGA GTT CAG GCT TTT TCA TGT TGG CTA GTG TTG CTT AGG TCG CTT GCT GCT G-3') (SEQ ID NO: 40)

ubi-hygro F (57 mer; 5'-AGC GAC CTA AGC AAC ACT AGGC CAA CAT GAA AAA GCC TGA ACT CAC CGC GAC GTC TG-3') (SEQ ID NO: 41)

hygro R (29 mer; 5'-CTA TTC CTT TGC CCT CGG ACG AGT GCT GG-3') (SEQ ID NO: 42)

The oligonucleotide primers ubi-600p F/ubi-hygro R were used for the amplification of the *T. aureum* ATCC 34304-derived ubiquitin promoter sequence using the *T. aureum* ATCC 34304 genomic DNA of Example 2-5 as a template. The oligonucleotide primers ubi-hygro F/hygro R were used for the amplification of the artificial Hygr using pcDNA 3.1 Zeo (Invitogen) as a template. The PCR reaction was performed at a denature temperature of 98° C. for 10 seconds, and the annealing and the extension reaction were appropriately adjusted according to the primer Tm and the amplification product length.

As a result, a 1,636-bp (SEQ ID NO: 43) joining *T. aureum* ATCC 34304-derived ubiquitin promoter sequence/Hygr was successfully obtained, and the sequence after TA cloning with a pGEM-T easy Vector (Promega) was named pTub600Hygr.

By using the pTub600Hygr as a template, a PCR was performed with PrimeSTAR HS DNA polymerase (Takara Bio) to prepare a *T. aureum* ATCC 34304-derived ubiquitin promoter sequence/Hygr DNA fragment containing NheI and XbaI sites added to the 5' end and the 3' end, respectively. The PCR was run under the following conditions using a set of oligonucleotide primers ubi-600p F NheI (33 mer: 5'-GTG CTA GCC GCA GCG CCT GGT GCA CCC GCC GGG-3') (SEQ ID NO: 44) and hygro R XbaI (37 mer: 5'-GTT CTA GAC TAT TCC TTT GCC CTC GGA CGA GTG CTG G-3') (SEQ ID NO: 45) [PCR cycles: 98° C. 2 min/98° C. 10 sec, 68° C. 3 min, cycles/68° C. 10 min/4° C. ∞]. Separately, by using the pTKONeor of Example 2-6 as a template, a PCR was performed with PrimeSTAR HS DNA polymerase (Takara Bio) to prepare a linear vector that did not contain the Neor of the pTKONeor of Experiment Example 2-6 and to which NheI and XbaI sites were added to the 3' end and the 5' end, respectively. The PCR was run under the following conditions using a set of oligonucleotide primers KO vec F XbaI (37 mer: 5'-GTT CTA GAC CTG TTT CCG GCT GGC TCC CGA GCC ATG C-3') (SEQ ID NO: 46) and KO vec R NheI (40 mer: 5'-GTG CTA GCG GTC GCG TTT ACA AAG CAG CGC AGC AAC AGA A-3') (SEQ ID NO: 47) [PCR cycles: 98° C. 2 min/98° C. 10 sec, 68° C. 3 min, 30 cycles/68° C. 10 min/4° C. ∞]. The both DNA fragments were digested with restriction enzymes NheI and XbaI, and purified with an agarose gel to construct a cyclic vector using a Ligation Convenience Kit (Nippon Gene).

The TaELO2 targeting vector using Hygr as a selection marker thus constructed used the pGEM-T easy Vector (Promega) as the platform, and contained a 3,537-bp insert sequence (SEQ ID NO: 48) of TaELO2 ORF upstream sequence/*T. aureum* ATCC 34304-derived ubiquitin promoter sequence/Hygr/TaELO2 ORF downstream sequence. This was named pTKOub600Hygr.

Example 2-12

Reintroduction of KOub600Hygr, and Evaluation of Transfectants by PCR Using Genomic DNA as Template, and by Southern Blotting and RT-PCR The constructed TaELO2 targeting vector pTKOub600Hygr (Example 2-11) using Hygr as a selection marker was used as a template, and the TaELO2 ORF upstream sequence/*T. aureum* ATCC 34304-derived ubiquitin promoter sequence/Hygr/TaELO2 ORF downstream sequence was amplified with a PrimeSTAR HS DNA polymerase (Takara Bio), using a set of oligonucleotide primers KO Pro F SmaI (Example 2-6, SEQ ID NO: 26)/KO Term R SmaI (Example 2-8, SEQ ID NO: 31) [PCR cycles: 98° C. 2 min/98° C. 10 sec, 68° C. 3.5 min, 30 cycles/68° C. 10 min/4° C. ∞]. The resulting DNA fragment was named KOub600Hygr. This was introduced to the transfectants obtained in Example 2-6 by using the technique described therein, and statically cultured on a 1 mg/ml G418 (nacalai tesque)-containing PDA agar plate medium for 24 hours. The cells were collected, and statically cultured on a PDA agar plate medium supplemented with 1 mg/ml G418 (nacalai tesque) and 2 mg/ml hygromycin B (Wako Pure Chemical Industries, Ltd.). As a result, large numbers of transfectants were obtained (introduction efficiency: $1.02 \times 10^3$ cfu/μg DNA).

Fifty clones were collected, and subcultured multiple times in a GY liquid medium supplemented with 1 mg/ml G418 (nacalai tesque) and 2 mg/ml hygromycin B (Wako Pure Chemical Industries, Ltd.). Then, genomic DNA was extracted by using the same technique used in Example 2-5, and dissolved in a suitable amount of TE after ethanol precipitation. The levels of extracted genomic DNA and the purity were assayed by O.D.260 and O.D.280 measurements. By using the genomic DNAs of the resulting transfectants and the wild-type strain as templates, a PCR was performed with various oligonucleotide primer sets [PCR cycles: 98° C. 2 min/98° C. 10 sec, 68° C. 1 min, 30 cycles/68° C. 10 min/4° C. ∞]. The following oligonucleotide primer sets were used.

(1) TaELO2 ORF detection: SNeoF (Example 2-6; SEQ ID NO: 28) and SNeoR (Example 2-6; SEQ ID NO: 29)

(2) KO verification: E2 KO Pro F EcoRV (Example 2-8; SEQ ID NO: 33) and ubi-hygro R (Example 2-11; SEQ ID NO: 40) (FIG. 6A).

It was suggested that 14 out of the 50 clones analyzed were transfectants that underwent homologous recombination through TaELO2 ORF replacement (FIG. 6B, arrow). It was also confirmed that the TaELO2 ORF was not amplified in these clones (FIG. 6C).

This was followed by southern blotting using the same technique used in Example 2-10. Specifically, the genomic DNAs of the wild-type strain and the transfectants digested with EcoRV and PstI were subjected to southern blotting using a chromogenic method (NBT/BCIP solution), using DIG-labeled probes prepared with a set of oligonucleotide primers uprobe F (SEQ ID NO: 37) and uprobe R (SEQ ID NO: 38). Here, about a 1.2-kbp DNA fragment was detected for the wild-type allele. In contrast, about a 2.5-kbp DNA fragment was detected for the mutant allele that underwent the homologous recombination replacement of TaELO2 ORF with Neor, and about a 1.9-kbp DNA fragment was detected for the mutant allele that underwent the homologous recombination replacement of TaELO2 ORF with Hygr (FIG. 7A).

Figure 7:
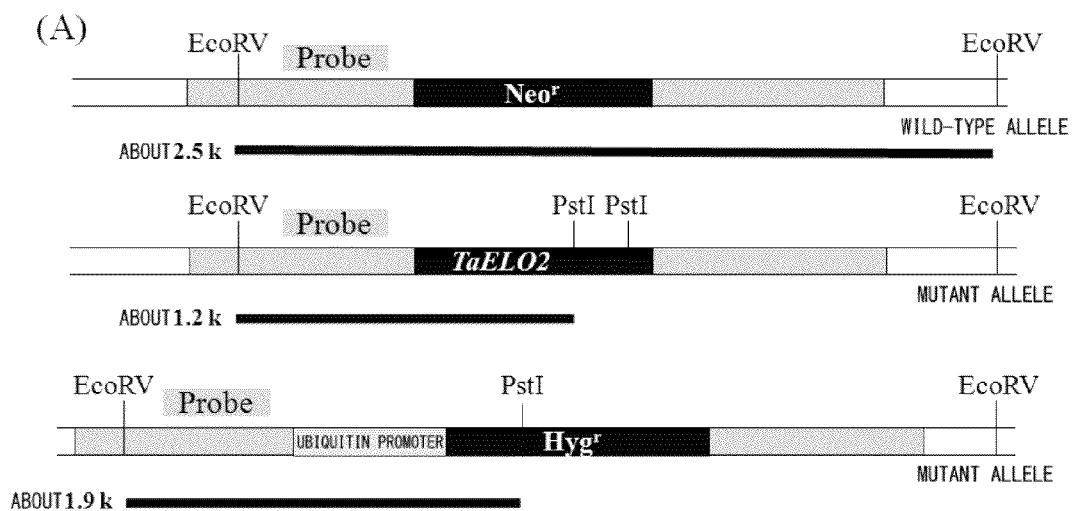
FIG. 7 represents the southern blotting evaluation of the transfectants obtained by KOub600Hygr reintroduction in Example 2-12. (A), a schematic view representing the southern blotting performed for the detection of a wild-type allele, a KONeor-introduced mutant allele, and a KOub600Hygr-introduced mutant allele; (B), the result of southern blotting. [Brief Description of Reference Numerals] 1, 9: wild-type strains; 2-8 and 10-16: TaELO2-deficient homozygotes.

The analysis revealed that the wild-type allele band of about a 2.5 kbp was absent in the resulting transfectants, and a new band, about 1.9 kbp, was detected for the mutant allele in which the TaELO2 ORF was replaced with Hygr (FIG. 7B).

Southern blotting using a chromogenic method (NBT/BCIP solution) was also performed for the genomic DNAs of the wild-type strain and the transfectants (clones 1, 8, 9, and 10) digested with EcoRV, using TaELO2-detecting DIG-labeled probes prepared by PCR using a set of oligonucleotide primers TaELO2 probe F (30 mer: 5'-ATG GCG ACG CGC ACC TCG AAG AGC GCT CCG-3') (SEQ ID NO: 49) and TaELO2 probe R (30 mer: 5'-AGG ATC ATC ATG AAC GTG TCG CTC CAG TCG-3') (SEQ ID NO: 50) [PCR cycles: 98° C. 2 min/98° C. 30 sec, 65° C. 30 sec, 72° C. 1 min, 30 cycles/72° C. 7 min/4° C. ∞]. Here, TaELO2 was detected as about a 2.5-kbp DNA fragment (FIG. 7A).

Figure 8:
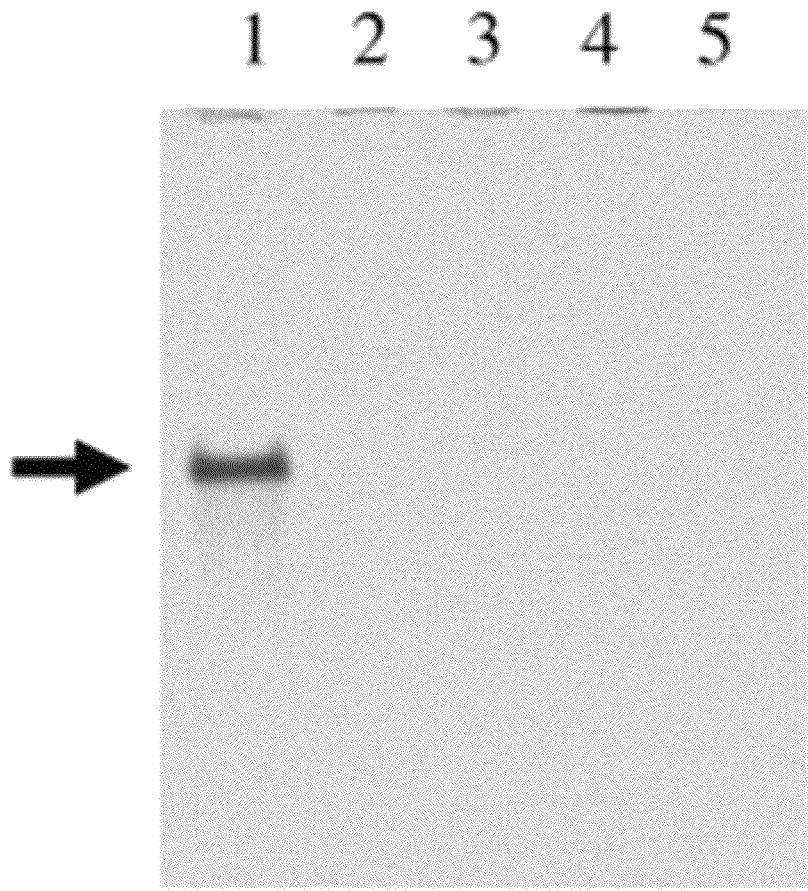
FIG. 8 represents the result of the southern blotting performed for the detection of TaELO2 in Example 2-12. [Brief Description of Reference Numerals] 1: wild-type strain; 2-5: T TaELO2-deficient homozygotes.

The analysis revealed that in contrast to the wild-type strain in which the TaELO2 was detected (FIG. 8, lane 1), TaELO2 was not detected in any of the transfectants (FIG. 8, lanes 2 to 5).

To examine the TaELO2 disruption at the mRNA level, TaELO2 mRNA detection was performed by RT-PCR. Total RNA was extracted from the cells of the wild-type strain and the transfectants (clones 1, 8, 9, and 10) cultured for 3 days in GY liquid media, using Sepasol-RNA I Super (nacalai tesque) as in Example 2-1. The total RNA (50 μg) was cleaned up using an RNeasy Mini Kit (QIAGEN) according to the manufacturer's protocol, and treated at 37° C. for 1 hour using 50 U Recombinant DNase I (Takara Bio) to degrade and remove the contaminated genomic DNA. By using the resulting total RNA as a template, a single-stranded cDNA library was created using oligo(dT) primer (Novagen) and PrimeScript Reverse Transcriptase (Takara Bio) according to the manufacturers' protocols. By using the resulting single-stranded cDNA library as a template, the TaELO2 ORF was amplified with a set of oligonucleotide primers E2 HindIII (Example 2-4; SEQ ID NO: 20) and E2 XbaI (Example 2-4; SEQ ID NO:21), and LA taq Hot Start Version (Takara Bio) [PCR cycles: 98° C. 2 min/98° C. 10 sec, 68° C. 1 min, 30 cycles/68° C. 10 min/4° C. ∞].

It was found as a result that the TaELO2 mRNA detected in the wild-type strain (FIG. 9, lane 5) was not detected in any of the transfectants (clones 1, 8, 9, and 10) (FIG. 9, lanes 1 to 4).

As demonstrated above, TaELO2-deficient homozygotes with the complete disruption of TaELO2 were successfully obtained. It was also found that the *T. aureum* ATCC 34304 was a diploid.

Example 2-13

Comparison of Fatty Acid Compositions of Wild-Type Strain and TaELO2-Deficient Homozygote The fatty acid compositions of the TaELO2-deficient homozygote and the wild-type strain of Example 2-12 were compared by the GC analysis of methylesterificated fatty acids. Specifically, the cells of the TaELO2-deficient homozygotes and the wild-type strain cultured for 5 days in GY liquid media were collected, and the fatty acids from these cells were extracted and methylesterificated by using the methods described in Example 2-4, and subjected to GC analysis. The GC analysis was performed with a gas chromatograph GC-2014 (Shimadzu Corporation) under the following conditions:

Column: HR-SS-10 (30 m×0.25 mm; Shinwa Chemical Industries Ltd.

Column temperature: 150° C.→(5° C./min)→220° C. (10 min) Carrier gas: He (1.3 mL/min).

As a result, the level of the EPA as a TaELO2 substrate showed about a two-fold increase in the TaELO2-deficient homozygote compared to the wild-type strain, whereas the level of the downstream metabolite DHA was lower than in the wild-type strain (FIG. 10).

The present invention is the first example of the modification of fatty acid compositions through disruption of genes that form the desaturase/elongase pathways in *Labyrinthula*. Specifically, the present invention has elucidated the involvement of the desaturase/elongase pathways in the PUFA biosynthesis in the *Labyrinthula T. aureum*, and shows that modification of fatty acid composition is possible by knocking out the constitutive genes. In the future, it would be possible to perform molecular breeding of Labyrinthulomycetes that selectively produce industrially useful PUFAs in large quantities in a PUFA biosynthetic pathway artificially created from combinations of genetic modifications such as overexpression of foreign desaturase/elongase genes, and PUFA-PKS gene knockouts.

Example 3

Disruption of *Parietichytrium sarkarianum* C20 Elongase Gene

Example 3-1

Subcloning of SV40 Terminator Sequence

An SV40 terminator sequence was amplified with PrimeSTAR HS DNA polymerase (Takara Bio), using a pcDNA 3.1 Myc-His vector as a template. The PCR primers used are as follows. RHO58 was set on the SV40 terminator sequence, and contains BglII and BamHI linker sequences. RHO52 was set on the SV40 terminator sequence, and contains a BglII sequence [RHO58: 34mer: 5'-CAG ATC TGG ATC CGC GAA ATG ACC GAC CAA GCG A-3' (SEQ ID NO: 51), RHO52: 24mer: 5'-ACG CAA TTA ATG TGA GAT CTA GCT-3' (SEQ ID NO: 52)]. The sequence was cloned into a pGEM-T easy vector (Promega) after being amplified under the following conditions [PCR cycles: 98° C. 2 min/98° C. 30 sec, 60° C. 30 sec, 72° C. 1 min, 30 cycles/72° C. 1 min]. The sequence was confirmed with a Dye Terminator Cycle Sequencing Kit (BECKMAN COULTER) after being amplified with *Escherichia coli*, and was named pRH27.

Figure 11:
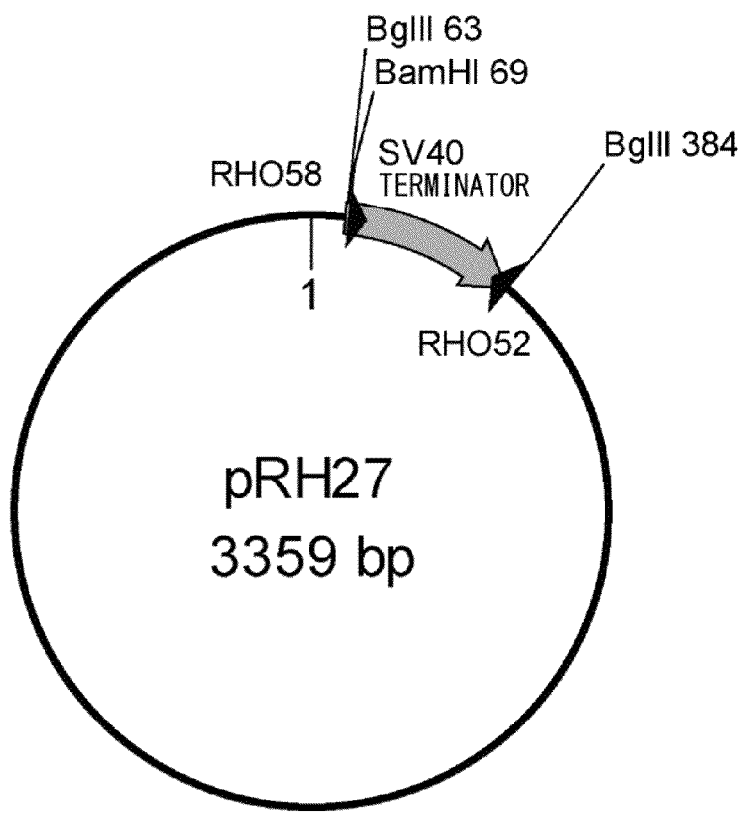
FIG. 11 represents a plasmid containing the SV40 terminator sequence derived from a subcloned pcDNA 3.1 Myc-His vector.

A plasmid (pRH27) containing the subcloned SV40 terminator sequence (342 bp, SEQ ID NO: 53) is shown in FIG. 11.

Example 3-2

Production of Artificial Neomycin-Resistant Gene Cassette

The *Thraustochytrium aureum* ATCC 34304 strain was cultured in GY medium, and cells at the late stage of the logarithmic growth phase were centrifuged at 4° C., 3,500×g for 5 min to obtain a pellet. The pellet was then disrupted after being frozen with liquid nitrogen. The cell disruption liquid was extracted with phenol, and precipitated with ethanol. The precipitate was then dissolved in a TE solution. The nucleic acids dissolved in the TE solution were treated with RNase at 37° C. for 30 min to degrade the RNA, and extracted again with phenol. After ethanol precipitation, the precipitate was dissolved in a TE solution. The DNA concentration was calculated by measuring A260/280.

By using this as a template, a ubiquitin promoter sequence (619 bp, SEQ ID NO: 54) was amplified using a PrimeSTAR HS DNA polymerase with GC Buffer (Takara Bio). The PCR primers used are as follows. RHO53 was set on the ubiquitin promoter sequence, and contains a BglII linker sequence. The TKO1 contains the ubiquitin promoter sequence and an artificial neomycin-resistant gene sequence [RHO53: 36mer: 5'-CCC AGA TCT GCC GCA GCG CCT GGT GCA CCC GCC GGG-3' (SEQ ID NO: 55), TKO1: 58mer: 5'-CGT GAA GGC CGT CCT GTT CAA TCA TGT TGG CTA GTG TTG CTT AGG TCG CTT GCT GCT G-3' (SEQ ID NO: 56)] [PCR cycles: 98° C. 2 min/98° C. 10 sec, 68° C. 1 min, 30 cycles/68° C. 1 min].

An artificial neomycin-resistant gene sequence (826 bp, SEQ ID NO: 57) was amplified with a PrimeSTAR HS DNA polymerase with GC Buffer (Takara Bio), using the artificial neomycin-resistant gene sequence as a template. The PCR primers used are as follows. TKO2 contains the ubiquitin promoter sequence and the artificial neomycin-resistant gene sequence. RHO57 contains the artificial neomycin-resistant gene sequence, and has a BglII linker sequence [TKO2: 54mer: 5'-AGC GAC CTA AGC AAC ACT AGC CAA CAT GAT TGA ACA GGA CGG CCT TCA CGC TGG-3' (SEQ ID NO: 58), RHO57: 26mer: 5'-CAG ATC TCA AAA GAA CTC GTC CAG GA-3' (SEQ ID NO: 59)] [PCR cycles: 98° C. 2 min/98° C. 10 sec, 68° C. 1 min, 30 cycles/68° C. 1 min].

Figure 12:
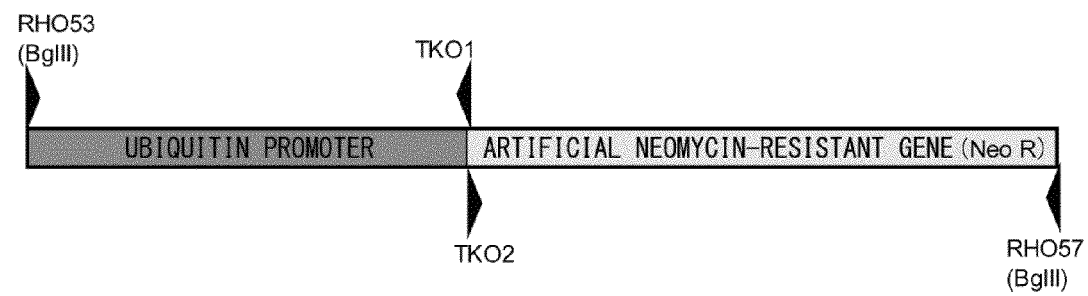
FIG. 12 is a schematic view showing the primers used for fusion PCR, and the product. The end product is the fused sequence of a *Thraustochytrium aureum* ATCC 34304-derived ubiquitin promoter and an artificial neomycin-resistant gene.

By using SEQ ID NOS: 54 and 57 as templates, a fusion PCR was performed with RHO53 (SEQ ID NO: 55) and RHO57 (SEQ ID NO: 59) according to the method described in Non-Patent Document 19. The product was amplified under the following conditions by using an LA taq Hot start version (Takara Bio) as an enzyme, and digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.) (FIG. 12).

The fused product *Thraustochytrium aureum* ATCC 34304-derived ubiquitin promoter-artificial neomycin-resistant gene sequence (1,395 bp, SEQ ID NO: 60) was digested with BglII, and ligated to the BamHI site of the pRH27 of Example 3-1. The resulting plasmid was amplified with *Escherichia coli*, and the sequence was confirmed by using a Dye Terminator Cycle Sequencing Kit (BECKMAN COULTER) and named pRH31.

Figure 13:
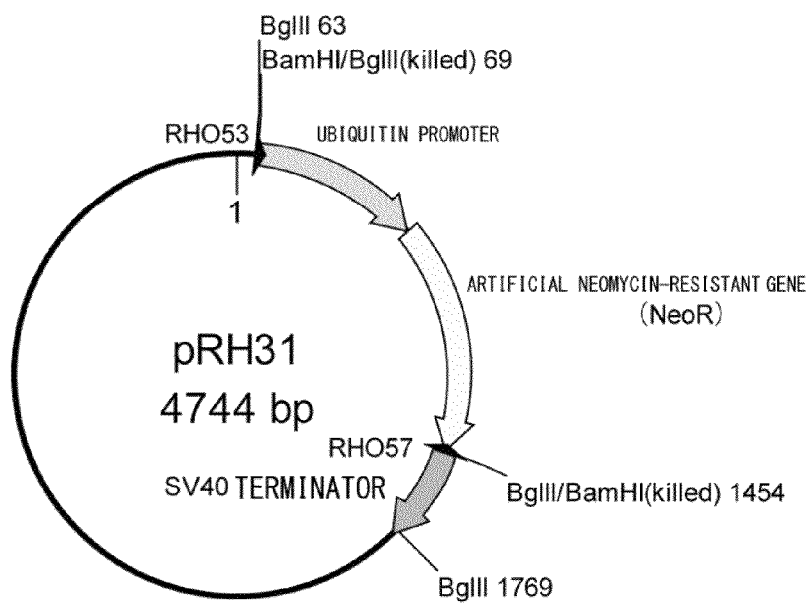
FIG. 13 represents a BglII cassette of the produced artificial neomycin-resistant gene.

The product artificial neomycin-resistant gene cassette (pRH31) is shown in FIG. 13.

Example 3-3

Production of Hygromycin-Resistant Gene Cassette

By using the genomic DNA of the *Thraustochytrium aureum* ATCC 34304 as a template, a ubiquitin promoter sequence (617 bp, SEQ ID NO: 61) was amplified with a PrimeSTAR HS DNA polymerase with GC Buffer (Takara Bio). The PCR primers used are as follows. RHO53 was set on the ubiquitin promoter sequence, and contains a BglII linker sequence. KSO8 contains the ubiquitin promoter sequence and a hygromycin-resistant gene sequence [RHO53: 36mer: 5'-CCC AGA TCT GCC GCA GCG CCT GGT GCA CCC GCC GGG-3' (Example 3-2; SEQ ID NO: 55), KSO8: 58mer: 5'-TCG CGG TGA GTT CAG GCT TTT TCA TGT TGG CTA GTG TTG CTT AGG TCG CTT GCT GCT G-3' (SEQ ID NO: 62)] [PCR cycles: 98° C. 2 min/98° C. 30 sec, 68° C. 2 min, 30 cycles/68° C. 2 min].

By using a pcDNA 3.1/Hygro (invitrogen) as a template, a hygromycin-resistant gene (1,058 bp, SEQ ID NO: 63) was amplified with a PrimeSTAR HS DNA polymerase with GC Buffer (Takara Bio). The PCR primers used are as follows. KSO7 contains the ubiquitin promoter sequence and the hygromycin-resistant gene sequence. RHO56 contains the hygromycin-resistant gene, and has a BglII linker sequence [KSO7: 56mer: 5'-AGC GAC CTA AGC AAC ACT AGC CAA CAT GAA AAA GCC TGA ACT CAC CGC GAC GTC TG-3' (SEQ ID NO: 64), RHO56: 36mer: 5'-CAG ATC TCT ATT CCT TTG CCC TCG GAC GAG TGC TGG-3' (SEQ ID NO: 65)] [PCR cycles: 98° C. 2 min/98° C. 30 sec, 68° C. 2 min, 30 cycles/68° C. 2 min].

Figure 14:
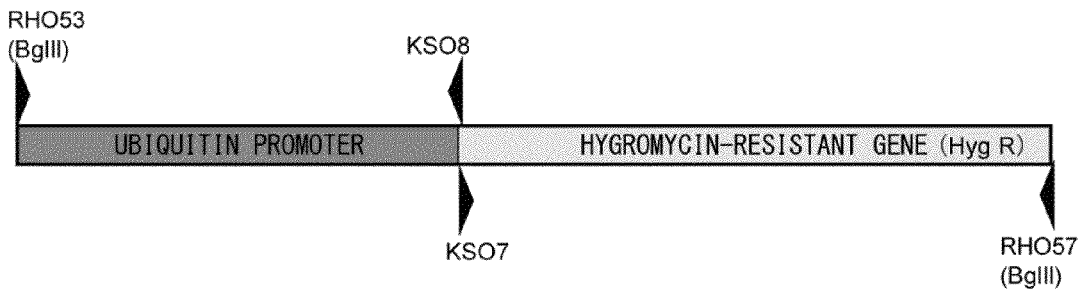
FIG. 14 is a schematic view showing the primers used for fusion PCR, and the product. The end product is the fused sequence of a *Thraustochytrium aureum* ATCC 34304-derived ubiquitin promoter and a pcDNA 3.1/Hygro-derived hygromycin-resistant gene.

By using SEQ ID NOS: 61 and 63 as templates, a fusion PCR was performed with RHO53 (Example 3-2; SEQ ID NO: 55) and RHO56 (SEQ ID NO: 65) according to the method described in Non-Patent Document 19. The product was amplified under the following conditions using an LA taq Hot start version (Takara Bio) as an enzyme, and digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.)] (FIG. 14).

The fused product *Thraustochytrium aureum* ATCC 34304-derived ubiquitin promoter-pcDNA 3.1/Hygro (invitrogen)-derived hygromycin-resistant gene (1,625 bp, SEQ ID NO: 66) was digested with BglII, and ligated to the BamHI site of the pRH27 of Example 3-1 (FIG. 11). The resulting plasmid was amplified with *Escherichia coli*, and the sequence was confirmed by using a Dye Terminator Cycle Sequencing Kit (BECKMAN COULTER). This was named pRH32.

Figure 15:
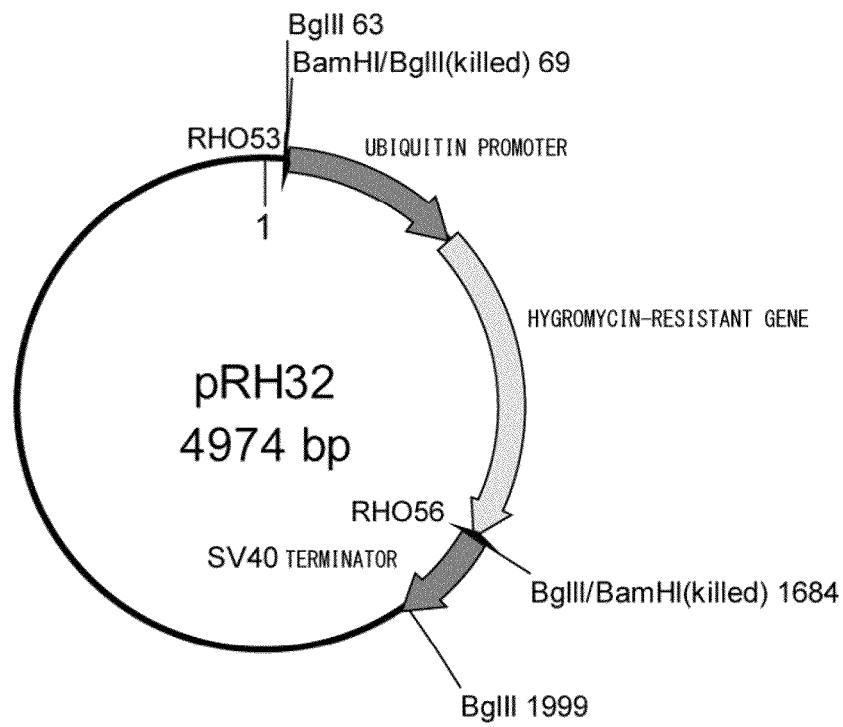
FIG. 15 represents a BglII cassette of the produced pcDNA 3.1/Hygro-derived hygromycin-resistant gene.

The product artificial neomycin-resistant gene cassette (pRH32) is shown in FIG. 15.

Example 3-4

Cloning of *Parietichytrium* C20 Elongase Gene

The *Parietichytrium sarkarianum* SEK364 genomic DNA extracted by using the method of Example 3-2 was extracted, and the genome was decoded.

A forward oligonucleotide (PsTaELO2 F1; 5'-CCT TCG GCG CTC CTC TTA TGT ATG T-3') (SEQ ID NO: 67) and a reverse oligonucleotide (PsTaELO2 R2; 5'-CAA TGC AAG AGG CGA ACT GGG AGA G-3') (SEQ ID NO: 68) were synthesized by targeting a conserved region in the C20 elongase gene. The oligonucleotides PsTaELO2 F1 and PsTaELO2 R2 were then used for a PCR performed with an LA taq Hot start version (TaKaRa) using the *Parietichytrium sarkarianum* SEK364 genomic DNA prepared by using the method of Example 3-2 as a template [PCR cycles: 98° C. 1 min/98° C. 10 sec, 60° C. 30 sec, 72° C. 1 min, 30 cycles/72° C. 7 min/4° C. ∞]. The resulting specific amplification product was gel purified, and the base sequence was analyzed by direct sequencing. The sequence showed significant homology with the sequence of a known C20 elongase gene, suggesting that the sequence was a partial sequence of the *Parietichytrium sarkarianum* SEK364-derived C20 elongase gene.

This was followed by cloning of the *Parietichytrium sarkarianum* SEK364-derived C20 elongase gene by 3'- and 5'-RACE, as in Example 2-2. First, forward oligonucleotide primers (PsRACE F1; 5'-TGG GGC TCT GGA ACC GCT GCT TAC G-3') (SEQ ID NO: 69) and (PsRACE F2; 5'-CTT CCA GCT CTC CCA GTT CGC CTC T-3') (SEQ ID NO: 70), and reverse oligonucleotide primers (PsRACE R1; 5'-CGG GTT GTT GAT GTT GAG CGA GGT G-3') (SEQ ID NO: 71) and (PsRACE R2; 5'-CCC ACG CCA TCC ACG AGC ACA CCA C-3') (SEQ ID NO: 72) were designed. This was followed by 3'- and 5'-RACE using a synthetic adapter-specific oligonucleotide and the oligonucleotide PsRACE F1 or PsRACE R1, using the cDNA library created with the SMART™ RACE cDNA Amplification Kit (Clontech) as a template [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C. ∞]. By using the resulting both RACE products as templates, a nested PCR was performed using a synthetic adapter-specific oligonucleotide, and the oligonucleotide PsRACE F2 or PsRACE R2 [PCR cycles: 94° C. 1 min/94° C. 30 sec, 68° C. 30 sec, 72° C. 3 min, 25 cycles/72° C. 10 min/4° C. ∞]. The resulting specific product was gel purified, and the base sequence was analyzed after being TA cloned with a pGEM-T easy Vector (Promega). The result confirmed that the product was a *Parietichytrium sarkarianum* SEK364-derived C20 elongase gene.

A sequence (957 bp, SEQ ID NO: 73) containing the C20 elongase gene sequence was amplified with an LA taq Hot start version (Takara Bio), using the *Parietichytrium* genomic DNA extracted by using the method of Example 3-2 as a template. The PCR primers used are as follows. RHO153 contains a start codon, and has a BamHI site as a linker sequence. RHO154 contains a stop codon, and has a BamHI site as a linker sequence [RHO153: 32 mer: 5'-CCC GGA TCC ATG GCA GCT CGC GTG GAG AAA CA-3' (SEQ ID NO: 74), RHO154: 33 mer: 5'-CCC GGA TCC TTA CTG AGC CTT CTT GGA GGT CTC-3' (SEQ ID NO: 75)] [PCR cycles: 98° C. 2 min/98° C. 10 sec, 68° C. 1 min, 30 cycles/68° C. 2 min].

The resulting DNA fragment was cloned into a pGEM-T easy vector, and amplified with *Escherichia coli*. Then, the sequence was confirmed with a Dye Terminator Cycle Sequencing Kit (BECKMAN COULTER).

Figure 16:
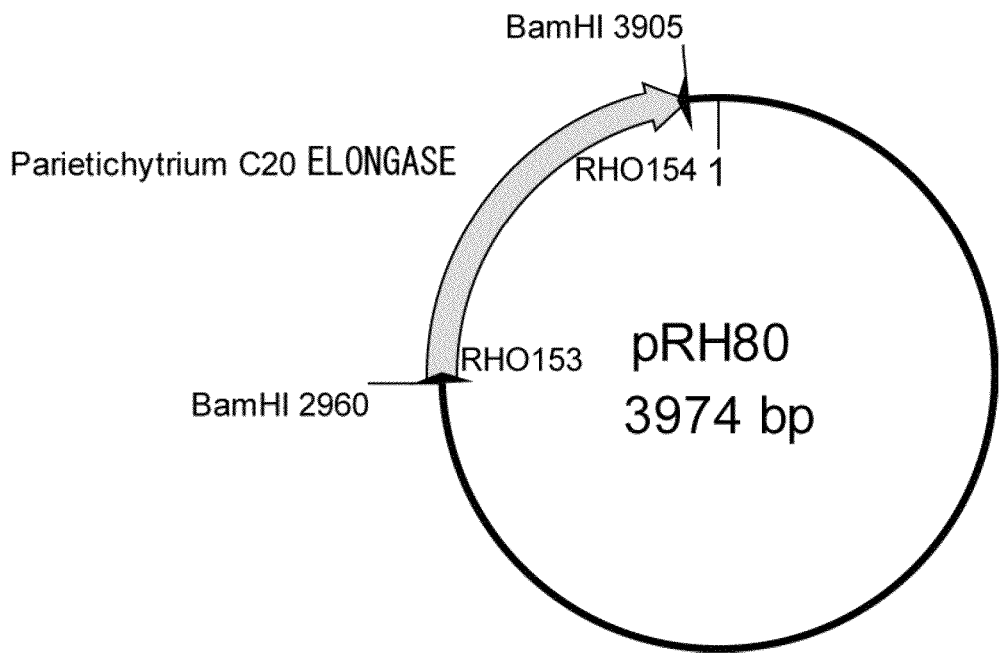
FIG. 16 represents a plasmid containing a cloned *Parietichytrium* C20 elongase sequence.

The 936-bp *Parietichytrium* C20 elongase gene (SEQ ID NO: 76) was cloned, and named pRH80 (FIG. 16). The amino acid sequence is represented by SEQ ID NO: 77.

Example 3-5

Production of Base Plasmid for *Parietichytrium* C20 Elongase Gene Targeting Vector Production By using the pRH80 produced in Example 3-4 (FIG. 16) as a template, amplification was performed with a PrimeSTAR Max DNA Polymerase (Takara Bio), using a primer set of the reverse orientation prepared for the insertion of the BglII site in a portion halfway along the C20 elongase gene sequence. The PCR primers used were as follows, and the both primers have BglII linker sequences [RHO155: 26 mer: 5'-ACA AAG ATC TCG ACT GGA CCG ACA CC-3' (SEQ ID NO: 78), RHO156: 27 mer: 5'-AGT CGA GAT CTT TGT CAG GAG GTG GAC-3' (SEQ ID NO: 79)] [PCR cycles: 98° C. 2 min/98° C. 10 sec, 56° C. 15 sec, 72° C. 1 min, 30 cycles/72° C. 1 min]. After the amplification under these conditions, the product was digested with BglII, and allowed to self-ligate. The ligated sample was amplified with *Escherichia coli*, and the sequence was confirmed by using a Dye Terminator Cycle Sequencing Kit (BECKMAN COULTER). This was named pRH83. The 935-bp C20 elongase gene sequence with the inserted BglII site is represented by SEQ ID NO: 80.

Figure 17:
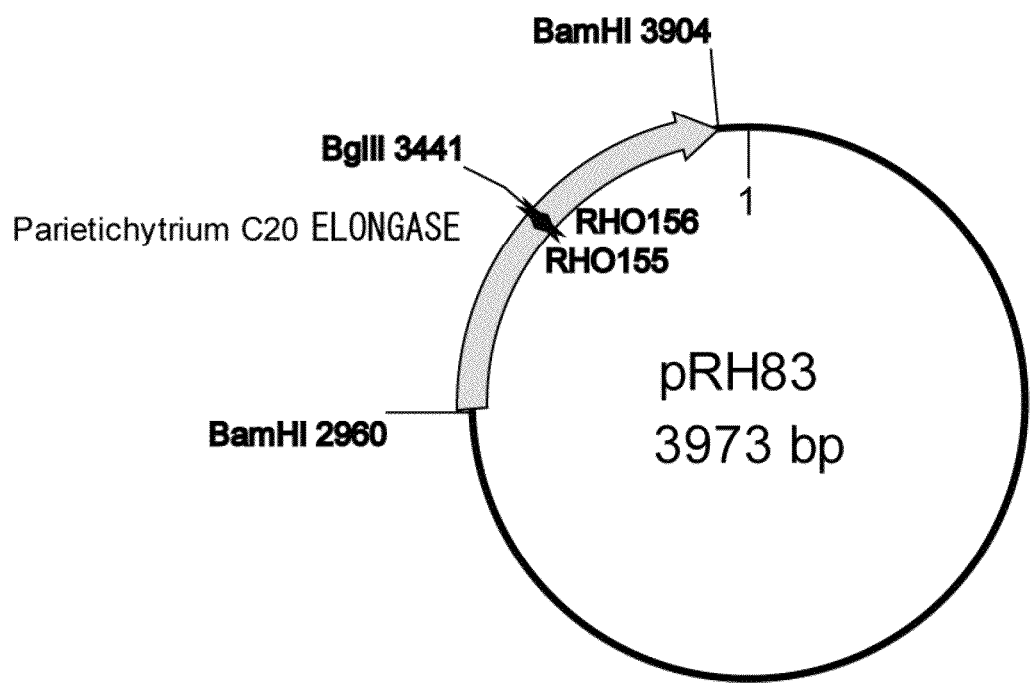
FIG. 17 represents a plasmid with a BglII site inserted into the *Parietichytrium* C20 elongase sequence of the plasmid of FIG. 16.

The produced base plasmid (pRH83) for *Parietichytrium* C20 elongase gene targeting vector production is shown in FIG. 17.

Example 3-6

Production of Targeting Vectors (Artificial Neomycin-Resistant Gene and Hygromycin-Resistant Gene)

The pRH31 (FIG. 13) of Example 3-2 was digested with BglII, and a DNA fragment containing an artificial neomycin-resistant gene cassette was ligated to the BglII site of the pRH83 (FIG. 17) of Example 3-5. This was named pRH85.

The pRH32 (FIG. 15) of Example 3-3 was digested with BglII, and a DNA fragment containing a hygromycin-resistant gene cassette was ligated to the BglII site of the pRH83 (FIG. 17) of Example 3-5. This was named pRH86.

The two targeting vectors (pRH85 and 86) produced are shown in FIG. 18.

Example 3-7

Introduction of C20 Elongase Gene Targeting Vector

By using the two targeting vectors produced in Example 3-6 as templates, the gene was amplified with a PrimeSTAR Max DNA polymerase (Takara Bio), using the RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was then calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (SEQ ID NO: 81). The introduced fragment obtained from using the pRH86 (FIG. 18) of Example 3-6 as a template was 2,892 bp, and had the following sequence order: First half of *Parietichytrium* C20 elongase gene-SV40 terminator sequence-hygromycin-resistant gene sequence-ubiquitin promoter sequence-second half of *Parietichytrium* C20 elongase gene (SEQ ID NO: 82).

The *Parietichytrium sarkarianum* SEK364 strain was cultured in a GY medium for 4 days, and cells in the logarithmic growth phase were used for gene introduction. The DNA fragment (0.625 µg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,550 PSI). After a 24-hour recovery time, the cells with the introduced gene were applied onto a PDA agar plate medium (containing 2 mg/ml G418 or 2 mg/ml hygromycin). As a result, 10 to 20 drug resistant strains were obtained per penetration.

Example 3-8

Identification of C20 Elongase Gene Gene Targeting Homologous Recombinant

Genomic DNA was extracted from the *Parietichytrium sarkarianum* SEK364 strain, the C20 elongase gene hetero homologous recombinant, and the C20 elongase gene homo homologous recombinant (gene disrupted strain) by using the method described in Example 3-2, and the DNA concentration was calculated by measuring A260/280. By using this as a template, a PCR was performed with an LA taq Hot start version (Takara Bio) to confirm the genome structure. The positions of the primers, combinations used for the amplification, and the expected sizes of the amplification products are shown in FIG. 19. RHO184 and RHO185 were set on the upstream and downstream sides, respectively, of the C20 elongase. RHO142 and RHO143 were set on the artificial neomycin-resistant gene. RHO140 and RHO141 were set on the hygromycin-resistant gene [RHO140: 20 mer: 5'-GGT TGA CGG CAA TTT CGA TG-3' (SEQ ID NO: 83), RHO141: 22 mer: 5'-CCT CCT ACA TCG AAG CTG AAA G-3' (SEQ ID NO: 84), RHO142: 21 mer: 5'-CTT CTC GGG CTT TAT CGA CTG-3' (SEQ ID NO: 85), RHO143: 22 mer: 5'-TAA GGT CGG TCT TGA CAA ACA G-3' (SEQ ID NO: 86), RHO184: 24 mer: 5'-AGT AGT CCC CGA TTT GGT AGT TGA-3' (SEQ ID NO: 87), RHO185: 22 mer: 5'-GGC AGA GAG CAA AAA CAC GAG C-3' (SEQ ID NO: 88)] [PCR cycles: 98° C. 2 min/98° C. 10 sec, 68° C. 4 min, 30 cycles/68° C. 7 min].

C20 elongase knockout strains were obtained that showed no amplification of the wild-type allele (Wt allele) and the artificial neomycin-resistant gene allele (NeoR allele) and the hygromycin-resistant gene allele (HygR allele) (FIG. 20).

Example 3-9

Changes in Fatty Acid Composition by C20 Elongase Disruption

*Parietichytrium sarkarianum* SEK364, and the gene disrupted strains were cultured in GY media. Cells from the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. After further centrifugation at 3,000 rpm for 10 min, the cells were freeze dried after removing the supernatant.

Then, 2 ml of methanolic KOH (7.5% KOH in 95% methanol) was added to the freeze dried cells, and, after being vortexed, the cells were ultrasonically disrupted (80° C., 30 min). The cells were vortexed after adding sterile water (500 µl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.5 ml), and 1 µl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Parietichytrium sarkarianum* SEK364 caused reduction of fatty acids of 22 or greater carbon chain length, and increased fatty acids of 20 carbon chain length (FIG. 21). FIG. 22 represents the proportions relative to the wild-type strain taken as 100%. As can be seen from these results, the arachidonic acid increased about ten-fold, and the EPA showed about an eight-fold increase. The DPA and DHA reduced to about ¼ and about ⅕, respectively.

Example 4

Disruption of *Thraustochytrium aureum* PUFA PKS Pathway-Associated Gene OrfA

Example 4-1

Cloning of PUFA PKS Pathway-Associated Gene OrfA Upstream Sequence

Genomic DNA was extracted from the *Thraustochytrium aureum* ATCC 34304 by using the method described in Example 3-2, and the DNA concentration was calculated by measuring A260/280. By using this, a genome cassette library was produced with an LA PCR™ in vitro Cloning Kit (Takara Bio). A PCR lower primer [RHO20: 23mer: 5'-CGA TGA AAG GTC ACA GAA GAG TC-3' (SEQ ID NO: 89)] was set on the PUFA PKS pathway-associated gene OrfA described in Patent Document 7, and the DNA was amplified by using this primer in combination with the cassette primer attached to the kit [1st PCR cycles: 98° C. 2 min/98° C. 30 sec, 56° C. 30 sec, 72° C. 4 min, 30 cycles/72° C. 5 min]. The 1st PCR amplification product was diluted 100 times, and amplified with the PCR lower primer [RHO20] and the nested primer attached to the kit [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 3,377-bp (SEQ ID NO: 91) DNA fragment containing the upstream 3,181 bp (SEQ ID NO: 90) of OrfA was cloned. The OrfA upstream DNA sequence was found to be 3,181 bp.

Example 4-2

Cloning of PUFA PKS Pathway-Associated Gene OrfA Downstream Sequence

The genome cassette library produced in Example 4-1 was used as a template. The DNA was amplified by using the method described in Example 4-1, using a PCR upper primer [RHO21: 21mer: 5'-CAG GGC GAG CGA GTG TGG TTC-3' (SEQ ID NO: 92)] set on the PUFA PKS pathway-associated gene OrfA described in Patent Document 7. The resulting DNA fragment was cloned into a pGEM-T easy vector, amplified with *Escherichia coli*, and the sequence was confirmed by using a Dye Terminator Cycle Sequencing Kit (BECKMAN COULTER). The 1,204-bp DNA fragment (SEQ ID NO: 94) containing the downstream 1,160 bp (SEQ ID NO: 93) of OrfA was cloned.

The DNA was amplified by using the method described in Example 4-1 using the PCR upper primer [RHO28: 20mer: 5'-TGA TGC CGA TGC TAC AAA AG-3' (SEQ ID NO: 95] produced on SEQ ID NO: 94. The resulting DNA fragment was cloned into a pGEM-T easy vector, amplified with *Escherichia coli*, and the sequence was confirmed by using a Dye Terminator Cycle Sequencing Kit (BECKMAN COULTER).

The 1,488-bp DNA fragment (SEQ ID NO: 96) containing the downstream sequence was cloned. The downstream DNA sequence of OrfA was found to be 2,551 bp in total (SEQ ID NO: 97).

Example 4-3

Production of PUFA PKS Pathway-Associated Gene OrfA Targeting Vector

By using the genomic DNA of *Thraustochytrium aureum* ATCC 34304 as a template, an 18S rDNA sequence (1,835 bp, SEQ ID NO: 98) was amplified with a PrimeSTAR HS DNA polymerase (Takara Bio). The PCR primers used are as follows. TMO30 was set on the 18S rDNA sequence. TMO31 contains the 18S rDNA sequence and an EF1α promoter sequence [TMO30: 30mer: 5'-CGA ATA TTC CTG GTT GAT CCT GCC AGT AGT-3' (SEQ ID NO: 99), TMO31: 46mer: 5'-GTA ACG GCT TTT TTT GAA TTG CAG GTT CAC TAC GCT TGT TAG AAA C-3' (SEQ ID NO: 100)] [PCR cycles: 98° C. 10 sec/98° C. 10 sec, 58° C. 30 sec, 72° C. 2 min, 30 cycles/72° C. 2 min]. Separately, by using the *Thraustochytrium aureum* ATCC 34304 genomic DNA as a template, the EF1α promoter sequence (661 bp, SEQ ID NO: 101) was amplified with a PrimeSTAR HS DNA polymerase (Takara Bio). The PCR primers used are as follows. TMO32 contains the 18S rDNA sequence and the EF1α promoter sequence. TMO33 contains the EF1α promoter sequence and an artificial neomycin-resistant gene sequence [TMO32: 46mer: 5'-GGT TTC CGT AGT GAA CCT GCA ATT CAA AAA AAG CCG TTA CTC ACA T-3' (SEQ ID NO: 102), TMO33: 46mer: 5'-GCG TGA AGG CCG TCC TGT TCA ATC ATC TAG CCT TCC TTT GCC GCT G-3' (SEQ ID NO: 103)] [PCR cycles: 98° C. 10 sec/98° C. 10 sec, 58° C. 30 sec, 72° C. 1 min, 30 cycles/72° C. 1 min].

By using the artificial neomycin-resistant gene as a template, the artificial neomycin-resistant gene sequence (835 bp, SEQ ID NO: 104) was amplified with a PrimeSTAR HS DNA polymerase (Takara Bio). The PCR primers used are as follows. TMO34 contains the EF1α promoter sequence and the artificial neomycin-resistant gene sequence. TMO35 contains the artificial neomycin-resistant gene sequence and the EF1α terminator sequence [TMO34: 45mer: 5'-CAT CGG CAA AGG AAG GCT AGA TGA TTG AAC AGG ACG GCC TTC ACG-3' (SEQ ID NO: 105), TMO 35: 46mer: 5'-GCG CAT AGC CGG CGC GGA TCT CAA AAG AAC TCG TCC AGG AGG CGG T-3' (SEQ ID NO: 106)] [PCR cycles: 98° C. 10 sec/98° C. 10 sec, 58° C. 30 sec, 72° C. 1 min, 30 cycles/72° C. 1 min].

Further, by using the *Thraustochytrium aureum* ATCC 34304 genomic DNA as a template, the EF1α terminator sequence (1249 bp, SEQ ID NO: 107) was amplified with a PrimeSTAR HS DNA polymerase (Takara Bio). The PCR primers used are as follows. TMO36 contains the artificial neomycin-resistant gene sequence and the EF1α terminator sequence. TMO37 was set within the EF1α terminator [TMO36: 46mer: 5'-TCC TGG ACG AGT TCT TTT GAG ATC CGC GCC GGC TAT GCG CCC GTG C-3' (SEQ ID NO: 108), TMO37: 30mer: 5'-CAC TGC AGC GAA AGA CGG GCC GTA AGG ACG-3' (SEQ ID NO: 109)] [PCR cycles: 98° C. 10 sec/98° C. 10 sec, 58° C. 30 sec, 72° C. 2 min, 30 cycles/72° C. 2 min].

Figure 23:
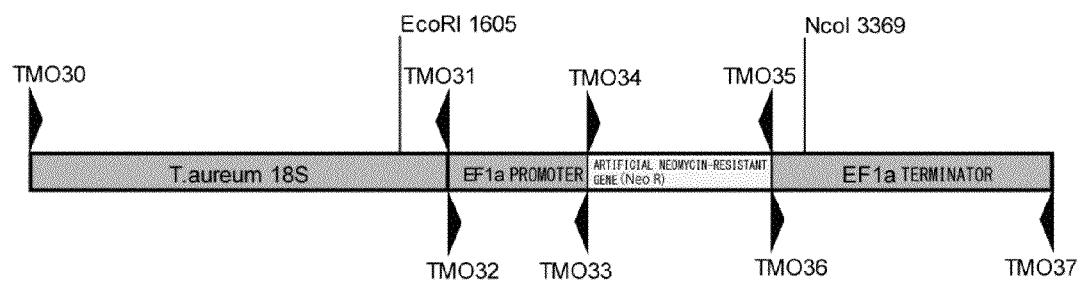
FIG. 23 is a schematic view of the primers used for fusion PCR, and the product. The end product is the fused sequence of *Thraustochytrium aureum* ATCC 34304-derived 18S rDNA, *Thraustochytrium aureum* ATCC 34304-derived EF1α promoter, artificial neomycin-resistant gene, and *Thraustochytrium aureum* ATCC 34304-derived EF1α terminator.

By using SEQ ID NOS: 98, 101, 104, and 107 as templates, a fusion PCR was performed according to the method described in Non-Patent Document 19. An LA taq Hot start version (Takara Bio) was used as the enzyme. The TMO30 (SEQ ID NO: 99) and TMO33 (SEQ ID NO: 103) set, and the TMO34 (SEQ ID NO: 105) and TMO37 (SEQ ID NO: 109) set were used for the first amplification. The TMO30 (SEQ ID NO: 99) and TMO37 (SEQ ID NO: 109) set was used for the second amplification. The PCR reaction was performed at a denature temperature of 98° C. for 10 seconds, and the annealing and the extension reaction were appropriately adjusted according to the primer Tm value and the amplification fragment length (FIG. 23).

The DNA fragment (FIG. 23, SEQ ID NO: 110, 4,453 bp) joined as above was cut at the EcoRI site of the *T. aureum* 18S rDNA, and the NcoI site of the *T. aureum* EF1α terminator, and ligated to a pGEM-T easy vector-derived vector. This was named pRH5 (FIG. 24).

By using the *Thraustochytrium aureum* ATCC 34304 genomic DNA as a template, the DNA was amplified with a PrimeSTAR HS DNA polymerase with GC Buffer (Takara Bio), using PCR primers set in the upstream sequence found in Example 4-1 (SEQ ID NO: 90, and PUFA PKS pathway-associated gene OrfA described in Patent Document 7). The amplification yielded a 1,218-bp DNA fragment (SEQ ID NO: 111). This was used as the 5' homologous region of the targeting vector. The PCR primers used are as follows. An EcoRI site or a HindIII site was added as a linker sequence [RHO33: 32mer: 5'-CCC GAA TTC GGA CGA CGA TGA CTG ACT GAC TGA TT-3' (SEQ ID NO: 112), RHO34: 28mer: 5'-CCC AAG CTT GTC TGC CTC GGC TCT TGG T-3' (SEQ ID NO: 113)] [PCR cycles: 98° C. 2 min/98° C. 30 sec, 57° C. 30 sec, 72° C. 1 min, 30 cycles/72° C. 3 min].

By using the *Thraustochytrium aureum* ATCC 34304 genomic DNA as a template, the DNA was amplified with a PrimeSTAR HS DNA polymerase with GC Buffer (Takara Bio) using the PCR primers set in the downstream sequence (SEQ ID NO: 97) found in Example 4-2. The amplification yielded a 1,000-bp DNA fragment (SEQ ID NO: 114). This was used as the 3' homologous region of the targeting vector. The PCR primers used are as follows. A linker sequence NcoI site was added to the both primers [RHO29: 28mer: 5'-CCC CCA TGG TGT TGC TGT GGG ATT GGT C-3' (SEQ ID NO: 115), RHO30: 30mer: 5'-CCC CCA TGG CTC GGT TAC ATC TCT GAG GAA-3' (SEQ ID NO: 116)] [PCR cycles: 98° C. 2 min/98° C. 30 sec, 57° C. 30 sec, 72° C. 1 min, 30 cycles/72° C. 3 min].

Figure 24:
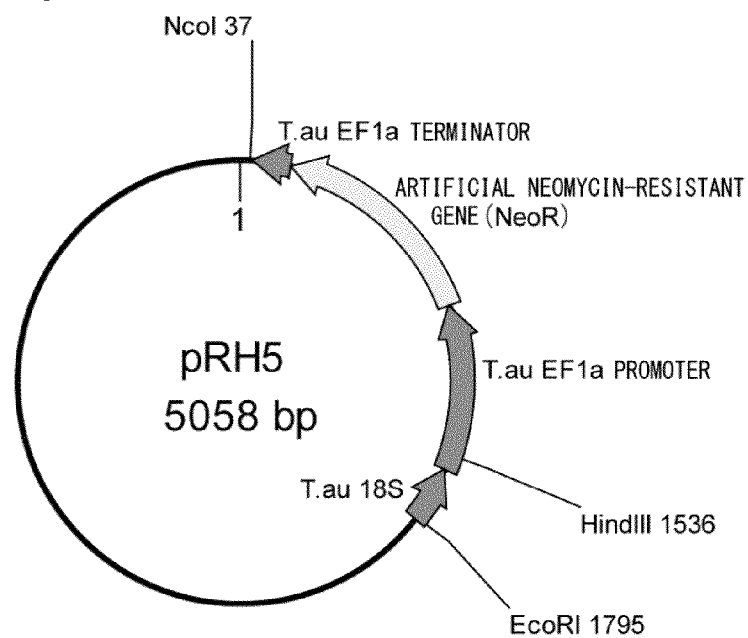
FIG. 24 represents a plasmid obtained by partial cloning of the DNA fragment joined in FIG. 23. The plasmid contains a partial sequence on the 3'-end side of the EcoRI site of the *Thraustochytrium aureum* ATCC 34304-derived 18S rDNA, the *Thraustochytrium aureum* ATCC 34304-derived EF1α promoter, the artificial neomycin-resistant gene, and a partial sequence on the 5'-end side of the NcoI site of the *Thraustochytrium aureum* ATCC 34304-derived EF1α terminator.

The amplified upstream sequence was joined to the EcoRI site and the HindIII site in the pRH5 of FIG. 24. The amplified downstream sequence was joined to the NcoI site. This vector was named pRH21.

Figure 25:
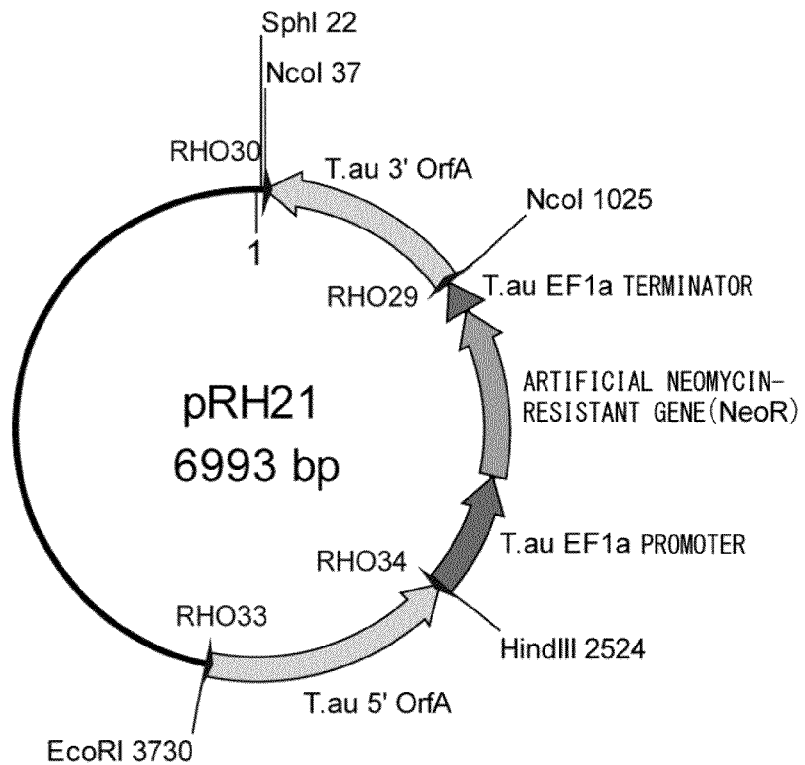
FIG. 25 represents a produced *Thraustochytrium aureum* ATCC 34304 PKS pathway-associated gene orfA targeting vector. The vector has a neomycin-resistant gene as a drug-resistance marker.

The produced targeting vector (pRH21) using the artificial neomycin-resistant gene is shown in FIG. 25.

Example 4-4

Production of PUFA PKS Pathway-Associated Gene OrfA Targeting Vector (Hygromycin-Resistant Gene)

By using the pRH32 (FIG. 15) of Example 3-3 as a template, a ubiquitin promoter-hygromycin-resistant gene fragment (1,632 bp, SEQ ID NO: 117) was amplified with a PrimeSTAR HS DNA polymerase with GC Buffer (Takara Bio). The PCR primers used are as follows. RHO59 was set on the ubiquitin promoter, and a linker sequence HindIII site was added. RHO60 contains a hygromycin-resistant gene sequence stop codon, and has linker sequences SphI and SalI [RHO59: 36mer: 5'-CCC AAG CTT GCC GCA GCG CCT GGT GCA CCC GCC GGG-3' (SEQ ID NO: 118), RHO60: 43mer: 5'-CCC GCA TGC GTC GAC TAT TCC TTT GCC CTC GGA CGA GTG CTG G-3' (SEQ ID NO: 119)] [PCR cycles: 98° C. 2 min/98° C. 30 sec, 68° C. 2 min, 30 cycles/68° C. 2 min].

Figure 26:
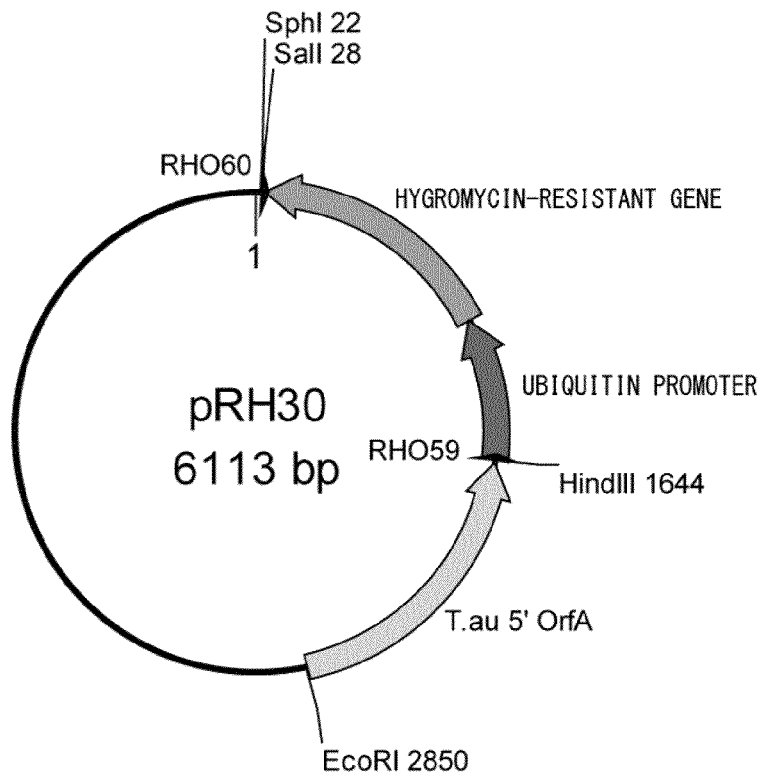
FIG. 26 represents a plasmid containing the upstream sequence of *Thraustochytrium aureum* ATCC 34304 PKS pathway-associated gene orfA, a *Thraustochytrium aureum* ATCC 34304-derived ubiquitin promoter, and a hygromycin-resistant gene.

The amplified fragment was joined to the HindIII and SphI sites of the pRH21 (FIG. 25) of Example 4-3 (FIG. 26, pRH30).

By using the *Thraustochytrium aureum* ATCC 34304 genomic DNA as a template, the gene was amplified with a PrimeSTAR HS DNA polymerase with GC Buffer (Takara Bio) using the PCR primers produced in the downstream sequence (SEQ ID NO: 97) found in Example 4-2. The amplification yielded a 1,000-bp DNA fragment (SEQ ID NO: 120). This was used as the 3' homologous region of the targeting vector. The PCR primers used are as follows. A linker sequence SalI site was added to the both primers [RHO61: 29mer: 5'-CCC GTC GAC GTG TTG CTG TGG GAT TGG TC-3' (SEQ ID NO: 121), RHO62: 29mer: 5'-CCC GTC GAC TCG GTT ACA TCT CTG AGG AA-3' (SEQ ID NO: 122)] [PCR cycles: 98° C. 2 min/98° C. 30 sec, 57° C. 30 sec, 72° C. 1 min, 30 cycles/72° C. 3 min].

Figure 27:
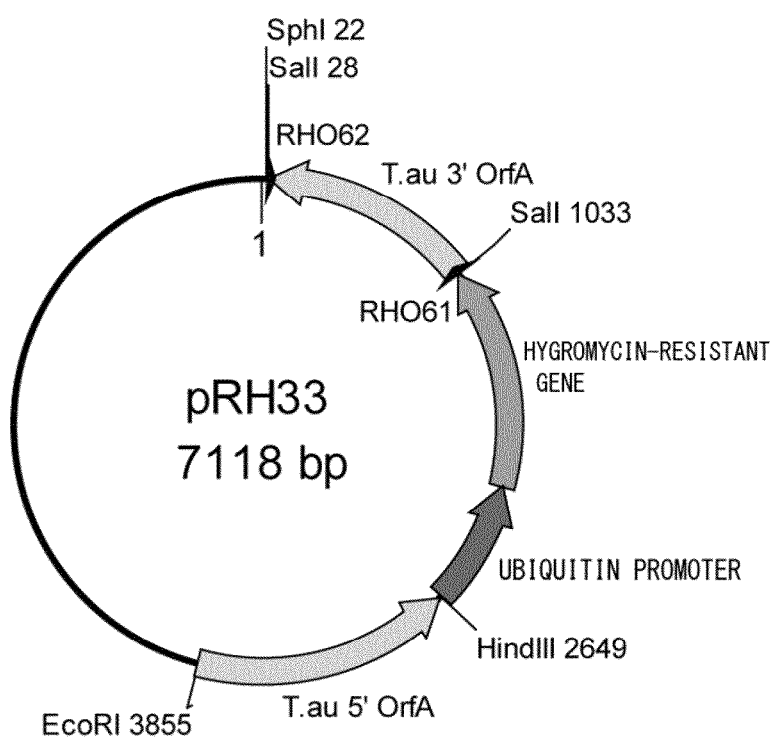
FIG. 27 represents a produced *Thraustochytrium aureum* ATCC 34304 PKS pathway-associated gene orfA targeting vector. The vector has a hygromycin-resistant gene as a drug-resistance marker.

The amplified downstream sequence was joined to the SalI site of pRH30 (FIG. 26). This was named pRH33. The produced targeting vector (pRH33) using the hygromycin-resistant gene is shown in FIG. 27.

Example 4-5

Introduction of PUFA PKS Pathway-Associated Gene OrfA Targeting Vector

By using the targeting vectors produced in Examples 4-3 and 4-4 as templates, the gene was amplified with a Prime-STAR Max DNA polymerase (Takara Bio) using the RHO30 (Example 4-3; SEQ ID NO: 116) and RHO33 (Example 4-3; SEQ ID NO: 112) as primers [PCR cycles: 98° C. 2 min/98° C. 30 sec, 60° C. 30 sec, 72° C. 1 min, 30 cycles/72° C. 3 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH21 (FIG. 25) of Example 4-3 as a template was 3,705 bp, and had the following sequence order: *Thraustochytrium aureum* OrfA gene upstream-EF1α promoter sequence-artificial neomycin-resistant gene sequence-*Thraustochytrium aureum* OrfA gene downstream (SEQ ID NO: 123). The introduced fragment obtained from using the pRH33 (FIG. 27) of Example 4-4 as a template was 3,826 bp, and had the following sequence order: Upstream of *Thraustochytrium aureum* OrfA gene-ubiquitin promoter sequence-hygromycin-resistant gene sequence-downstream of *Thraustochytrium aureum* OrfA gene (SEQ ID NO: 124).

The *Thraustochytrium aureum* ATCC 34304 strain was cultured in a GY medium for 4 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied onto a PDA agar plate medium (containing 2 mg/ml G418 or 2 mg/ml hygromycin). As a result, 100 to 200 drug resistant strains were obtained per penetration.

Example 4-6

Identification of PUFA PKS Pathway-Associated Gene OrfA Gene Targeting Homologous Recombinant Genomic DNA was extracted from the *Thraustochytrium aureum* ATCC 34304, the hetero homologous recombinant, and the homo homologous recombinant (PKS pathway-associated gene disrupted strain) by using the method described in Example 3-2. The DNA concentration was calculated by measuring A260/280.

The genomic DNA was cut with restriction enzymes, and electrophoresed in about 2 to 3 μg per well with a 0.7% SeaKem GTG agarose gel (Takara Bio). This was transferred to a nylon membrane, and hybridized at 54° C. for 16 hours with the probes produced by using a DIG system (Roche Applied Science). The following primers were used for the probe production.

5' end [RHO37: 22mer: 5'-GAA GCG TCC CGT AGA TGT GGT C-3' (SEQ ID NO: 125), RHO38: 21mer: 5'-GCC CGA GAG GTC AAA GTA CGC-3' (SEQ ID NO: 126)]

3' end [RHO39: 20mer: 5'-GCG AGC CCA GGT CCA CTT GC-3'(SEQ ID NO: 127), RHO40: 22mer: 5'-CAG CCC GAT GAA AAA CTT GGT C-3' (SEQ ID NO: 128)]

Figure 28:
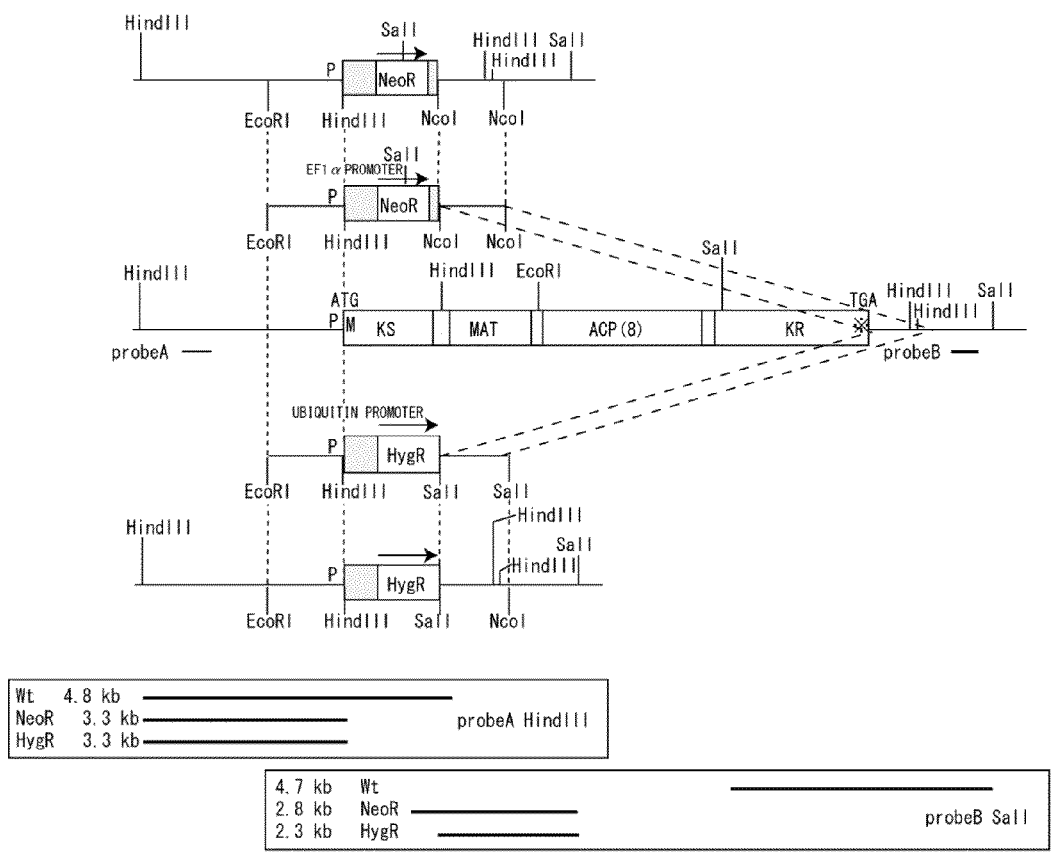
FIG. 28 is a schematic view representing the positions of the southern hybridization analysis probes used for the identification of the PKS pathway-associated gene orfA disrupted strain of *Thraustochytrium aureum* ATCC 34304, and the expected gene fragment sizes.

PCR cycles: 98° C. 2 min/98° C. 30 sec, 60° C. 30 sec, 72° C. 2 min, 30 cycles/72° C. 3 min The restriction enzymes used and the probe positions are as shown in FIG. 28. Detection of the hybridized probes was made by using the chromogenic method (NBT/BCIP solution).

Figure 29:
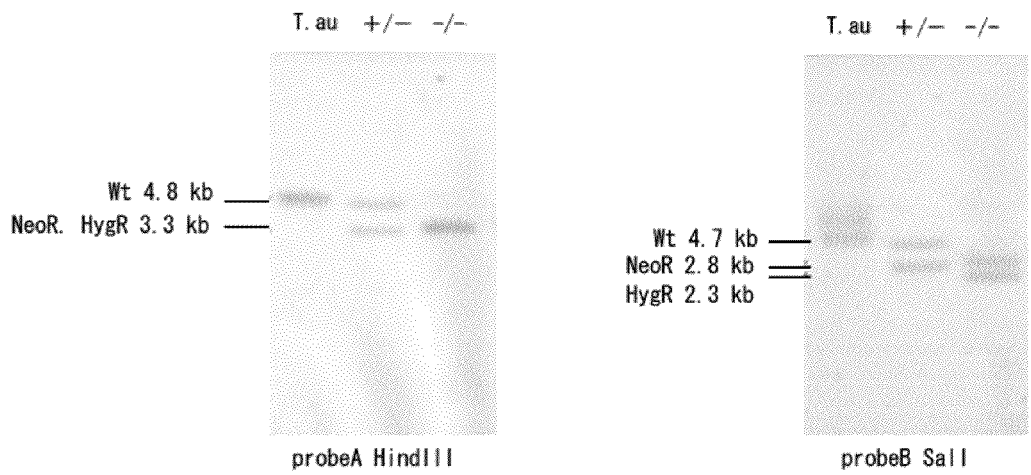
FIG. 29 represents the evaluation of PKS pathway-associated gene orfA disruption performed by southern hybridization using the *Thraustochytrium aureum* ATCC 34304 genomic DNA. [Description of Reference Numerals] T. au.

Bands of the sizes expected from the homologous recombination of the drug resistant genes were observed in the analyses of both the 5' end and the 3' end (FIG. 29).

Example 4-7

Changes in Fatty Acid Composition by Disruption of PUFA PKS Pathway-Associated Gene OrfA The *Thraustochytrium aureum* ATCC 34304 and the gene disrupted strain were cultured and freeze dried according to the methods of Example 3-9, and the fatty acids were methylesterificated, and GC analyzed.

FIG. 30 represents changes in fatty acid composition. FIG. 31 represents the proportions relative to the wild-type strain taken as 100%. As can be seen from these results, disrupting the PUFA PKS pathway-associated gene OrfA in the *Thraustochytrium aureum* tended to increase the DPA (C22: 5n-6) and decrease the DHA (C22: 6n-3).

Example 5

Disruption of C20 Elongase Gene in *Thraustochytrium aureum* OrfA Disrupted Strain Example 5-1

Cloning of Upstream Sequence of *Thraustochytrium aureum* C20 Elongase Gene

The genome cassette library produced in Example 4-1 was used as a template. A PCR lower primer [RHO71: 22mer: 5'-GGG AGC GCA GGG AAA ACG GTC T-3' (SEQ ID NO: 129)] was produced on the C20 elongase gene upstream sequence (SEQ ID NO: 24) of Example 2-5, and the gene was amplified by using this primer with the cassette primer attached to the kit used in Example 4-1 [1st PCR cycles: 98° C. 2 min/98° C. 30 sec, 56° C. 30 sec, 72° C. 4 min, 30 cycles/72° C. 5 min]. The 1st PCR amplification product was diluted 100 times, and the gene was amplified by using the PCR lower primer [RHO72: 20mer: 5'-CCA GCC CAC GTC GTC GGA GC-3' (SEQ ID NO: 130)] with the nested primer attached to the kit used in Example 4-1 [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 2,297-bp DNA fragment (SEQ ID NO: 131) containing the upstream −3,277 bp to −981 bp region of the C20 elongase gene was cloned.

Example 5-2

Cloning of C20 Elongase Gene Downstream Sequence

The genome cassette library produced in Example 4-1 was used as a template. A PCR upper primer [RHO87: 23 mer: 5'-GCC GCT CAT GCC CAC GCT CAA AC-3' (SEQ ID NO: 132)] was produced on the C20 elongase gene downstream sequence (SEQ ID NO: 25) of Example 2-5, and the gene was amplified by using this primer with the cassette primer attached to the kit used in Example 4-1 [1st PCR cycles: 98° C. 2 min/98° C. 30 sec, 56° C. 30 sec, 72° C. 4 min, 30 cycles/72° C. 5 min]. The 1st PCR amplification product was diluted 100 times, and the gene was amplified by using the PCR lower primer [RHO73: 23 mer: 5'-CTT TCG GCT GCC AGG AAT CTA CG-3' (SEQ ID NO: 133)] with the nested primer attached to the kit used in Example 4-1 [2nd PCR cycles: 98° C. 2 min/98° C. 30 sec, 56° C. 30 sec, 72° C. 4 min, 30 cycles/72° C. 5 min]. The resulting DNA fragment was cloned into a pGEM-T easy vector, amplified with *Escherichia coli*, and the sequence was confirmed by using a Dye Terminator Cycle Sequencing Kit (BECKMAN COULTER).

The 2,189-bp DNA fragment (SEQ ID NO: 134) containing the downstream 1,106 bp to 3,294 bp region of the C20 elongase gene was cloned.

Example 5-3

Production of Blasticidin-Resistant Gene Cassette

A ubiquitin promoter sequence (618 bp, SEQ ID NO:135) was amplified with a PrimeSTAR HS DNA polymerase with GC Buffer (Takara Bio), using the *Thraustochytrium aureum* ATCC 34304 genomic DNA as a template. The PCR primers used are as follows. RHO53 was set on the ubiquitin promoter sequence, and contains a BglII linker sequence (Example 3-2, SEQ ID NO: 55). RHO48 contains the ubiquitin promoter sequence and a blasticidin-resistant gene sequence [RHO48: 58mer: 5'-CTT CTT GAG ACA AAG GCT TGG CCA TGT TGG CTA GTG TTG CTT AGG TCG CTT GCT GCT G-3' (SEQ ID NO: 136)] [PCR cycles: 98° C. 2 min/98° C. 10 sec, 68° C. 1 min, 30 cycles/68° C. 1 min].

By using pTracer-CMV/Bsd/lacZ as a template, the blasticidin-resistant gene (432 bp, SEQ ID NO: 137) was amplified with a PrimeSTAR HS DNA polymerase with GC Buffer. The PCR primers used are as follows. RHO47 contains the ubiquitin promoter sequence and the blasticidin-resistant gene sequence. RHO49 contains the blasticidin-resistant gene sequence, and has a BglII linker sequence [RHO47: 54mer:5'-AGC GAC CTA AGC AAC ACT AGC CAA CAT GGC CAA GCC TTT GTC TCA AGA AGA ATC-3' (SEQ ID NO: 138), RHO49: 38mer: 5'-CCC AGA TCT TAG CCC TCC CAC ACA TAA CCA GAG GGC AG-3' (SEQ ID NO: 139)] [PCR cycles: 98° C. 2 min/98° C. 10 sec, 68° C. 1 min, 30 cycles/68° C. 1 min].

By using SEQ ID NOS: 135 and 137 as templates, a fusion PCR was performed with RHO53 (Example 3-2, SEQ ID NO: 55) and RHO49 (SEQ ID NO: 139) according to the method described in Non-Patent Document 19. An LA taq Hot start version (Takara Bio) was used as the enzyme. After the amplification performed under the following conditions, the product was digested with BglII [PCR cycles: 94° C. 2 min/94° C. 20 sec, 55° C. 30 sec, 68° C. 1 min, 30 cycles/68° C. 1 min (1° C./10 sec from 55° C. to 68° C.)] (FIG. 32).

The fused *Thraustochytrium aureum* ATCC 34304-derived ubiquitin promoter-pTracer-CMV/Bsd/lacZ-derived blasticidin-resistant gene (1,000 bp, SEQ ID NO: 140) was digested with BglII, and ligated to the BamHI site of the pRH27 (FIG. 11) of Example 3-1. The resulting plasmid was amplified with *Escherichia coli*, and the sequence was confirmed by using a Dye Terminator Cycle Sequencing Kit (BECKMAN COULTER). This was named pRH38.

The product blasticidin-resistant gene cassette (pRH38) is shown in FIG. 33.

Example 5-4

Production of GFP-Fused Zeocin-Resistant Gene Cassette

By using the *Thraustochytrium aureum* ATCC 34304 genomic DNA as a template, a ubiquitin promoter sequence (812 bp, SEQ ID NO: 141) was amplified with a PrimeSTAR HS DNA polymerase with GC Buffer (Takara Bio). The PCR primers used are as follows. TMO38 was set on the ubiquitin promoter sequence. TMO39 contains the ubiquitin promoter sequence and an enhanced GFP gene sequence [TMO38: 29mer: 5'-TCG GTA CCC GTT AGA ACG CGT AAT ACG AC-3' (SEQ ID NO: 142), TMO39: 41mer: 5'-TCC TCG CCC TTG CTC ACC ATG TTG GCT AGT GTT GCT TAG GT-3' (SEQ ID NO: 143)] [PCR cycles: 98° C. 10 sec/98° C. 10 sec, 58° C. 30 sec, 72° C. 1 min, 30 cycles/72° C. 1 min].

By using the enhanced GFP gene sequence (clontech) as a template, an enhanced GFP gene sequence (748 bp, SEQ ID NO: 144) was amplified with a PrimeSTAR HS DNA polymerase (Takara Bio). The PCR primers used are as follows. TMO40 contains the ubiquitin promoter sequence and the enhanced GFP gene sequence. RHO91 contains the enhanced GFP sequence and a zeocin-resistant gene sequence [TMO40: 41mer: 5'-ACC TAA GCA ACA CTA GCC AAC ATG GTG AGC AAG GGC GAG GA-3' (SEQ ID NO: 145), RHO91: 58mer: 5'-GAA CGG CAC TGG TCA ACT TGG CGT CCA TGC CGA GAG TGA TCC CGG CGG CGG TCA CGA A-3' (SEQ ID NO: 146)] [PCR cycles: 98° C. 10 sec/98° C. 10 sec, 58° C. 30 sec, 72° C. 2 min, 30 cycles/72° C. 2 min].

By using SEQ ID NOS: 141 and 144 as templates, a fusion PCR was performed with an LA taq Hot start version (Takara Bio) according to the method described in Non-Patent Document 19. TMO38 (SEQ ID NO: 142) and RHO91 (SEQ ID NO: 146) were used as primers, and the reaction was performed under the following conditions [PCR cycles: 94° C. 2 min/94° C. 20 sec, 55° C. 30 sec, 68° C. 2 min, 30 cycles/68° C. 2 min (1° C./10 sec from 55° C. to 68° C.)] (FIG. 34, 1,519 bp, SEQ ID NO: 147).

By using SEQ ID NO: 147 as a template, the ubiquitin promoter sequence-enhanced GFP gene sequence (1,319 bp, SEQ ID NO: 148) was amplified with a PrimeSTAR HS DNA polymerase (Takara Bio). The primers used are as follows. RHO53 (Example 3-2, SEQ ID NO: 55) contains the ubiquitin promoter sequence, and has a BglII site. RHO91 (SEQ ID NO: 146) contains the enhanced GFP sequence and the zeocin-resistant gene sequence [PCR cycles: 98° C. 2 min/98° C. 10 sec, 68° C. 2 min, 30 cycles/68° C. 2 min].

By using pcDNA3.1 Zeo(+) as a template, the zeocin-resistant gene sequence (408 bp, SEQ ID NO: 149) was amplified with a PrimeSTAR HS DNA polymerase (Takara Bio). RHO92 contains the enhanced GFP sequence and the zeocin-resistant gene sequence. RHO64 contains the zeocin-resistant gene sequence, and has a BglII site [RHO92: 54mer: 5'-CGC CGC CGG GAT CAC TCT CGG CAT GGA CGC CAA GTT GAC CAG TGC CGT TCC GGT-3' (SEQ ID NO: 150), RHO64: 38mer: 5'-CCC AGA TCT CAG TCC TGC TCC TCG GCC ACG AAG TGC AC-3' (SEQ ID NO: 151)] [PCR cycles: 98° C. 2 min/98° C. 10 sec, 68° C. 1 min, 30 cycles/68° C. 1 min].

By using SEQ ID NOS: 148 and 149 as templates, a fusion PCR was performed with an LA taq Hot start version (Takara Bio) according to the method described in Non-Patent Document 19. RHO53 (Example 3-2, SEQ ID NO: 55) and RHO64 (SEQ ID NO: 151) were used as primers, and the reaction was performed under the following conditions [PCR cycles: 94° C. 2 min/94° C. 20 sec, 68° C. 2 min, 30 cycles/68° C. 2 min (1° C./10 sec from 55° C. to 68° C.)] (FIG. 35).

The fused *Thraustochytrium aureum* ATCC 34304-derived ubiquitin promoter-enhanced GFP gene-pcDNA3.1 Zeo (+)-derived zeocin-resistant gene (FIG. 35, 1,677 bp, SEQ ID NO: 152) was digested with BglII, and ligated to the BamHI site of the pRH27 (FIG. 11) of Example 3-1. The resulting plasmid was amplified with *Escherichia coli*, and the sequence was confirmed by using a Dye Terminator Cycle Sequencing Kit (BECKMAN COULTER). This was named pRH51.

The product GFP-fused zeocin-resistant gene cassette (pRH51) is shown in FIG. 36.

Example 5-5

Production of Base Plasmid for C20 Elongase Gene Targeting Vector Production

By using the *Thraustochytrium aureum* ATCC 34304 genomic DNA as a template, the C20 elongase gene and the nearby sequences (2,884 bp, SEQ ID NO: 153) were PCR amplified with a PrimeSTAR HS DNA polymerase (Takara Bio). The PCR primers used are as follows. The both primers contain EcoRI linker sequences. KSO9 was set upstream of the C20 elongase gene (SEQ ID NO: 24), and KSO10 downstream of the C20 elongase gene (SEQ ID NO: 25) [KSO9: 50mer: 5'-CCC GAA TTC ACT AGT GAT TCT CCC GGG TGG ACC TAG CGC GTG TGT CAC CT-3' (SEQ ID NO: 154), KSO10: 40mer: 5'-CCC GAA TTC GAT TAT CCC GGG GCC GAG AAC GGG GTC GCC C-3' (SEQ ID NO: 155)] [PCR cycles: 98° C. 2 min/98° C. 10 sec, 68° C. 3.5 min, 30 cycles/68° C. 10 min]. A PrimeSTAR HS DNA Polymerase (Takara Bio) was used as the enzyme. After the amplification, the product was digested with EcoRI, and cloned into the EcoRI site of the pBluescript (SK) (stratagene) vector. After amplification with *Escherichia coli*, the sequence was confirmed by using a Dye Terminator Cycle Sequencing Kit (BECKMAN COULTER) (FIG. 37).

By using the plasmid of FIG. 37 as a template, amplification was performed with a PrimeSTAR Max DNA Polymerase (Takara Bio), using a primer set of the reverse orientation prepared for the deletion of the C20 elongase gene sequence portion and the insertion of a BglII site (1,939 bp, SEQ ID NO: 156). The PCR primers used are as follows. The both primers have BglII linker sequences [RHO69: 38mer: 5'-CCC AGA TCT ACC TGT TTC CGG CTG GCT CCC GAG CCA TG-3' (SEQ ID NO: 157), RHO70: 38mer: 5'-CCC AGA TCT GGT CGC GTT TAC AAA GCA GCG CAG CAA CA-3' (SEQ ID NO: 158)] [PCR cycles: 98° C. 2 min/98° C. 10 sec, 68° C. 1.5 min, 30 cycles/68° C. 1.5 min]. After the amplification performed under these conditions, the product was digested with BglII, and allowed to self ligate. The ligated sample was amplified with *Escherichia coli*, and the sequence was confirmed with a Dye Terminator Cycle Sequencing Kit (BECKMAN COULTER). This was named pRH40.

The produced base plasmid (pRH40) for the production of the C20 elongase gene targeting vector is shown in FIG. 38.

Example 5-6

Production of Targeting Vectors
(Blasticidin-Resistant Gene and GFP-Fused Zeocin-Resistant Gene)

The pRH38 (FIG. 33) of Example 5-3 was digested with BglII, and the DNA fragment containing the blasticidin-resistant gene cassette was ligated to the BglII site of the pRH40 (FIG. 38) of Example 5-5. This was named pRH43.

The pRH51 (FIG. 36) of Example 5-4 was digested with BglII, and the DNA fragment containing the GFP-fused zeocin-resistant gene cassette was ligated to the BglII site of the pRH40 (FIG. 38) of Example 5-5. This was named pRH54.

The two targeting vectors (pRH43 and 54) produced are shown in FIG. 39.

Example 5-7

Introduction of C20 Elongase Gene Targeting Vector into *Thraustochytrium aureum* OrfA Disrupted Strain By using the two targeting vectors produced in Example 5-6 as templates, the gene was amplified with a PrimeSTAR Max DNA polymerase (TakaraBio), using KSO11 and KSO12 as primers. KSO11 was set upstream of the *Thraustochytrium aureum* C20 elongase gene, and KSO12 downstream of the *Thraustochytrium aureum* C20 elongase gene [KSO11: 31mer: 5'-CTC CCG GGT GGA CCT AGC GCG TGT GTC ACC T-3' (SEQ ID NO: 159), KSO12: 27mer: 5'-ATC CCG GGG CCG AGA ACG CCC TCG CCC-3' (SEQ ID NO: 160)] [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH43 (FIG. 39) of Example 5-6 as a template was 3,215 bp, and had the following sequence order: Upstream of *Thraustochytrium aureum* C20 elongase gene-ubiquitin promoter-blasticidin-resistant gene sequence-SV40 terminator sequence-downstream of *Thraustochytrium aureum* C20 elongase gene (SEQ ID NO: 161). The introduced fragment obtained from using the pRH54 (FIG. 39) of Example 5-6 as a template was 3,887 bp, and had the following sequence order: Upstream of *Thraustochytrium aureum* C20 elongase gene-ubiquitin promoter-enhanced GFP gene sequence-zeocin-resistant gene sequence-SV40 terminator sequence-downstream of *Thraustochytrium aureum* C20 elongase gene (SEQ ID NO: 162).

The disrupted strain of the PUFA PKS pathway-associated gene OrfA gene described in Example 4 was cultured in a GY medium for 4 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied onto a PDA agar plate medium (containing 2 mg/ml G418 or 2 mg/ml hygromycin). As a result, 100 to 200 drug resistant strains were obtained per penetration.

Example 5-8

Identification of C20 Elongase Gene Gene Targeting Homologous Recombinant

Genomic DNA was extracted from the *Thraustochytrium aureum* and the C20 elongase gene disrupted strain of the *Thraustochytrium aureum* OrfA disrupted strain by using the method described in Example 3-2. The DNA concentration was calculated by measuring A260/280.

The genomic DNA was cut with restriction enzymes, and electrophoresed in about 2 to 3 μg per well in a 0.7% SeaKem GTG agarose gel (Takara Bio). This was transferred to a nylon membrane, and hybridized at 51° C. for 16 hours with the probes produced by using a DIG system (Roche Applied Science). The following primers were used for the probe production.

5' end [RHO94: 21mer: 5'-ACG TCC GCT TCA AAC ACC TCG-3' (SEQ ID NO: 163), RHO95: 24mer: 5'-TCG GAA CAA CTG GAA CAA CTA AAG-3' (SEQ ID NO: 164)]

3' end [RHO96: 22mer: 5'-ATG TCG CTC TCC TTC TTC TCA G-3' (SEQ ID NO: 165), RHO97: 21mer: 5'-TCG GCT CCT GGA AAG TGC TCT-3' (SEQ ID NO: 166)]

PCR cycles: 98° C. 2 min/98° C. 30 sec, 58° C. 30 sec, 72° C. 1 min, 30 cycles/72° C. 3 min The restriction enzymes used and the probe positions are as shown in FIG. 40. Detection of the hybridized probes was made by using a chromogenic method (NBT/BCIP solution).

Bands of the sizes expected from the homologous recombination of the drug resistant genes were observed in the analyses of both the 5' end and the 3' end (FIG. 41). It was found by the experiment that the *Thraustochytrium aureum* ATCC 34304 strain did not become auxotrophic even with the deletion of the PKS pathway-associated gene OrfA and the C20 elongase gene.

Example 5-9

**Changes in Fatty Acid Composition by Disruption of C20 Elongase Gene in *Thraustochytrium aureum* OrfA Disrupted Strain**

The *Thraustochytrium aureum* ATCC 34304 and the gene disrupted strain were cultured and freeze dried according to the method of Example 3-9, and the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 42. FIG. 43 represents the proportions relative to the wild-type strain taken as 100%.

As can be seen from these results, disrupting the C20 elongase gene in the *Thraustochytrium aureum* OrfA disrupted strain increased the C20:4n-6 (AA) about eight-fold, and the C20:5n3 (EPA) about four-fold, and decreased the C22:6n-3 (DHA) to about ⅕.

Example 6

**Expression of ω3 Desaturase Gene in *Thraustochytrium aureum* OrfA Disrupted Strain**

Example 6-1

**Cloning of *Saprolegnia diclina*-Derived ω3 Desaturase Gene and Production of Gene Expression Plasmid**

Genomic DNA was extracted from the *Thraustochytrium aureum* ATCC 34304 by using the method of Example 3-2, and the DNA concentration was calculated by measuring A260/280. By using this as a template, the ubiquitin promoter sequence (longer) (812 bp, SEQ ID NO: 167) was amplified with an LA Taq with GC Buffer (Takara Bio, Buffer II was used). The PCR primers used are as follows. TMO42 was set on the ubiquitin promoter sequence, upstream of RHO53 (Example 3-2, SEQ ID NO: 55), and contains a KpnI linker sequence. TMO43 contains the ubiquitin promoter sequence and a *Saprolegnia diclina*-derived ω3 desaturase gene sequence [TMO42: 29mer: 5'-TCG GTA CCC GTT AGA ACG CGT AAT ACG AC-3' (SEQ ID NO: 168), TMO43: 45mer: 5'-TTC GTC TTA TCC TCA GTC ATG TTG GCT AGT GTT GCT TAG GTC GCT-3' (SEQ ID NO: 169)] [PCR cycles: 96° C. 2 min/98° C. 20 sec, 60° C. 30 sec, 72° C. 1 min, 30 cycles/72° C. 1 min].

Then, *Saprolegnia diclina* was cultured in a medium (adjusted with deionized water) containing D-Glucose (31.8 g) and yeast extract (10.6 g) per liter. Cells in the late stage of the logarithmic growth phase were centrifuged at 4° C., 3,500×g for 5 min to form a pellet, and disrupted by being frozen with liquid nitrogen. After being extracted with phenol, the cell disruption liquid was precipitated with ethanol, and the precipitate was dissolved in a TE solution. The nucleic acids dissolved in the TE solution were treated with RNase at 37° C. for 30 min to degrade RNA. After being reextracted with phenol, the product was precipitated with ethanol, and the precipitate was dissolved in a TE solution. The DNA purity and concentration were calculated by measuring A260/280.

By using the resulting *Saprolegnia diclina* genomic DNA as a template, the *Saprolegnia diclina*-derived ω3 desaturase gene sequence (1,116 bp, SEQ ID NO: 170) was amplified with an LA Taq with GC Buffer (Takara Bio, Buffer II was used). The PCR primers used are as follows. TMO44 contains the ubiquitin promoter sequence and the *Saprolegnia diclina*-derived ω3 desaturase gene sequence. TMO45 contains the *Saprolegnia diclina*-derived ω3 desaturase gene sequence and the ubiquitin terminator [TMO44: 43mer: 5'-CCT AAG CAA CAC TAG CCA ACA TGA CTG AGG ATA AGA CGA AGG T-3' (SEQ ID NO: 171), TMO45: 40mer: 5'-ATA CTA CAG ATA GCT TAG TTT TAG TCC GAC TTG GCC TTG G-3' (SEQ ID NO: 172)] [PCR cycles: 96° C. 2 min/98° C. 20 sec, 60° C. 30 sec, 72° C. 1 min 30 sec, 30 cycles/72° C. 1 min 30 sec].

By using the *Thraustochytrium aureum* ATCC 34304 genomic DNA as a template, the ubiquitin terminator sequence (614 bp, SEQ ID NO: 173) was amplified with an LA Taq with GC Buffer (Takara Bio, Buffer II was used). The primers used are as follows. TMO46 contains the *Saprolegnia diclina*-derived ω3 desaturase gene sequence and the ubiquitin terminator. TMO47 was designed on the ubiquitin terminator sequence, and contains a KpnI linker sequence [TMO46: 44mer: 5'-CCA AGG CCA AGT CGG ACT AAA ACT AAG CTA TCT GTA GTA TGT GC-3' (SEQ ID NO: 174), TMO47: 45mer: 5'-TCG GTA CCA CCG CGT AAT ACG ACT CAC TAT AGG GAG ACT GCA GTT-3' (SEQ ID NO: 175)] [PCR cycles: 96° C. 2 min/98° C. 20 sec, 60° C. 30 sec, 72° C. 1 min, 30 cycles/72° C. 1 min].

By using SEQ ID NOS: 167, 170, and 173 as templates, a fusion PCR was performed with TMO42 (SEQ ID NO: 168) and TMO47 (SEQ ID NO: 175) according to the method described in Non-Patent Document 19. An LA Taq with GC Buffer (Takara Bio, Buffer II was used) was used as the enzyme, and the amplification was performed under the following conditions [PCR cycles: 96° C. 2 min/98° C. 20 sec, 55° C. 30 sec, 68° C. 3 min, 30 cycles/68° C. 3 min (1° C./10 sec from 55° C. to 68° C.] (FIG. 44, 2,463 bp, SEQ ID NO: 176).

By using the pRH38 (FIG. 33) of Example 5-3 as a template, a PCR was performed with RHO84 (SEQ ID NO: 177, the sequence is presented below) and RHO52 (Example 3-1, SEQ ID NO: 52). RHO84 was set on the ubiquitin promoter, and has a KpnI linker sequence. RHO52 was set on the SV40 terminator sequence, and has a BglII linker. An LA taq Hot start version was used as the enzyme, and, after the amplification performed under the following conditions, the product was cloned into a pGEM-T easy vector [RHO84: 36mer: 5'-CCC GGT ACC GCC GCA GCG CCT GGT GCA CCC GCC GGG-3' (SEQ ID NO: 177)] [PCR cycles: 98° C. 2 min/98° C. 10 sec, 68° C. 1 min 30 sec, 30 cycles/68° C. 3 min]. After amplification with *Escherichia coli*, the sequence was confirmed by using a Dye Terminator Cycle Sequencing Kit (BECKMAN COULTER). This was named pRH45 (FIG. 45).

The fused *Thraustochytrium aureum* ATCC 34304-derived ubiquitin promoter-*Saprolegnia diclina*-derived ω3 desaturase gene-*Thraustochytrium aureum* ATCC 34304-derived ubiquitin terminator (SEQ ID NO: 176; FIG. 44) was digested with KpnI, and ligated to the KpnI site of pRH45 (FIG. 45). The resulting plasmid was amplified with *Escherichia coli*, and the sequence was confirmed by using a Dye Terminator Cycle Sequencing Kit (BECKMAN COULTER). This was named pRH48.

The product *Saprolegnia diclina*-derived ω3 desaturase gene expression plasmid (pRH48) is shown in FIG. 46.

Example 6-2

Introduction of *Saprolegnia diclina*-Derived ω3 Desaturase Expression Plasmid into *Thraustochytrium aureum* OrfA Disrupted Strain By using the targeting vector produced in Example 6-1 as a template, DNA was amplified with a PrimeSTAR Max DNA polymerase (Takara Bio), using TMO42 (SEQ ID NO: 168) and RHO52 (Example 3-1, SEQ ID NO: 52) as primers [PCR cycles: 94° C. 30 sec, 72° C. 1 min, 5 cycles/94° C. 30 sec, 70° C. 30 sec, 72° C. 1 min, 5 cycles/94° C. 30 sec, 68° C. 30 sec, 72° C. 1 min, 25 cycles/72° C. 2 min]. The amplification product was collected from the 1.0% agarose gel, and precipitated with ethanol. The precipitate was then dissolved in 0.1×TE. The DNA concentration was calculated by measuring A260/280. The introduced fragment obtained by PCR was 3,777 bp, and had the following sequence order: ubiquitin promoter-ω3 desaturase gene-ubiquitin terminator-ubiquitin promoter-blasticidin-resistant gene sequence-SV40 terminator sequence (SEQ ID NO: 178).

The *Thraustochytrium aureum* OrfA disrupted strain produced in Example 4 was cultured in a GY medium for 4 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied to a PDA agar plate medium (containing 0.2 mg/ml blasticidin). As a result, 20 to 30 drug resistant strains were obtained per penetration.

Example 6-3

Acquisition of *Saprolegnia diclina*-Derived ω3 Desaturase Gene Expression Strain Genomic DNA was extracted from the *Thraustochytrium aureum* OrfA disrupted strain produced in Example 3 and the ω3 desaturase gene expressing strain by using the method described in Example 3-2. The DNA concentration was calculated by measuring A260/280. By using this as a template, a PCR was performed with an LA taq Hot start version to confirm the genome structure. The positions of the primers, combinations used for the amplification, and the expected size of the amplification product are shown in FIG. 47. TMO42 (Example 6-1, SEQ ID NO: 168) was set on the ubiquitin promoter. RHO49 (Example 5-3, SEQ ID NO: 139) was set on the blasticidin-resistant gene [PCR cycles: 98° C. 2 min/98° C. 10 sec, 68° C. 4 min, 30 cycles/68° C. 7 min].

The result of the amplification confirmed a band of the expected size (FIG. 48). That is, a strain was isolated that contained the introduced expression fragment stably introduced into its genome.

Example 6-4

Changes in Fatty Acid Composition by ω3 Desaturase Expression in PUFA PKS Pathway Disrupted Strain The *Thraustochytrium aureum* OrfA disrupted strain produced in Example 4, and the ω3 desaturase expressing strain produced in Example 6-3 were cultured by using the method described in Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

The ω3 desaturase expressing strain had reduced levels of the n-6 series fatty acids, and there was a tendency for the n-3 series fatty acids to increase (FIG. 49). FIG. 50 represents the proportions relative to the wild-type strain taken as 100%.

As a result, the arachidonic acid was reduced to about ⅐, and the DPA to about ¹/₁₀. EPA and DHA increased by a factor of about 3.

Example 7

Disruption of *Thraustochytrium roseum* C20 Elongase Gene

Example 7-1

Cloning of *T. roseum*-Derived C20 Elongase Gene

A forward denatured oligonucleotide (ELO20F; 5'-ATH GAR TWY TKB RTI TTY GTI CA-3') (SEQ ID NO: 179) and a reverse denatured oligonucleotide (ELO20R; 5'-TAR TRI SWR TAC ATI ADI AMR TG-3') (SEQ ID NO: 180) were synthesized by targeting a conserved region in the C20 elongase gene of the *Thraustochytrium roseum* ATCC 28210 strain. Then, a PCR was performed with an Advantage 2 Polymerase Mix (Clontech), using the *T. roseum* genomic DNA extracted by using the same technique described in the method of Example 2-5 as a template [PCR cycles: 94° C. 1 min/94° C. 30 sec, 55° C. 30 sec, 72° C. 1 min, 30 cycles/72° C. 7 min/4° C. ∞]. The resulting specific product was isolated by 2% agarose gel electrophoresis, and purified. The DNA fragment was then TA cloned with a pGEM-T easy Vector (Promega), and the base sequence was analyzed. The sequence showed significant sequence identity with the sequence of a known *T. aureum*-derived C20 elongase gene, suggesting that the sequence was a partial sequence of the *T. roseum*-derived C20 elongase gene.

This was followed by cloning of the *T. roseum*-derived C20 elongase gene by 3'- and 5'-RACE, as in Example 2-2. First, the following oligonucleotide primers were designed.

Forward oligonucleotide primer (8 F1; 5'-CTG ACA AAG TTT CTC GAC TGG AGC GAC A-3') (SEQ ID NO: 181)

Reverse oligonucleotide primers (8 R1; 5'-TAC GCG GCG GTG CCC GAG CCC CAG-3') (SEQ ID NO: 182) and (8 R2; 5'-TGC CGA TCG TTG CGT GGT GGA ACA CCT G-3') (SEQ ID NO: 183)

This was followed by 3'- and 5'-RACE using a synthetic adapter-specific oligonucleotide, and the oligonucleotide 8 F1 or 8 R1, using the cDNA library created with a SMART™ RACE cDNA Amplification Kit (clontech) as a template [PCR cycles: 94° C. 30 sec 5 cycles/94° C. 30 sec, 70° C. 30 sec, 72° C. 3 min, 5 cycles/94° C. 30 sec, 68° C. 30 sec, 72° C. 3 min, 25 cycles/4° C. ∞]. In the 5' RACE, a nested PCR was performed by using a synthetic adapter-specific oligonucleotide and the oligonucleotide 8 R2, using the RACE product as a template [PCR cycles: 94° C. 1 min/94° C. 30 sec, 68° C. 30 sec, 72° C. 3 min, 25 cycles/72° C. 10 min/4° C. ∞]. The both specific products were gel purified, and the base sequence was analyzed after being TA cloned with a pGEM-T easy Vector (Promega). There was a complete match with the *T. aureum* ATCC 34304-derived C20 elongase (TaELO2) (SEQ ID NO: 16) of Example 2-2.

Then, a forward oligonucleotide (8 ORF F; 5'-ATG GCG ACG CGC ACC TCG AA-3') (SEQ ID NO: 184) and a reverse oligonucleotide (8 ORF R; 5'-TTA CTC GGA CTT GGT GGG GGC G-3') (SEQ ID NO: 185) for amplifying a putative translated sequence were synthesized, and a PCR was performed with an Advantage GC 2 polymerase Mix (Clontech), using the *T. roseum* genomic DNA as a template [PCR cycles: 94° C. 1 min/94° C. 30 sec, 65° C. 30 sec, 72° C. 1 min, 30 cycles/72° C. 7 min/4° C. ∞]. The resulting specific product was gel purified, and the base sequence was analyzed by direct sequencing. The *T. roseum*-derived C20 elongase gene was found to be identical to the TaELO2. As demonstrated above, the sequence had a complete match with the sequence of the *Thraustochytrium aureum* C20 elongase. The base sequence is represented by SEQ ID NO: 186, and the amino acid sequence by SEQ ID NO: 187.

Example 7-2

Production of Base Plasmid for C20 Elongase Gene Targeting Vector Production

The *Thraustochytrium aureum* ATCC 34304 strain was cultured in a GY medium. Cells at the late stage of the logarithmic growth phase were centrifuged at 4° C., 3,500×g for 5 min to form a pellet, and disrupted after being frozen with liquid nitrogen. After being extracted with phenol, the cell disruption liquid was precipitated with ethanol, and the precipitate was dissolved in a TE solution. The nucleic acids dissolved in the TE solution were treated with RNase at 37° C. for 30 min to degrade the RNA. After being reextracted with phenol, the product was precipitated with ethanol, and the precipitate was dissolved in a TE solution. The DNA concentration was calculated by measuring A260/280. By using this as a template, the sequence (3,193 bp, SEQ ID NO: 188) containing the C20 elongase gene sequence was amplified with an LA taq Hot start version (Takara Bio) [PCR cycles: 98° C. 2 min/98° C. 10 sec, 68° C. 1 min, 30 cycles/68° C. 2 min]. The E2 KO ProF EcoRV (SEQ ID NO: 33) and E2KO TermR EcoRV (SEQ ID NO: 34) of Example 2-8 were used as PCR primers. The resulting DNA fragment was cloned into a pGEM-T easy vector (Promega), amplified with *Escherichia coli*, and the sequence was confirmed by using a Dye Terminator Cycle Sequencing Kit (BECKMAN COULTER). This was named pRH59 (FIG. 51).

By using the pRH59 (FIG. 51) as a template, amplification was performed with a PrimeSTAR Max DNA Polymerase (Takara Bio) using a primer set of the reverse orientation prepared for the insertion of the BglII site in a portion halfway along the C20 elongase gene sequence. The primers used are as follows. The both primers have BglII linker sequences [RHO120: 27 mer: 5'-GAC AAA GAT CTC GAC TGG AGC GAC CAC-3' (SEQ ID NO: 189), RHO121: 27 mer: 5'-GTC GAG ATC TTT TGT CAG GAG GTG CAC-3' (SEQ ID NO: 190)] [PCR cycles: 98° C. 2 min/98° C. 10 sec, 56° C. 15 sec, 72° C. min, 30 cycles/72° C. 1 min]. After the amplification performed under these conditions, the product was digested with BglII, and allowed to self ligate. The ligated sample was amplified with *Escherichia coli*, and the sequence was confirmed by using a Dye Terminator Cycle Sequencing Kit (BECKMAN COULTER). This was named pRH64. The C20 elongase gene sequence 951 bp with the inserted BglII site is represented by SEQ ID NO: 191.

The produced base plasmid (pRH64) for the production of the *Thraustochytrium roseum* C20 elongase gene targeting vector is shown in FIG. 52.

Example 7-3

Production of Targeting Vectors (Artificial Neomycin-Resistant Gene and Hygromycin-Resistant Gene)

The pRH31 (FIG. 13) of Example 3-2 was digested with BglII, and the DNA fragment containing an artificial neomycin-resistant gene cassette was ligated to the BglII site of the pRH64 (FIG. 52) of Example 7-2. This was named pRH65.

The pRH32 (FIG. 15) of Example 3-3 was digested with BglII, and the DNA fragment containing a hygromycin-resistant gene cassette was ligated to the BglII site of the pRH64 (FIG. 52) of Example 7-2. This was named pRH66.

The two targeting vectors (pRH65 and 66) produced are shown in FIG. 53.

Example 7-4

Introduction of C20 Elongase Gene Targeting Vector

By using the two targeting vectors produced in Example 7-3 as templates, the gene was amplified with a PrimeSTAR GXL polymerase (Takara Bio), using a forward primer containing a translation initiation site (RHO130: 5'-ATG GCG ACG CGC ACC TCG AAG AG-3') (SEQ ID NO: 192) and a reverse primer containing a translation termination site (RHO131: 5'-TTA CTC GGA CTT GCT GGG GGC GC) (SEQ ID NO: 193) as primers [PCR cycles: 98° C. 2 min/98° C. 30 sec, 60 30 sec, 72° C. 3 min, 30 cycles]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH65 (FIG. 53) of Example 7-3 as a template was 2,655 bp, and had the following sequence order: First half of *Thraustochytrium aureum* C20 elongase gene-SV40 terminator sequence-artificial neomycin-resistant gene sequence-ubiquitin promoter sequence-second half of *Thraustochytrium aureum* C20 elongase gene (SEQ ID NO: 194). The introduced fragment obtained from using the pRH66 (FIG. 53) of Example 7-3 as a template was 2,887 bp, and had the following sequence order: First half of *Thraustochytrium aureum* C20 elongase gene-ubiquitin promoter sequence-hygromycin-resistant gene sequence-SV40 terminator sequence-second half of *Thraustochytrium aureum* C20 elongase gene (SEQ ID NO: 195).

The *Thraustochytrium roseum* strain was cultured in a GY medium for 7 days, and cells in the logarithmic growth phase were used for gene introduction. The DNA fragment (0.625 µg) was then introduced into cells corresponding to OD600=1 to 1.5 using the gene-gun technique under the following conditions (microcarrier: 0.6-micron gold particles, target distance: 6 cm, chamber vacuum: 26 mmHg, rupture disk: 900 PSI). After a 24-hour recovery time, the cells with the introduced gene were applied to a PDA plate medium (containing 2 mg/ml G418 or 2 mg/ml hygromycin).

As a result, about 20 drug resistant strains were obtained per penetration.

Example 7-5

Identification of C20 Elongase Gene Gene Targeting Homologous Recombinant

The *Thraustochytrium roseum* ATCC 28210 strain, the C20 elongase gene hetero homologous recombinant, and the C20 elongase gene homo homologous recombinant (gene disrupted strain) were cultured in GY media. The resulting cells were centrifuged at 4° C., 3,000 rpm for 10 min to form a pellet, and lysed at 55° C., 6 h/99.9° C., 5 min after being suspended in a 20-µl SNET solution [20 mM Tris-HCl; pH 8.0, 5 mM NaCl, 0.3% SDS, 200 µg/ml Proteinase K (nacalai tesque)]. The resulting cell lysate was diluted 10 times and used as a template in a PCR performed with a Mighty Amp DNA polymerase (Takara Bio) to confirm the genome structure. The positions of the primers, combinations used for the amplification, and the expected sizes of the amplification products are shown in FIG. 54. RoseumF and RoseumR were set upstream and downstream of the C20 elongase, respectively. NeoF and NeoR were set on the artificial neomycin-resistant gene. HygF and HygR were set on the hygromycin-resistant gene [RoseumF: 26 mer: 5'-GCT CGG CTG GAA GTT GAG TAG TTT GC-3' (SEQ ID NO: 196), RoseumR: 24 mer: 5'-TCT TTC TTC GTC GAC GTC CCA CTG-3' (SEQ ID NO: 197), NeoF: 24 mer: 5'-ATG ATT GAA CAG GAC GGC CTT CAC-3' (SEQ ID NO: 198), NeoR: 24 mer: 5'-TCA AAA GAA CTC GTC CAG GAG GCG-3' (SEQ ID NO: 199), HygF: 24 mer: 5'-ATG AAA AAG CCT GAA CTC ACC GCG-3' (SEQ ID NO: 200), HygR: 25 mer: 5'-CTA TTC CTT TGC CCT CGG ACG AGT G-3' (SEQ ID NO: 201)] [PCR cycles: 98° C. 2 min/98° C. 10 sec, 60° C. 15 sec, 68° C. 4 min, 30 cycles].

C20 elongase knockout strains were obtained that showed no amplification of the wild-type allele (Wt allele) but showed amplification of the artificial neomycin-resistant gene allele (NeoR allele) and hygromycin-resistant gene allele (HygR allele) (FIG. 55).

Example 7-6

Changes in Fatty Acid Composition by C20 Elongase Disruption

The *Thraustochytrium roseum* ATCC 28210 strain and the gene disrupted strain were cultured in GY media. Cells at the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. This was centrifuged at 3,000 rpm for 10 min, and freeze dried after removing the supernatant. Then, 2 ml-methanolic KOH (7.5% KOH in 95% methanol) was added to the freeze dried cells, and, after being vortexed, the cells were ultrasonically disrupted (80° C., 30 min). The cells were vortexed after adding sterile water (500 µl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.2 ml), and 2 µl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Thraustochytrium roseum* increased fatty acids of 20 carbon chain length (FIG. 56). FIG. 57 represents the proportions relative to the wild-type strain taken as 100%.

As can be seen from these results, the arachidonic acid increased about 1.2-fold, EPA about 1.6-fold, DPA about 1.2-fold, and DHA about 1.5-fold.

Example 8

Disruption of Δ4 Desaturase Gene in *Thraustochytrium aureum* ATCC 34304 OrfA Disrupted Strain

Example 8-1

Cloning of Sequence from 1,071 bp Upstream of Δ4 Desaturase Gene to 1,500 bp within Δ4 Desaturase Gene in *Thraustochytrium aureum* ATCC 34304 Strain The genomic DNA of the *Thraustochytrium aureum* ATCC 34304 strain extracted by using the method described in Example 3-2 was decoded. Then, a search was made for a gene sequence highly homologous to a known Δ4 desaturase, and two PCR primers were designed by using the search result. TMO3 is a sequence located 1,071 to 1,049 bp upstream of the Δ4 desaturase gene of the *Thraustochytrium aureum* ATCC 34304 strain. TMO4 is a sequence within the protein coding region, located 1,477 to 1,500 bp from the start codon [TMO3: 23 mer: 5'-GGC GGA GCG AAG TGT GAA AGT TA-3' (SEQ ID NO: 202), TMO4: 24 mer: 5'-GCG ACA GCA TCT TGA AAT AGG CAG-3' (SEQ ID NO: 203)]. By using the genomic DNA of the *Thraustochytrium aureum* ATCC 34304 strain as a template, the sequence from 1,071 bp upstream of the Δ4 desaturase gene to 1,500 bp within the Δ4 desaturase gene of the *Thraustochytrium aureum* ATCC 34304 strain was amplified with the two primers, using an LA taq Hot start version (Takara Bio). The amplification was performed under the following conditions [PCR cycles: 98° C. 2 min/98° C. 20 sec, 60° C. 30 sec, 72° C. 3 min, 30 cycles/72° C. 8 min]. The resulting DNA fragment was cloned into a pGEM-T easy vector, amplified with *Escherichia coli*, and the sequence was confirmed by using a Dye Terminator Cycle Sequencing Kit (BECKMAN COULTER). This was named pTM1 (FIG. 58).

Example 8-2

Production of Base Plasmid for Δ4 Desaturase Gene Targeting Vector Production

By using the pTM1 (FIG. 58) of Example 8-1 as a template, a primer set of the reverse orientation was prepared in a manner that allows the 60 bp upstream of the Δ4 desaturase gene and a 556-bp sequence containing the start codon within the Δ4 desaturase gene (616 bp, SEQ ID NO: 205) to be deleted, and a BglII site to occur in the deleted portion. TMO7 and TMO8 both contain BglII sequences. A PrimeSTAR Max DNA Polymerase (Takara Bio) was used for the amplification [TMO7: 25 mer: 5'-CAG GAG ATC TCC AAG TCG CGA TTC A-3' (SEQ ID NO: 206), TMO8: 26 mer: 5'-CTT GGA GAT CTC CTG CCC GTC CCG AA-3' (SEQ ID NO: 207)] [PCR cycles: 98° C. 3 min/98° C. 10 sec, 55° C. 15 sec, 72° C. 30 sec, 30 cycles/72° C. 30 sec]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pTM2.

The product base plasmid (pTM2) for the Δ4 desaturase gene targeting vector production is shown in FIG. 59.

Example 8-3

Production of Targeting Vectors (Blasticidin-Resistant Gene and GFP-Fused Zeocin-Resistant Gene)

The pRH38 (FIG. 33) of Example 5-3 was digested with BglII, and the DNA fragment containing a blasticidin-resistant gene cassette was ligated to the BglII site of the pTM2 (FIG. 59) of Example 8-2. This was named pTM6.

The pRH51 (FIG. 36) of Example 5-4 was digested with BglII, and the DNA fragment containing a GFP-fused zeocin-resistant gene cassette was ligated to the BglII site of the pTM2 (FIG. 59) of Example 8-2. This was named pTM8.

The two targeting vectors (pTM6 and 8) produced are shown in FIG. 60.

Example 8-4

Introduction of Δ4 Desaturase Gene Targeting Vector into *Thraustochytrium aureum* OrfA Disrupted Strain By using the two targeting vectors produced in Example 8-3 as templates, the gene was amplified with a PrimeSTAR HS DNA polymerase (Takara Bio), using TMO3 (Example 8-1; SEQ ID NO: 202) and TMO4 (Example 8-1; SEQ ID NO: 203) as primers [PCR cycles: 98° C. 3 min/98° C. 10 sec, 55° C. 5 sec, 72° C. 4 min, 30 cycles/72° C. 3 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pTM6 (FIG. 60) of Example 8-3 as a template was 3,264 bp, and had the following sequence order: Upstream of *Thraustochytrium aureum* Δ4 desaturase gene-SV40 terminator sequence-blasticidin-resistant gene sequence-ubiquitin promoter-sequence within *Thraustochytrium aureum* Δ4 desaturase gene (SEQ ID NO: 208). The introduced fragment obtained from using the pTM8 (FIG. 60) of Example 8-3 as a template was 3,935 bp, and had the following sequence order: Upstream of *Thraustochytrium aureum* Δ4 desaturase gene-SV40 terminator sequence-zeocin-resistant gene sequence-enhanced GFP gene sequence-ubiquitin promoter-sequence within *Thraustochytrium aureum* Δ4 desaturase gene (SEQ ID NO: 209).

The gene disrupted strain of the PUFA PKS pathway-associated gene OrfA of Example 4 was cultured in a GY medium for 4 days, and cells in the logarithmic growth phase were used for gene introduction. The DNA fragment (0.625 μg) was then introduced into cells corresponding to OD600=1 to 1.5 by using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene was applied to a PDA agar plate medium (containing 20 mg/ml Zeocin or 0.2 mg/ml blasticidin). As a result, 100 to 200 drug resistant strains were obtained per penetration.

Example 8-5

Identification of Δ4 Desaturase Gene Gene Targeting Homologous Recombinant

Genomic DNA was extracted from *Thraustochytrium aureum*, and the Δ4 desaturase gene disrupted strain of the *Thraustochytrium aureum* OrfA disrupted strain by using the method of Example 3-2. The DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are shown in FIG. 61. TMO1 was set upstream of the Δ4 desaturase gene. TMO2 was set downstream of the Δ4 desaturase gene. RHO198 and RHO49 (Example 5-3; SEQ ID NO: 139) were set on the blasticidin-resistant gene. RHO128 was set on the enhanced GFP gene. RHO64 (Example 5-4; SEQ ID NO: 151) was set on the zeocin-resistant gene [TMO1: 23 mer: 5'-AAA AGA ACA AGC CCT CTC CTG GA-3' (SEQ ID NO: 210), TMO2: 23 mer: 5'-GAG GTT TGT ATG TTC GGC GGT TT-3' (SEQ ID NO: 211), RHO198: 26 mer: 5'-TGG GGG ACC TTG TGC AGA ACT CGT GG-3' (SEQ ID NO: 212), RHO128: 22 mer: 5'-GAC CTA CGG CGT GCA GTG CTT C-3' (SEQ ID NO: 213)] [PCR cycles: 98° C. 2 min/98° C. 10 sec, 68° C. 4 min 30 sec, 30 cycles/68° C. 4 min].

Δ4 desaturase gene knockout strains were obtained that showed no amplification of the wild-type allele (Wt allele) but showed amplification of the blasticidin-resistant gene allele (BlaR allele) and zeocin-resistant gene allele (ZeoR allele) (FIG. 62). It was found by the experiment that the *Thraustochytrium aureum* ATCC 34304 strain did not become auxotrophic even with the deletion of the PKS pathway-associated gene OrfA and the Δ4 desaturase gene.

Example 8-6

Changes in Fatty Acid Composition by Disruption of Δ4 Desaturase Gene in *Thraustochytrium aureum* OrfA Disrupted Strain The *Thraustochytrium aureum* ATCC 34304 and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 63. FIG. 64 represents the proportions relative to the wild-type strain taken as 100%.

As can be seen from the results, disrupting the Δ4 desaturase gene in the *Thraustochytrium aureum* OrfA disrupted strain resulted in hardly performing C22:5n-6 (DPA) and C22:6n-3(DHA) biosyntheses, and C22:4n-6 (DTA) and C22:5n-3 (DPA) accumulated.

Example 9

Disruption of C20 Elongase Gene in *Parietichytrium* sp. SEK358 Strain

Example 9-1

Introduction of C20 Elongase Gene Targeting Vector into *Parietichytrium* sp. SEK358 Strain By using the targeting vector produced with the pRH85 (FIG. 18) of Example 3-6 as a template, the gene was amplified with a PrimeSTAR Max DNA polymerase (TakaraBio), using RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (Example 3-7; SEQ ID NO: 81). The *Parietichytrium* sp. SEK358 strain was cultured in a GY medium for 3 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 900 PSI). After a 24-hour recovery time, the cells with the introduced gene were applied to a PDA agar plate medium containing 0.5 mg/ml G418. As a result, 10 to 30 drug resistant strains were obtained per penetration.

Example 9-2

Identification of C20 Elongase Gene Gene Targeting Homologous Recombinant

Genomic DNA was extracted from the *Parietichytrium* sp. SEK358 strain and the C20 elongase gene disrupted strain by using the method of Example 3-2. The DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are as described in Example 3-8 (FIG. 19).

RHO184 (Example 3-8; SEQ ID NO: 87) was set upstream of the C20 elongase. RHO185 (Example 3-8; SEQ ID NO: 88) was set downstream of the C20 elongase. RHO142 (Example 3-8; SEQ ID NO: 85) and RHO143 (Example 3-8; SEQ ID NO: 86) were set on the artificial neomycin-resistant gene [PCR cycles: 98° C. 2 min/98° C. 10 sec, 68° C. 2 min, 30 cycles/68° C. 7 min].

C20 elongase knockout strains were obtained that showed no amplification of the wild-type allele (Wt allele), but showed amplification of the artificial neomycin-resistant gene allele (NeoR allele) (FIG. 65).

Example 9-3

Changes in Fatty Acid Composition by Disruption of C20 Elongase

The *Parietichytrium* sp. SEK358 strain and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 66. FIG. 67 represents the proportions relative to the wild-type strain taken as 100%. As can be seen from the results, knocking out the C20 elongase in the *Parietichytrium* sp. SEK358 strain caused reduction of fatty acids of 22 or greater carbon chain length, and increased fatty acids of 20 carbon chain length. Specifically, the arachidonic acid increased about seven-fold, and the EPA about eleven-fold. The DPA and DHA reduced to about 1/15 and about 1/8, respectively.

Example 10

Disruption of C20 Elongase Gene in *Parietichytrium* sp. SEK571 Strain

Example 10-1

Introduction of C20 Elongase Gene Targeting Vector into *Parietichytrium* sp. SEK571 Strain By using the targeting vector produced with the pRH85 (FIG. 18) of Example 3-6 as a template, the gene was amplified with a PrimeSTAR Max DNA polymerase (TakaraBio), using RHO153 (Example 3-4; SEQ ID NO: 74) and RHO154 (Example 3-4; SEQ ID NO: 75) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment obtained from using the pRH85 (FIG. 18) of Example 3-6 as a template was 2,661 bp, and had the following sequence order: First half of *Parietichytrium* C20 elongase gene-SV40 terminator sequence-artificial neomycin-resistant gene sequence-ubiquitin promoter sequence-second half of *Parietichytrium* C20 elongase gene (Example 3-7; SEQ ID NO: 81). The *Parietichytrium* sp. SEK571 strain was cultured in a GY medium for 3 days, and cells in the logarithmic growth phase were used for gene introduction. The DNA fragment (0.625 μg) was then introduced into cells corresponding to OD600=1 to 1.5 using the gene-gun technique (microcarrier: 0.6-micron gold particles, target distance: 6 cm, chamber vacuum: 26 mmHg, rupture disk: 1550 PSI). After a 24-hour recovery time, the cells with the introduced gene were applied to a PDA agar plate medium containing 0.5 mg/ml G418. As a result, 5 to 15 drug resistant strains were obtained per penetration.

Example 10-2

Identification of C20 Elongase Gene Gene Targeting Homologous Recombinant

Genomic DNA was extracted from the *Parietichytrium* sp. SEK571 strain and the C20 elongase gene disrupted strain by using the method of Example 3-2, and the DNA concentration was calculated by measuring A260/280. By using this as a template, a PCR was performed with a Mighty Amp DNA polymerase (Takara Bio) to confirm the genome structure. The positions of the primers, combinations used for the amplification, and the expected sizes of the amplification products are as described in Example 3-8 (FIG. 19).

RHO184 (Example 3-8; SEQ ID NO: 87) was set upstream of the C20 elongase. RHO185 (Example 3-8; SEQ ID NO: 88) was set downstream of the C20 elongase. RHO142 (Example 3-8; SEQ ID NO: 85) and RHO143 (Example 3-8; SEQ ID NO: 86) were set on the artificial neomycin-resistant gene [PCR cycles: 98° C. 2 min/98° C. 10 sec, 68° C. 2 min, 30 cycles/68° C. 7 min].

C20 elongase knockout strains were obtained that showed no amplification of the wild-type allele (Wt allele), but showed amplification of the artificial neomycin-resistant gene allele (NeoR allele) (FIG. 68).

Example 10-3

Changes in Fatty Acid Composition by C20 Elongase Disruption

The *Parietichytrium* sp. SEK571 strain and the gene disrupted strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 69. FIG. 70 represents the proportions relative to the wild-type strain taken as 100%. As can be seen from the results, knocking out the C20 elongase in the *Parietichytrium* sp. SEK571 strain caused reduction of fatty acids of 22 or greater carbon chain length, and increased fatty acids of 20 carbon chain length. Specifically, the arachidonic acid increased about four-fold, and the EPA about eight-fold. The DPA and DHA both reduced to about 1/12.

Example 11

Disruption of *Thraustochytrium aureum* ATCC 34304-Derived Δ12 Desaturase Gene

Example 11-1

Isolation of *Thraustochytrium aureum* ATCC 34304-Derived Δ12 Desaturase Gene

By using the genomic DNA of the *Thraustochytrium aureum* ATCC 34304 as a template, a *Thraustochytrium aureum* ATCC 34304-derived Δ12 desaturase gene was amplified by a PCR performed with a forward oligonucleotide primer Tw3-F1 (22 mer: 5'-ATG TGC AAG GTC GAT GGG ACA A-3') (SEQ ID NO: 214) and a reverse oligonucleotide primer Tw3-R1 (22 mer: 5'-TCA CAA ACA TCG CAG CCT TCG G-3') (SEQ ID NO: 215) (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. ∞). As a result, a novel gene sequence having a 1,185-bp (SEQ ID NO: 217) ORF, encoding 395 amino acids (SEQ ID NO: 216) was obtained. In the amino acid sequence of the gene, three histidine boxes commonly conserved in desaturases, believed to construct the active site were conserved (FIG. 71). Further, because the gene showed high identity (41%, 44%, 41%) at the amino acid level with the *Thalassiosira pseudonana*-, *Micromonas* sp.-, and *Phaeodactylum tricornutum*-derived Δ12 desaturases in a Blast search (FIG. 71), it was strongly suggested that the gene was a *Thraustochytrium aureum* ATCC 34304-derived Δ12 desaturase gene. In the following, the gene will be referred to as TΔ12d.

Example 11-2

Expression of TΔ12d using Budding Yeast *Saccharomyces cerevisiae* as Host, and Analysis of Fatty Acid Composition of Gene Introduced Strain By using the genomic DNA of the *Thraustochytrium aureum* ATCC 34304 as a template, a DNA fragment containing HindIII and Xba I sites added to the both ends of TΔ12d was prepared in a PCR performed with a forward oligonucleotide primer Tw3-Hind3-F (30 mer: 5'-GGA AGC TTA TGT GCA AGG TCG ATG GGA CAA-3') (SEQ ID NO: 218) and a reverse oligonucleotide primer Tw3-Xba1-R (29 mer: 5'-TTC TAG ACT AGA GCT TTT TGG CCG CAC GC-3') (SEQ ID NO: 219) (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. ∞). The DNA fragment was then incorporated in the HindIII/Xba I site of a pYES2/CT vector to construct a TΔ12d expression vector pYESTD12. The pYESTD12 and pYES2/CT were then introduced into yeasts by using the lithium acetate method. In the GC analysis of the fatty acid composition of the TΔ12d overexpressing strain (pYESTD12 introduced strain), novel peaks were confirmed at positions corresponding to the retention times of LA (C18:2Δ9,12) and C16:2Δ9, 12, but not in the mock introduced strain (pYES2/CT introduced strain). FIG. 72 represents a GC analysis chart, and fatty acid levels per dry cell. On the other hand, no conversion activity for other fatty acids [LA, GLA (C18:3Δ6,9,12), C20: 2Δ11,14, DGLA (C20:3Δ8,11,14), ARA (C20:4Δ5,8,11,14), DTA (C22:4Δ7, 10,13,16)] was confirmed in the TΔ12d overexpressing strain. It became clear from these results that the TΔ12d was a *Thraustochytrium aureum* ATCC 34304-derived Δ12 desaturase gene.

Example 11-3

Construction of TΔ12d Targeting Vector

By using the genomic DNA of the *Thraustochytrium aureum* ATCC 34304 as a template, the upstream and downstream sequences (1,001 bp each) of the TΔ12d ORF were amplified in a PCR performed under the following conditions (enzyme used: PrimeSTAR GXL, TaKaRa); PCR cycles: 98° C. 2 min/98° C. 30 sec, 53° C. 30 sec, 72° C. 1 min, 30 cycles/72° C. 7 min/4° C. ∞). The following forward and reverse oligonucleotide primers were used.

TD12d-up-F (23 mer: 5'-AGT CAG CCC AGG CAC CGA TGA CG-3') (SEQ ID NO: 220) and TD12d-up-R (39 mer: 5'-AGC CAG AGC TAG ATC TCT TGT GCT CCT TTT CAA TCC TTT-3') (SEQ ID NO: 221)

TD12d-down-F (39 mer: 5'-GGA GCA CAA GAG ATC TAG CTC TGG CTC AAG GGA CAC CGT-3') (SEQ ID NO: 222) and TD12d-down-R (24 mer: 5'-CAC AGA AAC TGC CTT CAC GGG TCT-3') (SEQ ID NO: 223)

The resulting both DNA fragments were joined by fusion PCR with a BglII site inserted therebetween, and incorporated in a pGEM-T easy Vector (Promega). Then, the hygromycin-resistant gene cassette of Example 3-3, and the blasticidin-resistant gene cassette of Example 5-3 were incorporated at the BglII site of the resulting vector to construct TΔ12d KO targeting vectors. These were named pTD12dKOHyg and pTD12dKOBla. The construction scheme of the TΔ12d KO targeting vectors are shown in FIG. 73.

Example 11-4

Introduction of TΔ12d Targeting Vector to *Thraustochytrium aureum* ATCC 34304, and Acquisition of TΔ12d Disrupted Strain In order to obtain an efficient homologous recombinant by using a split marker method, two homologous recombination fragments were amplified by a PCR performed by using pTD12dKOHyg as a template [enzyme used: LA taq Hot Start Version, TaKaRa; PCR cycles: 98° C. 2 min/98° C. 30 sec, 60° C. 30 sec, 72° C. X min (X=1 min/kbp), 30 cycles/72° C. 7 min/4° C. ∞] (FIG. 74). The fragments were then introduced to the *Thraustochytrium aureum* ATCC 34304 by using the gene-gun technique. The following forward and reverse oligonucleotide primers were used for the amplification of the homologous recombination fragments.

TD12d-up-F (SEQ ID NO: 220) and Hyg-Knock-R (24 mer: 5'-TGT TAT GCG GCC ATT GTC CGT CAG-3') (SEQ ID NO: 224), and Hyg-Knock-F (24 mer: 5'-TGC GAT CGC TGC GGC CGA TCT TAG-3') (SEQ ID NO: 225) and TD12d-down-R (SEQ ID NO: 223)

As a result, a homologous recombinant with the disrupted TΔ12d first allele was obtained. Thereafter, by using pTD12dKOBla as a template, a homologous recombination fragment for disrupting the second allele was amplified by a PCR performed with the forward and reverse oligonucleotide primers TD12d-up-F (SEQ ID NO: 220) and TD12d-down-R (SEQ ID NO: 223) (enzyme used: LA taq Hot Start Version, TaKaRa) [PCR cycles: 98° C. 2 min/98° C. 30 sec, 60° C. 30 sec, 72° C. 3 min, 30 cycles/72° C. 7 min/4° C. ∞]. The fragment was then introduced to the homologous recombinant containing the disrupted first allele. Complete disruption of TΔ12d was verified by a PCR (using the genomic DNA below as a template) and a RT-PCR performed for the detection of hygromycin-resistant gene, blasticidin-resistant gene, and TΔ12d, or by southern blotting.

FIG. 75 represents the amplification results for the hygromycin-resistant gene, blasticidin-resistant gene, and TΔ12d amplified by a PCR performed by using the genomic DNAs of the wild-type strain, the TΔ12d first allele disrupted strain, and the TΔ12d disrupted strain (two alleles are disrupted) as templates.

As a result, amplification of the hygromycin-resistant gene and the blasticidin-resistant gene contained in the introduced homologous recombination fragment was confirmed in the TΔ12d disrupted strain. However, no amplification of the disrupted TΔ12d was confirmed. The following forward and reverse oligonucleotide primers were used for the amplification of the hygromycin-resistant gene, blasticidin-resistant gene, and TΔ12d.

Hyg-F (26 mer: 5'-ATG AAA AAG CCT GAA CTC ACC GCG AC-3') (SEQ ID NO: 226) and Hyg-R (25 mer: 5'-CTA TTC CTT TGC CCT CGG ACG AGT G-3') (SEQ ID NO: 227), Bla-F (27 mer: 5'-ATG GCC AAG CCT TTG TCT CAA GAA GAA-3') (SEQ ID NO: 228), and Bla-R (30 mer: 5'-TTA GCC CTC CCA CAC ATA ACC AGA GGG CAG-3') (SEQ ID NO: 229), Tw3-F1 (SEQ ID NO: 214), and Tw3-R1 (SEQ ID NO: 215)

FIG. 76 represents the results of the mRNA detection performed by RT-PCR for the hygromycin-resistant gene, blasticidin-resistant gene, and TΔ12d in the wild-type strain, the TΔ12d first allele disrupted strain, and the TΔ12d disrupted strain. As a result, mRNA was detected for the hygromycin-resistant gene and the blasticidin-resistant gene contained in the introduced homologous recombination fragment in the TΔ12d disrupted strain. However, mRNA was not detected for the disrupted TΔ12d. Note that the primers used are the same primers as used for the PCR in which the genomic DNA was used as a template.

By using the genomic DNA of the *Thraustochytrium aureum* ATCC 34304 as a template, two DIG-labeled probes were prepared, and southern blotting was performed with these probes. The following forward and reverse oligonucleotide primers were used for the preparation of the DIG-labeled probes.

KO up-probe-F1 (23 mer: 5'-GGG GTC GGC CGG TGC AGC CTT AG-3') (SEQ ID NO: 230) and KO up-probe-R1 (24 mer: 5'-GGC GGT CAG CGA TCG GTC GGA CTC-3') (SEQ ID NO: 231), and KO down-probe-F3 (23 mer: 5'-GCT TGC GGC TCC TGT TGG GTG AC-3') (SEQ ID NO: 232) and KO down-probe-R3 (23 mer: 5'-ACG CCT GGC TGC CCA CCA TAA AC-3') (SEQ ID NO: 233)

As a result, the bands of the wild-type allele (upstream side 2,028 bp, downstream side 2,334 bp) disappeared in the TΔ12d disrupted strain, and bands of the homologous recombination fragments (upstream side 5,880 bp and 5,253 bp; downstream side 1,496 bp and 2,334 bp) containing the hygromycin-resistant gene and the blasticidin-resistant gene were detected instead (FIG. 77).

The PCR using the genomic DNA as a template, the RT-PCR, and southern blotting made it clear that the TΔ12d was disrupted.

Example 11-5

Phenotypic Analysis of TΔ12d Disrupted Strain

Cells cultured in a 250-ml GY liquid medium for 5 days were collected in 10 ml portions, and absorbance at OD 600 nm was measured (n=3). After the measurement, the cells were collected, and washed once with sterilized ultrapure water. After freeze drying, the dry cell weight was measured after 1-hour drying with a desiccator (n=3). As a result, no significant difference was observed in the proliferation among the wild-type strain, the first allele disrupted strain, and the TΔ12d disrupted strain (FIG. 78). The wild-type strain, the first allele disrupted strain, and the TΔ12d disrupted strain were GC analyzed for their fatty acid compositions.

As a result, large fatty acid composition changes were observed. Accumulation of C18:1n9 (OA) in the TΔ12d disrupted strain was particularly prominent. FIG. 79 represents the proportion of each component in the fatty acid composition. FIG. 80 represents fatty acid levels per milligram of dry cells.

Example 12

Disruption of C20 Elongase Gene and Expression of ω3 Desaturase Gene in *Thraustochytrium aureum* ATCC 34304 OrfA Gene Disrupted Strain

Example 12-1

Production of C20 Elongase Gene Targeting and *Saprolegnia diclina*-Derived ω3 Desaturase Expression Vector (Blasticidin-Resistant Gene)

By using the pRH43 (FIG. 39) of Example 5-6 as a template, a primer set of the reverse orientation was prepared in a manner that allows the two restriction enzyme KpnI sites to be deleted, and a BamHI site to occur in the deleted portion. RHO189 and RHO190 both contain BamHI sequences. A PrimeSTAR Max DNA Polymerase (Takara Bio) was used for the amplification [RHO189: 28 mer: 5'-TTA GCG GGA TCC AAT TCG CCT AGT-3' (SEQ ID NO: 234), RHO190: 27 mer: 5'-AAT TGG GAT CCC GCT AAG TAT CTC CCG-3' (SEQ ID NO: 235)] [PCR cycles: 98° C. 2 min/98° C. 10 sec, 55° C. 15 sec, 72° C. 40 sec, 31 cycles/72° C. 1 min]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pRH101 (FIG. 81).

By using the pRH101 as a template, a primer set of the reverse orientation was prepared in a manner that allows for insertion of a restriction enzyme KpnI site. RHO191 and RHO192 both contain KpnI sequences. A PrimeSTAR Max DNA Polymerase (Takara Bio) was used for the amplification [RHO191: 28 mer: 5'-AGA TCT GGT ACC GCA GCG CCT GGT GCA C-3' (SEQ ID NO: 236), RHO192: 27 mer: 5'-GCT GCG GTA CCA GAT CTG GTC GCG TTT-3' (SEQ ID NO: 237)] [PCR cycles: 98° C. 2 min/98° C. 10 sec, 55° C. 15 sec, 72° C. 40 sec, 31 cycles/72° C. 1 min]. After the amplification performed under these conditions, the product was electrophoresed on an agarose gel, and purified. The resulting DNA fragment was introduced into *Escherichia coli* and amplified, and the sequence was confirmed by using a Dye Terminator Cycle Sequencing Kit (BECKMAN COULTER). This was named pRH102 (FIG. 82).

The pRH48 (FIG. 46) of Example 6-1 was digested with KpnI, and a DNA fragment containing a *Saprolegnia diclina*-derived ω3 desaturase expression cassette was ligated to the KpnI site of the pRH102 (FIG. 82). This was named pRH103.

The product C20 elongase gene targeting and *Saprolegnia diclina*-derived ω3 desaturase expression vector pRH103 is shown in FIG. 83.

Example 12-2

Introduction of C20 Elongase Gene Targeting and *Saprolegnia diclina*-Derived ω3 Desaturase Expression Vector into *Thraustochytrium aureum* OrfA Disrupted Strain By using the C20 elongase gene targeting vector pRH54 (FIG. 39) of Example 5-6 as a template, the gene was amplified with a PrimeSTAR Max DNA polymerase (Takara Bio) using KSO11 (Example 5-7; SEQ ID NO: 159) and KSO12 (Example 5-7; SEQ ID NO: 160) as primers [PCR cycles: 98° C. 2 min/98° C. 30 sec, 68° C. 2 min, 30 cycles/68° C. 2 min]. After being extracted with phenol-chloroform and then with chloroform, the DNA was precipitated with ethanol, and the precipitate was dissolved in 0.1×TE. The DNA concentration was calculated by measuring A260/280. The introduced fragment was 3,887 bp, and had the following sequence order: Upstream of *Thraustochytrium aureum* C20 elongase gene-ubiquitin promoter-Enhanced GFP gene sequence-zeocin-resistant gene sequence-SV40 terminator sequence-downstream of *Thraustochytrium aureum* C20 elongase gene (Example 5-7; SEQ ID NO: 162). The C20 elongase gene targeting and *Saprolegnia diclina*-derived ω3 desaturase expression vector pRH103 (FIG. 83) of Example 12-1 was digested with a restriction enzyme BamHI. After being extracted with phenol-chloroform and then with chloroform, the DNA was precipitated with ethanol, and the precipitate was dissolved in 0.1×TE. The DNA concentration was calculated by measuring A260/280. The introduced fragment was 5,611 bp, and had the following sequence order: Upstream of *Thraustochytrium aureum* C20 elongase gene-ubiquitin promoter-*Saprolegnia diclina*-derived ω3 desaturase gene sequence-ubiquitin terminator-ubiquitin promoter-blasticidin-resistant gene sequence-SV40 terminator-downstream of *Thraustochytrium aureum* C20 elongase gene (SEQ ID NO: 238).

The PUFA PKS pathway-associated gene OrfA gene disrupted strain of Example 4 was cultured in a GY medium for 4 days, and cells in the logarithmic growth phase were used for gene introduction. The DNA fragment (0.625 μg) was introduced into cells corresponding to OD600=1 to 1.5 by using the gene-gun technique (microcarrier: 0.6-micron gold particles, target distance: 6 cm, chamber vacuum: 26 mmHg, rupture disk: 1,100 PSI). After a 4- to 6-hour recovery time, the cells with the introduced gene were applied to a PDA agar plate medium (containing 20 mg/ml Zeocin or 0.2 mg/ml blasticidin). As a result, 20 to 60 drug resistant strains were obtained.

Example 12-3

Introduction of Homologous Recombinant Containing C20 Elongase Gene Targeting and *Saprolegnia diclina*-Derived ω3 Desaturase Expression Vector Inserted in Genome Genomic DNA was extracted from the *Thraustochytrium aureum* PUFA PKS pathway-associated gene OrfA disrupted strain, the C20 elongase gene first allele homologous recombinant of the *Thraustochytrium aureum* OrfA disrupted strain, and the disrupted strain by using the method described in Example 3-2. The DNA concentration was then calculated by measuring A260/280.

The genomic DNA was cut with restriction enzymes, and electrophoresed on a 0.7% SeaKem GTG agarose gel (Takara Bio) in about 2 to 3 μg per well. This was transferred to a nylon membrane, and hybridized at 51° C. for 16 hours with probes produced with a DIG system (Roche Applied Science). RHO94 (Example 5-8; SEQ ID NO: 163) and RHO95 (Example 5-8; SEQ ID NO: 164) were used for the production of the 5'-end probe. RHO96 (Example 5-8; SEQ ID NO:165) and RHO97 (Example 5-8; SEQ ID NO: 166) were used for the production of the 3'-end probe. The amplification was performed under the following conditions, and an LA taq Hot start version (Takara Bio) was used for the amplification [PCR cycles: 98° C. 2 min/98° C. 30 sec, 58° C. 30 sec, 72° C. 1 min, 30 cycles/72° C. 3 min]. The restriction enzymes used, and the probe positions are as shown in FIG. 84. Detection of the hybridized probes was made by using a chromogenic method (NBT/BCIP solution). Bands of the sizes expected from the homologous recombination of the drug resistant genes were observed in the analyses of both the 5' end and the 3' end (FIG. 85).

Example 12-4

Disruption of C20 Elongase Gene in *Thraustochytrium aureum* OrfA Disrupted Strain and Changes in Fatty Acid Composition by *Saprolegnia diclina*-Derived ω3 Desaturase Expression The *Thraustochytrium aureum* ATCC 34304wild-type strain, and the *Saprolegnia diclina*-derived ω3 desaturase expressing strain with the double disruption of the PKS pathway (orfA gene) and the C20 elongase gene were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

Changes in fatty acid composition are represented in FIG. 86. FIG. 87 represents the proportions relative to the wild-type strain taken as 100%.

It was found as a result that disrupting the C20 elongase gene and expressing the *Saprolegnia diclina*-derived ω3 desaturase in the *Thraustochytrium aureum* OrfA disrupted strain increases the C20:4n-6 (AA) about six-fold and the C20:5n3 (EPA) about ten-fold, and decreases the C22: 6n-3 (DHA) to about ¹⁄₁₆.

Example 13

Expression of ω3 Desaturase Gene in *Parietichytrium* sp. SEK571 C20 Elongase Gene Disrupted Strain Example 13-1

Production of *Saprolegnia diclina*-Derived ω3 Desaturase Expression Plasmid Using Hygromycin as Drug-Resistance Marker For the production of a *Saprolegnia diclina*-derived ω3 desaturase expression plasmid using hygromycin as a drug-resistance marker, a plasmid pRH107 (FIG. 88) was used as the base plasmid after partially modifying the restriction enzyme site by subcloning the *Parietichytrium* C20 elongase upstream sequence (904 bp, SEQ ID NO: 239) and *Parietichytrium* C20 elongase downstream sequence (721 bp, SEQ ID NO: 240) into a pGEM-T easy vector. For reference, the total pRH107 sequence is presented (4,592 bp, SEQ ID NO: 241). The sequence as the base of the expression plasmid production is not actively used for the introduction of cells in this experiment, and as such it is not necessarily required to use pRH107 as the base vector in similar experiments. In conducting a similar experiment, a cloning vector having a KpnI site and a BamHI site in proximity can be used instead. Here, the sequence between the KpnI site and the BamHI site should be as short as possible, because it is introduced into cells as a linker between the ω3 desaturase gene expression cassette and the drug resistant gene expression cassette. In this experiment example, the sequence corresponds to the *Parietichytrium* C20 elongase downstream sequence 37 bp (SEQ ID NO: 242).

The pRH48 (FIG. 46) of Example 6-1 was digested with KpnI, and the DNA fragment containing the *Saprolegnia diclina*-derived ω3 desaturase gene cassette was ligated to the KpnI site of pRH107 (FIG. 88). This was named pRH108 (FIG. 89).

The pRH32 (FIG. 15) of Example 3-3 was digested with BglII, and the DNA fragment containing the hygromycin-resistant gene cassette was ligated to the BamHI site of pRH108 (FIG. 89). This was named pRH109 (FIG. 90).

Example 13-2

Introduction of *Saprolegnia diclina*-Derived ω3 Desaturase Expression Plasmid into *Parietichytrium* sp. SEK571 C20 Elongase Gene Disrupted Strain By using the pRH109 (FIG. 90) produced in Example 13-1 as a template, the DNA was amplified with a PrimeSTAR Max DNA polymerase (Takara Bio), using TMO42 (Example 6-1, SEQ ID NO: 168) and RHO52 (Example 3-1, SEQ ID NO: 52) as primers [PCR cycles: 94° C. 30 sec, 72° C. 1 min, 5 cycles/94° C. 30 sec, 70° C. 30 sec, 72° C. 1 min, 5 cycles/ 94° C. 30 sec, 68° C. 30 sec, 72° C. 1 min, 25 cycles/72° C. 2 min]. The amplification product was collected form a 1.0% agarose gel, and precipitated with ethanol. The precipitate was then dissolved in 0.1×TE. The DNA concentration was calculated by measuring A260/280. The introduced fragment obtained by the PCR was 4,448 bp, and had the following sequence order: Ubiquitin promoter-ω3 desaturase gene-ubiquitin terminator-ubiquitin promoter-hygromycin-resistant gene sequence-SV40 terminator sequence (SEQ ID NO: 243).

The *Parietichytrium* sp. SEK571 C20 elongase gene disrupted strain produced in Example 10 was cultured in a GY medium for 3 days, and cells in the logarithmic growth phase were used for gene introduction. The DNA fragment (0.625 μg) was introduced into cells corresponding to OD600=1 to 1.5 by using the gene-gun technique (microcarrier: 0.6-micron gold particles, target distance: 6 cm, chamber vacuum: 26 mmHg, rupture disk: 1550 PSI). After a 24-hour recovery time, the cells with the introduced gene were applied to a PDA agar plate medium (containing 1.0 mg/ml hygromycin). As a result, 5 to 20 drug resistant strains were obtained per penetration.

Example 13-3

Acquisition of *Saprolegnia diclina*-Derived ω3 Desaturase Gene Expressing Strain Genomic DNA was extracted from the *Parietichytrium* sp. SEK571 C20 elongase gene disrupted strain produced in Example 10 and the ω3 desaturase gene expressing strain by using the method described in Example 3-2, and the DNA concentration was calculated by measuring A260/280. By using this as a template, a PCR was performed with an LA taq Hot start version to confirm the genome structure. The positions of the primers, combinations used for the amplification, and the expected size of the amplification product are shown in FIG. 91. RHO90 (27 mer: 5'-CGT TAG AAC GCG TAA TAC GAC TCA CTA-3' SEQ ID NO: 244) was set on the ubiquitin promoter, and RHO141 (Example 3-8, SEQ ID NO: 84) was set on the hygromycin-resistant gene [PCR cycles: 98° C. 2 min/98° C. 10 sec, 68° C. 4 min, 30 cycles/68° C. 7 min].

The result of amplification confirmed a band of the expected size (FIG. 92). That is, a strain was isolated that contained the introduced expression fragment stably introduced into its genome.

Example 13-4

Changes in Fatty Acid Composition by ω3 Desaturase Expression in *Parietichytrium* sp. SEK571 C20 Elongase Gene Disrupted Strain The *Parietichytrium* sp. SEK571 strain, and the ω3 desaturase gene expressing strain were cultured by using the method of Example 3-9. After freeze drying, the fatty acids were methylesterificated, and GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

The ω3 desaturase expressing strain reduced levels of the n-6 series fatty acids, and there was a tendency for the n-3 series fatty acids to increase (FIG. 93). FIG. 94 represents the proportions relative to the wild-type strain taken as 100%. As a result, the arachidonic acid was reduced to about ½, and EPA increased by a factor of about 1.4.

Example 14

Disruption of *Schizochytrium* C20 Elongase Gene

Example 14-1

Cloning of *Schizochytrium*-Derived C20 Elongase Gene

By using the genomic DNA extracted from *Schizochytrium* as a template, a *Schizochytrium*-derived C20 elongase gene was amplified by a PCR performed with a forward oligonucleotide primer RHO134 (32 mer: 5'-CCC GGA TCC ATG GTG GCC AGC GAG GTG CTC AG-3') (SEQ ID NO: 245) containing a BamHI site, and a reverse oligonucleotide primer RHO135 (34 mer: 5'-CCC GGA TCC TTA GTC GCG CTT GAG CTC AGC ATC C-3') (SEQ ID NO: 246) containing a BamHI site (enzyme used: LA taq Hot Start Version, TaKaRa; PCR cycles: 98° C. 2 min/98° C. 30 sec, 53° C. 30 sec, 72° C. 1 min, 30 cycles/72° C. 7 min/4° C. ∞). The both specific products were gel purified, cloned into a pGEM-T easy vector (Promega), and amplified with *Escherichia coli*. The sequence was then confirmed by using a Dye Terminator Cycle Sequencing Kit (BECKMAN COULTER). This was named pRH70 (FIG. 95). As a result of a base sequence analysis, a novel gene sequence having a 945-bp (SEQ ID NO: 248) ORF, encoding 315 amino acids (SEQ ID NO: 247) was obtained.

Example 14-2

Production of Base Plasmid for ?C20 Elongase Gene Targeting Vector Production

By using the pRH70 (FIG. 95) produced in Example 14-1 as a template, the gene was amplified with a Prime STAR Max DNA Polymerase (Takara Bio), using a primer set of the reverse orientation prepared for insertion of a BglII site in a portion halfway along the C20 elongase gene sequence. The primers used are as follows. The both had BglII linker sequences [RHO136: 25 mer: 5'-CAT CGA GAT CTT CGT GTT TGT CCA C-3' (SEQ ID NO: 249), RHO137: 25 mer: 5'-ACG AAG ATC TCG ATG CGG GCG TCC C-3' (SEQ ID NO: 250)] [PCR cycles: 98° C. 2 min/98° C. 10 sec, 56° C. 15 sec, 72° C. 1 min, 30 cycles/72° C. 1 min]. After the amplification performed under these conditions, the product was digested with BglII, and allowed to self ligate. The ligated sample was amplified with *Escherichia coli*, and the sequence was confirmed by using a Dye Terminator Cycle Sequencing Kit (BECKMAN COULTER). This was named pRH71. The C20 elongase gene sequence 945 bp with the inserted BglII site is represented by SEQ ID NO: 251.

The product base plasmid (pRH71) for the production of the *Schizochytrium* C20 elongase gene targeting vector is shown in FIG. 96.

Example 14-3

Production of Targeting Vectors (Artificial Neomycin-Resistant Gene and Hygromycin-Resistant Gene)

The pRH31 (FIG. 13) of Example 2-2 was digested with BglII, and the DNA fragment containing an artificial neomycin-resistant gene cassette was ligated to the BglII site of the pRH71 (FIG. 96) of Example 14-2. This was named pRH73.

The pRH32 (FIG. 15) of Example 2-3 was digested with BglII, and the DNA fragment containing a hygromycin-resistant gene cassette was ligated to the BglII site of the pRH71 (FIG. 96) of Example 14-2. This was named pKS-SKO.

The two targeting vectors (pRH73 and pKS-SKO) produced are shown in FIG. 97.

Example 14-4

Introduction of C20 Elongase Gene Targeting Vector

By using the two targeting vectors produced in Example 14-3 as templates, the gene was amplified with a Prime STAR GXL polymerase, using a forward primer (SorfF: 20 mer: 5'-AGA TGG TGG CCA GCG AGG TG-3') (SEQ ID NO: 252) containing a translation initiation site, and a reverse primer (SorfR: 25 mer: 5'-TTA GTC GCG CTT GAG CTC AGC ATC C-3') (SEQ ID NO: 253) containing a translation termination site [PCR cycles: 98° C. 2 min/98° C. 30 sec, 60

30 sec, 72° C. 3 min, 30 cycles]. After being extracted with phenol-chloroform and then with chloroform, the DNA was precipitated with ethanol, and the precipitate was dissolved in 0.1×TE. The DNA concentration was then calculated by measuring A260/280. The introduced fragment obtained from using the pRH73 (FIG. 97) of Example 14-3 as a template was 2,644 bp, and had the following sequence order: First half of *Schizochytrium* C20 elongase gene-SV40 terminator sequence-artificial neomycin-resistant gene sequence-ubiquitin promoter sequence-second half of *Schizochytrium* C20 elongase gene (SEQ ID NO: 254). The introduced fragment obtained from using the pKS-SKO (FIG. 97) of Example 14-3 as a template was 2,881 bp, and had the following sequence order: First half of *Schizochytrium* C20 elongase gene-ubiquitin promoter sequence-hygromycin-resistant gene sequence-SV40 terminator sequence-second half of *Schizochytrium* C20 elongase gene (SEQ ID NO: 255).

The *Schizochytrium* sp. TY12Ab strain was cultured in a GY medium for 7 days, and cells in the logarithmic growth phase were used for gene introduction. The DNA fragment (0.625 μg) was introduced into cells corresponding to OD600=1 to 1.5 using the gene-gun technique (microcarrier: 0.6-micron gold particles, target distance: 6 cm, chamber vacuum: 26 mmHg, rupture disk: 1,100 PSI). After a 24-hour recovery time, the cells with the introduced gene were applied to a PDA plate medium (containing 2 mg/ml G418 or 2 mg/ml hygromycin).

As a result, about 20 drug resistant strains were obtained per penetration.

Example 14-5

Identification of C20 Elongase Gene Gene Targeting Homologous Recombinant

The *Schizochytrium* sp. TY12Ab strain (FERM BP-11421), the C20 elongase gene hetero homologous recombinant, and the C20 elongase gene homo homologous recombinant (gene disrupted strain) were cultured in GY media, and the resulting cells were centrifuged at 4° C., 3,000 rpm for 10 min to form a pellet. The cells were then lysed at 55° C., 6 h/99.9° C., 5 min after being suspended in a 20-μl SNET solution [20 mM Tris-HCl; pH 8.0, 5 mM NaCl, 0.3% SDS, 200 μg/ml Proteinase K (nacalai tesque)]. The resulting cell lysate was diluted 10 times and used as a template in a PCR performed with a Mighty Amp DNA polymerase (Takara Bio) to confirm the genome structure. The positions of the primers, and the expected size of the amplification product are shown in FIG. 98. The primers were used in the SorfF and SorfR combination used in Example 14-4 [PCR cycles: 98° C. 2 min/98° C. 10 sec, 60° C. 15 sec, 68° C. 4 min, 30 cycles].

C20 elongase knockout strains were obtained that showed no amplification of the wild-type allele (Wt allele), but showed amplification of the artificial neomycin-resistant gene allele (NeoR allele) and hygromycin-resistant gene allele (HygR allele) (FIG. 99).

Example 14-6

Changes in Fatty Acid Composition by C20 Elongase Disruption

The *Schizochytrium* sp. TY12Ab strain and the gene disrupted strain were cultured in GY media. Cells at the late stage of the logarithmic growth phase were centrifuged at 4° C., 3,000 rpm for 10 min to form a pellet, suspended in 0.9% NaCl, and washed. The cells were further centrifuged at 4° C., 3,000 rpm for 10 min, and the pellet was suspended in sterile water, and washed. This was centrifuged at 3,000 rpm for 10 min, and freeze dried after removing the supernatant. Then, 2 ml-methanolic KOH (7.5% KOH in 95% methanol) was added to the freeze dried cells, and, after being vortexed, the cells were ultrasonically disrupted (80° C., 30 min).

The cells were vortexed after adding sterile water (500 μl), and vortexed again after adding n-hexane (2 ml). This was followed by centrifugation at 3,000 rpm for 10 min, and the upper layer was discarded. The cells were vortexed again after adding n-hexane (2 ml), and centrifuged at 3,000 rpm for 10 min. After discarding the upper layer, 6 N HCl (1 ml) was added to the remaining lower layer, and the mixture was vortexed. The mixture was vortexed again after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. The collected upper layer was then concentrated and dried with nitrogen gas. The concentrated dry sample was incubated overnight at 80° C. after adding 3 N methanolic HCl (2 ml).

The sample was allowed to cool to room temperature, and 0.9% NaCl (1 ml) was added. The mixture was vortexed after adding n-hexane (2 ml). This was followed by centrifugation at 3,000 rpm for 10 min, and the upper layer was collected. The mixture was further vortexed after adding n-hexane (2 ml), centrifuged at 3,000 rpm for 10 min, and the upper layer was collected. After adding a small amount of anhydrous sodium sulfate to the collected upper layer, the mixture was vortexed, and centrifuged at 3,000 rpm for 10 min. After collecting the upper layer, the upper layer was concentrated and dried with nitrogen gas. The concentrated dry sample was dissolved in n-hexane (0.2 ml), and 2 μl of the sample was GC analyzed. The GC analysis was performed with a gas chromatograph GC-2014 (Shimadzu Corporation) under the following conditions:

Column: HR-SS-10 (30 m×0.25 mm; Shinwa Chemical Industries Ltd.)

Column temperature: 150° C.→(5° C./min)→220° C. (10 min)

Carrier gas: He (1.3 mL/min).

As a result, knocking out the C20 elongase in the *Schizochytrium* sp. TY12Ab strain increased fatty acids of 20 carbon chain length (FIG. 100). FIG. 101 represents the proportions relative to the wild-type strain taken as 100%.

As can be seen from these results, the arachidonic acid increased about 1.7-fold, EPA about 1.3-fold, DPA (n-6) about 1.1-fold, and DHA about 0.9-fold.

INDUSTRIAL APPLICABILITY

The present invention provides a method for transforming stramenopile through disruption of stramenopile genes and/or inhibition of expression thereof, modification of the fatty acid composition produced by a stramenopile, and a method for highly accumulating fatty acids in a stramenopile. The present invention thus enables more efficient production of polyunsaturated fatty acids.

The invention claimed is:

1. A method for transforming Stramenopile, the method comprising disrupting a stramenopile gene and/or inhibiting expression thereof by genetic engineering in microorganisms belong to Stramenopile, wherein the microorganisms are selected from the group consisting of *Parietichvtrium sarkarianum* SEK 364 (FERM BP-11298), *Parietichvtrium* sp. SEK358 (FERM BP-11405), *Parietichvtrium* sp. SEK571 (FERM BP-11406), and *Schizochvtrium* sp. TY 12Ab (FERM BP-11421).

2. The method according to claim 1, wherein the stramenopile gene is a gene associated with fatty acid biosynthesis.

3. The method according to claim 2, wherein the gene associated with fatty acid biosynthesis is a gene associated with polyketide synthase, fatty acid chain elongase, and/or fatty acid desaturase.

4. The method according to claim 3, wherein the fatty acid chain elongase is a C20 elongase.

5. The method according to claim 3, wherein the fatty acid desaturase is a Δ12 desaturase.

6. The method according to claim 5, wherein the method used to disrupt the stramenopile gene by genetic engineering is electroporation or a gene-gun technique introducing a loss-of-function gene or a DNA fragment from which a coding region of the gene is deleted.

7. The method according to claim 6, wherein the method used to inhibit expression of the stramenopile gene by genetic engineering is an antisense technique or RNA interference.

8. The method according to claim 7, further comprising introducing a gene associated with fatty acid desaturase.

9. The method according to claim 8, wherein the gene associated with fatty acid desaturase is an ω3 desaturase.

10. A method for modifying the fatty acid composition of a Stramenopile, the method comprising disrupting a stramenopile gene and/or inhibiting expression thereof by genetic engineering in microorganisms wherein the microorganisms are selected from the group consisting of *Parietichvtrium sarkarianum* SEK 364 (FERM BP-11298), *Parietichvtrium* sp. SEK358 (FERM BP-11405), *Parietichvtrium* sp. SEK571 (FERM BP-11406), and *Schizochvtrium* sp. TY 12Ab (FERM BP-11421).

11. The method according to claim 10, wherein the stramenopile gene is a gene associated with fatty acid biosynthesis.

12. The method according to claim 11, wherein the gene associated with fatty acid biosynthesis is a gene associated with polyketide synthase, fatty acid chain elongase, and/or fatty acid desaturase.

13. The method according to claim 12, wherein the fatty acid chain elongase is a C20 elongase.

14. The method according to claim 12, wherein the fatty acid desaturase is a Δ12 desaturase.

15. The method according to claim 14, wherein the method used to disrupt the stramenopile gene by genetic engineering is electroporation or a gene-gun technique introducing a loss-of-function gene or a DNA fragment from which a coding region of the gene is deleted.

16. The method according to claim 15, wherein the method used to inhibit expression of the stramenopile gene by genetic engineering is an antisense technique or RNA interference.

17. The method according to claim 16, further comprising introducing a gene associated with fatty acid desaturase.

18. The method according to claim 17, wherein the gene associated with fatty acid desaturase is an ω3 desaturase.

19. A method for highly accumulating a fatty acid in a stramenopile, wherein the method uses the method of claim 18.

20. The method according to claim 19, wherein the fatty acid is an unsaturated fatty acid.

21. The method according to claim 20, wherein the unsaturated fatty acid is an unsaturated fatty acid of 18 to 22 carbon atoms.

22. A stramenopile transformed for the modification of the fatty acid composition through disruption of its gene and/or inhibition of expression thereof by genetic engineering in microorganisms wherein the microorganisms are selected from the group consisting of *Parietichvtrium sarkarianum* SEK 364 (FERM BP-11298), *Parietichvtrium* sp. SEK358 (FERM BP-11405), *Parietichvtrium* sp. SEK571 (FERM BP-11406), and *Schizochvtrium* sp. TY 12Ab (FERM BP-11421).

23. The stramenopile according to claim 22, wherein the stramenopile gene is a gene associated with fatty acid biosynthesis.

24. The stramenopile according to claim 23, wherein the gene associated with fatty acid biosynthesis is a gene associated with polyketide synthase, fatty acid chain elongase, and/or fatty acid desaturase.

25. The stramenopile according to claim 24, wherein the fatty acid chain elongase is a C20 elongase.

26. The stramenopile according to claim 24, wherein the fatty acid desaturase is a Δ12 desaturase.

27. The stramenopile according to claim 26, wherein the method used to disrupt the stramenopile gene by genetic engineering is electroporation or a gene-gun technique introducing a loss-of-function gene or a DNA fragment from which a coding region of the gene is deleted.

28. The stramenopile according to claim 27, wherein the method used to inhibit expression of the stramenopile gene by genetic engineering is an antisense technique or RNA interference.

29. The stramenopile according to claim 28, further comprising introducing a gene associated with fatty acid desaturase is introduced.

30. The stramenopile according to claim 29, wherein the gene associated with fatty acid desaturase is an ω3 desaturase.

31. The method according to claim 1, wherein the method used to disrupt the stramenopile gene by genetic engineering is electroporation or a gene-gun technique introducing a loss-of-function gene or a DNA fragment from which a coding region of the gene is deleted.

32. The method according to claim 31, wherein the method used to inhibit expression of the stramenopile gene by genetic engineering is an antisense technique or RNA interference.

33. The method according to claim 2, wherein the method used to disrupt the stramenopile gene by genetic engineering is electroporation or a gene-gun technique introducing a loss-of-function gene or a DNA fragment from which a coding region of the gene is deleted.

34. The method according to claim 33, wherein the method used to inhibit expression of the stramenopile gene by genetic engineering is an antisense technique or RNA interference.

35. The method according to claim 3, wherein the method used to disrupt the stramenopile gene by genetic engineering is electroporation or a gene-gun technique introducing a loss-of-function gene or a DNA fragment from which a coding region of the gene is deleted.

36. The method according to claim 35, wherein the method used to inhibit expression of the stramenopile gene by genetic engineering is an antisense technique or RNA interference.

37. The method according to claim 4, wherein the method used to disrupt the stramenopile gene by genetic engineering is electroporation or a gene-gun technique introducing a loss-of-function gene or a DNA fragment from which a coding region of the gene is deleted.

38. The method according to claim 37, wherein the method used to inhibit expression of the stramenopile gene by genetic engineering is an antisense technique or RNA interference.

\* \* \* \* \*

SEQUENCE LISTING

<160> NUMBER OF SEQ ID NOS: 255

<210> SEQ ID NO 1
<211> LENGTH: 21
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 1
ttyytncayg tntaycayca y                                              21

<210> SEQ ID NO 2
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 2
gcrtgrtgrt anacrtgnar raa                                            23

<210> SEQ ID NO 3
<211> LENGTH: 190
<212> TYPE: DNA
<213> ORGANISM: Artificial
<220> FEATURE:
<223> OTHER INFORMATION: cDNA (DNA fragment contains elo1)

<400> SEQUENCE: 3
cgccaccatc tttgctatct ggtttatgat cgccaagtac gccccgggcg gcgacgcata    60
ctttagcgtc atcctgaact cgttcgtgca caccgtcatg tacgcgtact acttcttctc   120
gtcgcagggc ttcgggttcg tcaagccgat caagccgtac atcacctcgc tgcagatgac   180
gcagttcatg                                                          190

<210> SEQ ID NO 4
<211> LENGTH: 210
<212> TYPE: DNA
<213> ORGANISM: Artificial
<220> FEATURE:
<223> OTHER INFORMATION: cDNA (DNA fragment contains elo2)

<400> SEQUENCE: 4
ccgacgacca gcacaccgag tgggtctcgt gcgtgcgctt ctcgccctcg accaccaacc    60
cgctgatcgt gtcgtgcggc tgggacaagc tcgtcaaggt ctggaacctc tcgaactgca   120
agcttcgggc caacctcatc ggccacgacg gctacctcaa ctcggtcacc gtcagcccgg   180
acggctccct gtgcgcttcg ggcggcaagg                                    210

```
<210> SEQ ID NO 5
<211> LENGTH: 200
<212> TYPE: DNA
<213> ORGANISM: Artificial
<220> FEATURE:
<223> OTHER INFORMATION: cDNA (DNA fragment contains elo3)

<400> SEQUENCE: 5
aagctaacct gggcgtagtt tttcttgagg atcatcatga acgtgtcgct ccagtcgaga      60
aactttgtca ggaggtgcac gaacacgaaa aactcgatgt tcgagtcgcg cgacttgttg     120
aggccgaaag ggttgccgtt ggccaggtcg acctgcggcc agaggcccca caccatccag     180
ccgcacaccg cgatttggac                                                 200

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
tatgatcgcc aagtacgccc c                                                21

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
gaactgcgtc atctgcagcg a                                                21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
tctcgccctc gaccaccaac                                                  20

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
cggtgaccga gttgaggtag cc                                               22

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10 caacccttc ggcctcaaca ag                                                22

<210> SEQ ID NO 11
```

```
<211> LENGTH: 26
<212> TYPE: DNA
<213> ORGANISM: Artificial
<220> FEATURE:
<223> OTHER INFORMATION: primer

<400> SEQUENCE: 11
ttcttgagga tcatcatgaa cgtgtc                                          26

<210> SEQ ID NO 12
<211> LENGTH: 1139
<212> TYPE: DNA
<213> ORGANISM: Artificial
<220> FEATURE:
<223> OTHER INFORMATION: cDNA (elo1)

<400> SEQUENCE: 12
ctaatacgac tcactatagg gcaagcagtg gtaacaacgc agagtacgcg gggaccccaa      60
acgcccgacg acaaccaaga agacagccag ccgaacaatc ggacgaagat gacgagcaac     120
atgagcgcgt ggggcgtcgc cgtcgaccag acgcagcagg tcgtcgacca gatcatgggc     180
ggcgccgagc cgtacaagct gacagaaggg cgcatgacga acgtcgagac gatgctggcg     240
atcgagtgcg gctacgccgc catgctgctg ttcctgaccc cgatcatgaa gcaggccgag     300
aagcccttcg agctcaagtc cttcaagctc gcccacaacc tgttcctgtt cgtcctgtcc     360
gcctacatgt gcctcgagac cgtccgccag gcctaccttg cgggctactc ggtgttcggc     420
aacgacatgg agaagggcag cgagccgcac gcgcacggca tggcccaaat cgtgtggatc     480
ttttacgtgt ccaaggcgta cgagttcgtg gacacgctga tcatgatcct gtgcaaaaag     540
ttcaaccagg tctccgtcct gcacgtgtac caccacgcca ccatctttgc tatctggttt     600
atgatcgcca agtacgcccc gggcggcgac gcatacttta gcgtcatcct gaactcgttc     660
gtgcacaccg tcatgtacgc gtactacttc ttctcgtcgc agggcttcgg gttcgtcaag     720
ccgatcaagc cgtacatcac ctcgctgcag atgacgcagt tcatggcgat gctcgtgcag     780
tcgctgtacg actaccttta cccgtgcgac tacccgcagg ggctcgtcaa gctcctcggc     840
gtgtacatgc tcaccctgct tgcgctcttc ggcaactttt tcgtgcagag ctacctcaag     900
aagtcgaaca agcccaaggc caagtcggcc taagccgacc cgctcgccgg caaccgagca     960
gcacctaggc gcatctcggc ccggaaccct ttcgacctgc tgtggagcgc gcgacgcgtt    1020
tcgcgaccgt ccgcgcgttc ttgacactct ttgctctgtg tgtttcgcac ttgacaacct    1080
ggaacagaca catacacgat acaaatcatc agaacagaca aaaacaacc tcaaattat     1139

<210> SEQ ID NO 13
<211> LENGTH: 1261
<212> TYPE: DNA
<213> ORGANISM: Artificial
<220> FEATURE:
<223> OTHER INFORMATION: cDNA (elo3)

<400> SEQUENCE: 13
ctaatacgac tcactatagg gcaagcagtg gtatcaacgc agagtacgcg gggaccccga      60
acgtgtttct cccaggacgt gccgctgtcg ctcgctgatc cacccgaagc gcggtcggct     120
ggcacggtcg ctcggctgga agttgagtag tttgctttct gttactgcgc tgctttgtaa     180
acgcgaccat ggcgacgcgc acctcgaaga gcgctccggc ggtttccaag tcggccaagg     240
ttgccgcgcc ggcgaagaag cggtcggtcg acaggagcga cggtttcttc cgcacgttca     300
acctgtgcgc cctgtacggg tctgccctcg cctatgcgta caagcacggc ccggtggaca     360
```

```
atgacggcca gggctgtac tttcacaagt cgcccatgta cgcgttcgcc gtgtcggacg    420
tcatgacctt cggcgcgccg ctgatgtacg tgctcggtgt gatgctgctc agcaggtaca    480
tggcggacaa aaagcccctg actggcttca tcaagaccta catccagccc gtctacaacg    540
tggtccaaat cgcggtgtgc ggctggatgg tgtggggcct ctggccgcag gtcgacctgg    600
ccaacggcaa cccttcggc ctcaacaagt cgcgcgactc gaacatcgag tttttcgtgt    660
tcgtgcacct cctgacaaag tttctcgact ggagcgacac gttcatgatg atcctcaaga    720
aaaactacgc ccaggttagc tttctgcagg tgttccacca cgcaacgatc ggcatggtgt    780
ggtcgttcct tcttcagcgt ggctgggct cgggcaccgc cgcgtacggt gctttcatca    840
actcggtcac gcacgtgatc atgtactcgc actactttgc cacctcgctc aacatcaaca    900
acccgttcaa gcggtacatc acgagcttcc agctcgccca gtttgcaagc tgcatcgtgc    960
atgccctact ggtgcttgcc ttcgaggagg tgtacccgct cgagtacgct acctgcaga    1020 tcagctacca catcatcatg ctctacctgt tcggacgccg catgaactgg agccccgagt    1080
ggtgcaccgg tgagatcgac ggccttgacg ccccaagcgc ccccaccaag tccgagtaaa    1140 cctgttccg gctggctccc gagccatgct accatgaat gaacctgcaa acagtctgag    1200
gtccttgtgc aaaccgctca gtgggacgtc gacgaagaaa gaaacaatgt gtactcgtcc    1260
c                                                                     1261
```

<210> SEQ ID NO 14
<211> LENGTH: 275
<212> TYPE: PRT
<213> ORGANISM: T. aureum ATCC 34304
<220> FEATURE:
<221> NAME/KEY: misc_feature
<222> LOCATION: (275)..(275)
<223> OTHER INFORMATION: Xaa can be any naturally occurring amino acid

<400> SEQUENCE: 14

```
Met Thr Ser Asn Met Ser Ala Trp Gly Val Ala Val Asp Gln Thr Gln
1               5                   10                  15

Gln Val Val Asp Gln Ile Met Gly Gly Ala Glu Pro Tyr Lys Leu Thr
            20                  25                  30

Glu Gly Arg Met Thr Asn Val Glu Thr Met Leu Ala Ile Glu Cys Gly
        35                  40                  45

Tyr Ala Ala Met Leu Leu Phe Leu Thr Pro Ile Met Lys Gln Ala Glu
    50                  55                  60

Lys Pro Phe Glu Leu Lys Ser Phe Lys Leu Ala His Asn Leu Phe Leu
65                  70                  75                  80

Phe Val Leu Ser Ala Tyr Met Cys Leu Glu Thr Val Arg Gln Ala Tyr
                85                  90                  95

Leu Ala Gly Tyr Ser Val Phe Gly Asn Asp Met Glu Lys Gly Ser Glu
            100                 105                 110

Pro His Ala His Gly Met Ala Gln Ile Val Trp Ile Phe Tyr Val Ser
        115                 120                 125

Lys Ala Tyr Glu Phe Val Asp Thr Leu Ile Met Ile Leu Cys Lys Lys
    130                 135                 140

Phe Asn Gln Val Ser Val Leu His Val Tyr His Ala Thr Ile Phe
145                 150                 155                 160

Ala Ile Trp Phe Met Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
```

```
                    180                 185                 190
Tyr Phe Phe Ser Ser Gln Gly Phe Gly Phe Val Lys Pro Ile Lys Pro
            195                 200                 205

Tyr Ile Thr Ser Leu Gln Met Thr Gln Phe Met Ala Met Leu Val Gln
        210                 215                 220

Ser Leu Tyr Asp Tyr Leu Tyr Pro Cys Asp Tyr Pro Gln Gly Leu Val
225                 230                 235                 240

Lys Leu Leu Gly Val Tyr Met Leu Thr Leu Leu Ala Leu Phe Gly Asn
                245                 250                 255

Phe Phe Val Gln Ser Tyr Leu Lys Lys Ser Asn Lys Pro Lys Ala Lys
                260                 265                 270

Ser Ala Xaa
        275

<210> SEQ ID NO 15
<211> LENGTH: 825
<212> TYPE: DNA
<213> ORGANISM: Artificial
<220> FEATURE:
<223> OTHER INFORMATION: cDNA (T. aureum ATCC 34304 elo1)

<400> SEQUENCE: 15
atgacgagca acatgagcgc gtggggcgtc gccgtcgacc agacgcagca ggtcgtcgac     60
cagatcatgg gcggcgccga gccgtacaag ctgacagaag gcgcatgac gaacgtcgag     120 acgatgctgg cgatcgagtg cggctacgcc gccatgctgc tgttcctgac cccgatcatg    180
aagcaggccg agaagccctt cgagctcaag tccttcaagc tcgcccacaa cctgttcctg    240
ttcgtcctgt ccgcctacat gtgcctcgag accgtccgcc aggcctacct tgcgggctac    300
tcggtgttcg gcaacgacat ggagaagggc agcgagccgc acgcgcacgg catggcccaa    360
atcgtgtgga tcttttacgt gtccaaggcg tacgagttcg tggacacgct gatcatgatc    420
ctgtgcaaaa agttcaacca ggtctccgtc ctgcacgtgt accaccacgc caccatctt    480 gctatctggt ttatgatcgc caagtacgcc ccgggcggcg acgcatactt tagcgtcatc    540
ctgaactcgt tcgtgcacac cgtcatgtac gcgtactact tcttctcgtc gcagggcttc    600
gggttcgtca agccgatcaa gccgtacatc acctcgctgc agatgacgca gttcatggcg    660
atgctcgtgc agtcgctgta cgactacctt tacccgtgcg actacccgca ggggctcgtc    720
aagctcctcg gcgtgtacat gctcaccctg cttgcgctct cggcaacttt tttcgtgcag    780
agctacctca gaagtcgaa caagcccaag gccaagtcgg cctaa                    825

<210> SEQ ID NO 16
<211> LENGTH: 317
<212> TYPE: PRT
<213> ORGANISM: T. aureum ATCC 34304
<220> FEATURE:
<221> NAME/KEY: misc_feature
<222> LOCATION: (317)..(317)
<223> OTHER INFORMATION: Xaa can be any naturally occurring amino acid

<400> SEQUENCE: 16

Met Ala Thr Arg Thr Ser Lys Ser Ala Pro Ala Val Ser Lys Ser Ala
1               5                   10                  15

Lys Val Ala Ala Pro Ala Lys Lys Arg Ser Val Asp Arg Ser Asp Gly
            20                  25                  30

Phe Phe Arg Thr Phe Asn Leu Cys Ala Leu Tyr Gly Ser Ala Leu Ala
        35                  40                  45
```

```
Tyr Ala Tyr Lys His Gly Pro Val Asp Asn Asp Gly Gln Gly Leu Tyr
         50                  55                  60

Phe His Lys Ser Pro Met Tyr Ala Phe Ala Val Ser Asp Val Met Thr
 65                  70                  75                  80

Phe Gly Ala Pro Leu Met Tyr Val Leu Gly Val Met Leu Leu Ser Arg
                 85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
                115                 120                 125

Trp Gly Leu Trp Pro Gln Val Asp Leu Ala Asn Gly Asn Pro Phe Gly
130                 135                 140

Leu Asn Lys Ser Arg Asp Ser Asn Ile Glu Phe Val Phe Val His
145                 150                 155                 160

Leu Leu Thr Lys Phe Leu Asp Trp Ser Asp Thr Phe Met Met Ile Leu
                165                 170                 175

Lys Lys Asn Tyr Ala Gln Val Ser Phe Leu Gln Val Phe His His Ala
            180                 185                 190

Thr Ile Gly Met Val Trp Ser Phe Leu Leu Gln Arg Gly Trp Gly Ser
                195                 200                 205

Gly Thr Ala Ala Tyr Gly Ala Phe Ile Asn Ser Val Thr His Val Ile
210                 215                 220

Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
                245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
                275                 280                 285

Gly Arg Arg Met Asn Trp Ser Pro Glu Trp Cys Thr Gly Glu Ile Asp
            290                 295                 300

Gly Leu Asp Ala Pro Ser Ala Pro Thr Lys Ser Glu Xaa
305                 310                 315

<210> SEQ ID NO 17
<211> LENGTH: 951
<212> TYPE: DNA
<213> ORGANISM: Artificial
<220> FEATURE:
<223> OTHER INFORMATION: cDNA (T. aureum ATCC 34304 elo3)

<400> SEQUENCE: 17
atggcgacgc gcacctcgaa gagcgctccg gcggtttcca gtcggccaa ggttgccgcg      60 ccggcgaaga gcggtcggt cgacaggagc gacggtttct tccgcacgtt caacctgtgc    120
gccctgtacg ggtctgccct cgcctatgcg tacaagcacg gccggtgga caatgacggc    180 caggggctgt actttcacaa gtcgcccatg tacgcgttcg ccgtgtcgga cgtcatgacc    240
ttcggcgcgc cgctgatgta cgtgctcggt gtgatgctgc tcagcaggta catggcggac    300
aaaaagcccc tgactggctt catcaagacc tacatccagc ccgtctacaa cgtggtccaa    360
atcgcggtgt gcggctggat ggtgtgggc ctctggccgc aggtcgacct ggccaacggc    420 aacccttcg gcctcaacaa gtcgcgcgac tcgaacatcg agttttttcgt gttcgtgcac    480 ctcctgacaa agtttctcga ctggagcgac acgttcatga tgatcctcaa gaaaaactac    540
```

```
gcccaggtta gctttctgca ggtgttccac cacgcaacga tcggcatggt gtggtcgttc    600
cttcttcagc gtggctgggg ctcgggcacc gccgcgtacg gtgctttcat caactcggtc    660
acgcacgtga tcatgtactc gcactacttt gccacctcgc tcaacatcaa caacccgttc    720
aagcggtaca tcacgagctt ccagctcgcc cagtttgcaa gctgcatcgt gcatgcccta    780
ctggtgcttg ccttcgagga ggtgtacccg ctcgagtacg cttacctgca gatcagctac    840
cacatcatca tgctctacct gttcggacgc gcatgaact  ggagcccga gtggtgcacc    900 ggtgagatcg acggccttga cgccccaagc gcccccacca agtccgagta a              951
```

```
<210> SEQ ID NO 18
<211> LENGTH: 38
<212> TYPE: DNA
<213> ORGANISM: Artificial
<220> FEATURE:
<223> OTHER INFORMATION: primer

<400> SEQUENCE: 18
ataagcttaa aatgtctagc aacatgagcg cgtggggc                              38

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
tgtctagaac gcgcggacgg tcgcgaaa                                         28

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20
taaagcttaa aatgtctacg cgcacctcga agagcgctcc                            40

<210> SEQ ID NO 21
<211> LENGTH: 31
<212> TYPE: DNA
<213> ORGANISM: Artificial
<220> FEATURE:
<223> OTHER INFORMATION: primer

<400> SEQUENCE: 21
catctagact cggacttggt gggggcgctt g                                     31

<210> SEQ ID NO 22
<211> LENGTH: 949
<212> TYPE: DNA
<213> ORGANISM: Artificial
<220> FEATURE:
<223> OTHER INFORMATION: cDNA (TaELO1 coding region)

<400> SEQUENCE: 22
ataagcttaa aatgacgagc aacatgagcg cgtggggcgt cgccgtcgac cagacgcagc     60
aggtcgtcga ccagatcatg ggcggcgccg agccgtacaa gctgacagaa gggcgcatga    120
cgaacgtcga gacgatgctg gcgatcgagt gcggctacgc cgccatgctg ctgttcctga    180
ccccgatcat gaagcaggcc gagaagccct tcgagctcaa gtccttcaag ctcgcccaca    240
```

```
acctgttcct gttcgtcctg tccgcctaca tgtgcctcga gaccgtccgc caggcctacc      300
ttgcgggcta ctcggtgttc ggcaacgaca tggagaaggg cagcgagccg cacgcgcacg      360
gcatggccca atcgtgtgg atcttttacg tgtccaaggc gtacgagttc gtggacacgc       420
tgatcatgat cctgtgcaaa aagttcaacc aggtctccgt cctgcacgtg taccaccacg      480
ccaccatctt tgctatctgg tttatgatcg ccaagtacgc cccgggcggc gacgcatact      540
ttagcgtcat cctgaactcg ttcgtgcaca ccgtcatgta cgcgtactac ttcttctcgt      600
cgcagggctt cgggttcgtc aagccgatca agccgtacat cacctcgctg cagatgacgc      660
agttcatggc gatgctcgtg cagtcgctgt acgactacct ttacccgtgc gactacccgc      720
aggggctcgt caagctcctc ggcgtgtaca tgctcaccct gcttgcgctc ttcggcaact      780
ttttcgtgca gagctacctc aagaagtcga acaagcccaa ggccaagtcg gcctaagccg      840
acccgctcgc cggcaaccga gcagcaccta ggcgcatctc ggcccggaac cttttcgacc      900
tgctgtggag cgcgcgacgc gtttcgcgac cgtccgcgcg ttctagaca                  949

<210> SEQ ID NO 23
<211> LENGTH: 967
<212> TYPE: DNA
<213> ORGANISM: Artificial
<220> FEATURE:
<223> OTHER INFORMATION: cDNA (TaELO2 coding region)

<400> SEQUENCE: 23
taaagcttaa aatggcgacg cgcacctcga agagcgctcc ggcggtttcc aagtcggcca       60
aggttgccgc gccggcgaag aagcggtcgg tcgacaggag cgacggtttc ttccgcacgt      120
tcaacctgtg cgccctgtac gggtctgccc tcgcctatgc gtacaagcac ggccggtgg       180 acaatgacgg ccaggggctg tactttcaca agtcgcccat gtacgcgttc gccgtgtcgg      240
acgtcatgac cttcggcgcg ccgctgatgt acgtgctcgg tgtgatgctg ctcagcaggt      300
acatggcgga caaaaagccc ctgactggct tcatcaagac ctacatccag cccgtctaca      360
acgtggtcca atcgcggtg tgcggctgga tggtgtgggg cctctggccg caggtcgacc      420
tggccaacgg caaccctttc ggcctcaaca agtcgcgcga ctcgaacatc gagttttttcg      480 tgttcgtgca cctcctgaca aagtttctcg actggagcga cacgttcatg atgatcctca      540
agaaaaacta cgcccaggtt agctttctgc aggtgttcca ccacgcaacg atcggcatgg      600
tgtggtcgtt ccttcttcag cgtggctggg gctcgggcac cgccgcgtac ggtgctttca      660
tcaactcggt cacgcacgtg atcatgtact cgcactactt tgccacctcg ctcaacatca      720
acaacccgtt caagcggtac atcacgagct ccagctcgc ccagtttgca agctgcatcg       780
tgcatgccct actggtgctt gccttcgagg aggtgtaccc gctcgagtac gcttacctgc      840
agatcagcta ccacatcatc atgctctacc tgttcggacg ccgcatgaac tggagccccg      900
agtggtgcac cggtgagatc gacggccttg acgcccaag cgcccccacc aagtccgagt      960
ctagatg                                                               967

<210> SEQ ID NO 24
<211> LENGTH: 1122
<212> TYPE: DNA
<213> ORGANISM: Artificial
<220> FEATURE:
<223> OTHER INFORMATION: cDNA (TaELO2 ORF upstream region)

<400> SEQUENCE: 24
```

```
cgttagaacg cgtaatacga ctcactatag ggatatcccc cgcgaggcga tggctgctcc      60
gacgacgtgg gctggcgacg tcgctcgcaa aggcgttccg caaccgcgcg ttccgctgta     120
acgagaccgt tttccctgcg ctgctgggtg gacctagcgc gtgtgtcacc tgccggcccc     180
cgttgcgtgc aaccgaattg atcgataata gaattacata acaaacaact tgctggatga     240
gtacaagacc agcgtagtgt ggctgtggga cgttgaacgg agcgggtcct gtgacggcgc     300
agaaaggaac tccgcccgag gtgaaacccc gatgcgcagg actctgcggc cacagcccct     360
ccgccagtat tccactaaaa atccgccccc tttgacaaag atcgcaaccc cgtcccatca     420
actcctcaca ataggctttc cactggcgga aacgtccccg gcacaggagt gcctcccgcg     480
gttctgcgca tacggctgac cactacgcag cgcgatatcc tccatccgcg tatatatccg     540
taaacaacgg aacattctcc ctctcaacga ggcgtggttt tcgaagccat gcctttcttc     600
cttcctactt gccttccttc tttctttctt tctttccttc ttttgcaagc gtgcgcgaac     660
ttgaaggtac tacttacact tgacagagag agatagagac ggcaattcga ccaagtactt     720
tccacgattt ttttttttt tgttttggtc gctttcgttg gtcgtgcatg atggatggcc     780
gggattttta caattggatg cgccaggctg ccacgcatgc cgtgacgctc gctcgcggcg     840
actcatgatg cttgccagtg gcagtgcatc cagctcttcc ctctgctcgt cgtgtactca     900
ctggcgatgc tctcggcgct cgttcaaggg ccatcgatcg atcgatcgat cgatcgatcg     960
atcaatcacg tttggtggac tcggcagacc ccgaacgtgt ttctcccagg acgtgccgct    1020
gtcgctcgct gatccacccg aagcgcggtc ggctggcacg gtcgctcggc tggaagttga    1080
gtagtttgct ttctgttgct gcgctgcttt gtaaacgcga cc                       1122

<210> SEQ ID NO 25
<211> LENGTH: 1204
<212> TYPE: DNA
<213> ORGANISM: Artificial
<220> FEATURE:
<223> OTHER INFORMATION: cDNA (TaELO2 downstream region)

<400> SEQUENCE: 25
acctgtttcc ggctggctcc cgagccatgc ttaccatgaa tgaacctgca acagtctga       60 ggtccttgtg caaaccgctc agtgggacgt cgacgaagaa agaaacaatg tgtactcgtc     120
ttgctctgct cccgcgccgt tttttatcgt tgttgagacc tctcgcgcag tttttgggaat    180 caaccaaaac aagagcccgg cgtcagcgtt tgcttcgccc tcggctgcac tcgctcggca    240
cgcaggtata actgggtgag taccaagccc gcatttgtc tgtccgcgat ccgcgcacgc     300
tgcgggtcag gacgacatcg cgctgcacgt cacagtgggt ccctttgac gtggctgcgg    360 cgatgaggag gcttggctcg gcttcatggc aaggcaacag actcgcttcc aggacgcgca    420
cgacgagcag cgctgctttg atcgaccttg cctgcgtcac cgcctcggct gctttgatcg    480
atcgttgtca ccggccgagt gaccgcgaac gcattgcccg cacggctcgg ctcggctcgg    540
accggaccgg ctcgccttgg cggcgcggcg cgatggcgac ccagacgcga ccggagccgc    600
gcgcggagga caaggccatg ttcatcttcg ggctcgggta cgttgggagc aggctcgcca    660
accagctggc ggaacagggg tggcgcgtcg cggggtcggt gagggagctc gggcgcgagg    720
acgactttgc cgagttcgaa aagtccaagc tgagcggcaa ggtgcaggtg ttccgactcc    780
cgcttgaggg cgaggacaac acgcccgctc gcgcgcggga gatacttagc gggtaccagc    840
acctgctgtt cacggcgcca gtggaccgcg cccggaactg tgaccccttc ttgggcgacc    900
ccgttctcgg ccccgtgatc gtcgagctag cagaggaggg ccgcatcgac tgggccggct    960
```

```
atctctcaac cacttcggtc tacggcaacc acgacggcga gtgggtggac gagaccacgc    1020
cgctcatgcc cacgctcaaa cgcggcgagc agcgcgtcat ggtggagcgc gccttcctgt    1080
acgagtcggg cctcccggcc catatctttc ggctgccagg aatctacggc ccagggcgcg    1140
gcccgatatc acgaattctc tccctatagt gagtcgtatt acgcgttcta acgacaatat    1200
gtac                                                                 1204

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
ctcccgggtg gacctagcgc gtgtgtcacc t                                   31

<210> SEQ ID NO 27
<211> LENGTH: 25
<212> TYPE: DNA
<213> ORGANISM: Artificial
<220> FEATURE:
<223> OTHER INFORMATION: primer

<400> SEQUENCE: 27
ggtcgcgttt acaaagcagc gcagc                                          25

<210> SEQ ID NO 28
<211> LENGTH: 52
<212> TYPE: DNA
<213> ORGANISM: Artificial
<220> FEATURE:
<223> OTHER INFORMATION: primer

<400> SEQUENCE: 28
gctgcgctgc tttgtaaacg cgaccatgat tgaacaggac ggccttcacg ct            52

<210> SEQ ID NO 29
<211> LENGTH: 52
<212> TYPE: DNA
<213> ORGANISM: Artificial
<220> FEATURE:
<223> OTHER INFORMATION: primer

<400> SEQUENCE: 29
tcgggagcca gccggaaaca ggttcaaaag aactcgtcca ggaggcggta ga            52

<210> SEQ ID NO 30
<211> LENGTH: 23
<212> TYPE: DNA
<213> ORGANISM: Artificial
<220> FEATURE:
<223> OTHER INFORMATION: primer

<400> SEQUENCE: 30
acctgtttcc ggctggctcc cga                                            23

<210> SEQ ID NO 31
<211> LENGTH: 27
<212> TYPE: DNA
<213> ORGANISM: Artificial
<220> FEATURE:
<223> OTHER INFORMATION: primer
```

<400> SEQUENCE: 31
atcccggggc cgagaacggg gtcgccc    27

<210> SEQ ID NO 32
<211> LENGTH: 2696
<212> TYPE: DNA
<213> ORGANISM: Artificial
<220> FEATURE:
<223> OTHER INFORMATION: cDNA (TaELO2 ORF upstream/Neor/TaELO2 ORF downstream)

<400> SEQUENCE: 32

| | | | | | |
|---|---|---|---|---|---|
| ctcccgggtg | gacctagcgc | gtgtgtcacc | tgccggcccc | cgttgcgtgc | aaccgaattg | 60 |
| atcgataata | gaattacata | acaaacaact | tgctggatga | gtacaagacc | agcgtagtgt | 120 |
| ggctgtggga | cgttgaacgg | agcgggtcct | gtgatggcgc | agaaaggaac | tccgcccgag | 180 |
| gtgaaacccc | gatgcgcagg | actctgcggc | cacagcccct | ccgccagtat | tccactaaaa | 240 |
| atccgccccc | tttgacaaag | atcgcaaccc | cgtcccatca | actcctcaca | ataggctttc | 300 |
| cactggcgga | aacgtccccg | gcacaggagt | gcctcccgcg | gttctgcgca | tacggctgac | 360 |
| cactacgcag | cgcgatatcc | tccatccgcg | tatatatccg | taaacaacgg | aacattctcc | 420 |
| ctctcaacga | ggcgtggttt | tcgaagccat | gcctttcttc | cttcctactt | gccttccttc | 480 |
| tttctttctt | tctttccttc | ttttgcaagc | gtgcgcgaac | ttgaaggtac | tacttacact | 540 |
| tgacagagag | agatagagac | ggcaattcga | ccaagtactt | tccacgattt | tttttttttt | 600 |
| tgttttggtc | gctttcgttg | gtcgtgcatg | atggatggcc | gggatttttta | caattggatg | 660 |
| cgccaggctg | ccacgcatgc | cgtgacgctt | gctcgcggcg | actcatgatg | cttgccagtg | 720 |
| gcagtgcatc | cagctcttcc | ctctgctcgt | cgtgtactca | ctggcgatgc | tctcggcgct | 780 |
| cgttcaaggg | ccatcgatcg | atcgatcgat | cgatcgatcg | atcaatcacg | tttggtggac | 840 |
| tcggcagacc | ccgaacgtgt | ttctcccagg | acgcgccgct | gtcgctcgct | gatccacccg | 900 |
| aagcgcggtc | ggctggcacg | gtcgctcggc | tggaagttga | gtagtttgct | ttctgttgct | 960 |
| gcgctgcttt | gtaaacgcga | ccatgattga | acaggacggc | cttcacgctg | gctcgcccgc | 1020 |
| tgcttgggtg | gaacggctgt | tcggctacga | ctgggctcag | cagacgatcg | gctgctcgga | 1080 |
| cgcggccgtg | ttccgcctta | gcgcgcaggg | ccggccggtc | ctgtttgtca | agaccgacct | 1140 |
| tagcggcgcc | ctcaacgagc | tccaggacga | agctgcccgc | tcagctggc | ttgccacgac | 1200 |
| gggggttccg | tgcgccgctg | tgctcgacgt | cgtcaccgaa | gccggccgcg | actggctgct | 1260 |
| cctcggggaa | gtgcccggcc | aggacctcct | cagcagccac | ctcgcgcccg | ctgagaaggt | 1320 |
| gtccatcatg | gccgacgcca | tgcgccgcct | gcacaccctc | gaccccgcca | cctgccccatt | 1380 |
| cgaccaccag | gcgaagcaca | ggatcgaacg | cgcccgcacg | cggatggagg | ctggcctcgt | 1440 |
| cgaccaagac | gacctcgacg | aggagcacca | gggcctcgcg | ccggcggaac | tgttcgccag | 1500 |
| gcttaaggct | aggatgccgg | acggcgagga | cctcgtggtc | acgcacgcg | acgcctgcct | 1560 |
| ccccaacatc | atggtcgaga | acggccgctt | ctcgggcttt | atcgactgcg | ggcgcctggg | 1620 |
| cgtggcggac | cgctaccaag | acatcgcgct | cgccacgcgg | gacatcgccg | aggagcttgg | 1680 |
| cggcgagtgg | gccgaccgct | ttctcgtgct | ctacggcatc | gccgcccgg | acagccagag | 1740 |
| gattgcgttc | taccgcctcc | tggacgagtt | cttttgaacc | tgtttccggc | tggctcccga | 1800 |
| gccatgctta | ccatgaatga | acctgcaaac | agtctgaggt | ccttgtgcaa | accgctcagt | 1860 |
| gggacgtcga | cgaagaaaga | aacaatgtgt | actcgtcttg | ctctgctccc | gcgccgtttt | 1920 |

```
ttatcgttgt tgagacctct cgcgcagttt tgggaatcaa ccaaaacaag agcccggcgt    1980
cagcgtttgc ttcgccctcg gctgcactcg ctcggcacgc aggtataact gggtgagtac    2040
caagccccgc atttgtctgt ccgcgatccg cgcacgctgc gggtcaggac gacatcgcgc    2100
tgcacgtcac agtgggtccc ttttgacgtg gctgcggcga tgaggaggct tggctcggct    2160
tcatggcaag gcaacagact cgcttccggg acgcgcacga cgagcagcgc tgctttgatc    2220
gaccttgcct gcgtcaccgc ctcggctgct ttgatcgatc gttgtcaccg gccgagtgac    2280
cgcgaacgca ttgcccgcac ggctcggctc ggcccggacc ggaccggctc gccttggcgg    2340
cgcggcgcga tggcgaccca gacgcggccg gagccgcgcg cggaggacaa ggccatgttc    2400
atcttcgggc tcgggtacgt tgggagcagg ctcgccaacc agctggcgga acaggggtgg    2460
cgcgtcgcgg ggtcggtgag ggagctcggg cgcgaggacg actttgccga gttcgaaaag    2520
tccaagctga gcggcaaggt gcaggtgttc cgactcccgc ttgagggcga ggacaacacg    2580
cccgctcgcg cgcgggagat acttagcggg taccagcacc tgctgttcac ggcgccagtg    2640
gaccgcgccc ggaactgtga ccccttcttg ggcgaccccg ttctcggccc cgggat        2696
```

<210> SEQ ID NO 33
<211> LENGTH: 30
<212> TYPE: DNA
<213> ORGANISM: Artificial
<220> FEATURE:
<223> OTHER INFORMATION: primer
<400> SEQUENCE: 33
ggatatcccc cgcgaggcga tggctgctcc                                       30

<210> SEQ ID NO 34
<211> LENGTH: 30
<212> TYPE: DNA
<213> ORGANISM: Artificial
<220> FEATURE:
<223> OTHER INFORMATION: primer
<400> SEQUENCE: 34
tgatatcggg ccgcgccctg ggccgtagat                                       30

<210> SEQ ID NO 35
<211> LENGTH: 25
<212> TYPE: DNA
<213> ORGANISM: Artificial
<220> FEATURE:
<223> OTHER INFORMATION: primer
<400> SEQUENCE: 35
gtacgtgctc ggtgtgatgc tgctc                                            25

<210> SEQ ID NO 36
<211> LENGTH: 24
<212> TYPE: DNA
<213> ORGANISM: Artificial
<220> FEATURE:
<223> OTHER INFORMATION: primer
<400> SEQUENCE: 36
gcggcgtccg aacaggtaga gcat                                             24

<210> SEQ ID NO 37
<211> LENGTH: 35
<212> TYPE: DNA
<213> ORGANISM: Artificial

```
<220> FEATURE:
<223> OTHER INFORMATION: primer

<400> SEQUENCE: 37
atccgcgtat atatccgtaa acaacggaac attct                              35

<210> SEQ ID NO 38
<211> LENGTH: 26
<212> TYPE: DNA
<213> ORGANISM: Artificial
<220> FEATURE:
<223> OTHER INFORMATION: primer

<400> SEQUENCE: 38
cttcgggtgg atcagcgagc gacagc                                        26

<210> SEQ ID NO 39
<211> LENGTH: 27
<212> TYPE: DNA
<213> ORGANISM: Artificial
<220> FEATURE:
<223> OTHER INFORMATION: primer

<400> SEQUENCE: 39
gccgcagcgc ctggtgcacc cgccggg                                       27

<210> SEQ ID NO 40
<211> LENGTH: 59
<212> TYPE: DNA
<213> ORGANISM: Artificial
<220> FEATURE:
<223> OTHER INFORMATION: primer

<400> SEQUENCE: 40
tcgcgggtga gttcaggctt tttcatgttg gctagtgttg cttaggtcgc ttgctgctg    59

<210> SEQ ID NO 41
<211> LENGTH: 57
<212> TYPE: DNA
<213> ORGANISM: Artificial
<220> FEATURE:
<223> OTHER INFORMATION: primer

<400> SEQUENCE: 41
agcgacctaa gcaacactag gccaacatga aaaagcctga actcaccgcg acgtctg      57

<210> SEQ ID NO 42
<211> LENGTH: 29
<212> TYPE: DNA
<213> ORGANISM: Artificial
<220> FEATURE:
<223> OTHER INFORMATION: primer

<400> SEQUENCE: 42
ctattccttt gccctcggac gagtgctgg                                     29

<210> SEQ ID NO 43
<211> LENGTH: 1636
<212> TYPE: DNA
<213> ORGANISM: Artificial
<220> FEATURE:
<223> OTHER INFORMATION: cDNA (T. aureum ATCC 34304 ubiruitin
      promoter/Hygr)

<400> SEQUENCE: 43
gctagccgca gcgcctggtg cacccgccgg gcgttggttg tgtgtgctat ttactatgcc   60
```

```
taccgagaga gagagcggag cggatgcata ggaaatcggg ccacgcggga gggccatgcg      120
ttcgccccac acgccactta taccacgccc gctctctctc cggccggcag gcagcgcata      180
actataccga cgctggcagg cttggtagca actggcaggg acaactcgcg cgcgggtccc      240
ggtcgttcga tgtgccaacc cgagagaatc cagccagcag ggcggttggc ctcatcgccc      300
acctgctatg gtgcagcgaa ccaactcccg aagcggccgg ttccgcgatt ccctcttctg      360
aattctgaat tctgaactga ttccggagga gaaccctctg gaagcgcggg ttgcctctcc      420
agttctgccg aactagacag gggagtgagc atgatgagtg accctgacgc gtgagctgag      480
ctggttgctg gaatatagtc gctgaacgct gggctgtgtc acgcgtccac ttcgggcaga      540
ccccaaacga caagcagaac aagcaacacc agcagcagca agcgacctaa gcaacactag      600
ccaacatgaa aaagcctgaa ctcaccgcga cgtctgtcga gaagtttctg atcgaaaagt      660
tcgacagcgt ctccgacctg atgcagctct cggagggcga agaatctcgt gctttcagct      720
tcgatgtagg agggcgtgga tatgtcctgc gggtaaatag ctgcgccgat ggtttctaca      780
aagatcgtta tgtttatcgg cactttgcat cggccgcgct cccgattccg gaagtgcttg      840
acattgggga attcagcgag agcctgacct attgcatctc ccgccgtgca cagggtgtca      900
cgttgcaaga cctgcctgaa accgaactgc ccgctgttct gcagccggtc gcggaggcca      960
tggatgcgat cgctgcggcc gatcttagcc agacgagcgg gttcggccca ttcggaccgc     1020
aaggaatcgg tcaatacact acatggcgtg atttcatatg cgcgattgct gatccccatg     1080
tgtatcactg gcaaactgtg atggacgaca ccgtcagtgc gtccgtcgcg caggctctcg     1140
atgagctgat gctttgggcc gaggactgcc ccgaagtccg gcacctcgtg cacgcggatt     1200
tcggctccaa caatgtcctg acggacaatg gccgcataac agcggtcatt gactggagcg     1260
aggcgatgtt cggggattcc caatacgagg tcgccaacat cttcttctgg aggccgtggt     1320
tggcttgtat ggagcagcag acgcgctact cgagcggag gcatccggag cttgcaggat     1380
cgccgcggct ccgggcgtat atgctccgca ttggtcttga ccaactctat cagagcttgg     1440
ttgacggcaa tttcgatgat gcagcttggg cgcagggtcg atgcgacgca atcgtccgat     1500
ccggagccgg gactgtcggg cgtacacaaa tcgcccgcag aagcgcggcc gtctggaccg     1560
atggctgtgt agaagtactc gccgatagtg gaaaccgacg ccccagcact cgtccgaggg     1620
caaaggaata gtctag                                                     1636
```

<210> SEQ ID NO 44
<211> LENGTH: 33
<212> TYPE: DNA
<213> ORGANISM: Artificial
<220> FEATURE:
<223> OTHER INFORMATION: primer

<400> SEQUENCE: 44
gtgctagccg cagcgcctgg tgcacccgcc ggg        33

<210> SEQ ID NO 45
<211> LENGTH: 37
<212> TYPE: DNA
<213> ORGANISM: Artificial
<220> FEATURE:
<223> OTHER INFORMATION: primer

<400> SEQUENCE: 45
gttctagact attcctttgc cctcggacga gtgctgg        37

<210> SEQ ID NO 46
<211> LENGTH: 37
<212> TYPE: DNA
<213> ORGANISM: Artificial
<220> FEATURE:
<223> OTHER INFORMATION: primer

<400> SEQUENCE: 46
gttctagacc tgtttccggc tggctcccga gccatgc                                37

<210> SEQ ID NO 47
<211> LENGTH: 40
<212> TYPE: DNA
<213> ORGANISM: Artificial
<220> FEATURE:
<223> OTHER INFORMATION: primer

<400> SEQUENCE: 47
gtgctagcgg tcgcgtttac aaagcagcgc agcaacagaa                             40

<210> SEQ ID NO 48
<211> LENGTH: 3537
<212> TYPE: DNA
<213> ORGANISM: Artificial
<220> FEATURE:
<223> OTHER INFORMATION: cDNA (TaELO2 ORF upstream region/T. aureum ATCC
      34304 ubiquitin promotor/Hygr/TaELO2 ORF downstream region)

<400> SEQUENCE: 48
ctcccgggtg gacctagcgc gtgtgtcacc tgccggcccc cgttgcgtgc aaccgaattg        60
atcgataata gaattacata caaacaact tgctggatga gtacaagacc agcgtagtgt       120
ggctgtggga cgttgaacgg agcgggtcct gtgacggcgc agaaaggaac tccgcccgag      180
gtgaaacccc gatgcgcagg actctgcggc cacagcccct ccgccagtat tccactaaaa      240
atccgccccc tttgacaaag atcgcaaccc cgtcccatca actcctcaca ataggctttc      300
cactggcgga acgtccccg gcacaggagt gcctcccgcg gttctgcgca tacggctgac      360
cactacgcag cgcgatatcc tccatccgcg tatatatccg taaacaacgg aacattctcc      420
ctctcaacga ggcgtggttt tcgaagccat gcctttcttc cttcctactt gccttccttc      480
tttctttctt tctttctttc ttttgtaagc gtgcgcgaac ttgaaggtac tacttacact      540
tgacagagag agatagagac ggcaattcga ccaagtactt ccacgatttt tttttttttt      600
tgttttggtc gctttcgttg gtcgtgcatg atggatggcc gggatttta caattggatg       660 cgccaggctc ccacgcatgc cgtgacgctc gctcgcggcg actcatggtg cttgccagtg      720
gcagtgcatc cagctcttcc ctctgctcgt cgtgtactca ctggcgatgc tctcggcgct      780
cgttcaaggg ccatcgatcg atcgatcgat cgatcgatcg atcaatcacg tttggtggac      840
tcggcagacc ccgaacgtgt ttctcccagg acgtgccgct gtcgctcgct gatccacccg      900
aagcgcggtc ggctggcacg gtcgctcggc tggaagttga gtagtttgct ttctgttgct      960
gcgctgcttt gtaaacgcga ccgctagccg cagcgcctgg tgcacccgcc gggcgttggt     1020
tgtgtgtgct atttactatg cctaccgaga gagagagcgg agcggatgca taggaaatcg     1080
ggccacgcgg gagggccatg cgttcgcccc acacgccact tataccacgc ccgctctctc     1140
tccggccggc aggcagcgca taactatacc gacgctggca ggcttggtag caactggcag     1200
ggacaactcg cgcgcgggtc ccggtcgttc gatgtgccaa cccgagagaa tccagccagc     1260
agggcggttg gcctcatcgc ccacctgcta tggtgcagcg aaccaactcc cgaagcggcc     1320

-continued

```
ggttccgcga ttccctcttc tgaattctga attctgaact gattccggag gagaaccctc    1380
tggaagcgcg ggttgcctct ccagttctgc cgaactagac aggggagtga gcatgatgag    1440
tgaccctgac gcgtgagctg agctggttgc tggaatatag tcgctgaacg ctgggctgtg    1500
tcacgcgtcc acttcgggca gaccccaaac gacaagcaga acaagcaaca ccagcagcag    1560
caagcgacct aagcaacact agccaacatg aaaaagcctg aactcaccgc gacgtctgtc    1620
gagaagtttc tgatcgaaaa gttcgacagc gtctccgacc tgatgcagct ctcggagggc    1680
gaagaatctc gtgctttcag cttcgatgta ggagggcgtg gatatgtcct gcgggtaaat    1740
agctgcgccg atggtttcta caaagatcgt tatgtttatc ggcactttgc atcggccgcg    1800
ctcccgattc cggaagtgct tgacattggg gaattcagcg agagcctgac ctattgcatc    1860
tcccgccgtg cacagggtgt cacgttgcaa gacctgcctg aaaccgaact gcccgctgtt    1920
ctgcagccgg tcgcggaggc catggatgcg atcgctgcgg ccgatcttag ccagacgagc    1980
gggttcggcc cattcggacc gcaaggaatc ggtcaataca ctacatgcg tgatttcata    2040 tgcgcgattg ctgatcccca tgtgtatcac tggcaaactg tgatggacga caccgtcagt    2100
gcgtccgtcg cgcaggctct cgatgagctg atgctttggg ccgaggactg ccccgaagtc    2160
cggcacctcg tgcacgcgga tttcggctcc aacaatgtcc tgacggacaa tggccgcata    2220
acagcggtca ttgactggag cgaggcgatg ttcggggatt cccaatacga ggtcgccaac    2280
atcttcttct ggaggccgtg gttggcttgt atggagcagc agacgcgcta cttcgagcgg    2340
aggcatccgg agcttgcagg atcgccgcgg ctccgggcgt atatgctccg cattggtctt    2400
gaccaactct atcagagctt ggttgacggc aatttcgatg atgcagcttg gcgcagggt    2460 cgatgcgacg caatcgtccg atccggagcc gggactgtcg ggcgtacaca aatcgcccgc    2520
agaagcgcgg ccgtctggac cgatggctgt gtagaagtac tcgccgatag tggaaaccga    2580
cgccccagca ctcgtccgag ggcaaaggaa tagtctagac ctgtttccgg ctggctcccg    2640
agccatgctt accatgaatg aacctgcaaa cagtctgagg tccttgtgca aaccgctcag    2700
tgggacgtcg acgaagaaag aaacaatgtg tactcgtctt gctctgctcc cgcgccgttt    2760
tttatcgttg ttgagacctc tcgcgcagtt ttgggaatca accaaaacaa gagcccggcg    2820
tcagcgtttg cttcgccctc ggctgcactc gctcggcacg caggtataac tgggtgagta    2880
ccaagccccg catttgtctg tccgcgatcc gcgcacgctg cgggtcagga cgacatcgcg    2940
ctgcacgtca cagtgggtcc ctttttgacgt ggctgcggcg atgaggaggc ttggctcggc    3000
ttcatggcaa ggcaacagac tcgcttccgg gacgcgcacg acgagcagcg ctgctttgat    3060
cgaccttgcc tgcgtcaccg cctcggctgc tttgatcgat cgttgtcacc ggccgagtga    3120
ccgcgaacgc attgcccgca cggctcggct cggcccggac cggaccggct cgccttggcg    3180
gcgcggcgcg atggcgaccc agacgcggcc ggagccgcgc gcggaggaca aggccatgtt    3240
catcttcggg ctcgggtacg ttgggagcag gctcgccaac cagctggcgg aacaggggtg    3300
gcgcgtcgcg gggtcggtga gggagctcgg gcgcgaggac gactttgccg agttcgaaaa    3360
gtccaagctg agcggcaagg tgcaggtgtt ccgactcccg cttgagggcg aggacaacac    3420
gcccgctcgc gcgcgggaga tacttagcgg gtaccagcac ctgctgttca cggcgccagt    3480
ggaccgcgcc cggaactgtg accccttctt gggcgacccc gttctcggcc ccgggat      3537
```

<210> SEQ ID NO 49
<211> LENGTH: 30
<212> TYPE: DNA
<213> ORGANISM: Artificial

```
<220> FEATURE:
<223> OTHER INFORMATION: primer

<400> SEQUENCE: 49
atggcgacgc gcacctcgaa gagcgctccg                                        30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
aggatcatca tgaacgtgtc gctccagtcg                                        30

<210> SEQ ID NO 51
<211> LENGTH: 34
<212> TYPE: DNA
<213> ORGANISM: Artificial
<220> FEATURE:
<223> OTHER INFORMATION: primer

<400> SEQUENCE: 51
cagatctgga tccgcgaaat gaccgaccaa gcga                                   34

<210> SEQ ID NO 52
<211> LENGTH: 24
<212> TYPE: DNA
<213> ORGANISM: Artificial
<220> FEATURE:
<223> OTHER INFORMATION: primer

<400> SEQUENCE: 52
acgcaattaa tgtgagatct agct                                              24

<210> SEQ ID NO 53
<211> LENGTH: 342
<212> TYPE: DNA
<213> ORGANISM: Artificial
<220> FEATURE:
<223> OTHER INFORMATION: SV40 terminator

<400> SEQUENCE: 53
cagatctgga tccgcgaaat gaccgaccaa gcgacgccca acctgccatc acgagatttc       60
gattccaccg ccgccttcta tgaaaggttg ggcttcggaa tcgttttccg ggacgccggc      120
tggatgatcc tccagcgcgg ggatctcatg ctggagttct cgcccaccc caacttgttt      180 attgcagctt ataatggtta caaataaagc aatagcatca caaatttcac aaataaagca      240
tttttttcac tgcattctag ttgtggtttg tccaaactca tcaatgtatc ttatcatgtc      300
tgtataccgt cgacctctag ctagatctca cattaattgc gt                         342

<210> SEQ ID NO 54
<211> LENGTH: 619
<212> TYPE: DNA
<213> ORGANISM: Artificial
<220> FEATURE:
<223> OTHER INFORMATION: ubiquitin promoter

<400> SEQUENCE: 54
cccagatctg ccgcagcgcc tggtgcaccc gccgggcgtt gttggtgtgc tcttcttgcc       60
tccgagagag agagcggagc ggatgcatag gaaatcgggc cacgcgggag ggccatgcgt      120
```

```
tcgccccaca cgccactttc cacgcccgct ctctctccgg ccggcaggca gcgcataact    180
ctccgacgct ggcaggctgg tagcaactgg cagggacaac tcgcgcgcgg gtcccggtcg    240
ttcgatgtgc caacccgaga gaatccagcc agcagggcgg ttggcctcat cgcccacctg    300
ctatggtgca gcgaaccaac tcccgaagcg gccggttctg cgattccctc ttctgaattc    360
tgaattctga actgattccg gaggagaacc ctctggaagc gcgggttgcc tctccagttc    420
tgccgaacta gacaggggag tgagcagaga gtgaccctga cgcgggagcg agctggttgc    480
tggaaaagtc gcgaacgctg ggctgtgtca cgcgtccact tcgggcagac cccaaacgac    540
aagcagaaca gcaacaccca gcagcagcaa gcgacctaag caacactagc caacatgatt    600
gaacaggacg gccttcacg                                                619
```

<210> SEQ ID NO 55
<211> LENGTH: 36
<212> TYPE: DNA
<213> ORGANISM: Artificial
<220> FEATURE:
<223> OTHER INFORMATION: primer

<400> SEQUENCE: 55

```
cccagatctg ccgcagcgcc tggtgcaccc gccggg                              36
```

<210> SEQ ID NO 56
<211> LENGTH: 58
<212> TYPE: DNA
<213> ORGANISM: Artificial
<220> FEATURE:
<223> OTHER INFORMATION: primer

<400> SEQUENCE: 56

```
cgtgaaggcc gtcctgttca atcatgttgg ctagtgttgc ttaggtcgct tgctgctg      58
```

<210> SEQ ID NO 57
<211> LENGTH: 826
<212> TYPE: DNA
<213> ORGANISM: Artificial
<220> FEATURE:
<223> OTHER INFORMATION: Neomycin resistance gene (Neor)

<400> SEQUENCE: 57

```
agcgacctaa gcaacactag ccaacatgat tgaacaggac ggccttcacg ctggctcgcc    60
cgctgcttgg gtggaacggc tgttcggcta cgactgggct cagcagacga tcggctgctc    120
ggacgcggcc gtgttccgcc ttagcgcgca gggccggccg gtcctgtttg tcaagaccga    180
ccttagcggc gccctcaacg agctccagga cgaagctgcc cgcctcagct ggcttgccac    240
gacgggggtt ccgtgcgccg ctgtgctcga cgtcgtcacc gaagccggcc gcgactggct    300
gctcctcggg gaagtgcccg gccaggacct cctcagcagc cacctcgcgc ccgctgagaa    360
ggtgtccatc atggccgacg ccatgcgccg cctgcacacc ctcgaccccg ccacctgccc    420
cttcgaccac caggcgaagc acaggatcga acgcgcccgc acgcggatgg aggctggcct    480
cgtcgaccaa gacgacctcg acgaggagca ccagggcctc gcgccggcgg aactgttcgc    540
caggcttaag gctaggatgc cggacggcga ggacctcgtg gtcacgcacg gcgacgcctg    600 cctcccaac atcatggtcg agaacggccg cttctcgggc tttatcgact gcgggcgcct    660
gggcgtggcg gaccgctacc aagacatcgc gctcgccacg cgggacatcg ccgaggagct    720
tggcggcgag tgggccgacc gctttctcgt gctctacgac atcgccgccc ggacagcca    780 gaggattgcg ttctaccgcc tcctggacga gttcttttga gatctg                   826
```

<210> SEQ ID NO 58
<211> LENGTH: 54
<212> TYPE: DNA
<213> ORGANISM: Artificial
<220> FEATURE:
<223> OTHER INFORMATION: primer

<400> SEQUENCE: 58

```
agcgacctaa gcaacactag ccaacatgat tgaacaggac ggccttcacg ctgg        54
```

<210> SEQ ID NO 59
<211> LENGTH: 26
<212> TYPE: DNA
<213> ORGANISM: Artificial
<220> FEATURE:
<223> OTHER INFORMATION: primer

<400> SEQUENCE: 59

```
cagatctcaa aagaactcgt ccagga                                      26
```

<210> SEQ ID NO 60
<211> LENGTH: 1395
<212> TYPE: DNA
<213> ORGANISM: Artificial
<220> FEATURE:
<223> OTHER INFORMATION: fusion DNA (T. aureum ATCC 34304 ubiquitin
      promoter/Neor)

<400> SEQUENCE: 60

```
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt   120
tcgccccaca cgccactttc cacgcccgct ctctctccgg ccggcaggca gcgcataact   180
ctccgacgct ggcaggctgg tagcaactgg cagggacaac tcgcgcgcgg gtcccggtcg   240
ttcgatgtgc caacccgaga gaatccagcc agcaggcgg ttggcctcat cgcccacctg    300
ctatggtgca gcgaaccaac tcccgaagcg gccggttctg cgattccctc ttctgaattc   360
tgaattctga actgattccg gaggagaacc ctctggaagc gcgggttgcc tctccagttc   420
tgccgaacta gacaggggag tgagcagaga gtgaccctga cgcgggagcg agctggttgc   480
tggaaaagtc gcgaacgctg ggctgtgtca cgcgtccact cgggcagac cccaaaacgac    540
aagcagaaca agcaacacca gcagcagcaa gcgacctaag caacactagc caacatgatt   600
gaacaggacg gccttcacgc tggctcgccc gctgcttggg tggaacggct gttcggctac   660
gactgggctc agcagacgat cggctgctcg gacgcggccg tgttccgcct tagcgcgcag   720
ggccggccgg tcctgtttgt caagaccgac cttagcggcg ccctcaacga gctccaggac   780
gaagctgccc gcctcagctg gcttgccacg acggggttc cgtgcgccgc tgtgctcgac    840
gtcgtcaccg aagccggccg cgactggctg ctcctcgggg aagtgcccgg ccaggacctc   900
ctcagcagcc acctcgcgcc cgctgagaag gtgtccatca tggccgacgc catgcgccgc   960
ctgcacaccc tcgaccccgc cacctgcccc ttcgaccacc aggcgaagca caggatcgaa  1020
cgcgcccgca cgcggatgga ggctggcctc gtcgaccaag acgacctcga cgaggagcac  1080
cagggcctcg cgcggcgga actgttcgcc aggcttaagg ctaggatgcc ggacggcgag    1140
gacctcgtgg tcacgcacgg cgacgcctgc ctccccaaca tcatggtcga aacggccgc    1200
ttctcgggct ttatcgactg cgggcgcctg ggcgtggcgg accgctacca agacatcgcg   1260
ctcgccacgc gggacatcgc cgaggagctt ggcggcgagt gggccgaccg ctttctcgtg   1320
```

```
ctctacggca tcgccgcccc ggacagccag aggattgcgt tctaccgcct cctggacgag    1380
ttcttttgag atctg                                                    1395

<210> SEQ ID NO 61
<211> LENGTH: 617
<212> TYPE: DNA
<213> ORGANISM: Artificial
<220> FEATURE:
<223> OTHER INFORMATION: ubiquitin promoter

<400> SEQUENCE: 61
cccagatctg ccgcagcgcc tggtgcaccc gccgggcgtt gttgtgtgct cttcttgcct      60
ccgagagaga gagcggagcg gatgcatagg aaatcgggcc acgcgggagg gccatgcgtt     120
cgccccacac gccactttcc acgcccgctc tctctccggc cggcaggcag cgcataactc     180
tccgacgctg gcaggctggt agcaactggc aggacaact cgcgcgcggg tcccggtcgt      240
tcgatgtgcc aacccgagag aatccagcca gcagggcggt tggcctcatc gcccacctgc    300
tatggtgcag cgaaccaact cccgaagcgg ccggttctgc gattccctct tctgaattct    360
gaattctgaa ctgattccgg aggagaaccc tctggaagcg cgggttgcct ctccagttct    420
gccgaactag acaggggagt gagcagagag tgaccctgac gcggagcgag ctggttgctg    480
gaaaagtcgc gaacgctggg ctgtgtcacg cgtccacttc gggcagaccc caaacgacaa    540
gcagaacaag caacaccagc agcagcaagc gacctaagca acactagcca acatgaaaaa    600
gcctgaactc accgcga                                                   617

<210> SEQ ID NO 62
<211> LENGTH: 58
<212> TYPE: DNA
<213> ORGANISM: Artificial
<220> FEATURE:
<223> OTHER INFORMATION: primer

<400> SEQUENCE: 62
tcgcggtgag ttcaggcttt ttcatgttgg ctagtgttgc ttaggtcgct tgctgctg       58

<210> SEQ ID NO 63
<211> LENGTH: 1058
<212> TYPE: DNA
<213> ORGANISM: Artificial
<220> FEATURE:
<223> OTHER INFORMATION: Hygromycin resistance gene (Hygr)

<400> SEQUENCE: 63
agcgacctaa gcaacactag ccaacatgaa aaagcctgaa ctcaccgcga cgtctgtcga     60
gaagtttctg atcgaaaagt tcgacagcgt ctccgacctg atgcagctct cggagggcga    120
agaatctcgt gctttcagct tcgatgtagg agggcgtgga tatgtcctgc gggtaaatag    180
ctgcgccgat ggtttctaca agatcgtta tgtttatcgg cactttgcat cggccgcgct    240
cccgattccg gaagtgcttg acattgggga attcagcgag agcctgacct attgcatctc    300
ccgccgtgca cagggtgtca cgttgcaaga cctgcctgaa accgaactgc ccgctgttct    360
gcagccggtc gcggaggcca tggatgcgat cgctgcggcc gatcttagcc agacgagcgg    420
gttcggccca ttcggaccgc aaggaatcgg tcaatacact acatggcgtg atttcatatg    480
cgcgattgct gatccccatg tgtatcactg gcaaactgtg atggacgaca ccgtcagtgc    540
gtccgtcgcg caggctctcg atgagctgat gctttgggcc gaggactgcc ccgaagtccg    600
```

```
gcacctcgtg cacgcggatt tcggctccaa caatgtcctg acggacaatg ccgcataac      660 agcggtcatt gactggagcg aggcgatgtt cggggattcc caatacgagg tcgccaacat     720
cttcttctgg aggccgtggt tggcttgtat ggagcagcag acgcgctact tcgagcggag     780
gcatccggag cttgcaggat cgccgcggct ccgggcgtat atgctccgca ttggtcttga     840
ccaactctat cagagcttgg ttgacggcaa tttcgatgat gcagcttggg cgcagggtcg     900
atgcgacgca atcgtccgat ccggagccgg gactgtcggg cgtacacaaa tcgcccgcag     960
aagcgcggcc gtctggaccg atggctgtgt agaagtactc gccgatagtg gaaaccgacg    1020
ccccagcact cgtccgaggg caaaggaata gagatctg                            1058
```

```
<210> SEQ ID NO 64
<211> LENGTH: 56
<212> TYPE: DNA
<213> ORGANISM: Artificial
<220> FEATURE:
<223> OTHER INFORMATION: primer

<400> SEQUENCE: 64
agcgacctaa gcaacactag ccaacatgaa aaagcctgaa ctcaccgcga cgtctg          56
```

```
<210> SEQ ID NO 65
<211> LENGTH: 36
<212> TYPE: DNA
<213> ORGANISM: Artificial
<220> FEATURE:
<223> OTHER INFORMATION: primer

<400> SEQUENCE: 65
cagatctcta ttcctttgcc ctcggacgag tgctgg                                36
```

```
<210> SEQ ID NO 66
<211> LENGTH: 1625
<212> TYPE: DNA
<213> ORGANISM: Artificial
<220> FEATURE:
<223> OTHER INFORMATION: fusion DNA (Thraustochytrium aureum ATCC 34304
      ubiquitin promoter-pcDNA 3.1/Hygr)

<400> SEQUENCE: 66
cccagatctg ccgcagcgcc tggtgcaccc gccgggcgtt gttgtgtgct cttcttgcct      60
ccgagagaga gagcggagcg gatgcatagg aaatcgggcc acgcgggagg gccatgcgtt    120
cgccccacac gccactttcc acgcccgctc tctctccggc cggcaggcag cgcataactc    180
tccgacgctg gcaggctggt agcaactggc agggacaact cgcgcgcggg tcccggtcgt    240
tcgatgtgcc aacccgagag aatccagcca gcagggcggt tggcctcatc gcccacctgc    300
tatggtgcag cgaaccaact cccgaagcgg ccggttctgc gattccctct ctgaattct     360 gaattctgaa ctgattccgg aggagaaccc tctggaagcg cgggttgcct ctccagttct    420
gccgaactag acagggagt gagcagagag tgaccctgac gcgagcgag ctggttgctg      480 gaaaagtcgc gaacgctggg ctgtgtcacg cgtccacttc gggcagaccc caaacgacaa    540
gcagaacaag caacaccagc agcagcaagc gacctaagca acactagcca acatgaaaaa    600
gcctgaactc accgcgacgt ctgtcgagaa gtttctgatc gaaaagttcg acagcgtctc    660
cgacctgatg cagctctcgg agggcgaaga atctcgtgct ttcagcttcg atgtaggagg    720
gcgtggatat gtcctgcggg taaatagctg cgccgatggt ttctacaaag atcgttatgt    780
ttatcggcac tttgcatcgg ccgcgctccc gattccggaa gtgcttgaca ttggggaatt    840
```

-continued

```
cagcgagagc ctgacctatt gcatctcccg ccgtgcacag ggtgtcacgt tgcaagacct      900
gcctgaaacc gaactgcccg ctgttctgca gccggtcgcg gaggccatgg atgcgatcgc      960
tgcggccgat cttagccaga cgagcgggtt cggcccattc ggaccgcaag gaatcggtca     1020
atacactaca tggcgtgatt tcatatgcgc gattgctgat ccccatgtgt atcactggca     1080
aactgtgatg gacgacaccg tcagtgcgtc cgtcgcgcag gctctcgatg agctgatgct     1140
ttgggccgag gactgccccg aagtccggca cctcgtgcac gcggatttcg gctccaacaa     1200
tgtcctgacg gacaatggcc gcataacagc ggtcattgac tggagcgagg cgatgttcgg     1260
ggattcccaa tacgaggtcg ccaacatctt cttctggagg ccgtggttgg cttgtatgga     1320
gcagcagacg cgctacttcg agcggaggca tccggagctt gcaggatcgc cgcggctccg     1380
ggcgtatatg ctccgcattg gtcttgacca actctatcag agcttggttg acggcaattt     1440
cgatgatgca gcttgggcgc agggtcgatg cgacgcaatc gtccgatccg gagccgggac     1500
tgtcgggcgt acacaaatcg cccgcagaag cgcggccgtc tggaccgatg gctgtgtaga     1560
agtactcgcc gatagtggaa accgacgccc cagcactcgt ccgagggcaa aggaatagag     1620
atctg                                                                 1625

<210> SEQ ID NO 67
<211> LENGTH: 25
<212> TYPE: DNA
<213> ORGANISM: Artificial
<220> FEATURE:
<223> OTHER INFORMATION: primer

<400> SEQUENCE: 67
ccttcggcgc tcctcttatg tatgt                                             25

<210> SEQ ID NO 68
<211> LENGTH: 25
<212> TYPE: DNA
<213> ORGANISM: Artificial
<220> FEATURE:
<223> OTHER INFORMATION: primer

<400> SEQUENCE: 68
caatgcaaga ggcgaactgg gagag                                             25

<210> SEQ ID NO 69
<211> LENGTH: 25
<212> TYPE: DNA
<213> ORGANISM: Artificial
<220> FEATURE:
<223> OTHER INFORMATION: primer

<400> SEQUENCE: 69
tggggctctg gaaccgctgc ttacg                                             25

<210> SEQ ID NO 70
<211> LENGTH: 25
<212> TYPE: DNA
<213> ORGANISM: Artificial
<220> FEATURE:
<223> OTHER INFORMATION: primer

<400> SEQUENCE: 70
cttccagctc tcccagttcg cctct                                             25

<210> SEQ ID NO 71
<211> LENGTH: 25
```

```
<212> TYPE: DNA
<213> ORGANISM: Artificial
<220> FEATURE:
<223> OTHER INFORMATION: primer

<400> SEQUENCE: 71
cgggttgttg atgttgagcg aggtg                                          25

<210> SEQ ID NO 72
<211> LENGTH: 25
<212> TYPE: DNA
<213> ORGANISM: Artificial
<220> FEATURE:
<223> OTHER INFORMATION: primer

<400> SEQUENCE: 72
cccacgccat ccacgagcac accac                                          25

<210> SEQ ID NO 73
<211> LENGTH: 957
<212> TYPE: DNA
<213> ORGANISM: Artificial
<220> FEATURE:
<223> OTHER INFORMATION: cDNA (Parietichytrium genomic DNA contains C20
      elongase coding region)

<400> SEQUENCE: 73
cccggatcca tggcagctcg cgtggagaaa cagcaggcac ctgcgaaggc cgccaagaag       60
gtggggtcgc gtgtggaccg cagtgatggg ttctttcgca ctttcaacct ctgtgcgctg      120
tacgaaagcg cgttcgcgta cgcttacaac aatgggccag tggacaacga cggcaagggc      180
ttgtactttt caaagtctcc attctacgca ttcctcgtct cggacgccat gaccttcggc      240
gctcctctta tgtatgtaat tgctgtcatg gcactcagcc gatacatggc agacaagcag      300
cccctcactg gcttcattaa aagctacatt cagccagttt acaacattgt gcaaatcgtg      360
gtgtgctcgt ggatggcgtg gggccttttg ccacaggtgg acatcttcaa cctcaacccca      420 ttcggtctca caagcagcg tgatgccaac atcgagttct tgtcatggt ccacctcctg       480 acaaagttcc tcgactggac cgacaccttc atcatgattt tcaagaagaa ctatgcacag      540 gtctctttc tccaggtgtt ccaccatgcc accatcggaa tggtgtggtc cttcctcctc      600
cagcgcggct ggggctctgg aaccgctgct tacgagcgt tcatcaactc ggtcacccat      660
gtcatcatgt acactcatta ctttgtcacc tcgctcaaca tcaacaaccc gttcaagagg      720
tacatcaccg gcttccagct ctcccagttc gcctcttgca ttgtacatgc tctcctcgtc      780
cttgccttcg aggaggtgta ccccctcgag tacgcttacc ttcagatcag ctaccacatc      840
atcatgctct acctcttcgg caggagaatg aactggagcc ctctctggtg cactggcgag      900
gtcgacgggc ttgacgtcaa cgtcgagacc tccaagaagg ctcagtaagg atccggg          957

<210> SEQ ID NO 74
<211> LENGTH: 32
<212> TYPE: DNA
<213> ORGANISM: Artificial
<220> FEATURE:
<223> OTHER INFORMATION: primer

<400> SEQUENCE: 74
cccggatcca tggcagctcg cgtggagaaa ca                                    32

<210> SEQ ID NO 75
<211> LENGTH: 33
```

-continued

<212> TYPE: DNA
<213> ORGANISM: Artificial
<220> FEATURE:
<223> OTHER INFORMATION: primer

<400> SEQUENCE: 75
cccggatcct tactgagcct tcttggaggt ctc                                    33

<210> SEQ ID NO 76
<211> LENGTH: 936
<212> TYPE: DNA
<213> ORGANISM: Artificial
<220> FEATURE:
<223> OTHER INFORMATION: genomic DNA (Parietichytrium C20 elongase gene)

<400> SEQUENCE: 76
atggcagctc gcgtggagaa acagcaggca cctgcgaagg ccgccaagaa ggtggggtcg        60
cgtgtggacc gcagtgatgg gttctttcgc actttcaacc tctgtgcgct gtacggaagc      120
gcgttcgcgt acgcttacaa caatgggcca gtggacaacg acggcaaggg cttgtacttt      180
tcaaagtctc cattctacgc attcctcgtc tcggacgcca tgaccttcgg cgctcctctt      240
atgtatgtaa ttgctgtcat ggcactcagc cgatacatgg cagacaagca gcccctcact      300
ggcttcatta aaagctacat tcagccagtt tacaacattg tgcaaatcgt ggtgtgctcg      360
tggatggcgt ggggcctttt gccacaggtg gacatcttca acctcaaccc attcggtctc      420
aacaagcagc gtgatgccaa catcgagttc tttgtcatgg tccacctcct gacaaagttc      480
ctcgactgga ccgacacctt catcatgatt ttcaagaaga actatgcaca ggtctctttt      540
ctccaggtgt tccaccatgc caccatcgga atggtgtggt ccttcctcct ccagcgcggc      600
tggggctctg gaaccgctgc ttacggagcg ttcatcaact cggtcaccca tgtcatcatg      660
tacactcatt actttgtcac ctcgctcaac atcaacaacc cgttcaagag gtacatcacc      720
ggcttccagc tctcccagtt cgcctcttgc attgtacatg ctctcctcgt ccttgccttc      780
gaggaggtgt accccctcga gtacgcttac cttcagatca gctaccacat catcatgctc      840
tacctcttcg gcaggagaat gaactggagc cctctctggt gcactggcga ggtcgacggg      900
cttgacgtca acgtcgagac ctccaagaag gctcag                                936

<210> SEQ ID NO 77
<211> LENGTH: 312
<212> TYPE: PRT
<213> ORGANISM: Parietichytrium

<400> SEQUENCE: 77

Met Ala Ala Arg Val Glu Lys Gln Gln Ala Pro Ala Lys Ala Lys
1               5                   10                  15

Lys Val Gly Ser Arg Val Asp Arg Ser Asp Gly Phe Phe Arg Thr Phe
            20                  25                  30

Asn Leu Cys Ala Leu Tyr Gly Ser Ala Phe Ala Tyr Ala Tyr Asn Asn
        35                  40                  45

Gly Pro Val Asp Asn Asp Gly Lys Gly Leu Tyr Phe Ser Lys Ser Pro
    50                  55                  60

Phe Tyr Ala Phe Leu Val Ser Asp Ala Met Thr Phe Gly Ala Pro Leu
65                  70                  75                  80

Met Tyr Val Ile Ala Val Met Ala Leu Ser Arg Tyr Met Ala Asp Lys
                85                  90                  95

Gln Pro Leu Thr Gly Phe Ile Lys Ser Tyr Ile Gln Pro Val Tyr Asn
            100                 105                 110

```
Ile Val Gln Ile Val Val Cys Ser Trp Met Ala Trp Gly Leu Leu Pro
        115                 120                 125

Gln Val Asp Ile Phe Asn Leu Asn Pro Phe Gly Leu Asn Lys Gln Arg
    130                 135                 140

Asp Ala Asn Ile Glu Phe Phe Val Met Val His Leu Leu Thr Lys Phe
145                 150                 155                 160

Leu Asp Trp Thr Asp Thr Phe Ile Met Ile Phe Lys Lys Asn Tyr Ala
                165                 170                 175

Gln Val Ser Phe Leu Gln Val Phe His His Ala Thr Ile Gly Met Val
            180                 185                 190

Trp Ser Phe Leu Leu Gln Arg Gly Trp Gly Ser Gly Thr Ala Ala Tyr
        195                 200                 205

Gly Ala Phe Ile Asn Ser Val Thr His Val Ile Met Tyr Thr His Tyr
    210                 215                 220

Phe Val Thr Ser Leu Asn Ile Asn Asn Pro Phe Lys Arg Tyr Ile Thr
225                 230                 235                 240

Gly Phe Gln Leu Ser Gln Phe Ala Ser Cys Ile Val His Ala Leu Leu
                245                 250                 255

Val Leu Ala Phe Glu Glu Val Tyr Pro Leu Glu Tyr Ala Tyr Leu Gln
            260                 265                 270

Ile Ser Tyr His Ile Ile Met Leu Tyr Leu Phe Gly Arg Arg Met Asn
        275                 280                 285

Trp Ser Pro Leu Trp Cys Thr Gly Glu Val Asp Gly Leu Asp Val Asn
    290                 295                 300

Val Glu Thr Ser Lys Lys Ala Gln
305                 310

<210> SEQ ID NO 78
<211> LENGTH: 26
<212> TYPE: DNA
<213> ORGANISM: Artificial
<220> FEATURE:
<223> OTHER INFORMATION: primer

<400> SEQUENCE: 78
acaaagatct cgactggacc gacacc                                           26

<210> SEQ ID NO 79
<211> LENGTH: 27
<212> TYPE: DNA
<213> ORGANISM: Artificial
<220> FEATURE:
<223> OTHER INFORMATION: primer

<400> SEQUENCE: 79
agtcgagatc tttgtcagga ggtggac                                          27

<210> SEQ ID NO 80
<211> LENGTH: 935
<212> TYPE: DNA
<213> ORGANISM: Artificial
<220> FEATURE:
<223> OTHER INFORMATION: BglII inserted C20 elongase

<400> SEQUENCE: 80
atggcagctc gcgtggagaa acagcaggca cctgcgaagg ccgccaagaa ggtggggtcg      60
cgtgtggacc gcagtgatgg gttctttcgc actttcaacc tctgtgcgct gtacggaagc     120
gcgttcgcgt acgcttacaa caatgggcca gtggacaacg acggcaaggg cttgtacttt    180
```

```
tcaaagtctc cattctacgc attcctcgtc tcggacgcca tgaccttcgg cgctcctctt    240
atgtatgtaa ttgctgtcat ggcactcagc cgatacatgg cagacaagca gccctcact     300 ggcttcatta aaagctacat tcagccagtt tacaacattg tgcaaatcgt ggtgtgctcg    360
tggatggcgt ggggccttt gccacaggtg gacatcttca acctcaaccc attcggtctc     420
aacaagcagc gtgatgccaa catcgagttc tttgtcatgg tccacctcct gacaaagatc    480
tcgactggac cgacaccttc atcatgattt caagaagaa ctatgcacag gtctcttttc     540
tccaggtgtt ccaccatgcc accatcggaa tggtgtggtc cttcctcctc cagcgcggct    600
ggggctctgg aaccgctgct tacgagcgt tcatcaactc ggtcacccat gtcatcatgt     660
acactcatta ctttgtcacc tcgctcaaca tcaacaaccc gttcaagagg tacatcaccg    720
gcttccagct ctcccagttc gcctcttgca ttgtacatgc tctcctcgtc cttgccttcg    780
aggaggtgta cccctcgag tacgcttacc ttcagatcag ctaccacatc atcatgctct     840
acctcttcgg caggagaatg aactggagcc ctctctggtg cactggcgag gtcgacgggc    900
ttgacgtcaa cgtcgagacc tccaagaagg ctcag                               935
```

<210> SEQ ID NO 81
<211> LENGTH: 2661
<212> TYPE: DNA
<213> ORGANISM: Artificial
<220> FEATURE:
<223> OTHER INFORMATION: fusion DNA (Parietichytrium C20 elongase 5' region/SV40 terminator/Neor/ubiquitin promoter/Parietichytrium C20 elongase 3' region)

<400> SEQUENCE: 81

```
cccggatcca tggcagctcg cgtggagaaa cagcaggcac ctgcgaaggc cgccaagaag     60
gtggggtcgc gtgtggaccg cagtgatggg ttctttcgca ctttcaacct ctgtgcgctg    120
tacggaagcg cgttcgcgta cgcttacaac aatgggccag tggacaacga cggcaagggc    180
ttgtactttt caaagtctcc attctacgca ttcctcgtct cggacgccat gaccttcggc    240
gctcctctta tgtatgtaat tgctgtcatg gcactcagcc gatacatggc agacaagcag    300 ccctcactg gcttcattaa aagctacatt cagccagttt acaacattgt gcaaatcgtg    360
gtgtgctcgt ggatggcgtg gggccttttg ccacaggtgg acatcttcaa cctcaaccca    420
ttcggtctca acaagcagcg tgatgccaac atcgagttct ttgtcatggt ccacctcctg    480
acaaagatct agctagaggt cgacggtata cagacatgat aagatacatt gatgagtttg    540
gacaaaccac aactagaatg cagtgaaaaa atgctttat ttgtgaaatt tgtgatgcta    600
ttgctttatt tgtaaccatt ataagctgca ataaacaagt tggggtgggc gaagaactcc    660
agcatgagat ccccgcgctg gaggatcatc cagccgcgt cccggaaaac gattccgaag    720
cccaaccttt catagaaggc ggcggtggaa tcgaaatctc gtgatggcag ttgggcgtc    780 gcttggtcgg tcatttcgcg gatctcaaaa gaactcgtcc aggaggcggt agaacgcaat    840
cctctggctg tccggggcgg cgatgccgta gagcacgaga aagcggtcgg cccactcgcc    900
gccaagctcc tcggcgatgt cccgcgtggc gagcgcgatg tcttggtagc ggtccgccac    960
gcccaggcgc ccgcagtcga taagcccga gaagcggcc ttctcgacca tgatgttggg    1020
gaggcaggcg tcgccgtgcg tgaccacgag gtcctcgccg tccggcatcc tagccttaag    1080
cctggcgaac agttccgccg gcgcgaggcc ctggtgctcc tcgtcgaggt cgtcttggtc    1140
gacgaggcca gcctccatcc gcgtgcgggc gcgttcgatc ctgtgcttcg cctggtggtc    1200
```

```
gaaggggcag gtggcggggt cgagggtgtg caggcggcgc atggcgtcgg ccatgatgga    1260
caccttctca gcgggcgcga ggtggctgct gaggaggtcc tggccgggca cttccccgag    1320
gagcagccag tcgcggccgg cttcggtgac gacgtcgagc acagcggcgc acggaacccc    1380
cgtcgtggca agccagctga ggcgggcagc ttcgtcctgg agctcgttga gggcgccgct    1440
aaggtcggtc ttgacaaaca ggaccggccg gccctgcgcg ctaaggcgga cacggccgc     1500 gtccgagcag ccgatcgtct gctgagccca gtcgtagccg aacagccgtt ccacccaagc    1560
agcgggcgag ccagcgtgaa ggccgtcctg ttcaatcatg ttggctagtg ttgcttaggt    1620
cgcttgctgc tgctggtgtt gcttgttctg cttgtcgttt ggggtctgcc cgaagtggac    1680
gcgtgacaca gcccagcgtt cgcgactttt ccagcaacca gctcgctccg cgtcagggtc    1740
actctctgct cactccctg tctagttcgg cagaactgga gaggcaaccc gcgcttccag     1800
agggttctcc tccggaatca gttcagaatt cagaattcag aagagggaat cgcagaaccg    1860
gccgcttcgg gagttggttc gctgcaccat agcaggtggg cgatgaggcc aaccgccctg    1920
ctggctggat tctctcgggt tggcacatcg aacgaccggg accgcgcgc gagttgtccc     1980 tgccagttgc taccagcctg ccagcgtcgg agagttatgc gctgcctgcc ggccggagag    2040
agagcgggcg tggaaagtgg cgtgtggggc gaacgcatgg ccctcccgcg tggcccgatt    2100
tcctatgcat ccgctccgct ctctctctcg gaggcaagaa gagcacacca acaacgcccg    2160
gcgggtgcac caggcgctgc ggcagatcca gatctcgact ggaccgacac cttcatcatg    2220
attttcaaga gaactatgc acaggtctct tttctccagg tgttccacca tgccaccatc     2280
ggaatggtgt ggtccttcct cctccagcgc ggctgggggct ctggaaccgc tgcttacgga   2340
gcgttcatca actcggtcac ccatgtcatc atgtacactc attactttgt cacctcgctc    2400
aacatcaaca cccgttcaa gaggtacatc accggcttcc agctctccca gttcgcctct    2460
tgcattgtac atgctctcct cgtccttgcc ttcgaggagg tgtacccct cgagtacgct     2520 taccttcaga tcagctacca catcatcatg ctctacctct tcggcaggag aatgaactgg    2580
agccctctct ggtgcactgg cgaggtcgac gggcttgacg tcaacgtcga gacctccaag    2640
aaggctcagt aaggatccgg g                                             2661

<210> SEQ ID NO 82
<211> LENGTH: 2892
<212> TYPE: DNA
<213> ORGANISM: Artificial
<220> FEATURE:
<223> OTHER INFORMATION: fusion DNA (Parietichytrium C20 elongase 5'
      region/SV40 terminator/Hygr/ubiquitin promoter/Parietichytrium C20
      elongase 3' region)

<400> SEQUENCE: 82
cccggatcca tggcagctcg cgtggagaaa cagcaggcac ctgcgaaggc cgccaagaag      60
gtggggtcgc gtgtggaccg cagtgatggg ttctttcgca cttcaacct ctgtgcgctg      120 tacggaagcg cgttcgcgta cgcttacaac aatgggccag tggacaacga cggcaagggc     180
ttgtactttt caaagtctcc attctacgca ttcctcgtct cggacgccat gaccttcggc     240
gctcctctta tgtatgtaat tgctgtcatg gcactcagcc gatacatggc agacaagcag     300
cccctcactg gcttcattaa aagctacatt cagccagttt acaacattgt gcaaatcgtg     360
gtgtgctcgt ggatggcgtg gggccttttg ccacaggtgg acatcttcaa cctcaaccca    420
ttcggtctca acaagcagcg tgatgccaac atcgagttct ttgtcatggt ccacctcctg     480
acaaagatct agctagaggt cgacggtata cagacatgat aagatacatt gatgagtttg    540
```

```
gacaaaccac aactagaatg cagtgaaaaa aatgctttat ttgtgaaatt tgtgatgcta    600
ttgctttatt tgtaaccatt ataagctgca ataaacaagt tggggtgggc gaagaactcc    660
agcatgagat ccccgcgctg gaggatcatc cagccggcgt cccggaaaac gattccgaag    720
cccaacctttt catagaaggc ggcggtggaa tcgaaatctc gtgatggcag gttgggcgtc    780
gcttggtcgg tcatttcgcg gatctctatt cctttgccct cggacgagtg ctggggcgtc    840
ggtttccact atcggcgagt acttctacac agccatcggt ccagacgcc gcgcttctgc    900
gggcgatttg tgtacgcccg acagtcccgg ctccggatcg gacgattgcg tcgcatcgac    960
cctgcgccca agctgcatca tcgaaattgc cgtcaaccaa gctctgatag agttggtcaa   1020
gaccaatgcg gagcatatac gcccggagcc gcggcgatcc tgcaagctcc ggatgcctcc   1080
gctcgaagta gcgcgtctgc tgctccatac aagccaacca cggcctccag aagaagatgt   1140
tggcgacctc gtattgggaa tccccgaaca tcgcctcgct ccagtcaatg accgctgtta   1200
tgcggccatt gtccgtcagg acattgttgg agccgaaatc cgcgtgcacg aggtgccgga   1260
cttcggggca gtcctcggcc caaagcatca gctcatcgag agcctgcgcg acggacgcac   1320
tgacggtgtc gtccatcaca gtttgccagt gatacacatg gggatcagca atcgcgcata   1380
tgaaatcacg ccatgtagtg tattgaccga ttccttgcgg tccgaatggg ccgaacccgc   1440
tcgtctggct aagatcggcc gcagcgatcg catccatggc ctccgcgacc ggctgcagaa   1500
cagcgggcag ttcggtttca ggcaggtctt gcaacgtgac accctgtgca cggcgggaga   1560
tgcaataggt caggctctcg ctgaattccc caatgtcaag cacttccgga atcgggagcg   1620
cggccgatgc aaagtgccga taaacataac gatctttgta gaaaccatcg gcgcagctat   1680
ttacccgcag gacatatcca cgccctccta catcgaagct gaaagcacga gattcttcgc   1740
cctccgagag ctgcatcagg tcggagacgc tgtcgaactt ttcgatcaga aacttctcga   1800
cagacgtcgc ggtgagttca ggcttttttca tgttggctag tgttgcttag gtcgcttgct   1860
gctgctggtg ttgcttgttc tgcttgtcgt ttggggtctg cccgaagtgg acgcgtgaca   1920
cagcccagcg ttcgcgactt ttccagcaac cagctcgctc cgcgtcaggg tcactctctg   1980
ctcactcccc tgtctagttc ggcagaactg gagaggcaac ccgcgcttcc agagggttct   2040
cctccggaat cagttcagaa ttcagaattc agaagaggga atcgcagaac cggccgcttc   2100
gggagttggt tcgctgcacc atagcaggtg ggcgatgagg ccaaccgccc tgctggctgg   2160
attctctcgg gttggcacat cgaacgaccg ggacccgcgc gcgagttgtc cctgccagtt   2220
gctaccagcc tgccagcgtc ggagagttat gcgctgcctg ccggccggag agagagcggg   2280
cgtggaaagt ggcgtgtggg gcgaacgcat ggccctcccg cgtggcccga tttcctatgc   2340
atccgctccg ctctctctct cggaggcaag aagagcacac aacaacgccc ggcgggtgca   2400
ccaggcgctg cggcagatcc agatctcgac tggaccgaca ccttcatcat gattttcaag   2460
aagaactatg cacaggtctc tttttctccag gtgttccacc atgccaccat cggaatggtg   2520
tggtccttcc tcctccagcg cggctgggc tctggaaccg ctgcttacgg agcgttcatc   2580
aactcggtca cccatgtcat catgtacact cattactttg tcacctcgct caacatcaac   2640
aacccgttca agaggtacat caccggcttc cagctctccc agttcgcctc ttgcattgta   2700
catgctctcc tcgtccttgc cttcgaggag gtgtaccccc tcgagtacgc ttaccttcag   2760
atcagctacc acatcatcat gctctacctc ttcggcagga gaatgaactg gagccctctc   2820
tggtgcactg gcgaggtcga cgggcttgac gtcaacgtcg agacctccaa gaaggctcag   2880
```
taaggatccg gg                                                    2892

<210> SEQ ID NO 83
<211> LENGTH: 20
<212> TYPE: DNA
<213> ORGANISM: Artificial
<220> FEATURE:
<223> OTHER INFORMATION: primer

<400> SEQUENCE: 83
ggttgacggc aatttcgatg                                              20

<210> SEQ ID NO 84
<211> LENGTH: 22
<212> TYPE: DNA
<213> ORGANISM: Artificial
<220> FEATURE:
<223> OTHER INFORMATION: primer

<400> SEQUENCE: 84
cctcctacat cgaagctgaa ag                                           22

<210> SEQ ID NO 85
<211> LENGTH: 21
<212> TYPE: DNA
<213> ORGANISM: Artificial
<220> FEATURE:
<223> OTHER INFORMATION: primer

<400> SEQUENCE: 85
cttctcgggc tttatcgact g                                            21

<210> SEQ ID NO 86
<211> LENGTH: 22
<212> TYPE: DNA
<213> ORGANISM: Artificial
<220> FEATURE:
<223> OTHER INFORMATION: primer

<400> SEQUENCE: 86
taaggtcggt cttgacaaac ag                                           22

<210> SEQ ID NO 87
<211> LENGTH: 24
<212> TYPE: DNA
<213> ORGANISM: Artificial
<220> FEATURE:
<223> OTHER INFORMATION: primer

<400> SEQUENCE: 87
agtagtcccc gatttggtag ttga                                         24

<210> SEQ ID NO 88
<211> LENGTH: 22
<212> TYPE: DNA
<213> ORGANISM: Artificial
<220> FEATURE:
<223> OTHER INFORMATION: primer

<400> SEQUENCE: 88
ggcagagagc aaaaacacga gc                                           22

<210> SEQ ID NO 89
<211> LENGTH: 23
<212> TYPE: DNA
<213> ORGANISM: Artificial

<220> FEATURE:
<223> OTHER INFORMATION: primer

<400> SEQUENCE: 89
cgatgaaagg tcacagaaga gtc                                                 23

<210> SEQ ID NO 90
<211> LENGTH: 3181
<212> TYPE: DNA
<213> ORGANISM: Artificial
<220> FEATURE:
<223> OTHER INFORMATION: genomic DNA (T. aureum ATCC 34304 OrfA
      upstream)

<400> SEQUENCE: 90
aagcttttgc tctgcggctc tgcttgttcg aagccaacgc gcctcgcgaa gtatctgcaa         60
tctgcactcc tccggagagt aagtacgtaa gtacgtgcgt ggtgcgcgcg gattgcggtg        120
acgaaagaga gggttgggtt ggagatgctg cggcatgccg ggcgactcga gcagcatgtc        180
gccgcgagag gacctggaaa gctttcggtt tggtccgctg ccgaggcgag gctggcagag        240
tactgcgggc ggagctctcg agggaatatg ctcctcaaag acggcgtgcg cgtttgtgcc        300
cccgaatccg aatgcggaga gtcctgcgcg tttcggcccg ccgcgcgtat ccggccacgg        360
gagcgccgct gtgacgacga ggggatcaat ctgggtgcca gagtcaacgc ccagggtcgg        420
ggggatcacg ccgcgctcca ttgcaaggag aaccttgcac attcccgcaa agccggccgc        480
gacgagggtg tgtccgaagt tgcctttcgt ggacccgatc cggggggcttg cgccctcaaa      540 gcaggctttg acggcttgga gctcgacggt gtcgccctgc ggcgtgccgg tggcgtggca        600
ctcgacgtac tggacgtctc ggggcggcac gccgacgagc tcgtaggtgg ctttcaagca        660
ggcctcctcg cttggctggt gcggcttgag aggaagcccg cagcctgcgt tgctcaagct        720
ggccccaaga agcgtcccgt agatgtggtc tccgtcgcgc tcggcgtccg cgaggcgctt        780
gagcaccatc accgagccgc cctcgccggg cgtcagccct tgcgtgtccc gatgaaacgg        840
catcgagaca ccgttctcac cgactggcat cgcgtggaac gtgctaaacc cagtcaggat        900
gaagaagggc tctgggaagc acgtcgctcc gcacagcatc aagtcagcct cgcccgagag        960
gaggtggtcc tgagcgagtc gcagaacgta aagggccgag gcgcaggcgg cgtcgagcga       1020
gtagtgcagc gggccgaggc cgagctgtcc ggcgacgaag gaggctgggt cgcggtgggt       1080
cctcgggtcc ccgggcagcg ggtgaagcgc tctggttcgc gtcgaccagg gcgtttggtc       1140
cgcgaagcaa tgcttgccaa tccgcctctc agcatgggct tggtaaaggt tgagcagctc       1200
gccttgcagg ttgtccatcg ggaaggacag gcagccgctg acaatgccgc agcgcttgag       1260
ctgcgctggg tcgaacttgc cgccgtcgct gcgcctgtcc tgcgcgtctt gaagcgcagc       1320
cgcggcgagg ccgaggagca ggtcgtgctc gttgtcgact ttgggatcga tgcatccgta       1380
cctctcgttg cagaacgtat cggcgtactt tgacctctcg ggcgcatagt gctcttctcg       1440
tcgtgctgac ccgaggcgat cgtctgagat acaggcagag ttgattttgc cgttcatgag       1500
cgtgtcccag aacgcttcct tgccgcggca ccctgcatac tcgaccgcca tgcccacgac       1560
agcgatccgc gtgtcagggc atgggtccgc gcgcgccacc gagacgccct cgtcattcct       1620
cccgccctgg ttcatctctt tctgagcctt gtggcctctt gctttcgatt tcgatcggca       1680
gctccaacgc gcagctcgat ggccgattgc ttgctaaggc ggcgtgcaga caaccgctgc       1740
tcgaggttct gggcaagccg aggttcgccg cagggttcgt ggaggcactg ggatgttgtt       1800
ttgcggcagc tgcagcgctt gcggagcgag cggcgcagga cgacgttttc cgcgttcgcg       1860

```
cgaagctgcc tctcggctat tgtgacccgc cgccgacgct ggcagagacg tcgccgtcgg      1920
ccaccgcacc tcgagatcaa ttcgcagagg ctggcagagc cggtagcatt gcggcgtggc      1980
attgcgtgtg ccatgtgcat gtgtggcaaa caaatccagc caacctccga gtcgggcaga      2040
ccgaccgtgt gagttctcgc tgttgactga tctcttgatt gagcccaata atgatcacgg      2100
cctgagatcc ttcgcgctga gagatgcatg cgggcgctcg ttcctgggtt ggcgacccaa      2160
cggcgagtca cgtcgcccac tccgccacgc cccacacatg gccgccgatc cctcccgcca      2220
cacgaacggc gggccaagat cgcacgcctc cgtcggacga tgactgactg actgattggc      2280
tgacgacggc cgccctcgtg cgcggcgtcg ggcgtcgtcg caaaccaggc aggcaggcag      2340
gaaggaagga aggaagggcc aggccctggt gcgaaacgct ggcctgctcc gctgcaagcc      2400
aagccgcgct cgcaggtgta cttccgagtc ctcgcgatga ttaggcaagc ctgagcgagc      2460
acgtaagctg cactgcggct gttcaaccag agagagagtt ggctctcttg cgtcaaggcg      2520
gcgcgcagcc cacttgcgtc gcggctgagg gcccctggag gggaggaagg aggccggcga      2580
gcggcgagtg gcggccctca ctggcaccag gtcgcaggag gccaggcagc ccgccacgga      2640
caggaatcct cagggcgcag cagcgcacta cgtagtgcag agacgcagag cgggccggat      2700
ccgcagtgcg gtcgcgccac cccgccgcgc agctcgctcg cggacggggt ccgtggccgc      2760
gcgaaaacgg acacggtgtg ggagcggaca tgggatcgag aacgccgttc gccctgctcg      2820
cgctgccagc agcaggagcc gtccgaagga cgagcggccg gccgcctgtc ccccctccgc      2880
gcactcgaag cgcgcccggc agcgcccat tgcgtgcgcg gatggcgtct ggctggtcc       2940 ctctcgaggc gcttgctcgt gctcgccacg ccttgtccgc ctcctcgctg agcaagcgat      3000
gagctgagca cggaccgcct gcaagtgcaa gtgttcttgt gctgcagggc gccgaagaat      3060
tggattctgg cccatgatca gtttgattgg gccgagggag ggagggaggc tgggcgagtg      3120
ggcgacacca gcaagccgga ctgcgagagg ggcggggcag gatgtgagcg caggaaagtg      3180
a                                                                     3181
```

<210> SEQ ID NO 91
<211> LENGTH: 3377
<212> TYPE: DNA
<213> ORGANISM: Artificial
<220> FEATURE:
<223> OTHER INFORMATION: genomic DNA (T. aureum ATCC 34304 OrfA upstream genomic DNA fragment)

<400> SEQUENCE: 91

```
gaattcgatt aatacgactc actatagggga gaagctttg ctctgcggct ctgcttgttc       60
gaagccaacg cgcctcgcga agtatctgca atctgcactc ctccggagag taagtacgta      120
agtacgtgcg tggtgcgcgc ggattgcggt gacgaaagag agggttgggt tggagatgct      180
gcggcatgcc gggcgactcg agcagcatgt cgccgcgaga ggacctggaa agctttcggt      240
ttggtccgct gccgaggcga ggctggcaga gtactgcggg cggagctctc gagggaatat      300
gctcctcaaa gacggcgtgc gcgtttgtgc ccccgaatcc gaatgcggag agtcctgcgc      360
gtttcggccc gccgcgcgta tccgccacgg ggagcgccgc tgtgacgacg aggggatcaa      420
tctgggtgcc agagtcaacg cccagggtcg gggggatcac gccgcgctcc attgcaagga      480
gaaccttgca cattcccgca aagccggccg cgacgagggt gtgtccgaag ttgccttcg       540 tggacccgat ccgggggctt gcgccctcaa agcaggcttt gacggcttgg agctcgacgg      600
tgtcgccctg cggcgtgccg gtggcgtggc actcgacgta ctggacgtct cggggcggca      660
```

```
cgccgacgag ctcgtaggtg gctttcaagc aggcctcctc gcttggctgg tgcggcttga    720
gaggaagccc gcagcctgcg ttgctcaagc tggcccaag aagcgtcccg tagatgtggt    780
ctccgtcgcg ctcggcgtcc gcgaggcgct tgagcaccat caccgagccg ccctcgccgg    840
gcgtcagccc ttgcgtgtcc cgatgaaacg gcatcgagac accgttctca ccgactggca    900
tcgcgtggaa cgtgctaaac ccagtcagga tgaagaaggg ctctgggaag cacgtcgctc    960
cgcacagcat caagtcagcc tcgcccgaga ggaggtggtc ctgagcgagt cgcagaacgt   1020
aaagggccga ggcgcaggcg gcgtcgagcg agtagtgcag cgggccgagg ccgagctgtc   1080
cggcgacgaa ggaggctggg tcgcggtggg tcctcgggtc cccgggcagc gggtgaagcg   1140
ctctggttcg cgtcgaccag ggcgtttggt ccgcgaagca atgcttgcca atccgcctct   1200
cagcatgggc ttggtaaagg ttgagcagct cgccttgcag gttgtccatc gggaaggaca   1260
ggcagccgct gacaatgccg cagcgcttga gctgcgctgg gtcgaacttg ccgccgtcgc   1320
tgcgcctgtc ctgcgcgtct tgaagcgcag ccgcggcgag gccgaggagc aggtcgtgct   1380
cgttgtcgac tttgggatcg atgcatccgt acctctcgtt gcagaacgta tcggcgtact   1440
ttgacctctc gggcgcatag tgctcttctc gtcgtgctga cccgaggcga tcgtctgaga   1500
tacaggcaga gttgattttg ccgttcatga gcgtgtccca gaacgcttcc ttgccgcggc   1560
accctgcata ctcgaccgcc atgcccacga cagcgatccg cgtgtcaggg catgggtccg   1620
cgcgcgccac cgagacgccc tcgtcatttc tcccgccctg gttcatctct ttctgagcct   1680
tgtggcctct tgctttcgat ttcgatcggc agctccaacg cgcagctcga tggccgattg   1740
cttgctaagg cggcgtgcag acaaccgctg ctcgaggttc tgggcaagcc gaggttcgcc   1800
gcagggttcg tggaggcact gggatgttgt tttgcggcag ctgcagcgct gcggagcga   1860 gcggcgcagg acgacgtttt ccgcgttcgc gcgaagctgc ctctcggcta ttgtgacccg   1920
ccgccgacgc tggcagagac gtcgccgtcg gccaccgcac ctcgagatca attcgcagag   1980
gctggcagag ccggtagcat tgcggcgtgg cattgcgtgt gccatgtgca tgtgtggcaa   2040
acaaatccag ccaacctccg agtcgggcag accgaccgtg tgagttctcg ctgttgactg   2100
atctcttgat tgagcccaat aatgatcacg gcctgagatc cttcgcgctg agagatgcat   2160
gcgggcgctc gttcctgggt tggcgaccca acggcgagtc acgtcgccca ctccgccacg   2220 cccccacacat ggccgccgat ccctcccgcc acacgaacgg cgggccaaga tcgcacgcct   2280
ccgtcggacg atgactgact gactgattgg ctgacgacgg ccgccctcgt gcgcggcgtc   2340
gggcgtcgtc gcaaaccagg caggcaggca ggaaggaagg aaggaagggc caggccctgg   2400
tgcgaaacgc tggcctgctc cgctgcaagc caagccgcgc tcgcaggtgt acttccgagt   2460
cctcgcgatg attaggcaag cctgagcgag cacgtaagct gcactgcggc tgttcaacca   2520
gagagagagt tggctctctt gcgtcaaggc ggcgcgcagc ccacttgcgt cgcggctgag   2580
ggcccctgga ggggaggaag gaggccgcg agcggcgagt ggcggccctc actgcaccac   2640
ggtcgcagga ggccaggcag cccgccacgg acaggaatcc tcagggcgca gcagcgcact   2700
acgtagtgca gagacgcaga gcgggccgga tccgcagtgc ggtcgcgcca ccccgccgcg   2760
cagctcgctc gcgacggggt ccgtggccg cgcgaaaacg gacacggtgt gggagcggac   2820
atgggatcga gaacgccgtt cgccctgctc gcgctgccag cagcaggagc cgtccgaagg   2880
acgagcggcc ggccgcctgt ccccccctccg cgcactcgaa gcgcgcccgg cagcgcccca   2940
ttgcgtgcgc ggatggcgtc ttggctggtc cctctcgagg cgcttgctcg tgctcgccac   3000
```

```
gccttgtccg cctcctcgct gagcaagcga tgagctgagc acggaccgcc tgcaagtgca    3060
agtgttcttg tgctgcaggg cgccgaagaa ttggattctg cccatgatc agtttgattg    3120 ggccgaggga gggagggagg ctgggcgagt gggcgacacc agcaagccgg actgcgagag    3180
gggcggggca ggatgtgagc gcaggaaagt gacgcaagtg catccggcca tcattgggcc    3240
atcattgggc catcattggt gttttgggcc gcgctttgcg gatcgtccgg ccgatcaggt    3300
acgaggccac gaacctacgt cgtttgccgc gctcaggctg gttggttgca cttggactct    3360
tctgtgacct ttcatcg                                                  3377

<210> SEQ ID NO 92
<211> LENGTH: 21
<212> TYPE: DNA
<213> ORGANISM: Artificial
<220> FEATURE:
<223> OTHER INFORMATION: primer

<400> SEQUENCE: 92
cagggcgagc gagtgtggtt c                                             21

<210> SEQ ID NO 93
<211> LENGTH: 1160
<212> TYPE: DNA
<213> ORGANISM: Artificial
<220> FEATURE:
<223> OTHER INFORMATION: genomic DNA (T. aureum ATCC 34304 OrfA
      downstream)

<400> SEQUENCE: 93
tggctctcga ccaaagccga gtagagtact ctactcagta ctcttttcac ataccggcag     60
gcagtgttgc tgtgggattg gtccgggggc tcttctgcac gcggcctccg tcgcgcgcag    120
aaatgccccg tcactggctg cccaggaggc agccgaatcc ctctagctag ctagctaggc    180
tagagcgtct tttccgtagt ttttcacaaa gccagtatca catggataac gaacgaaggt    240
ttcgggctcg cgctcgcagg cgttaggacg aagttgatcg ccccacgtca cttcaaacga    300
gtgaaccaag atcacgttgc atctgctcgc aagatcttct tcttccacgc cgcatcgatg    360
cgatggattt caaactcttt tcagggcttt taggtgagta tggcagcgct gttgtgcgtgg   420 cagcgctgtt tgcgtggttg tactctctaa aggtgcttcc acgcatgcgc gcacaaaggg    480
gcatggcatg gttggcggcg cactctggcc ctcatttgaa gcagactatc gaagggtcca    540
gttggtactg cggcaggtcc ggcgagagca agcgcggcgg tcgctcccac tcgtccctgc    600
acagttgctg gactggcgac ggctggcgca cctgactacg agaagactcg agacgcacag    660
aggtagtcag ggacgaccga ccgcaaagca caaaccgctc caaaacggcc gcaccaggca    720
gggcagtaaa ctaaaaacga atgtacctcc atcgcgcgta tctgccgagc ctcctcccac    780
gcttcggctg ggcttgattc accagtgtcc gcaagctgaa ccgaccgtct tcgatgtcat    840
gaagcttggc gcggcattag tcagacgacg cggcacgcca ggattctgtc ggtttctggg    900
aaatgggcat ctatatagct gattccctct gtcatgaggc ggccttgttc tggccctggg    960
ccgccgttcg gatgatctat gatgtcgttg tacgcataaa gcttgtcgaa aacgtcggcc   1020
atgtcttcct cagagatgta accgagcggc gcgtcgtggc gattgatgcc gatgctacaa   1080
aagccgccga gttagctcga atgtcagatg cattgcgggc tggcccgcat ggcgcgggcg   1140
cagcagcgag aggttctaga                                              1160

<210> SEQ ID NO 94
```

<211> LENGTH: 1204
<212> TYPE: DNA
<213> ORGANISM: Artificial
<220> FEATURE:
<223> OTHER INFORMATION: genomic DNA (T. aureum ATCC 34304 OrfA downstream genomic DNA fragment)

<400> SEQUENCE: 94

```
cagggcgagc gagtgtggtt ctgaacaagg ctctttcgtt ttgatggctc tcgaccaaag      60
ccgagtagag tactctactc agtactcttt tcacataccg gcaggcagtg ttgctgtggg     120
attggtccgg gggctcttct gcacgcggcc tccgtcgcgc gcagaaatgc cccgtcactg     180
gctgcccagg aggcagccga atccctctag ctagctagct aggctagagc gtcttttccg     240
tagttttttca caaagccagt atcacatgga taacgaacga aggtttcggg ctcgcgctcg    300
caggcgttag gacgaagttg atcgccccac gtcacttcaa acgagtgaac caagatcacg     360
ttgcatctgc tcgcaagatc ttcttcttcc acgccgcatc gatgcgatgg atttcaaact     420
cttttcaggg cttttaggtg agtatggcag cgctgtttgc gtggcagcgc tgtttgcgtg     480
gttgtactct ctaaaggtgc ttccacgcat gcgcgcacaa aggggcatgg catggttggc     540
ggcgcactct ggccctcatt tgaagcagac tatcgaaggg tccagttggt actgcggcag     600
gtccggcgag agcaagcgcg gcggtcgctc ccactcgtcc ctgcacagtt gctggactgg     660
cgacggctgg cgcacctgac tacgagaaga ctcgagacgc acagaggtag tcagggacga     720
ccgaccgcaa agcacaaacc gctccaaaac ggccgcacca ggcagggcag taaactaaaa     780
acgaatgtac ctccatcgcg cgtatctgcc gagcctcctc ccacgcttcg gctgggcttg     840
attcaccagt gtccgcaagc tgaaccgacc gtcttcgatg tcatgaagct tggcgcggca     900
ttagtcagac gacgcggcac gccaggattc tgtcggtttc tgggaaatgg gcatctatat     960
agctgattcc ctctgtcatg aggcggcctt gttctggccc tgggccgccg ttcggatgat    1020
ctatgatgtc gttgtacgca taaagcttgt cgaaaacgtc ggccatgtct tcctcagaga    1080
tgtaaccgag cggcgcgtcg tggcgattga tgccgatgct acaaaagccg ccgagttagc    1140
tcgaatgtca gatgcattgc gggctggccc gcatggcgcg ggcgcagcag cgagaggttc    1200
taga                                                                  1204
```

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95

```
tgatgccgat gctacaaaag                                                  20
```

<210> SEQ ID NO 96
<211> LENGTH: 1488
<212> TYPE: DNA
<213> ORGANISM: Artificial
<220> FEATURE:
<223> OTHER INFORMATION: genomic DNA (T. aureum ATCC 34304 OrfA downstream genomic DNA fragment)

<400> SEQUENCE: 96

```
aagcttgtac ggtgaaaagc cctttggcgc agcccgaaac aagtcttgct tctcctgccc      60
cgtcaaactc gcaaactctg gcagcaactc ccgcacgctc tgtaccacgg cgaacccaag     120
ggcaggcacg cggtgaaacg acttgcatgc ttgcacaaca accccttgc cgacgtcgac      180
```

```
gcggtcgcct tcggagagcc caaacacagc gaacgccgga tccgcctgcg cctctgcatg      240
cgcctctgca tgcgcctcga catgcgcctc ggcctccgtg cctgcttgcc gggccggcgg      300
ggcagcagga agtgcgtggc cgaggtccat cgcatcaaag gctcgcttcg cggcgtgaaa      360
ggcctcgagc gcctccgccg gcaagtacac cttggtcttg cacttgagca tgctcctgat      420
ccgcgcgtag aggaagacgg ccgcgcagtg gtccaggtgc ccgtgcgaca agaacacgtg      480
ctccgccctc gccgcggcct tgtccggctc gtccccgagc gacccgcagt cgaactgcaa      540
gcagacccgc gagcccaggt ccacttgcag cgccgtgccg cagccggccc tcgactgccc      600
cgtcacgcgc acgtgcgagg ccatctcccg ccgcgagcct ggagcgccag agcctcctgc      660
tgctgccgtg ccgcctcggg gggcgcgagg agggtctcgc ctgatgcagc gcgcggggcc      720
gacgcagcag cgcgggtgga ggaagactgc gctgtgggcg gcggccctcg ggctgctgct      780
cttgtggctc ctgtccgtgc gctcgttcgt gcacggcgtg gcggacaggg aggcggacgc      840
cgtcgccccg cgcgagggcc ccagggcgcc ggcgccaaag aggactggcg ggaggaatga      900
tatgcccgct gagcctgccg ctggtaggcc cgcgcacagc tcgcctcgag ggacgcccga      960
cggcaacgcg gtcgagtgct ccacgaccaa gggcccgttc cgcgtggtcc tcacgcctag     1020
cctagcgccg aacgggacca agttttttcat cgggctggtg gaagcaggct atttcgacca     1080
aggcatcgcc ttctttcgcg tcaacaaggc catcacgcag ttcgggatca ccaagcgaag     1140
gccacgcgat gaggatccgt tcgtgcagtt cagaggcggg gcccagcgcg acgagaaccc     1200
tttcggtggc gtggaggatg acgaggagag tgtccatcgc aggcacatgc acccgtggcg     1260
gcgcggcacg attgcctcga taggcggctt ccactttgtt gtcacgatcc gcggggacaa     1320
aaagtaagtt cttgaatgtt gtgaagtgcg ccaactcgcg ttcggagcgg acctggaccg     1380
atattcagca atctagaacc tctcgctgct gcgcccgcgc catgcgggcc agcccgcaat     1440
gcatctgaca ttcgagctaa ctcggcggct tttgtagcat cggcatca                  1488
```

<210> SEQ ID NO 97
<211> LENGTH: 2551
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 97

```
tggctctcga ccaaagccga gtagagtact ctactcagta ctcttttcac ataccggcag       60
gcagtgttgc tgtgggattg gtccgggggc tcttctgcac gcggcctccg tcgcgcgcag      120
aaatgccccg tcactggctg cccaggaggc agccgaatcc ctctagctag ctagctaggc      180
tagagcgtct tttccgtagt ttttcacaaa gccagtatca catggataac gaacgaaggt      240
ttcgggctcg cgctcgcagg cgttaggacg aagttgatcg ccccacgtca cttcaaacga      300
gtgaaccaag atcacgttgc atctgctcgc aagatcttct tcttccacgc cgcatcgatg      360
cgatggattt caaactcttt tcagggcttt taggtgagta tggcagcgct gtttgcgtgg      420
cagcgctgtt tgcgtggttg tactctctaa aggtgcttcc acgcatgcgc gcacaaaggg      480
gcatggcatg gttggcggcg cactctggcc ctcatttgaa gcagactatc gaagggtcca      540
gttggtactg cggcaggtcc ggcgagagca agcgcggcgg tcgctcccac tcgtccctgc      600
acagttgctg gactgcgac ggctggcgca cctgactacg agaagactcg agacgcacag      660
aggtagtcag ggacgaccga ccgcaaagca caaaccgctc caaaacggcc gcaccaggca      720
```

```
gggcagtaaa ctaaaaacga atgtacctcc atcgcgcgta tctgccgagc ctcctcccac      780
gcttcggctg ggcttgattc accagtgtcc gcaagctgaa ccgaccgtct tcgatgtcat      840
gaagcttggc gcggcattag tcagacgacg cggcacgcca ggattctgtc ggtttctggg      900
aaatgggcat ctatatagct gattccctct gtcatgaggc ggccttgttc tggccctggg      960
ccgccgttcg gatgatctat gatgtcgttg tacgcataaa gcttgtcgaa aacgtcggcc     1020
atgtcttcct cagagatgta accgagcggc gcgtcgtggc gattgatgcc gatgctacaa     1080
aagccgccga gttagctcga atgtcagatg cattgcgggc tggcccgcat ggcgcgggcg     1140
cagcagcgag aggttctaga ttgctgaata tcggtccagg tccgctccga acgcgagttg     1200
gcgcacttca caacattcaa gaacttactt tttgtccccg cggatcgtga caacaaagtg     1260
gaagccgcct atcgaggcaa tcgtgccgcg ccgccacggg tgcatgtgcc tgcgatggac     1320
actctcctcg tcatcctcca cgccaccgaa agggttctcg tcgcgctggg ccccgcctct     1380
gaactgcacg aacggatcct catcgcgtgg ccttcgcttg gtgatcccga actgcgtgat     1440
ggccttgttg acgcgaaaga aggcgatgcc ttggtcgaaa tagcctgctt ccaccagccc     1500
gatgaaaaac ttggtcccgt tcggcgctag gctaggcgtg aggaccacgc ggaacgggcc     1560
cttggtcgtg gagcactcga ccgcgttgcc gtcgggcgtc cctcgaggcg agctgtgcgc     1620
gggcctacca gcggcaggct cagcgggcat atcattcctc ccgccagtcc tctttggcgc     1680
cggcgccctg gggccctcgc gcggggcgac ggcgtccgcc tccctgtccg ccacgccgtg     1740
cacgaacgag cgcacggaca ggagccacaa gagcagcagc ccgagggccg ccgcccacag     1800
cgcagtcttc ctccacccgc gctgctgcgt cggccccgcg cgctgcatca ggcgagaccc     1860
tcctcgcgcc ccccgaggcg gcacggcagc agcaggaggc tctggcgctc caggctcgcg     1920
gcgggagatg gcctcgcacg tccgcgtgac ggggcagtcg agggccggct gcggcacggc     1980
gctgcaagtg gacctgggct cgcgggtctg cttgcagttc gactgcgggt cgctcgggga     2040
cgagccggac aaggccgcgg cgaggcggag cacgtgttc ttgtcgcacg ggcacctgga     2100
ccactgcgcg gccgtcttcc tctacgcgcg gatcaggagc atgctcaagt gcaagaccaa     2160
ggtgtacttg ccggcggagg cgctcgaggc ctttcacgcc gcgaagcgag cctttgatgc     2220
gatggacctc ggccacgcac ttcctgctgc cccgccggcc cggcaagcag gcacggaggc     2280
cgaggcgcat gtcgaggcgc atgcagaggc gcatgcagag gcgcaggcgg atccggcgtt     2340
cgctgtgttt gggctctccg aaggcgaccg cgtcgacgtc ggcaaggggg ttgttgtgca     2400
agcatgcaag tcgtttcacc gcgtgcctgc ccttgggttc gccgtggtac agagcgtgcg     2460
ggagttgctg ccagagtttg cgagtttgac ggggcaggag aagcaagact tgtttcgggc     2520
tgcgccaaag ggcttttcac cgtacaagct t                                    2551
```

<210> SEQ ID NO 98
<211> LENGTH: 1835
<212> TYPE: DNA
<213> ORGANISM: Artificial
<220> FEATURE:
<223> OTHER INFORMATION: 18S rDNA (T. aureum ATCC 34304)

<400> SEQUENCE: 98

```
cgaatattcc tggttgatcc tgccagtagt catacgctta tctcaaagat taagccatgc       60
atgtctaagt ataaaggctt atactctgaa actgcgaacg gctcattata tcagtttatag     120 tttctttgat agtgtttttt ctacatggat acttgtggca aatctagaaa caatacatgc      180
```

```
gtacaggcct gactttgggg gagggctgca tttatttgac ttaagccaat accccctcggg      240 gttgttttgg tgattcagaa taactgagcg aatcgcatag ctttcgggcg gcgatgaatc      300
atttcaagtt tctgccccat cagctgtcga tggtagggta taggcctacc atggctgtca      360
cgggtgacgg agaattaggg ttcgattccg gagagggagc ctgagagacg gctaccacat      420
ccaaggaagg cagcaggcgc gtaaattact caatgttgac tcgacgaagt agtgacgaga      480
attaacaatg cggagcgctc agcgttttgc aattggaatg agagcaatgt aaaagcctca      540
tcgaggatcc attggagggc aagtctggtg ccagcagccg cggtaattcc agctccaata      600
gcgtatacta aagttgttgc agttaaaaag ctcgtagttg aacctctggt agggccgacc      660
ttggcgcgcg gtgaatgccg cgtcgtttag aagcgtcgtg cccggccatc ctcccccggt      720
cttttgggct gggggtcgtt tactgtaaaa aaaatagagt gttccaagca ggggtaata      780 tcccggtata tagtagtatg gaataatgag ataggacttt ggtactattt tgttggtttg      840
catgccaagg taatgattaa gagggacagt tgggggtatt cgtatttaga tgtcagaggt      900
gaaattcttg gattttcgaa agacgaacta ctgcgaaagc atttaccaag gatgttttca      960
ttaatcaaga acgaaagtta ggggatcgaa gatgattaga taccatcgta gtcttaaccg     1020
taaactatgc cgacttgcga ttgtccggcg tcgcttttag atgacctggg cagcagcaca     1080
tgagaaatca aagtctttgg gttccggggg gagtatggtc gcaaggctga aacttaaagg     1140
aattgacgga agggcaccac caggagtgga gcctgcggct taatttgact caacacggga     1200
aaacttacca ggtccggaca taggaaggat tgacagattg agagctcttt cttgattcta     1260 tgggtggtg tgcatggccg ttcttagttg gtggagtgat ttgtctggtt aattccgtta     1320
acgaacgaga ccacagccta ctaaatagtg gccgttatgg cgacatagcg gtgaacttct     1380
tagagggaca tttcgggtat accggaagga agtttgtggc aataacaggt ctgtgatgcc     1440
cttagatgtt ctgggccgca cgcgcgctac actgatcggt tcaacgagta tttgtttttt     1500
tctcattttg ggagggggca gagtccttgg ccggaaggtc tgggtaatct tttgaatgcc     1560
gatcgtgatg gggctagatt tttgcaatta ttaatctcca acgaggaatt cctagtagac     1620
gcaagtcatc agcttgcatc gattacgtcc ctgcccttg tacacaccgc ccgtcgcacc     1680
taccgattga acgatccggt gagaccttgg gattctgttg tggctgattc attttggctg     1740
cgatgggaga acttgagcaa accttatcgt ttagaggaag gtgaagtcgt aacaaggttt     1800
ccgtagtgaa cctgcaattc aaaaaaagcc gttac                                1835
```

```
<210> SEQ ID NO 99
<211> LENGTH: 30
<212> TYPE: DNA
<213> ORGANISM: Artificial
<220> FEATURE:
<223> OTHER INFORMATION: primer

<400> SEQUENCE: 99
cgaatattcc tggttgatcc tgccagtagt                                        30

<210> SEQ ID NO 100
<211> LENGTH: 46
<212> TYPE: DNA
<213> ORGANISM: Artificial
<220> FEATURE:
<223> OTHER INFORMATION: primer

<400> SEQUENCE: 100
gtaacggctt ttttgaatt gcaggttcac tacgcttgtt agaaac                       46
```

<210> SEQ ID NO 101
<211> LENGTH: 661
<212> TYPE: DNA
<213> ORGANISM: Artificial
<220> FEATURE:
<223> OTHER INFORMATION: EF1 alpha promoter (T. aureum ATCC 34304)

<400> SEQUENCE: 101

```
ggtttccgta gtgaacctgc aattcaaaaa aagccgttac tcacatcagg ccgccactca      60
tccgggcgaa agcttcgcgc attcgtcctc gtcacctcgg gtcccctgtg tcgtgacgga     120
aagcgcgacg agacgcggcc gcagcagaga gccccggggg cccgcgtcac gggggggcctg    180
gcggcggtcc tccttaagcc aaaccgaggg ttagggctcc aggctgttcg gcggggtcgc    240
gggcgcggtg gacgcgcggg gccgcctagc acctcctagc gcgcgactac caggatagcc    300
cccgcgagtg cgcagggcgg tccgcggggc ggagggcggc ccagcagcgc ggcgcggcgg    360
gcgggtgcgg ctgcgtaagg tggcggcggg cgcgggcggt tagtgttggt gttaggtcgc    420
ggcggggctg tgttccgggc atccgcctta cggcggtgca tactggttgg ctgggaggcg    480
gtttgcgggg ttagataggc ggccaaggtg agctgcgttg ggcggataaa tccgtggagg    540
cgctcgttga cggcgcggca gagacggaac gcggagcagc acggagtagc aagcaggagt    600
agcaggagta gcaagcagcg gcaaaggaag gctagatgat tgaacaggac ggccttcacg    660
c                                                                     661
```

<210> SEQ ID NO 102
<211> LENGTH: 46
<212> TYPE: DNA
<213> ORGANISM: Artificial
<220> FEATURE:
<223> OTHER INFORMATION: primer

<400> SEQUENCE: 102

```
ggtttccgta gtgaacctgc aattcaaaaa aagccgttac tcacat                    46
```

<210> SEQ ID NO 103
<211> LENGTH: 46
<212> TYPE: DNA
<213> ORGANISM: Artificial
<220> FEATURE:
<223> OTHER INFORMATION: primer

<400> SEQUENCE: 103

```
gcgtgaaggc cgtcctgttc aatcatctag ccttcctttg ccgctg                    46
```

<210> SEQ ID NO 104
<211> LENGTH: 835
<212> TYPE: DNA
<213> ORGANISM: Artificial
<220> FEATURE:
<223> OTHER INFORMATION: Neomycin resistance gene (Neor)

<400> SEQUENCE: 104

```
catcggcaaa ggaaggctag atgattgaac aggacggcct tcacgctggc tcgcccgctg      60
cttgggtgga acggctgttc ggctacgact gggctcagca gacgatcggc tgctcggacg    120
cggccgtgtt ccgccttagc gcgcagggcc ggccggtcct gtttgtcaag accgacctta    180
gcggcgccct caacgagctc caggacgaag ctgcccgcct cagctggctt gccacgacgg    240
gggttccgtg cgccgctgtg ctcgacgtcg tcaccgaagc cggccgcgac tggctgctcc    300
```

|   |   |   |   |   |   |
|---|---|---|---|---|---|
| tcggggaagt | gcccggccag | gacctcctca | gcagccacct | cgcgcccgct | gagaaggtgt | 360 |
| ccatcatggc | cgacgccatg | cgccgcctgc | acaccctcga | ccccgccacc | tgccccttcg | 420 |
| accaccaggc | gaagcacagg | atcgaacgcg | cccgcacgcg | gatggaggct | ggcctcgtcg | 480 |
| accaagacga | cctcgacgag | gagcaccagg | gcctcgcgcc | ggcggaactg | ttcgccaggc | 540 |
| ttaaggctag | gatgccggac | ggcgaggacc | tcgtggtcac | gcacggcgac | gcctgcctcc | 600 |
| ccaacatcat | ggtcgagaac | ggccgcttct | cgggctttat | cgactgcggg | cgcctgggcg | 660 |
| tggcggaccg | ctaccaagac | atcgcgctcg | ccacgcggga | catcgccgag | gagcttggcg | 720 |
| gcgagtgggc | cgaccgcttt | ctcgtgctct | acggcatcgc | cgccccggac | agccagagga | 780 |
| ttgcgttcta | ccgcctcctg | gacgagttct | tttgagatcc | gcgccggcta | tgcgc | 835 |

<210> SEQ ID NO 105
<211> LENGTH: 45
<212> TYPE: DNA
<213> ORGANISM: Artificial
<220> FEATURE:
<223> OTHER INFORMATION: primer

<400> SEQUENCE: 105

|   |   |   |   |   |
|---|---|---|---|---|
| catcggcaaa | ggaaggctag | atgattgaac | aggacggcct | tcacg | 45 |

<210> SEQ ID NO 106
<211> LENGTH: 46
<212> TYPE: DNA
<213> ORGANISM: Artificial
<220> FEATURE:
<223> OTHER INFORMATION: primer

<400> SEQUENCE: 106

|   |   |   |   |   |
|---|---|---|---|---|
| gcgcatagcc | ggcgcggatc | tcaaaagaac | tcgtccagga | ggcggt | 46 |

<210> SEQ ID NO 107
<211> LENGTH: 1249
<212> TYPE: DNA
<213> ORGANISM: Artificial
<220> FEATURE:
<223> OTHER INFORMATION: EF1 alpha terminator (T. aureum ATCC 34304)

<400> SEQUENCE: 107

|   |   |   |   |   |   |
|---|---|---|---|---|---|
| tcctggacga | gttcttttga | gatccgcgcc | ggctatgcgc | ccgtgctcga | ctgccacact | 60 |
| gcccacattg | cctgcaagtt | cgctgagctc | cagaacaaga | tggaccgccg | ctcgggcaag | 120 |
| attctcgagg | agaccccccaa | gttcatcaag | tcgggtggac | tctgccatgg | tcaagatgta | 180 |
| tccccctccaa | gcgcatgtgc | gtcgagtcct | tcaccgagta | cccgccgctc | ggccgctttg | 240 |
| ccgtgcgcga | catgcgcgtc | accgtcgctg | tcggcgtcat | caagtccgtc | accaagggcg | 300 |
| acaaataaat | tctacgaaag | attttttttcc | tcaagaagcg | ccctaaagtt | gacccctagc | 360 |
| agcgacgact | gtgtgtgccg | ttgtgagtcg | agttgcgatg | tcgtgcagcg | cccgtcgcgt | 420 |
| cccatgctcg | cgcgcgactc | cgtctctgct | tttcatctca | agtcaagagt | gggaagttcc | 480 |
| cttgctttat | ctcactattt | agaggtcgct | cacggctgct | ggttcctcgt | cgcatgtagc | 540 |
| acagcctcgt | ccaatcgcag | cctgcaccac | cccgctcgcc | tgggaaaatg | cgctcagcgg | 600 |
| attcgcactg | gcactcctct | cctcggacag | gtgcgatgtg | gaagcggtca | catcctcggc | 660 |
| gccctcggcc | acgccagcat | ctgcgcaatc | gctctcctcg | ttctcagccg | caaccgcagg | 720 |
| caggccgacg | tcgtttaccct | cggaatccac | cgagcatttc | gagcccatcg | cgctggcgtc | 780 |
| cacctcgatc | ataccttctc | catcgccgtc | cgctgcggct | tccgattctt | ctgctgccgc | 840 |

```
aaccgcgacg tcggccccg tctcctccgt tctttccgat gccggcgcag tggccgcgcc      900
ctctgctcga accggctcgt gttcagcgtc agggcctgcg cttgagctcg gcggctctt      960 ccgagtgatc cggccccgcg aggcaaggaa tcggcggctc tggagtgtcg gggcagccgc    1020
tctcactgcc ggtcttggc tggctgcctg tcctgcctcg cgttggcctt tgcttttgcc     1080
taggctttcg ccttggtgac ggcgtttgcc tgctgcggcg acttggcgcg ccgcggaat     1140 agcgcctcaa agtcctgctc gaggcgcccc agctctgact tgatttgcga ggtcccggtg    1200
gcatgagctc cgctgccctc gtccttacgg cccgtctttc gctgcagtg                1249
```

<210> SEQ ID NO 108
<211> LENGTH: 46
<212> TYPE: DNA
<213> ORGANISM: Artificial
<220> FEATURE:
<223> OTHER INFORMATION: primer

<400> SEQUENCE: 108

```
tcctggacga gttcttttga gatccgcgcc ggctatgcgc ccgtgc                    46
```

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109

```
cactgcagcg aaagacgggc cgtaaggacg                                      30
```

<210> SEQ ID NO 110
<211> LENGTH: 4453
<212> TYPE: DNA
<213> ORGANISM: Artificial
<220> FEATURE:
<223> OTHER INFORMATION: fusion DNA (T. aureum ATCC 34304 18S rDNA/T.
      aureum ATCC 34304 EF1 alpha promoter/Neor/T. aureum ATCC 34304 EF1
      alpha terminator)

<400> SEQUENCE: 110

```
cgaatattcc tggttgatcc tgccagtagt catacgctta tctcaaagat taagccatgc      60
atgtctaagt ataaaggctt atactctgaa actgcgaacg gctcattata tcagtttatg     120
tttctttgat agtgtttttt ctacatggat acttgtggca aatctagaaa caatacatgc     180
gtacaggcct gactttgggg gagggctgca tttatttgac ttaagccaat acccctcggg    240
gttgttttgg tgattcagaa taactgagcg aatcgcatag ctttcgggcg gcgatgaatc    300
atttcaagtt tctgccccat cagctgtcga tggtaggta taggcctacc atggctgtca    360
cgggtgacgg agaattaggg ttcgattccg gagagggagc tgagagacg ctaccacat     420 ccaaggaagg cagcaggcgc gtaaattact caatgttgac tcgacgaagt agtgacgaga    480
attaacaatg cggagcgctc agcgttttgc aattggaatg agagcaatgt aaaagcctca    540
tcgaggatcc attggagggc aagtctggtg ccagcagccg cggtaattcc agctccaata    600
gcgtatacta aagttgttgc agttaaaaag ctcgtagtta aacctctggt agggccgacc    660
ttggcgcgcg gtgaatgccg cgtcgtttag aagcgtcgtg cccggccatc ctccccccgt    720
cttttgggct gggggtcgtt tactgtaaaa aaaatagagt gttccaagca gggggtaata    780
tcccggtata tagtagtatg gaataatgag ataggacttt ggtactattt tgttggttg     840
```

```
catgccaagg taatgattaa gagggacagt tgggggtatt cgtatttaga tgtcagaggt    900
gaaattcttg gattttcgaa agacgaacta ctgcgaaagc atttaccaag gatgttttca    960
ttaatcaaga acgaaagtta gggatcgaa gatgattaga taccatcgta gtcttaaccg    1020
taaactatgc cgacttgcga ttgtccggcg tcgcttttag atgacctggg cagcagcaca    1080
tgagaaatca aagtctttgg gttccggggg gagtatggtc gcaaggctga aacttaaagg    1140
aattgacgga agggcaccac caggagtgga gcctgcggct taatttgact caacacggga    1200
aaacttacca ggtccggaca taggaaggat tgacagattg agagctcttt cttgattcta    1260
tgggtggtgg tgcatggccg ttcttagttg gtggagtgat ttgtctggtt aattccgtta    1320
acgaacgaga ccacagccta ctaaatagtg gccgttatgg cgacatagcg gtgaacttct    1380
tagagggaca tttcgggtat accggaagga agtttgtggc aataacaggt ctgtgatgcc    1440
cttagatgtt ctgggccgca cgcgcgctac actgatcggt tcaacgagta tttgtttttt    1500
tctcattttg ggaggggggca gagtccttgg ccggaaggtc tgggtaatct tttgaatgcc    1560
gatcgtgatg gggctagatt tttgcaatta ttaatctcca acgaggaatt cctagtagac    1620
gcaagtcatc agcttgcatc gattacgtcc ctgcccttta cacaccgc ccgtcgcacc    1680
taccgattga acgatccggt gagaccttgg gattctgttg tggctgattc attttggctg    1740
cgatgggaga acttgagcaa accttatcgt ttagaggaag gtgaagtcgt aacaaggttt    1800
ccgtagtgaa cctgcaattc aaaaaaagcc gttactcaca tcaggccgcc actcatccgg    1860
gcgaaagctt cgcgcattcg tcctcgtcac ctcgggtccc ctgtgtcgtg acggaaagcg    1920
cgacgagacg cggccgcagc agagagcccc ggggcccgc gtcacgggggg gcctggcggc    1980
ggtcctcctt aagccaaacc gagggttagg gctccaggct gttcggcggg gtcgcgggcg    2040
cggtggacgc gcggggccgc ctagcacctc ctagcgcgcg actaccagga tagccccgc    2100
gagtgcgcag ggcggtccgc ggggcggagg gcggcccagc agcgcggcgc ggcgggcggg    2160
tgcggctgcg taaggtggcg gcgggcgcgg gcggttagtg ttggtgttag gtcgcggcgg    2220
ggctgtgttc cgggcatccg ccttacggcg gtgcatactg gttggctggg aggcggtttg    2280
cgggggttaga taggcggcca aggtgagctg cgttgggcgg ataaatccgt ggaggcgctc    2340
gttgacggcg cggcagagac ggaacgcgga gcagcacgga gtagcaagca ggagtagcag    2400
gagtagcaag catggcaaag gaaggctaga tgattgaaca ggacggcctt cacgctggct    2460
cgcccgctgc ttgggtggaa cggctgttcg gctacgactg ggctcagcag acgatcggct    2520
gctcggacgc ggccgtgttc cgccttagcg cgcagggccg gccggtcctg tttgtcaaga    2580
ccgaccttag cggcgccctc aacgagctcc aggacgaagc tgcccgcctc agctggcttg    2640
ccacgacggg ggttccgtgc gccgctgtgc tcgacgtcgt caccgaagcc ggccgcgact    2700
ggctgctcct cggggaagtg cccggccagg acctcctcag cagccacctc gcgcccgctg    2760
agaaggtgtc catcatggcc gacgccatgc cgccgctgca caccctcgac cccgccacct    2820
gccccttcga ccaccaggcg aagcacagga tcgaacgcgc ccgcacgcgg atggaggctg    2880
gcctcgtcga ccaagacgac ctcgacgagg agcaccaggg cctcgcgccg gcggaactgt    2940
tcgccaggct taaggctagg atgccggacg gcgaggacct cgtggtcacg cacggcgacg    3000
cctgcctccc caacatcatg gtcgagaacg gccgcttctc gggctttatc gactgcgggc    3060
gcctgggcgt ggcggaccgc taccaagaca tcgcgctcgc cacgcgggac atcgccgagg    3120
agcttggcgc cgagtgggcc gaccgctttc tcgtgctcta cggcatcgcc gccccggaca    3180
gccagaggat tgcgttctac cgcctcctgg acgagttctt ttgagatccg cgccggctat    3240
```

```
gcgcccgtgc tcgactgcca cactgcccac attgcctgca agttcgctga gctccagaac    3300
aagatggacc gccgctcggg caagattctc gaggagaccc ccaagttcat caagtcgggt    3360
ggactctgcc atggtcaaga tgtatcccct ccaagcgcat gtgcgtcgag tccttcaccg    3420
agtacccgcc gctcggccgc tttgccgtgc gcgacatgcg cgtcaccgtc gctgtcggcg    3480
tcatcaagtc cgtcaccaag ggcgacaaat aaattctacg aaagattttt ttcctcaaga    3540
agcgccctaa agttgacccc tagcagcgac gactgtgtgt gccgttgtga gtcgagttgc    3600
gatgtcgtgc agcgcccgtc gcgtcccatg ctcgcgcgcg actccgtctc tgcttttcat    3660
ctcaagtcaa gagtgggaag ttcccttgct ttatctcact atttagaggt cgctcacggc    3720
tgctggttcc tcgtcgcatg tagcacagcc tcgtccaatc gcagcctgca ccaccccgct    3780
cgcctgggaa aatgcgctca gcggattcgc actggcactc ctctcctcgg acaggtgcga    3840
tgtggaagcg gtcacatcct cggcgccctc ggccacgcca gcatctgcgc aatcgctctc    3900
ctcgttctca gccgcaaccg caggcaggcc gacgtcgttt acctcggaat ccaccgagca    3960
tttcgagccc atcgcgctgg cgtccacctc gatcatacct tctccatcgc cgtccgctgc    4020
ggcttccgat tcttctgctg ccgcaaccgc gacgtcggcc ccgtctcct ccgttctttc    4080 cgatgccggc gcagtggccg cgccctctgc tcgaaccggc tcgtgttcag cgtcagggcc    4140
tgcgcttgag ctcgggcggc tcttccgagt gatccggccc cgcgaggcaa ggaatcggcg    4200
gctctggagt gtcggggcag ccgctctcac tgccggtctt tggctggctg cctgtcctgc    4260
ctcgcgttgg cctttgcttt tgcctaggct ttcgccttgg tgacggcgtt tgcctgctgc    4320
ggcgacttgg cgcggccgcg aatagcgcc tcaaagtcct gctcgaggcg ccccagctct    4380
gacttgattt gcgaggtccc ggtggcatga gctccgctgc cctcgtcctt acggcccgtc    4440
tttcgctgca gtg                                                        4453
```

<210> SEQ ID NO 111
<211> LENGTH: 1218
<212> TYPE: DNA
<213> ORGANISM: Artificial
<220> FEATURE:
<223> OTHER INFORMATION: genomic DNA (T. aureum ATCC 34304 OrfA upstream genomic DNA fragment)

<400> SEQUENCE: 111

```
cccgaattcg gacgatgact gactgactga ttggctgacg acggccgccc tcgtgcgcgg     60
cgtcgggcgt cgtcgcaaac caggcaggca ggcaggaagg aaggaaggaa gggccaggcc    120
ctggtgcgaa acgctggcct gctccgctgc aagccaagcc gcgctcgcag gtgtacttcc    180
gagtcctcgc gatgattagg caagcctgag cgagcacgta agctgcactg cggctgttca    240
accagagaga gagttggctc tcttgcgtca aggcggcgcg cagcccactt gcgtcgcggc    300
tgagggcccc tggaggggag aaggaggcc ggcgagcggc gagtggcggc cctcactggc    360
accaggtcgc aggaggccag gcagcccgcc acggacagga atcctcaggg cgcagcagcg    420
cactacgtag tgcagagacg cagagcgggc cggatccgca gtgcggtcgc gccaccccgc    480
cgcgcagctc gctcgcggac ggggtccgtg ccgcgcgaa acggacacg tgtgggagc     540 ggacatggga tcgagaacgc cgttcgccct gctcgcgctg ccagcagcag gagccgtccg    600
aaggacgagc ggccggccgc ctgtcccccc tccgcgcact cgaagcgcgc ccggcagcgc    660
cccattgcgt gcgcggatgg cgtcttggct ggtccctctc gaggcgcttg ctcgtgctcg    720
ccacgccttg tccgcctcct cgctgagcaa gcgatgagct gagcacggac cgcctgcaag    780
```

```
tgcaagtgtt cttgtgctgc agggcgccga agaattggat tctggcccat gatcagtttg    840
attgggccga gggagggagg gaggctgggc gagtgggcga caccagcaag ccggactgcg    900
agaggggcgg ggcaggatgt gagcgcagga aagtgacgca agtgcatccg gccatcattg    960
ggccatcatt gggccatcat tggtgttttg ggccgcgctt tgcggatcgt ccggccgatc   1020
aggtacgagg ccacgaacct acgtcgtttg ccgcgctcag gctggttggt tgcacttgga   1080
ctcttctgtg acctttcatc gtgtgcaggc aaactcgatt tgcagacccg agacacggcg   1140
aaggatccgt gctgcaaacg caagtggagt gcgtcgagag caccgccgag accaagagcc   1200
gaggcagaca agcttggg                                                1218

<210> SEQ ID NO 112
<211> LENGTH: 32
<212> TYPE: DNA
<213> ORGANISM: Artificial
<220> FEATURE:
<223> OTHER INFORMATION: primer

<400> SEQUENCE: 112
cccgaattcg gacgatgact gactgactga tt                                  32

<210> SEQ ID NO 113
<211> LENGTH: 28
<212> TYPE: DNA
<213> ORGANISM: Artificial
<220> FEATURE:
<223> OTHER INFORMATION: primer

<400> SEQUENCE: 113
cccaagcttg tctgcctcgg ctcttggt                                       28

<210> SEQ ID NO 114
<211> LENGTH: 1000
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 114
cccccatggt gttgctgtgg gattggtccg ggggctcttc tgcacgcggc ctccgtcgcg     60
cgcagaaatg ccccgtcact ggctgcccag gaggcagccg aatccctcta gctagctagc    120
taggctagag cgtctttttcc gtagtttttc acaaagccag tatcacatgg ataacgaacg    180
aaggtttcgg gctcgcgctc gcaggcgtta ggacgaagtt gatcgcccca cgtcacttca    240
aacgagtgaa ccaagatcac gttgcatctg ctcgcaagat cttcttcttc cacgccgcat    300
cgatgcgatg gatttcaaac tcttttcagg gcttttaggt gagtatggca gcgctgtttg    360
cgtggcagcg ctgtttgcgt ggttgtactc tctaaaggtg cttccacgca tgcgcgcaca    420
aaggggcatg gcatggttgg cggcgcactc tggccctcat ttgaagcaga ctatcgaagg    480
gtccagttgg tactgcggca ggtccggcga gagcaagcgc ggcggtcgct cccactcgtc    540
cctgcacagt tgctggactg gcgacggctg gcgcacctga ctacgagaag actcgagacg    600
cacagaggta gtcagggacg accgaccgca aagcacaaac cgctccaaaa cggccgcacc    660
aggcagggca gtaaactaaa aacgaatgta cctccatcgc gcgtatctgc cgagcctcct    720
cccacgcttc ggctgggctt gattcaccag tgtccgcaag ctgaaccgac cgtcttcgat    780
gtcatgaagc ttggcgcggc attagtcaga cgacgcggca cgccaggatt ctgtcggttt    840
```

```
ctgggaaatg ggcatctata tagctgattc cctctgtcat gaggcggcct tgttctggcc      900
ctgggccgcc gttcggatga tctatgatgt cgttgtacgc ataaagcttg tcgaaaacgt      960
cggccatgtc ttcctcagag atgtaaccga gccatggggg                           1000
```

<210> SEQ ID NO 115
<211> LENGTH: 28
<212> TYPE: DNA
<213> ORGANISM: Artificial
<220> FEATURE:
<223> OTHER INFORMATION: primer

<400> SEQUENCE: 115

```
cccccatggt gttgctgtgg gattggtc                                          28
```

<210> SEQ ID NO 116
<211> LENGTH: 30
<212> TYPE: DNA
<213> ORGANISM: Artificial
<220> FEATURE:
<223> OTHER INFORMATION: primer

<400> SEQUENCE: 116

```
cccccatggc tcggttacat ctctgaggaa                                        30
```

<210> SEQ ID NO 117
<211> LENGTH: 1632
<212> TYPE: DNA
<213> ORGANISM: Artificial
<220> FEATURE:
<223> OTHER INFORMATION: fusion DNA (T. aureum ATCC 34304 ubiqitin
      promoter/Hygr)

<400> SEQUENCE: 117

```
cccaagcttg ccgcagcgcc tggtgcaccc gccgggcgtt gttgtgtgct cttcttgcct       60
ccgagagaga gagcggagcg gatgcatagg aaatcgggcc acgcgggagg gccatgcgtt      120
cgccccacac gccactttcc acgcccgctc tctctccggc cggcaggcag cgcataactc      180
tccgacgctg gcaggctggt agcaactggc agggacaact cgcgcgcggg tcccggtcgt      240
tcgatgtgcc aacccgagag aatccagcca gcagggcggt tggcctcatc gcccacctgc      300
tatggtgcag cgaaccaact cccgaagcgg ccggttctgc gattccctct tctgaattct      360
gaattctgaa ctgattccgg aggagaaccc tctggaagcg cgggttgcct ctccagttct      420
gccgaactag acaggggagt gagcagagag tgacccctgac gcggagcgag ctggttgctg      480
gaaaagtcgc gaacgctggg ctgtgtcacg cgtccacttc gggcagaccc caaacgacaa      540
gcagaacaag caacaccagc agcagcaagc gacctaagca acactagcca acatgaaaaa      600
gcctgaactc accgcgacgt ctgtcgagaa gtttctgatc gaaaagttcg acagcgtctc      660
cgacctgatg cagctctcgg agggcgaaga atctcgtgct ttcagcttcg atgtaggagg      720
gcgtggatat gtcctgcggg taaatagctg cgccgatggt ttctacaaag atcgttatgt      780
ttatcggcac tttgcatcgg ccgcgctccc gattccggaa gtgcttgaca ttggggaatt      840
cagcgagagc ctgacctatt gcatctcccg ccgtgcacag ggtgtcacgt tgcaagacct      900
gcctgaaacc gaactgcccg ctgttctgca gccggtcgcg gaggccatgg atgcgatcgc      960
tgcggccgat cttagccaga cgagcgggtt cggcccattc ggaccgcaag gaatcggtca     1020
atacactaca tggcgtgatt tcatatgcgc gattgctgat ccccatgtgt atcactggca     1080
aactgtgatg gacgacaccg tcagtgcgtc cgtcgcgcag gctctcgatg agctgatgct     1140
```

```
ttgggccgag gactgccccg aagtccggca cctcgtgcac gcggatttcg gctccaacaa    1200
tgtcctgacg gacaatggcc gcataacagc ggtcattgac tggagcgagg cgatgttcgg    1260
ggattcccaa tacgaggtcg ccaacatctt cttctggagg ccgtggttgg cttgtatgga    1320
gcagcagacg cgctacttcg agcggaggca tccggagctt gcaggatcgc gcggctccg     1380 ggcgtatatg ctccgcattg gtcttgacca actctatcag agcttggttg acggcaattt    1440
cgatgatgca gcttgggcgc agggtcgatg cgacgcaatc gtccgatccg agccgggac     1500 tgtcgggcgt acacaaatcg cccgcagaag cgcggccgtc tggaccgatg gctgtgtaga    1560
agtactcgcc gatagtggaa accgacgccc cagcactcgt ccgagggcaa aggaatagtc    1620
gacgcatgcg gg                                                        1632
```

<210> SEQ ID NO 118
<211> LENGTH: 36
<212> TYPE: DNA
<213> ORGANISM: Artificial
<220> FEATURE:
<223> OTHER INFORMATION: primer

<400> SEQUENCE: 118

```
cccaagcttg ccgcagcgcc tggtgcaccc gccggg                              36
```

<210> SEQ ID NO 119
<211> LENGTH: 43
<212> TYPE: DNA
<213> ORGANISM: Artificial
<220> FEATURE:
<223> OTHER INFORMATION: primer

<400> SEQUENCE: 119

```
cccgcatgcg tcgactattc ctttgccctc ggacgagtgc tgg                      43
```

<210> SEQ ID NO 120
<211> LENGTH: 1000
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 120

```
cccgtcgacg tgttgctgtg ggattggtcc gggggctctt ctgcacgcgg cctccgtcgc    60
gcgcagaaat gccccgtcac tggctgccca ggaggcagcc gaatccctct agctagctag    120
ctaggctaga gcgtcttttc cgtagttttt cacaaagcca gtatcacatg gataacgaac    180
gaaggtttcg ggctcgcgct cgcaggcgtt aggacgaagt tgatcgcccc acgtcacttc    240
aaacgagtga accaagatca cgttgcatct gctcgcaaga tcttcttctt ccacgccgca    300
tcgatgcgat ggatttcaaa ctcttttcag ggcttttagg tgagtatggc agcgctgttt    360
gcgtggcagc gctgtttgcg tggttgtact ctctaaaggt gcttccacgc atgcgcgcac    420 aaagggggcat ggcatggttg gcggcgcact ctggccctca tttgaagcag actatcgaag    480
ggtccagttg gtactgcggc aggtccggcg agagcaagcg cggcggtcgc tcccactcgt    540
ccctgcacag ttgctggact ggcgacggct ggcgcacctg actacgagaa gactcgagac    600
gcacagaggt agtcagggac gaccgaccgc aaagcacaaa ccgctccaaa acggccgcac    660
caggcagggc agtaaactaa aaacgaatgt acctccatcg cgcgtatctg ccgagcctcc    720
tcccacgctt cggctgggct tgattcacca gtgtccgcaa gctgaaccga ccgtcttcga    780
```

```
tgtcatgaag cttggcgcgg cattagtcag acgacgcggc acgccaggat tctgtcggtt      840
tctgggaaat gggcatctat atagctgatt ccctctgtca tgaggcggcc ttgttctggc      900
cctgggccgc cgttcggatg atctatgatg tcgttgtacg cataaagctt gtcgaaaacg      960
tcggccatgt cttcctcaga gatgtaaccg agtcgacggg                           1000

<210> SEQ ID NO 121
<211> LENGTH: 29
<212> TYPE: DNA
<213> ORGANISM: Artificial
<220> FEATURE:
<223> OTHER INFORMATION: primer

<400> SEQUENCE: 121
cccgtcgacg tgttgctgtg ggattggtc                                        29

<210> SEQ ID NO 122
<211> LENGTH: 29
<212> TYPE: DNA
<213> ORGANISM: Artificial
<220> FEATURE:
<223> OTHER INFORMATION: primer

<400> SEQUENCE: 122
cccgtcgact cggttacatc tctgaggaa                                        29

<210> SEQ ID NO 123
<211> LENGTH: 3705
<212> TYPE: DNA
<213> ORGANISM: Artificial
<220> FEATURE:
<223> OTHER INFORMATION: fusion DNA (T. aureum OrfA upstream/EF1 alpha
      promoter/Neor/T. aureum OrfA  downstream)

<400> SEQUENCE: 123
cccccatggc tcggttacat ctctgaggaa gacatggccg acgttttcga caagctttat       60
gcgtacaacg acatcataga tcatccgaac ggcggcccag ggccagaaca aggccgcctc      120
atgacagagg gaatcagcta tatagatgcc catttcccag aaaccgacag aatcctggcg      180
tgccgcgtcg tctgactaat gccgcgccaa gcttcatgac atcgaagacg gtcggttcag      240
cttgcggaca ctggtgaatc aagcccagcc gaagcgtggg aggaggctcg gcagatacgc      300
gcgatggagg tacattcgtt tttagtttac tgccctgcct ggtgcggccg ttttggagcg      360
gtttgtgctt tgcggtcggt cgtccctgac tacctctgtg cgtctcgagt cttctcgtag      420
tcaggtgcgc cagccgtcgc cagtccagca actgtgcagg gacgagtggg agcgaccgcc      480
gcgcttgctc tcgccggacc tgccgcagta ccaactggac ccttcgatag tctgcttcaa      540
atgagggcca gagtgcgccg ccaaccatgc catgcccctt tgtgcgcgca tgcgtggaag      600
cacctttaga gagtacaacc acgcaaacag cgctgccacg caaacagcgc tgccatactc      660
acctaaaagc cctgaaaaga gtttgaaatc catcgcatcg atgcggcgtg aagaagaag      720 atcttgcgag cagatgcaac gtgatcttgg ttcactcgtt tgaagtgacg tggggcgatc      780
aacttcgtcc taacgcctgc gagcgcgagc ccgaaacctt cgttcgttat ccatgtgata      840
ctggctttgt gaaaaactac ggaaaagacg ctctagccta gctagctagc tagagggatt      900
cggctgcctc ctgggcagcc agtgacgggg catttctgcg cgcgacggag gccgcgtgca      960
gaagagcccc cggaccaatc ccacagcaac accatgcgca agtcgcccga cttgatgaac     1020
ttgggggtct cctcgagaat cttgcccgag cggcggtcca tcttgttctg gagctcagcg     1080
```

```
aacttgcagg caatgtgggc agtgtggcgg tcgagcacgg gcgcatagcc ggcgcggatc    1140
tcaaaagaac tcgtccagga ggcggtagaa cgcaatcctc tggctgtccg gggcggcgat    1200
gccgtagagc acgagaaagc ggtcggccca ctcgccgcca agctcctcgg cgatgtcccg    1260
cgtggcgagc gcgatgtctt ggtagcggtc cgccacgccc aggcgcccgc agtcgataaa    1320
gcccgagaag cggccgttct cgaccatgat gttggggagg caggcgtcgc cgtgcgtgac    1380
cacgaggtcc tcgccgtccg gcatcctagc cttaagcctg cgaacagtt ccgccggcgc     1440
gaggccctgg tgctcctcgt cgaggtcgtc ttggtcgacg aggccagcct ccatccgcgt    1500
gcgggcgcgt tcgatcctgt gcttcgcctg gtggtcgaag gggcaggtgg cggggtcgag    1560
ggtgtgcagg cggcgcatgg cgtcggccat gatggacacc ttctcagcgg gcgcgaggtg    1620
gctgctgagg aggtcctggc cgggcacttc cccgaggagc agccagtcgc ggccggcttc    1680
ggtgacgacg tcgagcacag cggcgcacgg aaccccgtc gtggcaagcc agctgaggcg     1740
ggcagcttcg tcctggagct cgttgagggc gccgctaagg tcggtcttga caaacaggac    1800
cggccggccc tgcgcgctaa ggcggaacac ggccgcgtcc gagcagccga tcgtctgctg    1860
agcccagtcg tagccgaaca gccgttccac ccaagcagcg ggcgagccag cgtgaaggcc    1920
gtcctgttca atcatctagc cttcctttgc cgctgcttgc tactcctgct actcctgctt    1980
gttacttcgt gttgctccgc gttccgtctc tgccgcgccg tccacgagcg cctcacgga     2040
tttatccgcc caacgcggct caccttggcc gcctatctaa ccccgcaaac cgcctcccag    2100
ccaaccattg cgccgccgta aggcggattc ccagaacaca gccccgccgc gacctaaccc    2160
aacctaaccg cccgcgcccg ccgccacctt acgcagccgc accgcccgc cgcgccgcgc      2220
tgctgggccg ccctcgcccc gcagaccgcc ctgcgcgctc gcggggcta tcctggtagt     2280
cgcgcgctag gaggtgctag gcggccccgt gcttccacct cgcccgcgac cccgccgaac    2340
agcctggagc cctaaccctc ggtttggctt aaggaggact gccgccaggc ccccgtgac    2400
gcgggccccc ggggctctct gctgcggccg cgtctcgtcg cactttccgt cccgacacag    2460
gggacccgag gtgacgagga cgaatgcgcg aagcttgtct gcctcggctc ttggtctcgg    2520
cggtgctctc gacgcactcc acttgcgttt gcagcacgga tccttcgccg tgtctcgggt    2580
ctgcaaatcg agtttgcctg cacacgatga aaggtcacag aagagtccaa gtgcaaccaa    2640
ccagcctgag cgcggcaaac gacgtaggtt cgtggcctcg tacctgatcg gccggacgat    2700
ccgcaaagcg cggcccaaaa caccaatgat ggcccaatga tggcccaatg atggccggat    2760
gcacttgcgt cactttcctg cgctcacatc ctgccccgcc cctctcgcag tccggcttgc    2820
tggtgtcgcc cactcgccca gcctccctcc ctccctcggc ccaatcaaac tgatcatggg    2880
ccagaatcca attcttcggc gccctgcagc acaagaacac ttgcacttgc aggcggtccg    2940
tgctcagctc atcgcttgct cagcgaggag gcggacaagg cgtggcgagc acgagcaagc    3000
gcctcgagag ggaccagcca agacgccatc cgcgcacgca atgggcgct gccgggcgcg     3060
cttcgagtgc gcggaggggg gacaggcggc cggccgctcg tccttcggac ggctcctgct    3120
gctggcagcg cgagcagggc gaacggcgtt ctcgatccca tgtccgctcc cacaccgtgt    3180
ccgttttcgc gcggccacgg accccgtccg cgagcgagct gcgcggcggg gtggcgcgac    3240
cgcactgcgg atccggcccg ctctgcgtct ctgcactacg tagtgcgctg ctgcgccctg    3300
aggattcctg tccgtggcgg gctgcctggc ctcctgcgac ctggtgccag tgagggccgc    3360
cactcgccgc tcgccggcct ccttcctccc ctccaggggc cctcagccgc gacgcaagtg    3420
```

```
ggctgcgcgc cgccttgacg caagagagcc aactctctct ctggttgaac agccgcagtg    3480
cagcttacgt gctcgctcag gcttgcctaa tcatcgcgag gactcggaag tacacctgcg    3540
agcgcggctt ggcttgcagc ggagcaggcc agcgtttcgc accagggcct ggcccttcct    3600
tccttccttc ctgcctgcct gcctggtttg cgacgacgcc cgacgccgcg cacgagggcg    3660
gccgtcgtca gccaatcagt cagtcagtca tcgtccgaat tcggg                    3705
```

<210> SEQ ID NO 124
<211> LENGTH: 3826
<212> TYPE: DNA
<213> ORGANISM: Artificial
<220> FEATURE:
<223> OTHER INFORMATION: fusion DNA (T. aureum OrfA upstream/ubiquitin
      promoter/Hygr/T. aureum OrfA downstream)

<400> SEQUENCE: 124

```
cccccatggc tcggttacat ctctgaggaa gacatggccg acgttttcga caagctttat      60
gcgtacaacg acatcataga tcatccgaac ggcggcccag ggccagaaca aggccgcctc     120
atgacagagg gaatcagcta tatagatgcc catttcccag aaaccgacag aatcctggcg     180
tgccgcgtcg tctgactaat gccgcgccaa gcttcatgac atcgaagacg gtcggttcag     240
cttgcggaca ctggtgaatc aagcccagcc gaagcgtggg aggaggctcg gcagatacgc     300
gcgatggagg tacattcgtt tttagtttac tgccctgcct ggtgcggccg ttttggagtg     360
gtttgtgctt tgcggtcggt cgtccctgac tacctctgtg cgtctcgagt cttctcgtag     420
tcaggtgcgc cagccgtcgc cagtccagca actgtgcagg gacgagtggg agcgaccgcc     480
gcgcttgctc tcgccggacc tgccgcagta ccaactggac ccttcgatag tctgcttcaa     540
atgagggcca gagtgcgccg ccaaccatgc catgcccctt tgtgcgcgca tgcgtggaag     600
cacctttaga gagtacaacc acgcaaacag cgctgccacg caaacagcgc tgccacgcaa     660
acagcgctgc catactcacc taaaagccct gaaaagagtt tgaaatccat cgcgtcgatg     720
cggcgtggaa gaagaagatc ttgcgagcag acgcaacgtg atcttggttc actcgtttga     780
agtgacgcgg gacgatcaac ttcgtcctaa cgcctgcgag cgcgagcccg aaaccttcgt     840
tcgttatcca tgtgatactg gctttgtgaa aaactacgga aaagacgcta gctagaggga     900
ttcggctgcc tccttgggca gccagtgacg gggcatttct gcgcgcgacg gaggccgcgt     960
gcaaaagagc ccccgaccca atcccacagc aacacgtcga ctattccttt gccctcggac    1020
gagtgctggg gcgtcggttt ccactatcgg cgagtacttc tacacagcca tcggtccaga    1080
cggccgcgct tctgcgggcg atttgtgtac gcccgacagt cccggctccg gatcggacga    1140
ttgcgtcgca tcgaccctgc gcccaagctg catcatcgaa attgccgtca accaagctct    1200
gatagagttg gtcaagacca atgcggagca tatacgcccg gagccgcggc gatcctgcaa    1260
gctccggatg cctccgctcg aagtagcgcg tctgctgctc catacaagcc aaccacggcc    1320
tccagaagaa gatgttggcg acctcgtatt gggaatcccc gaacatcgcc tcgctccagt    1380
caatgaccgc tgttatgcgg ccattgtccg tcaggacatt gttggagccg aaatccgcgt    1440
gcacgaggtg ccggacttcg ggcagtcct cggcccaaag catcagctca tcgagagcct    1500
gcgcgacgga cgcactgacg gtgtcgtcca tcacagtttg ccagtgatac acatggggat    1560
cagcaatcgc gcatatgaaa tcacgccatg tagtgtattg accgattcct gcggtccga     1620 atgggccgaa cccgctcgtc tggctaagat cggccgcagc gatcgcatcc atggcctccg    1680
cgaccggctg cagaacagcg ggcagttcgg tttcaggcag gtcttgcaac gtgacaccct    1740
```

-continued

```
gtgcacggcg ggagatgcaa taggtcaggc tctcgctgaa ttccccaatg tcaagcactt    1800
ccggaatcgg gagcgcggcc gatgcaaagt gccgataaac ataacgatct ttgtagaaac    1860
catcggcgca gctatttacc cgcaggacat atccacgccc tcctacatcg aagctgaaag    1920
cacgagattc ttcgccctcc gagagctgca tcaggtcgga gacgctgtcg aacttttcga    1980
tcagaaactt ctcgacagac gtcgcggtga gttcaggctt tttcatgttg ctagtgttg    2040 cttaggtcgc ttgctgctgc tggtgttgct tgttctgctt gtcgtttggg gtctgcccga    2100
agtggacgcg tgacacagcc cagcgttcgc gacttttcca gcaaccagct cgctcccgcg    2160
tcagggtcac tctctgctca ctcccctgtc tagttcggca gaactggaga ggcaacccgc    2220
gcttccagag ggttctcctc cggaatcagt tcagaattca gaattcagaa gagggaatcg    2280
cagaaccggc cgcttcggga gttggttcgc tgcaccatag caggtgggcg atgaggccaa    2340
ccgccctgct ggctggattc tctcgggttg gcacatcgaa cgaccgggac ccgcgcgcga    2400
gttgtccctg ccagttgcta ccagcctgcc agcgtcggag agttatgcgc tgcctgccgg    2460
ccggagagag agcgggcgtg gaaagtggcg tgtggggcga acgcatggcc ctcccgcgtg    2520
gcccgatttc ctatgcatcc gctccgctct ctctctcgga ggcaagaaga gcacaccaac    2580
aacgcccggc gggtgcacca ggcgctgcgg caagcttgtc tgcctcggct cttggtctcg    2640
gcggtgctct cgacgcactc cacttgcgtt tgcagcacgg atccttcgcc gtgtctcggg    2700
tctgcaaatc gagtttgcct gcacacgatg aaaggtcaca gaagagtcca agtgcaacca    2760
accagcctga gcgcggcaaa cgacgtaggt tcgtggcctc gtacctgatc ggccggacga    2820
tccgcaaagc gcggcccaaa acaccaatga tggcccaatg atggcccaat gatgccggaa    2880
tgcacttgcg tcactttcct gcgctcacat cctgccccgc ccctctcgca gtccggcttg    2940
ctggtgtcgc ccactcgccc agcctccctc cctccctcgg cccaatcaaa ctgatcatgg    3000
gccagaatcc aattcttcgg cgccctgcag cacaagaaca cttgcacttg caggcggtcc    3060
gtgctcagct catcgcttgc tcagcgagga ggcggacaag gcgtggcgag cacgagcaag    3120
cgcctcgaga gggaccagcc aagacgccat ccgcgcacgc aatggggcgc tgccgggcgc    3180
gcttcgagtg cgcggagggg ggacaggcgg ccggccgctc gtccttcgga cggctcctgc    3240
tgctggcagc gcgagcaggg cgaacggcgt tctcgatccc atgtccgctc ccacaccgtg    3300
tccgttttcg cgcggccacg gaccccgtcc gcgagcgagc tgcgcggcgg ggtgggcgcga    3360 ccgcactgcg gatccggccc gctctgcgtc tctgcactac gtagtgcgct gctgcgccct    3420
gaggattcct gtccgtggcg ggctgcctgg cctcctgcga cctggtgcca gtgagggccg    3480
ccactcgccg ctcgccggcc tccttcctcc cctccagggg ccctcagccg cgacgcaagt    3540
gggctgcgcg ccgccttgac gcaagagagc caactctctc tctggttgaa cagccgcagt    3600
gcagcttacg tgctcgctca ggcttgccta atcatcgcga ggactcggaa gtacacctgc    3660
gagcgcggct tggcttgcag cggagcaggc cagcgtttcg caccagggcc tggcccttcc    3720
ttccttcctt cctgcctgcc tgcctggttt gcgacgacgc ccgacgccgc gcacgagggc    3780
ggccgtcgtc agccaatcag tcagtcagtc atcgtccgaa ttcggg                  3826
```

<210> SEQ ID NO 125
<211> LENGTH: 22
<212> TYPE: DNA
<213> ORGANISM: Artificial
<220> FEATURE:
<223> OTHER INFORMATION: primer

<400> SEQUENCE: 125
gaagcgtccc gtagatgtgg tc                                          22

<210> SEQ ID NO 126
<211> LENGTH: 21
<212> TYPE: DNA
<213> ORGANISM: Artificial
<220> FEATURE:
<223> OTHER INFORMATION: primer

<400> SEQUENCE: 126
gcccgagagg tcaaagtacg c                                           21

<210> SEQ ID NO 127
<211> LENGTH: 20
<212> TYPE: DNA
<213> ORGANISM: Artificial
<220> FEATURE:
<223> OTHER INFORMATION: primer

<400> SEQUENCE: 127
gcgagcccag gtccacttgc                                             20

<210> SEQ ID NO 128
<211> LENGTH: 22
<212> TYPE: DNA
<213> ORGANISM: Artificial
<220> FEATURE:
<223> OTHER INFORMATION: primer

<400> SEQUENCE: 128
cagcccgatg aaaaacttgg tc                                          22

<210> SEQ ID NO 129
<211> LENGTH: 22
<212> TYPE: DNA
<213> ORGANISM: Artificial
<220> FEATURE:
<223> OTHER INFORMATION: primer

<400> SEQUENCE: 129
gggagcgcag ggaaaacggt ct                                          22

<210> SEQ ID NO 130
<211> LENGTH: 20
<212> TYPE: DNA
<213> ORGANISM: Artificial
<220> FEATURE:
<223> OTHER INFORMATION: primer

<400> SEQUENCE: 130
ccagcccacg tcgtcggagc                                             20

<210> SEQ ID NO 131
<211> LENGTH: 2297
<212> TYPE: DNA
<213> ORGANISM: Artificial
<220> FEATURE:
<223> OTHER INFORMATION: genomic DNA (T. aureum ATCC 34304 C20 elongase
      upstream genomic DNA fragment)

<400> SEQUENCE: 131
ggccggggca gcccgcccag cacgccgctg cgctgctttc ggtcatgcga acctggctcc    60
ccacagcaat gctgcgcggt cgctgcgcct cttgaggctc ggcgacgttg gcccggtttg   120
gggcaccctg acgttgcacg aacgtccgct gcatctcagg cgcactcgga tcgacaactg   180

```
tgcaaccggt cagcctttcg cggcagattg ggcacttgcc gcgctcgcgt atccgcgtgg      240
cgcattcttc gcacacgcag gcgtgccggc agggaagcag gagggtgttt atcgtggcgt      300
ccatgtagac cttgcacagc cgcggctcac tttccctcgg cgcagtcccg tgcccaacgt      360
cggggccggg cgccggcgcc ggcgagggcg tcggttctgg gatgggatca ggatccgccg      420
aggctgcaga ttgctgtgcg ggggtgccgg ggcgcggccc attagcaccg tcctgcggaa      480
tatccaggag ggtgctcatc acggaagcca tgtccgggcg ctggctgccg tcttcgtgcg      540
tgcaacgatc caccaggtca aggagcaccc gagccacgtt ttggcgggtg cgaaaagcgg      600
cttggtcaac gcagcgctcc gggtcgaagc cgttgtcgcg catccagtac ggaagcaggt      660
cgaggccgcg gcggcaggga agcaaggcg gcttgccgga cacaagctcg ccgagcacga      720
cgccaaaggc gtaaacgtcc acggggcgat tgtactcgac atgggtggcg ccctccaggt      780
cggagatctc gggcgccatg tagccaagcg tgcccacttg tgtcatcgtt tgcatggtgt      840
ggagcgtggt actggcggcc accttggaca cgccaaagtc cgtccagcac agccttaggc      900
ccgcgccctt gttcaggttg accagagcgt tgtcgctctt ggatgtctct gtgcagcacg      960
ccagcagcgt gcagcgccct gaggccgtgc gccgcctggt atgccagcgc ctcgcgagcg     1020
ctgccgtcca aaagcggcgc gctccccgaa tcatcgcgga gctggatggc cttcttgagc     1080
gacatttcca tgcggggcat gatgatcgca aacctgccgc cgctctgtgg ctcgagcgcg     1140
gtcgccagga ccgtgagcac gttctcgtgc gttgcgctcg ccatccgcga ggcctcagcg     1200
cgaaagtcat cgaggacgcc gagcgtctgc ccgggccgcg gtaccttgac agcgcagcgc     1260
ccgaacggcg ccacgtccgc ttcaaacacc tcgccaaagg cgccttgtcc gagcagctcg     1320
ccccagccgc agccgcgacc actcgatctc gggcacgcgt gccatcgacc cttgcagcgt     1380
ggccttgcca agtcacagtc cagcgcgcag ttcagtgtct gccgcgccag gtccaccacg     1440
atcaattcat ccgagtcggc tgcgaactgg acaagtgcca tttgggtgcg ggcaacgcgc     1500
aagatcaccc agcactggca tgaagaccat gaatgaatga atgaccgtgc gcgagtgacc     1560
gaccaacacg agtccagccg actccttctt cttctccttc ttcttcttct tcttcttctc     1620
gtagcgggcg tcaacagcat caatcaggca tggcggcatt cactctgcgc gatggatggc     1680
acgagcgctg gaggtgatga acgcactgcc cggattggct ctcggtcact gtcagcacat     1740
gatgcctgtg cttgcgcgga gcgcgctatg tctcgttctg tgtcaagaca caggcgcaac     1800
tcttgatgga ttcttgaagc gcatgtaact gaagtctgac agactcggaa gtccattgtg     1860
aacaatgttg ttccacaatt gctccaattg ttccgattat tccacaattg ttgttccaat     1920
tgttccaatt gttccgatta ttccgattat tccactttag ttgttccagt tgttccgatt     1980
gttccacaat tgttgttccg attattccag ttgttccagt tgttccaatt attccaattg     2040
ttccagttcc ttactcttga catcggggga ataacgggtg tgtatttagg ggttcggcga     2100
aagcagaatg gccgaacgta acagcggaga ggaacctctt tagcggggtt tgcgtatcgg     2160
ggaaaccagg tgttgtgctg gcgaggagga tccccgcga ggcgatggct gctccgacga     2220
cgtgggctgg cgacgtcgct cgcaaaggcg ttccgcaacc gcgcgttccg ctgtaacgag     2280
accgttttcc ctgcgct                                                   2297
```

<210> SEQ ID NO 132
<211> LENGTH: 23
<212> TYPE: DNA
<213> ORGANISM: Artificial
<220> FEATURE:

```
<223> OTHER INFORMATION: primer

<400> SEQUENCE: 132
gccgctcatg cccacgctca aac                                              23

<210> SEQ ID NO 133
<211> LENGTH: 23
<212> TYPE: DNA
<213> ORGANISM: Artificial
<220> FEATURE:
<223> OTHER INFORMATION: primer

<400> SEQUENCE: 133
ctttcggctg ccaggaatct acg                                              23

<210> SEQ ID NO 134
<211> LENGTH: 2189
<212> TYPE: DNA
<213> ORGANISM: Artificial
<220> FEATURE:
<223> OTHER INFORMATION: genomic DNA (T. aureum ATCC 34304 OrfA
      downstream genomic DNA fragment)

<400> SEQUENCE: 134
ctttcggctg ccaggaatct acggcccagg gcgcggcccg atctcacgaa ttcgcaaggg      60
ccaggcccgc agtatcgtca aggagggcca ggtcttctcg cgggcgcacg tcgacgatat     120
caccggtgcg atccgcgctt cgctggccaa cccaaacccg ggccgcgcct acaacgtttg     180
cgacgacgag cctgcaatga accatgtcgt gacagagttt gcctgcgaac tcatggacgt     240
cccgcccccg aagcgcgaag actttgacaa ggtgcgcgag accatgtcaa gcatgtcgct     300
ctccttcttc tcagagagca agcgggtctt caacaagcgg ctcaaggaag agctgcggta     360
cgcgctattg tacccgacct accgcgaagg gatcaaagcc caactggagg aggagcttgc     420
caacggctgg acgctcatcg acgcctcggg tgcttctgct ggaaccgact ccctgcctc      480 gcccaaagcg cccgccccca tcgccgcctc aagtgacgag tcgagcgggc agagcgcgac     540
agcggccgag ccggtgcgcc ggcgcaggcg ccccgagcgc aaggcgctcc cgcctgctgg     600
gccgagtggg ccgtcggtct tgcagagggt ttctcgggca atttatgggc cgttcagttg     660
gctcctcggt cgcctgtttg ggccacttcc gagccgcgct gtcggcttgt ttcgcggctg     720
ggcgcactgg ctgttgcgtc tcgtggggct gcgcgcatcc gcgccgggcg gcggccgtac     780
aacctgcctc cttgttgaca acggctcgct caaaccagag cctttcgcc agctgcgcgt      840 gcacgcggcg aacctcgaag agtctcttag gagcgacgcg cgtgccccac atcccgtgca     900
ggtggtggcc gtcagcgcga ggtacagcga ccgcatcgac gcctcccttc tggacggcaa     960
gcccggcgtc gccctcgccg ggttcctgag ttccttcaag gccgacgccg agtcgcagcc    1020
agcaaccagc gaggttggcc gcatcatcgc gctcccctac tttctgggcc caagcaagac    1080
ggccacgtcg tatgttgctt cccagctcgc agagcacttt ccaggagccg agcgcaccat    1140
tgccgctccg ctcgtgtcgc gggacggcgc cattgcgcag ctcctcgctg acatggtcca    1200
tgacgtcgct cgggcgcgcg cgctgcaggc cccgtacgcg gtagttctcg tcgaccacgg    1260
gtccccgagc cgagccggtca accgcgttcg gcgggccatc gctgcgcgga tgcgccgccg    1320
ccttggcccg aacgcgcgct gcgttgtcga ctgctccatg gagcgccgcg agggcgacgc    1380
tttcgccttc aacgagcctc tgctagagtc ggttttcacc aagggtggtc tcgactctgg    1440
cgacgtcatt ctcgcgatgg cattttttggc gcctggtcgc cacgctggcg agggcggcga    1500
```

| | | | |
|---|---|---|---|
| tatcgcggag | atccttgacg | aggctatcgc aaagtcggct | ggcaagctgc gcgttcacca | 1560 |
| aacgcggttg | attggtgacg | tggacaggaa cggtacgcag | atttgcgccc tcctcaagaa | 1620 |
| caggccgctt | gccgcgctgt | aacggcaaga gcatccacaa | ttcctgacct gagcaaacca | 1680 |
| gcccacgcga | gagaccgaac | acgtcaagcc gatgaggcgc | agaaaacaaa gaaaaaaagc | 1740 |
| aaaaagaaca | aaaacccaag | gcaaaatgat ggcaattttc | ttggtatgga agccgatga | 1800 |
| tcgccgagtg | tcgctggcta | tttgctctgg tggggcatcg | agctcgatga ccgaaatcca | 1860 |
| ccaattatct | gcgtgtcaat | catttggagc ataagacccg | ggaaggcctt gagcaagcga | 1920 |
| agaaaccggc | gcgtgttcac | acgatagtac gagacgtcgc | tctctgcgcg gatctcaatc | 1980 |
| tgagccttct | tgtctccgcg | gatgaaagtg ttcatgtccc | cgacaagggc gccgcgccca | 2040 |
| acccctcgtt | tgggctgcgc | cgcgctactg gaaatggtga | ttccgcgaaa cgtgcccgat | 2100 |
| tcgcctttct | caacagggct | caccgtgaca gaaccctcag | cgacaagaac gatgccgtca | 2160 |
| atcttttcgc | cgggcgaggc | tttctgcag | | 2189 |

<210> SEQ ID NO 135
<211> LENGTH: 618
<212> TYPE: DNA
<213> ORGANISM: Artificial
<220> FEATURE:
<223> OTHER INFORMATION: genomic DNA (T. aureum ATCC 34304 ubiquitin promoter)

<400> SEQUENCE: 135

| | | | |
|---|---|---|---|
| cccagatctg | ccgcagcgcc | tggtgcaccc gccgggcgtt | gttggtgtgc tcttcttgcc | 60 |
| tccgagagag | agagcggagc | ggatgcatag gaaatcgggc | cacgcgggag ggccatgcgt | 120 |
| tcgccccaca | cgccactttc | cacgcccgct ctctctccgg | ccggcaggca gcgcataact | 180 |
| ctccgacgct | ggcaggctgg | tagcaactgg cagggacaac | tcgcgcgcgg gtcccggtcg | 240 |
| ttcgatgtgc | caacccgaga | gaatccagcc agcagggcgg | ttggcctcat cgcccacctg | 300 |
| ctatggtgca | gcgaaccaac | tcccgaagcg gccggttctg | cgattccctc ttctgaattc | 360 |
| tgaattctga | actgattccg | gaggagaacc ctctggaagc | gcgggttgcc tctccagttc | 420 |
| tgccgaacta | gacaggggag | tgagcagaga gtgaccctga | cgcggagcga gctggttgct | 480 |
| ggaaaagtcg | cgaacgctgg | gctgtgtcac gcgtccactt | cgggcagtcc ccaaacgaca | 540 |
| agcagaacaa | gcaacaccag | cagcagcaag cgacctaagc | aacactagcc aacatggcca | 600 |
| agcctttgtc | tcaagaag | | | 618 |

<210> SEQ ID NO 136
<211> LENGTH: 58
<212> TYPE: DNA
<213> ORGANISM: Artificial
<220> FEATURE:
<223> OTHER INFORMATION: primer

<400> SEQUENCE: 136
cttcttgaga caaaggcttg gccatgttgg ctagtgttgc ttaggtcgct tgctgctg     58

<210> SEQ ID NO 137
<211> LENGTH: 432
<212> TYPE: DNA
<213> ORGANISM: Artificial
<220> FEATURE:
<223> OTHER INFORMATION: Blasticidin resistance gene (Blar)

<400> SEQUENCE: 137

```
agcgacctaa gcaacactag ccaacatggc caagcctttg tctcaagaag aatccaccct    60
cattgaaaga gcaacggcta caatcaacag catccccatc tctgaagact acagcgtcgc   120
cagcgcagct ctctctagcg acggccgcat cttcactggt gtcaatgtat atcattttac   180
tgggggacct tgtgcagaac tcgtggtgct gggcactgct gctgctgcgg cagctggcaa   240
cctgacttgt atcgtcgcga tcggaaatga gaacaggggc atcttgagcc cctgcggacg   300
gtgccgacag gtgcttctcg atctgcatcc tgggatcaaa gccatagtga aggacagtga   360
tggacagccg acggcagttg ggattcgtga attgctgccc tctggttatg tgtgggaggg   420
ctaagatctg gg                                                        432

<210> SEQ ID NO 138
<211> LENGTH: 54
<212> TYPE: DNA
<213> ORGANISM: Artificial
<220> FEATURE:
<223> OTHER INFORMATION: primer

<400> SEQUENCE: 138
agcgacctaa gcaacactag ccaacatggc caagcctttg tctcaagaag aatc           54

<210> SEQ ID NO 139
<211> LENGTH: 38
<212> TYPE: DNA
<213> ORGANISM: Artificial
<220> FEATURE:
<223> OTHER INFORMATION: primer

<400> SEQUENCE: 139
cccagatctt agccctccca cacataacca gagggcag                             38

<210> SEQ ID NO 140
<211> LENGTH: 1000
<212> TYPE: DNA
<213> ORGANISM: Artificial
<220> FEATURE:
<223> OTHER INFORMATION: fusion DNA (T. aureum ATCC 34304 ubiquitin
      promoter/pTracer-CMV/Bsd/lacZ Blar)

<400> SEQUENCE: 140
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt   120
tcgccccaca cgccactttc cacgcccgct ctctctccgg ccggcaggca gcgcataact   180
ctccgacgct ggcaggctgg tagcaactgg cagggacaac tcgcgcgcgg gtcccggtcg   240
ttcgatgtgc caacccgaga gaatccagcc agcagggcgg ttggcctcat cgcccacctg   300
ctatggtgca gcgaaccaac tcccgaagcg gccggttctg cgattccctc ttctgaattc   360
tgaattctga actgattccg gaggagaacc ctctggaagc gcgggttgcc tctccagttc   420
tgccgaacta gacaggggag tgagcagaga gtgaccctga cgcggagcga gctggttgct   480
ggaaaagtcg cgaacgctgg gctgtgtcac gcgtccactt cgggcagtcc ccaaacgaca   540
agcagaacaa gcaacaccag cagcagcaag cgacctaagc aacactagcc aacatggcca   600
agcctttgtc tcaagaagaa tccaccctca ttgaaagagc aacggctaca atcaacagca   660
tccccatctc tgaagactac agcgtcgcca gcgcagctct ctctagcgac ggccgcatct   720
tcactggtgt caatgtatat catttttactg ggggaccttg tgcagaactc gtggtgctgg   780
gcactgctgc tgctgcggca gctggcaacc tgacttgtat cgtcgcgatc ggaaatgaga   840
```

```
acagggcat cttgagcccc tgcggacggt gccgacaggt gcttctcgat ctgcatcctg    900
ggatcaaagc catagtgaag gacagtgatg gacagccgac ggcagttggg attcgtgaat    960
tgctgccctc tggttatgtg tgggagggct aagatctggg                         1000
```

<210> SEQ ID NO 141
<211> LENGTH: 812
<212> TYPE: DNA
<213> ORGANISM: Artificial
<220> FEATURE:
<223> OTHER INFORMATION: cDNA (T.aureum ATCC 34304 ubiquitin promoter)

<400> SEQUENCE: 141

```
tcggtacccg ttagaacgcg taatacgact cactataggg agagtcgact gagcacaact     60
ctgctgcgag cgggcctcga gagcgtttgc ttcgagccgc ggagcaaggg ggatggatcg    120
ctcatgcggt cgtgcggccc tcggtcaccc ggtgggtcct gcactgacgc atctgttctg    180
atcagacaca cgaacgaaca aaccgaggag ccgcagcgcc tggtgcaccc gccgggcgtt    240
gttgtgtgct cttcttgcct ccgagagaga gagcggagcg gatgcatagg aaatcgggcc    300
acgcgggagg gccatgcgtt tgccccacac gccactttcc acgcccgctc tctctccggc    360
cggcaggcag cgcataactc tccgacgctg gcaggctggt agcaactggc agggacaact    420
cgcgcgcggg tcccggtcgt tcgatgtgcc aacccgagag aatccagcca gcagggcggt    480
tggcctcatc gcccacctgc tatggtgcag cgaaccaact cccgaagctg ccggttctgc    540
gattccctct tctgaattct gaattctgaa ctgattccgg aggagaaccc tctggaagcg    600
cgggttgcct ctccagttct gccgaactag acaggggagt gagcagagag tgaccctgac    660
gcggagcgag ctggttgctg gaaaagtcgc gaacgctggg ctgtgtcacg cgtccacttc    720
gggcagaccc caaacgacaa gcagaacaag caacaccagc agcagcaagc gatctaagca    780
acactagcca acatggtgag caagggcgag ga                                  812
```

<210> SEQ ID NO 142
<211> LENGTH: 29
<212> TYPE: DNA
<213> ORGANISM: Artificial
<220> FEATURE:
<223> OTHER INFORMATION: primer

<400> SEQUENCE: 142

```
tcggtacccg ttagaacgcg taatacgac                                       29
```

<210> SEQ ID NO 143
<211> LENGTH: 41
<212> TYPE: DNA
<213> ORGANISM: Artificial
<220> FEATURE:
<223> OTHER INFORMATION: primer

<400> SEQUENCE: 143

```
tcctcgccct tgctcaccat gttggctagt gttgcttagg t                         41
```

<210> SEQ ID NO 144
<211> LENGTH: 748
<212> TYPE: DNA
<213> ORGANISM: Artificial
<220> FEATURE:
<223> OTHER INFORMATION: Enhanced GFP gene (Enhanced GFP DNA fragment)

<400> SEQUENCE: 144

```
acctaagcaa cactagccaa catggtgagc aagggcgagg agctgttcac cggggtggtg     60
```

```
cccatcctgg tcgagctgga cggcgacgta acggccaca agttcagcgt gtccggcgag      120
ggcgagggcg atgccaccta cggcaagctg accctgaagt tcatctgcac caccggcaag    180
ctgcccgtgc cctggcccac cctcgtgacc accctgacct acggcgtgca gtgcttcagc    240
cgctaccccg accacatgaa gcagcacgac ttcttcaagt ccgccatgcc cgaaggctac    300
gtccaggagc gcaccatctt cttcaaggac gacggcaact acaagacccg cgccgaggtg    360
aagttcgagg gcgacaccct ggtgaaccgc atcgagctga agggcatcga cttcaaggag    420
gacggcaaca tcctggggca caagctggag tacaactaca acagccacaa cgtctatatc    480
atggccgaca gcagaagaa cggcatcaag gtgaacttca gatccgcca caacatcgag       540 gacggcagcg tgcagctcgc cgaccactac cagcagaaca cccccatcgg cgacggcccc    600
gtgctgctgc ccgacaacca ctacctgagc acccagtccg ccctgagcaa agaccccaac    660
gagaagcgcg atcacatggt cctgctggag ttcgtgaccg ccgccgggat cactctcggc    720
atggacgcca agttgaccag tgccgttc                                        748

<210> SEQ ID NO 145
<211> LENGTH: 41
<212> TYPE: DNA
<213> ORGANISM: Artificial
<220> FEATURE:
<223> OTHER INFORMATION: primer

<400> SEQUENCE: 145
acctaagcaa cactagccaa catggtgagc aagggcgagg a                          41

<210> SEQ ID NO 146
<211> LENGTH: 58
<212> TYPE: DNA
<213> ORGANISM: Artificial
<220> FEATURE:
<223> OTHER INFORMATION: primer

<400> SEQUENCE: 146
gaacggcact ggtcaacttg gcgtccatgc cgagagtgat cccggcggcg gtcacgaa       58

<210> SEQ ID NO 147
<211> LENGTH: 1519
<212> TYPE: DNA
<213> ORGANISM: Artificial
<220> FEATURE:
<223> OTHER INFORMATION: fusion DNA (T. aureum ATCC 34304 ubiquitin
      promoter/Enhanced GFP)

<400> SEQUENCE: 147
tcggtacccg ttagaacgcg taatacgact cactataggg agagtcgact gagcacaact      60
ctgctgcgag cgggcctcga gagcgtttgc ttcgagccgc ggagcaaggg ggatggatcg     120
ctcatgcggt cgtgcggccc tcggtcaccc ggtgggtcct gcactgacgc atctgttctg    180
atcagacaca cgaacgaaca aaccgaggag ccgcagcgcc tggtgcaccc gccgggcgtt    240
gttgtgtgct cttcttgcct ccgagagaga gagcggagcg gatgcatagg aaatcgggcc    300
acgcgggagg gccatgcgtt tgccccacac gccactttcc acgcccgctc tctctccggc    360
cggcaggcag cgcataactc tccgacgctg gcaggctggt agcaactggc agggacaact    420
cgcgcgcggg tcccggtcgt tcgatgtgcc aacccgagag aatccagcca gcagggcggt    480
tggcctcatc gcccacctgc tatggtgcag cgaaccaact cccgaagctg ccggttctgc    540
gattccctct tctgaattct gaattctgaa ctgattccgg aggagaaccc tctggaagcg    600
```

```
cggggttgcct ctccagttct gccgaactag acaggggagt gagcagagag tgaccctgac      660
gcggagcgag ctggttgctg gaaaagtcgc gaacgctggg ctgtgtcacg cgtccacttc      720
gggcagaccc caaacgacaa gcagaacaag caacaccagc agcagcaagc gacctaagca      780
acactagcca acatggtgag caagggcgag gagctgttca ccggggtggt gcccatcctg      840
gtcgagctgg acggcgacgt aaacggccac aagttcagcg tgtccggcga gggcgagggc      900
gatgccacct acggcaagct gaccctgaag ttcatctgca ccaccggcaa gctgcccgtg      960
ccctggccca ccctcgtgac caccctgacc tacggcgtgc agtgcttcag ccgctacccc     1020
gaccacatga gcagcacga cttcttcaag tccgccatgc ccgaaggcta cgtccaggag     1080
cgcaccatct tcttcaagga cgacggcaac tacaagaccc gcgccgaggt gaagttcgag     1140
ggcgacaccc tggtgaaccg catcgagctg aagggcatcg acttcaagga ggacggcaac     1200
atcctggggc acaagctgga gtacaactac aacagccaca cgtctatat catggccgac     1260 aagcagaaga acggcatcaa ggtgaacttc aagatccgcc acaacatcga ggacggcagc     1320
gtgcagctcg ccgaccacta ccagcagaac ccccccatcg gcgacggccc cgtgctgctg     1380
cccgacaacc actacctgag cacccagtcc gccctgagca agacccccaa cgagaagcgc     1440
gatcacatgg tcctgctgga gttcgtgacc gccgccggga tcactctcgg catggacgcc     1500
aagttgacca gtgccgttc                                                   1519

<210> SEQ ID NO 148
<211> LENGTH: 1319
<212> TYPE: DNA
<213> ORGANISM: Artificial
<220> FEATURE:
<223> OTHER INFORMATION: fusion DNA (T. aureum ATCC 34304 ubiquitin
      promoter/Enhanced GFP)

<400> SEQUENCE: 148
cccagatctg ccgcagcgcc tggtgcaccc gccgggcgtt gttgtgtgct cttcttgcct       60
ccgagagaga gagcggagcg gatgcatagg aaatcgggcc acgcgggagg gccatgcgtt      120
tgccccacac gccactttcc acgcccgctc tctctccggc cggcaggcag cgcataactc      180
tccgacgctg gcaggctggt agcaactggc agggacaact cgcgcgcggg tcccggtcgt      240
tcgatgtgcc aacccgagag aatccagcca gcagggcggt tggcctcatc gcccaccttgc     300 tatggtgcag cgaaccaact cccgaagctg ccggttctgc gattccctct tctgaattct      360
gaattctgaa ctgattccgg aggagaaccc tctggaagcg cggggttgcct ctccagttct    420 gccgaactag acaggggagt gagcagagag tgaccctgac gcggagcgag ctggttgctg      480
gaaaagtcgc gaacgctggg ctgtgtcacg cgtccacttc gggcagaccc caaacgacaa      540
gcagaacaag caacaccagc agcagcaagc gacctaagca acactagcca acatggtgag      600
caagggcgag gagctgttca ccggggtggt gcccatcctg gtcgagctgg acggcgacgt      660
aaacggccac aagttcagcg tgtccggcga gggcgagggc gatgccacct acggcaagct      720
gaccctgaag ttcatctgca ccaccggcaa gctgcccgtg ccctggccca ccctcgtgac      780
caccctgacc tacggcgtgc agtgcttcag ccgctacccc gaccacatga gcagcacga     840 cttcttcaag tccgccatgc ccgaaggcta cgtccaggag cgcaccatct tcttcaagga      900
cgacggcaac tacaagaccc gcgccgaggt gaagttcgag ggcgacaccc tggtgaaccg      960
catcgagctg aagggcatcg acttcaagga ggacggcaac atcctggggc acaagctgga     1020
gtacaactac aacagccaca cgtctatat catggccgac aagcagaaga acggcatcaa     1080
```

```
ggtgaacttc aagatccgcc acaacatcga ggacggcagc gtgcagctcg ccgaccacta    1140
ccagcagaac accccatcg gcgacggccc cgtgctgctg cccgacaacc actacctgag     1200
cacccagtcc gccctgagca aagaccccaa cgagaagcgc gatcacatgg tcctgctgga    1260
gttcgtgacc gccgccggga tcactctcgg catggacgcc aagttgacca gtgccgttc    1319
```

<210> SEQ ID NO 149
<211> LENGTH: 408
<212> TYPE: DNA
<213> ORGANISM: Artificial
<220> FEATURE:
<223> OTHER INFORMATION: cDNA (Zeor)

<400> SEQUENCE: 149

```
cgccgccggg atcactctcg gcatggacgc caagttgacc agtgccgttc cggtgctcac      60
cgcgcgcgac gtcgccggag cggtcgagtt ctggaccgac cggctcgggt tctcccggga    120
cttcgtggag gacgacttcg ccggtgtggt ccgggacgag gtgaccctgt tcatcagcgc    180
ggtccaggac caggtggtgc cggacaacac cctggcctgg gtgtgggtgc gcggcctgga    240
cgagctgtac gccgagtggt cggaggtcgt gtccacgaac ttccgggacg cctccgggcc    300
ggccatgacc gagatcggcg agcagccgtg ggggcgggag ttcgccctgc gcgacccggc    360
cggcaactgc gtgcacttcg tggccgagga gcaggactga gatctggg                408
```

<210> SEQ ID NO 150
<211> LENGTH: 54
<212> TYPE: DNA
<213> ORGANISM: Artificial
<220> FEATURE:
<223> OTHER INFORMATION: primer

<400> SEQUENCE: 150

```
cgccgccggg atcactctcg gcatggacgc caagttgacc agtgccgttc cggt           54
```

<210> SEQ ID NO 151
<211> LENGTH: 38
<212> TYPE: DNA
<213> ORGANISM: Artificial
<220> FEATURE:
<223> OTHER INFORMATION: primer

<400> SEQUENCE: 151

```
cccagatctc agtcctgctc ctcggccacg aagtgcac                              38
```

<210> SEQ ID NO 152
<211> LENGTH: 1677
<212> TYPE: DNA
<213> ORGANISM: Artificial
<220> FEATURE:
<223> OTHER INFORMATION: fusion DNA (T. aureum ATCC 34304 ubiquitin
      promoter/Enhanced GFP/pcDNA3.1 Zeo(+) Zeor)

<400> SEQUENCE: 152

```
cccagatctg ccgcagcgcc tggtgcaccc gccgggcgtt gttgtgtgct cttcttgcct      60
ccgagagaga gagcggagcg gatgcatagg aaatcgggcc acgcgggagg gcatgcgtt     120 tgccccacac gccactttcc acgcccgctc tctctccggc cggcaggcag cgcataactc    180
tccgacgctg gcaggctggt agcaactggc agggacaact cgcgcgcggg tcccggtcgt    240
tcgatgtgcc aacccgagag aatccagcca gcagggcggt tggcctcatc gcccacctgc    300
tatggtgcag cgaaccaact cccgaagctg ccggttctgc gattccctct tctgaattct    360
```

```
gaattctgaa ctgattccgg aggagaaccc tctggaagcg cggggttgcct ctccagttct    420 gccgaactag acaggggagt gagcagagag tgaccctgac gcggagcgag ctggttgctg    480
gaaaagtcgc gaacgctggg ctgtgtcacg cgtccacttc gggcagaccc caaacgacaa    540
gcagaacaag caacaccagc agcagcaagc gacctaagca acactagcca acatggtgag    600
caagggcgag gagctgttca ccggggtggt gcccatcctg gtcgagctgg acggcgacgt    660
aaacggccac aagttcagcg tgtccggcga gggcgagggc gatgccacct acggcaagct    720
gaccctgaag ttcatctgca ccaccggcaa gctgcccgtg ccctggccca cctcgtgac     780 caccctgacc tacggcgtgc agtgcttcag ccgctacccc gaccacatga gcagcacga    840 cttcttcaag tccgccatgc ccgaaggcta cgtccaggag cgcaccatct tcttcaagga    900
cgacggcaac tacaagaccc gcgccgaggt gaagttcgag ggcgacaccc tggtgaaccg    960
catcgagctg aagggcatcg acttcaagga ggacggcaac atcctggggc acaagctgga   1020
gtacaactac aacagccaca acgtctatat catggccgac aagcagaaga acggcatcaa   1080
ggtgaacttc aagatccgcc acaacatcga ggacggcagc gtgcagctcg ccgaccacta   1140
ccagcagaac acccccatcg gcgacggccc cgtgctgctg cccgacaacc actacctgag   1200
cacccagtcc gccctgagca agaccccaa cgagaagcgc gatcacatgg tcctgctgga    1260
gttcgtgacc gccgccggga tcactctcgg catggacgcc aagttgacca gtgccgttcc   1320
ggtgctcacc gcgcgcgacg tcgccggagc ggtcgagttc tggaccgacc ggctcgggtt   1380
ctcccgggac ttcgtggagg acgacttcgc cggtgtggtc cggacgacg tgaccctgtt    1440 catcagcgcg gtccaggacc aggtggtgcc ggacaacacc ctggcctggg tgtgggtgcg   1500
cggcctggac gagctgtacg ccgagtggtc ggaggtcgtg tccacgaact tccgggacgc   1560
ctccgggccg gccatgaccg agatcggcga gcagccgtgg gggcgggagt tcgccctgcg   1620
cgacccggcc ggcaactgcg tgcacttcgt ggccgaggag caggactgag atctggg      1677
```

<210> SEQ ID NO 153
<211> LENGTH: 2884
<212> TYPE: DNA
<213> ORGANISM: Artificial
<220> FEATURE:
<223> OTHER INFORMATION: genomic DNA (T. aureum ATCC 34304 C20 elongase upstream/C20 elongase/C20 elongase downstream)

<400> SEQUENCE: 153

```
cccgaattca ctagtgattc tcccgggtgg acctagcgcg tgtgtcacct gccggccccc     60
gttgcgtgca accgaattga tcgataatag aattacataa caaacaactt gctggatgag    120
tacaagacca gcgtagtgtg gctgtgggac gttgaacgga gcgggtcctg tgatggcgca    180
gaaaggaact ccgcccgagg tgaaacccg atgcgcagga ctctgcggcc acagcccctc     240
cgccagtatt ccactaaaaa tccgcccct ttgacaaaga tcgcaacccc gtcccatcaa     300
ctcctcacaa taggctttcc actggcggaa acgtccccgg cacaggagtg cctcccgcgg    360
ttctgcgcat acggctgacc actacgcagc gcgatatcct ccatccgcgt atatatccgt    420
aaacaacgga acattctccc tctcaacgag gcgtggtttt cgaagtcatg cctttcttcc    480
ttcctacttt ccttccttct ttctttcttt cttttccttc ttttgcaagcg tgcgcgaact    540 tgaaggtact acttacactt gacagagaga gatagagacg gcaattcgac caagtacttt    600
ccacgatttt ttttttttt gttttggtcg ctttcgttgg tcgtgcatga tggatggccg     660 ggattttac aattggatgc gccaggctgc cacgcatgcc gtgacgcttg ctcgcggcga    720
```

-continued

```
ctcatgatgc ttgccagtgg cagtgcatcc agctcttccc tctgctcgtc gtgtactcac    780
tggcgatgct ctcggcgctc gttcaagggc catcgatcga tcgatcgatc gatcgatcga    840
tcaatcacgt ttggtggact cggcagaccc cgaacgtgtt tctcccagga cgcgccgctg    900
tcgctcgcta atccacccga agcgcggtcg gctggcacgg tcgctcggct ggaagttgag    960
tagtttgctt tctgttgctg cgctgctttg taaacgcgac catggcgacg cgcacctcga    1020
agagcgctcc ggcggtttcc aagtcggcca aggttgccgc gccggcgaag aagcggtcgg    1080
tcgacaggag cgacggtttc ttccgcacgt tcaacctgtg cgccctgtac gggtctgccc    1140
tcgcctatgc gtacaagcac ggcccggtgg acaatgacgg ccaggggctg tactttcaca    1200
agtcgcccat gtacgcgttc gccgtgtcgg acgtcatgac cttcggcgcg ccgctgatgt    1260
acgtgctcgg tgtgatgctg ctcagcaggt acatggcgga caaaaagccc ctgactggct    1320
tcatcaagac ctacatccag cccgtctaca acgtggtcca atcgcggtg tgcggctgga    1380
tggtgtgggg cctctggccg caggtcgacc tggccaacgg caacccttc ggcctcaaca    1440
agtcgcgcga ctcgaacatc gagttttcg tgttcgtgca cctcctgaca aagtttctcg    1500
actggagcga cacgttcatg atgatcctca agaaaaacta cgcccaggtt agcttctgc    1560
aggtgttcca ccacgcaacg atcggcatgg tgtggtcgtt ccttcttcag cgtggctggg    1620
gctcgggcac cgccgcgtac ggtgctttca tcaactcggt cacgcacgtg atcatgtact    1680
cgcactactt tgccacctcg ctcaacatca acaacccgtt caagcggtac atcacgagct    1740
tccagctcgc ccagtttgca agctgcatcg tgcatgccct actggtgctt gccttcgagg    1800
aggtgtaccc gctcgagtac gcttacctgc agatcagcta ccacatcatc atgctctacc    1860
tgttcggacg ccgcatgaac tggagccccg agtggtgcac cggtgagatc gacggccttg    1920
acgccccaag cgcccccacc aagtccgagt aaacctgttt ccggctggct cccgagccat    1980
gcttaccatg aatgaacctg caaacagtct gaggtccttg tgcaaaccgc tcagtgggac    2040
gtcgacgaag aaagaaacaa tgtgtactcg tcttgctctg ctcccgcgcc gttttttatc    2100
gttgttgaga cctctcgcgc agttttggga atcaaccaaa acaagagccc ggcgtcagcg    2160
tttgcttcgc cctcggctgc actcgctcgg cacgcaggta taactgggtg agtaccaagc    2220
cccgcatttg tctgtccgcg atccgcgcac gctgcgggtc aggacgacat cgcgctgcac    2280
gtcacagtgg gtcccttttg acgtggctgc ggcgatgagg aggcttggct cggcttcatg    2340
gcaaggcaac agactcgctt ccgggacgcg cacgacgagc agcgctgctt tgatcgacct    2400
tgcctgcgtc accgctcgg ctgctttgat cgatcgttgt caccggccga gtgaccgcga    2460
acgcattgcc cgcacggctc ggctcggccc ggaccggacc ggctcgcctt ggcggcgcgg    2520
cgcgatggca acccagacgc ggccggagcc gcgcgcggag gacaaggcca tgttcatctt    2580
cgggctcggg tacgttggga gcaggctcgc caaccagctg gcggaacagg ggtggcgcgt    2640
cgcggggtcg gtgagggagc tcgggcgcga ggacgacttt gccgagttcg aaaagtccaa    2700
gctgagcggc aaggtgcagg tgttccgact cccgcttgag ggcgaggaca acacgcccgc    2760
tcgcgcgcgg gagatactta gcgggtacca gcacctgctg ttcacggcgc cagtggaccg    2820
cgccccggaac tgtgaccct tcttgggcga ccccgttctc ggccccggga taatcgaatt    2880
cggg                                                                 2884
```

<210> SEQ ID NO 154
<211> LENGTH: 50
<212> TYPE: DNA

<213> ORGANISM: Artificial
<220> FEATURE:
<223> OTHER INFORMATION: primer

<400> SEQUENCE: 154

```
cccgaattca ctagtgattc tcccgggtgg acctagcgcg tgtgtcacct       50
```

<210> SEQ ID NO 155
<211> LENGTH: 40
<212> TYPE: DNA
<213> ORGANISM: Artificial
<220> FEATURE:
<223> OTHER INFORMATION: primer

<400> SEQUENCE: 155

```
cccgaattcg attatcccgg ggccgagaac ggggtcgccc       40
```

<210> SEQ ID NO 156
<211> LENGTH: 1939
<212> TYPE: DNA
<213> ORGANISM: Artificial
<220> FEATURE:
<223> OTHER INFORMATION: fusion DNA (T. aureum ATCC 34304 C20 elongase
      upstream/C20 elongase downstream)

<400> SEQUENCE: 156

```
cccgaattca ctagtgattc tcccgggtgg acctagcgcg tgtgtcacct gccggcccc      60
gttgcgtgca accgaattga tcgataatag aattacataa caaacaactt gctggatgag    120
tacaagacca gcgtagtgtg gctgtgggac gttgaacgga gcgggtcctg tgatggcgca    180
gaaaggaact ccgcccgagg tgaaacccg atgcgcagga ctctgcggcc acagcccctc     240
cgccagtatt ccactaaaaa tccgcccct ttgacaaaga tcgcaacccc gtcccatcaa     300
ctcctcacaa taggctttcc actggcggaa acgtccccgg cacaggagtg cctcccgcgg    360
ttctgcgcat acggctgacc actacgcagc gcgatatcct ccatccgcgt atatatccgt    420
aaacaacgga acattctccc tctcaacgag gcgtggtttt cgaagtcatg ccttctctt    480
ttcctacttt ccttccttct ttctttcttt ctttccttct tttgcaagcg tgcgcgaact    540
tgaaggtact acttacactt gacagagaga gatagagacg gcaattcgac caagtacttt    600
ccacgatttt ttttttttt gttttggtcg ctttcgttgg tcgtgcatga tggatggccg    660
ggattttac aattggatgc gccaggctgc cacgcatgcc gtgacgcttg ctcgcggcga    720
ctcatgatgc ttgccagtgg cagtgcatcc agctcttccc tctgctcgtc gtgtactcac    780
tggcgatgct ctcggcgctc gttcaagggc atcgatcga tcgatcgatc gatcgatcga    840
tcaatcacgt ttggtggact cggcagaccc cgaacgtgtt tctcccagga gcgccgctg     900
tcgctcgcta atccacccga agcgcggtcg gctggcacgg tcgctcggct ggaagttgag    960
tagtttgctt tctgttgctg cgctgctttg taaacgcgac cagatctacc tgtttccggc    1020
tggctcccga gccatgctta ccatgaatga acctgcaaac agtctgaggt ccttgtgcaa    1080
accgctcagt gggacgtcga cgaagaaaga acaatgtgt actcgtcttg ctctgctccc    1140
gcgccgtttt tatcgttgt tgagacctct cgcgcagttt tgggaatcaa ccaaaacaag    1200
agcccggcgt cagcgtttgc ttcgcccctcg gctgcactcg ctcggcacgc aggtataact    1260
gggtgagtac caagccccgc atttgtctgt ccgcgatccg cgcacgctgc gggtcaggac    1320
gacatcgcgc tgcacgtcac agtgggtccc tttgacgtg gctgcggcga tgaggaggct   1380
tggctcggct tcatggcaag gcaacagact cgcttccggg acgcgcacga cgagcagcgc    1440
```

-continued

```
tgctttgatc gaccttgcct gcgtcaccgc ctcggctgct ttgatcgatc gttgtcaccg   1500
gccgagtgac cgcgaacgca ttgcccgcac ggctcggctc ggcccggacc ggaccggctc   1560
gccttggcgg cgcggcgcga tggcgaccca gacgcggccg gagccgcgcg cggaggacaa   1620
ggccatgttc atcttcgggc tcgggtacgt tgggagcagg ctcgccaacc agctggcgga   1680
acaggggtgg cgcgtcgcgg ggtcggtgag ggagctcggg cgcgaggacg actttgccga   1740
gttcgaaaag tccaagctga gcggcaaggt gcaggtgttc cgactcccgc ttgagggcga   1800
ggacaacacg cccgctcgcg cgcgggagat acttagcggg taccagcacc tgctgttcac   1860
ggcgccagtg gaccgcgccc ggaactgtga ccccttcttg ggcgaccccg ttctcggccc   1920
cgggataatc gaattcggg                                                1939
```

<210> SEQ ID NO 157
<211> LENGTH: 38
<212> TYPE: DNA
<213> ORGANISM: Artificial
<220> FEATURE:
<223> OTHER INFORMATION: primer

<400> SEQUENCE: 157

```
cccagatcta cctgtttccg gctggctccc gagccatg                             38
```

<210> SEQ ID NO 158
<211> LENGTH: 38
<212> TYPE: DNA
<213> ORGANISM: Artificial
<220> FEATURE:
<223> OTHER INFORMATION: primer

<400> SEQUENCE: 158

```
cccagatctg gtcgcgttta caaagcagcg cagcaaca                             38
```

<210> SEQ ID NO 159
<211> LENGTH: 31
<212> TYPE: DNA
<213> ORGANISM: Artificial
<220> FEATURE:
<223> OTHER INFORMATION: primer

<400> SEQUENCE: 159

```
ctcccgggtg gacctagcgc gtgtgtcacc t                                    31
```

<210> SEQ ID NO 160
<211> LENGTH: 27
<212> TYPE: DNA
<213> ORGANISM: Artificial
<220> FEATURE:
<223> OTHER INFORMATION: primer

<400> SEQUENCE: 160

```
atcccggggc cgagaacgcc ctcgccc                                         27
```

<210> SEQ ID NO 161
<211> LENGTH: 3215
<212> TYPE: DNA
<213> ORGANISM: Artificial
<220> FEATURE:
<223> OTHER INFORMATION: fusion DNA (T. aureum C20 elongase
      upstream/ubiquitin promoter/Blar/SV40 terminator/T. aureum C20
      elongase downstream)

<400> SEQUENCE: 161

```
ctcccgggtg gacctagcgc gtgtgtcacc tgccggcccc cgttgcgtgc aaccgaattg     60
```

```
atcgataata gaattacata acaaacaact tgctggatga gtacaagacc agcgtagtgt    120
ggctgtggga cgttgaacgg agcgggtcct gtgatggcgc agaaaggaac tccgcccgag    180
gtgaaacccc gatgcgcagg actctgcggc cacagcccct ccgccagtat tccactaaaa    240
atccgccccc tttgacaaag atcgcaaccc cgtcccatca actcctcaca ataggctttc    300
cactggcgga aacgtccccg gcacaggagt gcctcccgcg gttctgcgca tgcggctgac    360
cactacgcag cgcgatatcc tccatccgcg tatatatccg taaacaacgg aacattctcc    420
ctctcaacga ggcgtggttt tcgaagtcat gcctttcttc cttcctactt tccttccttc    480
tttctttctt tctttccttc ttttgcaagc gtgcgcgaac ttgaaggtac tacttacact    540
tgacagagag agatagagac ggcaattcga ccaagtactt tccacgattt tttttttttt    600
tgttttggtc gctttcgttg gtcgtgcatg atggatggcc gggattttta caattggatg    660
cgccaggctg ccacgcatgc cgtgacgctt gctcgcggcg actcatgatg cttgccagtg    720
gcagtgcatc cagctcttcc ctctgctcgt cgtgtactca ctggcgatgc tctcggcgct    780
cgttcaaggg ccatcgatcg atcgatcgat cgatcgatcg atcaatcacg tttggtggac    840
tcggcagacc ccgaacgtgt ttctcccagg acgcgccgct gtcgctcgct aatccacccg    900
aagcgcggtc ggctggcacg gtcgctcggc tggaagttga gtagtttgct ttctgttgct    960
gcgctgcttt gtaaacgcga ccagatctgg atctgccgca gcgcctggtg cacccgccgg   1020
gcgttgttgt gtgctcttct tgcctccgag agagagagcg gagcggatgc ataggaaatc   1080
gggccacgcg ggagggccat gcgttcgccc cacacgccac tttccacgcc cgctctctct   1140
ccggccggca ggcagcgcat aactctccga cgctggcagg ctggtagcaa ctggcaggga   1200
caactcgcgc gcgggtcccg gtcgttcgat gtgccaaccc gagagaatcc agccagcagg   1260
gcggttggcc tcatcgccca cctgctatgg tgcagcgaac caactcccga agcggccggt   1320
tctgcgattc cctcttctga attctgaatt ctgaactgat tccggaggag aaccctctgg   1380
aagcgcgggt tgcctctcca gttctgccga actagacagg ggagtgagca gagagtgacc   1440
ctgacgcgga gcgagctggt tgctggaaaa gtcgcgaacg ctgggctgtg tcacgcgtcc   1500
acttcgggca gtccccaaac gacaagcaga acaagcaaca ccagcagcag caagcgacct   1560
aagcaacact agccaacatg gccaagcctt tgtctcaaga agaatccacc ctcattgaaa   1620
gagcaacggc tacaatcaac agcatcccca tctctgaaga ctacagcgtc gccagcgcag   1680
ctctctctag cgacggccgc atcttcactg gtgtcaatgt atatcatttt actggggac    1740
cttgtgcaga actcgtggtg ctgggcactg ctgctgctgc ggcagctggc aacctgactt   1800
gtatcgtcgc gatcggaaat gagaacaggg gcatcttgag cccctgcgga cggtgccgac   1860
aggtgcttct cgatctgcat cctgggatca aagccatagt gaaggacagt gatggacagc   1920
cgacggcagt tgggattcgt gaattgctgc cctctggtta tgtgtgggag ggctaagatc   1980
cgcgaaatga ccgaccaagc gacgcccaac ctgccatcac gagatttcga ttccaccgcc   2040
gccttctatg aaaggttggg cttcggaatc gttttccggg acgccggctg gatgatcctc   2100
cagcgcgggg atctcatgct ggagttcttc gcccaccccc aacttgtttat tgcagcttat   2160
aatggttaca aataaagcaa tagcatcaca aatttcacaa ataaagcatt ttttttcactg   2220
cattctagtt gtggtttgtc caaactcatc aatgtatctt atcatgtctg tataccgtcg   2280
acctctagct agatctacct gtttccggct ggctcccgag ccatgcttac catgaatgaa   2340
cctgcaaaca gtctgaggtc cttgtgcaaa ccgctcagtg ggacgtcgac gaagaaagaa   2400
```

| | |
|---|---|
| acaatgtgta ctcgtcttgc tctgctcccg cgccgttttt tatcgttgtt gagacctctc | 2460 |
| gcgcagtttt gggaatcaac caaaacaaga gcccggcgtc agcgtttgct tcgccctcgg | 2520 |
| ctgcactcgc tcggcacgca ggtataactg ggtgagtacc aagccccgca tttgtctgtc | 2580 |
| cgcgatccgc gcacgctgcg ggtcaggacg acatcgcgct gcacgtcaca gtgggtccct | 2640 |
| tttgacgtgg ctgcggcgat gaggaggctt ggctcggctt catggcaagg caacagactc | 2700 |
| gcttccggga cgcgcacgac gagcagcgct gctttgatcg accttgcctg cgtcaccgcc | 2760 |
| tcggctgctt tgatcgatcg ttgtcaccgg ccgagtgacc gcgaacgcat tgcccgcacg | 2820 |
| gctcggctcg gcccgaccg gaccggctcg ccttggcggc gcggcgcgat ggcgacccag | 2880 |
| acgcggccgg agccgcgcgc ggaggacaag gccatgttca tcttcgggct cgggtacgtt | 2940 |
| gggagcaggc tcgccaacca gctggcggaa caggggtggc gcgtcgcggg gtcggtgagg | 3000 |
| gagctcgggc gcgaggacga cttttgccgag ttcgaaaagt ccaagctgag cggcaaggtg | 3060 |
| caggtgttcc aactcccgct tgagggcgag gacaacacgc ccgctcgcgc gcgggagata | 3120 |
| cttagcgggt accagcacct gctgttcacg gcgccagtgg accgcgcccg gaactgtgac | 3180 |
| cccttcttgg gcgaccccgt tctcggcccc gggat | 3215 |

<210> SEQ ID NO 162
<211> LENGTH: 3887
<212> TYPE: DNA
<213> ORGANISM: Artificial
<220> FEATURE:
<223> OTHER INFORMATION: fusion DNA (T. aureum C20 elongase
       upstream/ubiquitin promoter/Enhanced GFP/Zeor/SV40 terminator/T.
       aureum C20 elongase downstream)

<400> SEQUENCE: 162

| | |
|---|---|
| ctcccgggtg gacctagcgc gtgtgtcacc tgccggcccc cgttgcgtgc aaccgaattg | 60 |
| atcgataata gaattacata acaaacaact tgctggatga gtacaagacc agcgtagtgt | 120 |
| ggctgtggga cgttgaacgg agcgggtcct gtgatgcgc agaaaggaac tccgcccgag | 180 |
| gtgaaacccc gatgcgcagg actctgcggc cacagcccct ccgccagtat tccactaaaa | 240 |
| atccgccccc tttgacaaag atcgcaaccc cgtcccatca actcctcaca ataggctttc | 300 |
| cactggcgga aacgtccccg gcacaggagt gcctcccgcg gttctgcgca tacggctgac | 360 |
| cactacgcag cgcgatatcc tccatccgcg tatatatccg taaacaacgg aacattctcc | 420 |
| ctctcaacga ggcgtggttt tcgaagtcat gcctttcttc cttcctactt tccttccttc | 480 |
| tttctttctt tctttccttc ttttgcaagc gtgcgcgaac ttgaaggtac tacttacact | 540 |
| tgacagagag agatagagac ggcaattcga ccaagtactt tccacgattt ttttttttt | 600 |
| tgttttggtc gctttcgttg gtcgtgcatg atggatggcc gggatttta caattggatg | 660 |
| cgccaggctg ccacgcatgc cgtgacgctt gctcgcggcg actcatgatg cttgccagtg | 720 |
| gcagtgcatc cagctcttcc ctctgctcgt cgtgtactca ctggcgatgc tctcggcgct | 780 |
| cgttcaaggg ccatcgatcg atcgatcgat cgatcgatc atcaatcacg tttggtggac | 840 |
| tcggcagacc ccgaacgtgt ttctcccagg acgcgccgct gtcgctcgct aatccacccg | 900 |
| aagcgcggtc ggctggcacg gtcgctcggc tggaagttga gtagtttgct ttctgttgct | 960 |
| gcgctgcttt gtaaacgcga ccagatctgc cgcagcgcct ggtgcacccg ccgggcgttg | 1020 |
| ttgtgtgctc ttcttgcctc cgagagagag agcggagcgg atgcatagga aatcgggcca | 1080 |
| cgcgggaggg ccatgcgttt gccccacacg ccacttttcca cgcccgctct ctctccggcc | 1140 |
| ggcaggcagc gcataactct ccgacgctgg caggctggta gcaactggca gggacaactc | 1200 |

```
gcgcgcgggt cccggtcgtt cgatgtgcca acccgagaga atccagccag cagggcggtt    1260
ggcctcatcg cccacctgct atggtgcagc gaaccaactc ccgaagctgc cggttctgcg    1320
attccctctt ctgaattctg aattctgaac tgattccgga ggagaaccct ctggaagcgc    1380
gggttgcctc tccagttctg ccgaactaga caggggagtg agcagagagt daccctgacg    1440
cggagcgagc tggttgctgg aaaagtcgcg aacgctgggc tgtgtcacgc gtccacttcg    1500
ggcagacccc aaacgacaag cagaacaagc aacaccagca gcagcaagcg atctaagcaa    1560
cactagccaa catggtgagc aagggcgagg agctgttcac cggggtggtg cccatcctgg    1620
tcgagctgga cggcgacgta aacggccaca agttcagcgt gtccggcgag ggcgagggcg    1680
atgccaccta cggcaagctg accctgaagt tcatctgcac caccggcaag ctgcccgtgc    1740
cctggcccac cctcgtgacc accctgacct acggcgtgca gtgcttcagc cgctaccccg    1800
accacatgaa gcagcacgac ttcttcaagt ccgccatgcc cgaaggctac gtccaggagc    1860
gcaccatctt cttcaaggac gacggcaact acaagacccg cgccgaggtg aagttcgagg    1920
gcgacaccct ggtgaaccgc atcgagctga agggcatcga cttcaaggag gacggcaaca    1980
tcctggggca caagctggag tacaactaca acagccacaa cgtctatatc atggccgaca    2040
agcagaagaa cggcatcaag gtgaacttca gatccgcca caacatcgag gacggcagcg    2100
tgcagctcgc cgaccactac cagcagaaca cccccatcgg cgacggcccc gtgctgctgc    2160
ccgacaacca ctacctgagc acccagtccg ccctgagcaa agaccccaac gagaagcgcg    2220
atcacatggt cctgctggag ttcgtgaccg ccgccgggat cactctcggc atggacgcca    2280
agttgaccag tgccgttccg gtgctcaccg cgcgcgacgt cgccggagcg gtcgagttct    2340
ggaccgaccg gctcgggttc tcccgggact tcgtggagga cgacttcgcc ggtgtggtcc    2400
gggacgacgt gaccctgttc atcagcgcgg tccaggacca ggtggtgccg gacaacaccc    2460
tggcctgggt gtgggtgcgc ggcctggacg agctgtacgc cgagtggtcg gaggtcgtgt    2520
ccacgaactt ccgggacgcc tccgggccgg ccatgaccga gatcggcgag cagccgtggg    2580
ggcgggagtt cgccctgcgc gacccggccg gcaactgcgt gcacttcgtg gccgaggagc    2640
aggactgaga tccgcgaaat gaccgaccaa gcgacgccca acctgccatc acgagatttc    2700
gattccaccg ccgccttcta tgaaaggttg ggcttcggaa tcgttttccg ggacgccggc    2760
tggatgatcc tccagcgcgg ggatctcatg ctggagttct tcgcccaccc caacttgttt    2820
attgcagctt ataatggtta caaataaagc aatagcatca caaatttcac aaataaagca    2880 ttttttttcac tgcattctag ttgtggtttg tccaaactca tcaatgtatc ttatcatgtc    2940
tgtataccgt cgacctctag ctagatctac ctgtttccgg ctggctcccg agccatgctt    3000
accatgaatg aacctgcaaa cagtctgagg tccttgtgca aaccgctcag tgggacgtcg    3060
acgaagaaag aaacaatgtg tactcgtctt gctctgctcc cgcgccgttt tttatcgttg    3120
ttgagacctc tcgcgcagtt ttgggaatca accaaaacaa gagcccggcg tcagcgtttg    3180
cttcgccctc ggctgcactc gctcggcacg caggtataac tgggtgagta ccaagccccg    3240
catttgtctg tccgcgatcc gcgcacgctg cgggtcagga cgacatcgcg ctgcacgtca    3300
cagtgggtcc cttttgacgt ggctgcgcg atgaggaggc ttggctcggc ttcatggcaa    3360
ggcaacagac tcgcttccgg gacgcgcacg acgagcagcg ctgctttgat cgaccttgcc    3420
tgcgtcaccg cctcggctgc tttgatcgat cgttgtcacc ggcgagtga ccgcgaacgc    3480 attgcccgca cggctcggct cggcccggac cggaccggct cgccttggcg gcgcggcgcg    3540
```

-continued

| | |
|---|---|
| atggcgaccc agacgcggcc ggagccgcgc gcggaggaca aggccatgtt catcttcggg | 3600 |
| ctcgggtacg ttgggagcag gctcgccaac cagctggcgg aacaggggtg gcgcgtcgcg | 3660 |
| gggtcggtga gggagctcgg gcgcgaggac gactttgccg agttcgaaaa gtccaagctg | 3720 |
| agcggcaagg tgcaggtgtt ccgactcccg cttgagggcg aggacaacac gcccgctcgc | 3780 |
| gcgcgggaga tacttagcgg gtaccagcac ctgctgttca cggcgccagt ggaccgcgcc | 3840 |
| cggaactgtg accccttctt gggcgacccc gttctcggcc ccgggat | 3887 |

<210> SEQ ID NO 163
<211> LENGTH: 21
<212> TYPE: DNA
<213> ORGANISM: Artificial
<220> FEATURE:
<223> OTHER INFORMATION: primer

<400> SEQUENCE: 163

| | |
|---|---|
| acgtccgctt caaacacctc g | 21 |

<210> SEQ ID NO 164
<211> LENGTH: 24
<212> TYPE: DNA
<213> ORGANISM: Artificial
<220> FEATURE:
<223> OTHER INFORMATION: primer

<400> SEQUENCE: 164

| | |
|---|---|
| tcggaacaac tggaacaact aaag | 24 |

<210> SEQ ID NO 165
<211> LENGTH: 22
<212> TYPE: DNA
<213> ORGANISM: Artificial
<220> FEATURE:
<223> OTHER INFORMATION: primer

<400> SEQUENCE: 165

| | |
|---|---|
| atgtcgctct ccttcttctc ag | 22 |

<210> SEQ ID NO 166
<211> LENGTH: 21
<212> TYPE: DNA
<213> ORGANISM: Artificial
<220> FEATURE:
<223> OTHER INFORMATION: primer

<400> SEQUENCE: 166

| | |
|---|---|
| tcggctcctg gaaagtgctc t | 21 |

<210> SEQ ID NO 167
<211> LENGTH: 812
<212> TYPE: DNA
<213> ORGANISM: Artificial
<220> FEATURE:
<223> OTHER INFORMATION: ubiquitin promoter

<400> SEQUENCE: 167

| | |
|---|---|
| tcggtacccg ttagaacgcg taatacgact cactataggg agagtcgact gagcacaact | 60 |
| ctgctgcgag cgggcctcga gagcgtttgc ttcgagccgc ggagcaaggg ggatggatcg | 120 |
| ctcatgcggt cgtgcggccc tcggtcaccc ggtgggtcct gcactgacgc atctgttctg | 180 |
| atcagacaca cgaacgaaca aaccgaggag ccgcagcgcc tggtgcaccc gccgggcgtt | 240 |
| gttgtgtgct cttcttgcct ccgagagaga gagcggagcg gatgcatagg aaatcgggcc | 300 |

```
acgcgggagg gccatgcgtt cgccccacac gccactttcc acgcccgctc tctctccggc    360
cggcaggcag cgcataactc tccgacgctg gcaggctggt agcaactggc agggacaact    420
cgcgcgcggg tcccggtcgt tcgatgtgcc aacccgagag aatccagcca gcagggcggt    480
tggcctcatc gcccacctgc tatggtgcag cgaaccaact cccgaagcgg ccggttctgc    540
gattccctct tctgaattct gaattctgaa ctgattccgg aggagaaccc tctggaagcg    600
cgggttgcct ctccagttct gccgaactag acagggagt gagcagagag tgaccctgac     660
gcggagcgag ctggttgctg aaaagtcgc gaacgctggg ctgtgtcacg cgtccacttc     720
gggcagaccc caaacgacaa gcagaacaag caacaccagc agcagcaagc gacctaagca    780
acactagcca acatgactga ggataagacg aa                                 812
```

<210> SEQ ID NO 168
<211> LENGTH: 29
<212> TYPE: DNA
<213> ORGANISM: Artificial
<220> FEATURE:
<223> OTHER INFORMATION: primer

<400> SEQUENCE: 168

```
tcggtacccg ttagaacgcg taatacgac                                      29
```

<210> SEQ ID NO 169
<211> LENGTH: 45
<212> TYPE: DNA
<213> ORGANISM: Artificial
<220> FEATURE:
<223> OTHER INFORMATION: primer

<400> SEQUENCE: 169

```
ttcgtcttat cctcagtcat gttggctagt gttgcttagg tcgct                    45
```

<210> SEQ ID NO 170
<211> LENGTH: 1116
<212> TYPE: DNA
<213> ORGANISM: Artificial
<220> FEATURE:
<223> OTHER INFORMATION: cDNA (Saprolegnia diclina omega3 desaturase)

<400> SEQUENCE: 170

```
cctaagcaac actagccaac atgactgagg ataagacgaa ggtcgagttc ccgacgctca    60
cggagctcaa gcactcgatc ccgaacgcgt gctttgagtc gaacctcggc ctctcgctct   120
actacacggc ccgcgcgatc ttcaacgcgt cggcctcggc ggcgctgctc tacgcggcgc   180
gctcgacgcc gttcattgcc gataacgttc tgctccacgc gctcgtttgc gccacctaca   240
tctacgtgca gggcgtcatc ttctggggct tcttcacggt cggccacgac tgcggccact   300
cggccttctc gcgctaccac agcgtcaact ttatcatcgg ctgcatcatg cactctgcga   360
ttttgacgcc gttcgagagc tggcgcgtga cgcaccgcca ccaccacaag aacacgggca    420
acattgataa ggacgagatc ttttacccgc accggtcggt caaggacctc caggacgtgc    480
gccaatgggt ctacacgctc ggcggtgcgt ggtttgtcta cttgaaggtc gggtatgccc    540
cgcgcacgat gagccacttt gacccgtggg acccgctcct ccttcgccgc gcgtcggccg    600
tcatcgtgtc gctcggcgtc tgggccgcct tcttcgccgc gtacgcgtac ctcacatact   660
cgctcggctt tgccgtcatg ggcctctact actatgcgcc gctctttgtc tttgcttcgt   720
tcctcgtcat tacgaccttc ttgcaccaca acgacgaagc gacgccgtgg tacggcgact   780
```

```
cggagtggac gtacgtcaag ggcaacctct cgagcgtcga ccgctcgtac ggcgcgttcg      840
tggacaacct gagccaccac attggcacgc accaggtcca ccacttgttc ccgatcattc      900
cgcactacaa gctcaacgaa gccaccaagc actttgcggc cgcgtacccg cacctcgtgc      960
gcaagaacga cgagcccatc atctcggcct tcttcaagac cgcgcacctc tttgtcaact     1020
acggcgctgt gcccgagacg gcgcagatct tcacgctcaa agagtcggcc gcggccgcca     1080
aggccaagtc ggactaaact aagctatctg tagtat                               1116
```

<210> SEQ ID NO 171  
<211> LENGTH: 43  
<212> TYPE: DNA  
<213> ORGANISM: Artificial  
<220> FEATURE:  
<223> OTHER INFORMATION: primer

<400> SEQUENCE: 171

```
cctaagcaac actagccaac atgactgagg ataagacgaa ggt                         43
```

<210> SEQ ID NO 172  
<211> LENGTH: 40  
<212> TYPE: DNA  
<213> ORGANISM: Artificial  
<220> FEATURE:  
<223> OTHER INFORMATION: primer

<400> SEQUENCE: 172

```
atactacaga tagcttagtt ttagtccgac ttggccttgg                             40
```

<210> SEQ ID NO 173  
<211> LENGTH: 614  
<212> TYPE: DNA  
<213> ORGANISM: Artificial  
<220> FEATURE:  
<223> OTHER INFORMATION: ubiquitin terminator

<400> SEQUENCE: 173

```
ccaaggccaa gtcggactaa actaagctat ctgtagtatg tgctatactc gaatcatgct       60
gccctgtacg tacctaccta tatctgattg agcgtgctgc gtcgaccata gacgcgggaa      120
cgcgggccag cctaccacgt tgccgccgcc ggtatccacg ggcacgccaa agcattggtc      180
gataacgctc tgcccagggc ttcctggcga ggacccgagg ccaacatgca tgcatgtgct      240
atcagcggtc atcatcgccc tcatcagcgc gcatcggcga gctcgcgcac gaacggcaag      300
cgcccaactc aactcactta ctcacactat ggtcttgccg ttggcggttg cttagctaat      360
gcgtgacgtc actctgcctc caacatcgcg aggcagagtc gcgagcagtg cagaggccac      420
ggcggacgcc aacaaagcgc caaccagcgc aacgcaccag cgggtctgtg ggcgtagctc      480
gagcgggcgt cttcaagagc cgccgtggag ccgacgcccc tgcgaagggc tcgagtgcaa      540
gcggggccgt tgagccgcgt ggtaggaaca actgcagtct ccctatagtg agtcgtatta      600
cgcggtggta ccga                                                        614
```

<210> SEQ ID NO 174  
<211> LENGTH: 44  
<212> TYPE: DNA  
<213> ORGANISM: Artificial  
<220> FEATURE:  
<223> OTHER INFORMATION: primer

<400> SEQUENCE: 174

```
ccaaggccaa gtcggactaa aactaagcta tctgtagtat gtgc                       44
```

<210> SEQ ID NO 175
<211> LENGTH: 45
<212> TYPE: DNA
<213> ORGANISM: Artificial
<220> FEATURE:
<223> OTHER INFORMATION: primer

<400> SEQUENCE: 175

```
tcggtaccac cgcgtaatac gactcactat agggagactg cagtt            45
```

<210> SEQ ID NO 176
<211> LENGTH: 2463
<212> TYPE: DNA
<213> ORGANISM: Artificial
<220> FEATURE:
<223> OTHER INFORMATION: fusion DNA (T. aureum ATCC 34304 ubiquitin
      promoter/Saprolegnia diclina omega3 desaturase/T. aureum
      ATCC 34304 ubiquitin terminator)

<400> SEQUENCE: 176

```
tcggtacccg ttagaacgcg taatacgact cactataggg agagtcgact gagcacaact    60
ctgctgcgag cgggcctcga gagcgtttgc ttcgagccgc ggagcaaggg ggatggatcg   120
ctcatgcggt cgtgcggccc tcggtcaccc ggtgggtcct gcactgacgc atctgttctg   180
atcagacaca cgaacgaaca aaccgaggag ccgcagcgcc tggtgcaccc gccgggcgtt   240
gttgtgtgct cttcttgcct ccgagagaga gagcggagcg gatgcatagg aaatcgggcc   300
acgcgggagg gccatgcgtt cgccccacac gccactttcc acgcccgctc tctctccggc   360
cggcaggcag cgcataactc tccgacgctg gcaggctggt agcaactggc agggacaact   420
cgcgcgcggg tcccggtcgt tcgatgtgcc aacccgagag aatccagcca gcagggcggt   480
tggcctcatc gcccacctgc tatggtgcag cgaaccaact cccgaagcgg ccggttctgc   540
gattccctct tctgaattct gaattctgaa ctgattccgg aggagaaccc tctggaagcg   600
cgggttgcct ctccagttct gccgaactag acaggggagt gagcagagag tgaccctgac   660
gcggagcgag ctggttgctg gaaaagtcgc gaacgctggg ctgtgtcacg cgtccacttc   720
gggcagaccc caaacgacaa gcagaacaag caacaccagc agcagcaagc gacctaagca   780
acactagcca acatgactga ggataagacg aaggtcgagt tcccgacgct cacggagctc   840
aagcactcga tcccgaacgc gtgctttgag tcgaacctcg gcctctcgct ctactacacg   900
gcccgcgcga tcttcaacgc gtcggcctcg gcggcgctgc tctacgcggc gcgctcgacg   960
ccgttcattg ccgataacgt tctgctccac gcgctcgttt gcgccaccta catctacgtg  1020
cagggcgtca tcttctgggg cttcttcacg gtcggccacg actgcggcca ctcggccttc  1080
tcgcgctacc acagcgtcaa ctttatcatc ggctgcatca tgcactctgc gattttgacg  1140
ccgttcgaga gctggcgcgt gacgcaccgc caccaccaca gaacacgggg caacattgat  1200
aaggacgaga tcttttaccc gcaccggtcg gtcaaggacc tccaggacgt gcgccaatgg  1260
gtctacacgc tcggcggtgc gtggtttgtc tacttgaagg tcgggtatgc cccgcgcacg  1320
atgagccact ttgacccgtg ggacccgctc ctccttcgcc gcgcgtcggc cgtcatcgtg  1380
tcgctcggcg tctgggccgc cttcttcgcc gcgtacgcgt acctcacata tcgctcggc   1440 tttgccgtca tgggcctcta ctactatgcg ccgctctttg tctttgcttc gttcctcgtc  1500
attacgacct tcttgcacca caacgacgaa gcgacgccgt ggtacggcga tcggagtgg   1560 acgtacgtca agggcaacct ctcgagcgtc gaccgctcgt acggcgcgtt cgtggacaac  1620
```

```
ctgagccacc acattggcac gcaccaggtc caccacttgt tcccgatcat tccgcactac    1680
aagctcaacg aagccaccaa gcactttgcg gccgcgtacc cgcacctcgt gcgcaagaac    1740
gacgagccca tcatctcggc cttcttcaag accgcgcacc tctttgtcaa ctacggcgct    1800
gtgcccgaga cggcgcagat cttcacgctc aaagagtcgg ccgcggccgc caaggccaag    1860
tcggactaaa ctaagctatc tgtagtatgt gctatactcg aatcatgctg ccctgtacgt    1920
acctacctat atctgattga gcgtgctgcg tcgaccatag acgcgggaac gcgggccagc    1980
ctaccacgtt gccgccgccg gtatccacgg gcacgccaaa gcattggtcg ataacgctct    2040
gcccagggct tcctggcgag gacccgaggc caacatgcat gcatgtgcta tcagcggtca    2100
tcatcgccct catcagcgcg catcggcgag ctcgcgcacg aacggcaagc gcccaactca    2160
actcacttac tcacactatg gtcttgccgt tggcggttgc ttagctaatg cgtgacgtca    2220
ctctgcctcc aacatcgcga ggcagagtcg cgagcagtgc agaggccacg gcggacgcca    2280
acaaagcgcc aaccagcgca acgcaccagc gggtctgtgg gcgtagctcg agcgggcgtc    2340
ttcaagagcc gccgtggagc cgacgcccct gcgaagggct cgagtgcaag cggggccgtt    2400
gagccgcgtg gtaggaacaa ctgcagtctc cctatagtga gtcgtattac gcggtggtac    2460
cga                                                                 2463
```

<210> SEQ ID NO 177
<211> LENGTH: 36
<212> TYPE: DNA
<213> ORGANISM: Artificial
<220> FEATURE:
<223> OTHER INFORMATION: primer

<400> SEQUENCE: 177

```
cccggtaccg ccgcagcgcc tggtgcaccc gccggg                               36
```

<210> SEQ ID NO 178
<211> LENGTH: 3777
<212> TYPE: DNA
<213> ORGANISM: Artificial
<220> FEATURE:
<223> OTHER INFORMATION: fusion DNA (ubiquitin promoter/omega 3
      desaturase/ubiquitin terminator/ubiquitin promoter/Blar/SV40
      terminator)

<400> SEQUENCE: 178

```
tcggtacccg ttagaacgcg taatacgact cactataggg agagtcgact gagcacaact     60
ctgctgcgag cgggcctcga gagcgtttgc ttcgagccgc ggagcaaggg ggatggatcg    120
ctcatgcggt cgtgcggccc tcggtcaccc ggtgggtcct gcactgacgc atctgttctg    180
atcagacaca cgaacgaaca aaccgaggag ccgcagcgcc tggtgcaccc gccgggcgtt    240
gttgtgtgct cttcttgcct ccgagagaga gagcggagcg gatgcatagg aaatcgggcc    300
acgcgggagg gccatgcgtt cgccccacac gccactttcc acgcccgctc tctctccggc    360
cggcaggcag cgcataactc tccgacgctg gcaggctggt agcaactggc agggacaact    420
cgcgcgcggg tcccggtcgt tcgatgtgcc aacccgagag aatccagcca gcagggcggt    480
tggcctcatc gcccacctgc tatggtgcag cgaaccaact cccgaagcgg ccggttctgc    540
gattccctct tctgaattct gaattctgaa ctgattccgg aggagaaccc tctggaagcg    600
cgggttgcct ctccagttct gccgaactag acaggggagt gagcagagag tgaccctgac    660
gcggagcgag ctggttgctg gaaaagtcgc gaacgctggg ctgtgtcacg cgtccacttc    720
gggcagaccc caaacgacaa gcagaacaag caacaccagc agcagcaagc gacctaagca    780
```

```
acactagcca acatgactga ggataagacg aaggtcgagt tcccgacgct cacggagctc    840
aagcactcga tcccgaacgc gtgctttgag tcgaacctcg gcctctcgct ctactacacg    900
gcccgcgcga tcttcaacgc gtcggcctcg gcggcgctgc tctacgcggc gcgctcgacg    960
ccgttcattg ccgataacgt tctgctccac gcgctcgttt gcgccaccta catctacgtg   1020
cagggcgtca tcttctgggg cttcttcacg gtcggccacg actgcggcca ctcggccttc   1080
tcgcgctacc acagcgtcaa ctttatcatc ggctgcatca tgcactctgc gattttgacg   1140
ccgttcgaga gctggcgcgt gacgcaccgc caccaccaca agaacacggg caacattgat   1200
aaggacgaga tcttttaccc gcaccggtcg gtcaaggacc tccaggacgt gcgccaatgg   1260
gtctacacgc tcggcggtgc gtggtttgtc tacttgaagg tcgggtatgc cccgcgcacg   1320
atgagccact ttgacccgtg ggacccgctc ctccttcgcc gcgcgtcggc cgtcatcgtg   1380
tcgctcggcg tctgggccgc cttcttcgcc gcgtacgcgt acctcacata ctcgctcggc   1440
tttgccgtca tgggcctcta ctactatgcg ccgctctttg tctttgcttc gttcctcgtc   1500
attacgacct tcttgcacca caacgacgaa gcgacgccgt ggtacggcga ctcggagtgg   1560
acgtacgtca agggcaacct ctcgagcgtc gaccgctcgt acggcgcgtt cgtggacaac   1620
ctgagccacc acattggcac gcaccaggtc caccacttgt tcccgatcat tccgcactac   1680
aagctcaacg aagccaccaa gcactttgcg ccgcgtacc cgcacctcgt gcgcaagaac   1740
gacgagccca tcatctcggc cttcttcaag accgcgcacc tctttgtcaa ctacggcgct   1800
gtgcccgaga cggcgcagat cttcacgctc aaagagtcgg ccgcggccgc caaggccaag   1860
tcggactaaa ctaagctatc tgtagtatgt gctatactcg aatcatgctg ccctgtacgt   1920
acctacctat atctgattga gcgtgctgcg tcgaccatag acgcgggaac gcgggccagc   1980
ctaccacgtt gccgccgccg gtatccacgg gcacgccaaa gcattggtcg ataacgctct   2040
gcccagggct tcctggcgag gacccgaggc caacatgcat gcatgtgcta tcagcggtca   2100
tcatcgccct catcagcgcg catcggcgag ctcgcgcacg aacggcaagc gcccaactca   2160
actcacttac tcacactatg gtcttgccgt tggcggttgc ttagctaatg cgtgacgtca   2220
ctctgcctcc aacatcgcga ggcagagtcg cgagcagtgc agaggccacg gcggacgcca   2280
acaaagcgcc aaccagcgca acgcaccagc gggtctgtgg gcgtagctcg agcgggcgtc   2340
ttcaagagcc gccgtggagc cgacgcccct gcgaagggct cgagtgcaag cggggccgtt   2400
gagccgcgtg gtaggaacaa ctgcagtctc cctatagtga gtcgtattac gcggtggtac   2460
cgccgcagcc cctggtgcac ccgccgggcg ttgttgtgtg ctcttcttgc ctccgagaga   2520
gagagcggag cggatgcata ggaaatcggg ccacgcggga gggccatgcg ttcgcccac   2580 acgccacttt ccacgcccgc tctctctccg gccggcaggc agcgcataac tctccgacgc   2640
tggcaggctg gtagcaactg gcagggacaa ctcgcgcgcg ggtcccggtc gttcgatgtg   2700
ccaacccgag agaatccagc cagcagggcg gttggcctca tcgcccacct gctatggtgc   2760
agcgaaccaa ctcccgaagc ggccggttct gcgattccct cttctgaatt ctgaattctg   2820
aactgattcc ggaggagaac cctctggaag cgcgggttgc ctctccagtt ctgccgaact   2880
agacagggga gtgagcagag agtgaccctg acgcggagcg agctggttgc tggaaaagtc   2940
gcgaacgctg ggctgtgtca cgcgtccact tcgggcagtc cccaaacgac aagcagaaca   3000
agcaacacca gcagcagcaa gcgacctaag caacactagc caacatggcc aagcctttgt   3060
ctcaagaaga atccaccctc attgaaagag caacggctac aatcaacagc atccccatct   3120
```

| | |
|---|---|
| ctgaagacta cagcgtcgcc agcgcagctc tctctagcga cggccgcatc ttcactggtg | 3180 |
| tcaatgtata tcattttact gggggacctt gtgcagaact cgtggtgctg ggcactgctg | 3240 |
| ctgctgcggc agctggcaac ctgacttgta tcgtcgcgat cggaaatgag aacaggggca | 3300 |
| tcttgagccc ctgcggacgg tgccgacagg tgcttctcga tctgcatcct gggatcaaag | 3360 |
| ccatagtgaa ggacagtgat ggacagccga cggcagttgg gattcgtgaa ttgctgccct | 3420 |
| ctggttatgt gtgggagggc taagatccgc gaaatgaccg accaagcgac gcccaacctg | 3480 |
| ccatcacgag atttcgattc caccgccgcc ttctatgaaa ggttgggctt cggaatcgtt | 3540 |
| ttccgggacg ccggctggat gatcctccag cgcggggatc tcatgctgga gttcttcgcc | 3600 |
| cacccccaact tgtttattgc agcttataat ggttacaaat aaagcaatag catcacaaat | 3660 |
| ttcacaaata aagcattttt ttcactgcat tctagttgtg gtttgtccaa actcatcaat | 3720 |
| gtatcttatc atgtctgtat accgtcgacc tctagctaga tctcacatta attgcgt | 3777 |

```
<210> SEQ ID NO 179
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is inosine.
<220> FEATURE:
<221> NAME/KEY: misc_feature
<222> LOCATION: (21)..(21)
<223> OTHER INFORMATION: n is inosine.

<400> SEQUENCE: 179
```

| | |
|---|---|
| athgartwyt kbrtnttygt nca | 23 |

```
<210> SEQ ID NO 180
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is inosine.
<220> FEATURE:
<221> NAME/KEY: misc_feature
<222> LOCATION: (15)..(15)
<223> OTHER INFORMATION: n is inosine.
<220> FEATURE:
<221> NAME/KEY: misc_feature
<222> LOCATION: (18)..(18)
<223> OTHER INFORMATION: n is inosine.

<400> SEQUENCE: 180
```

| | |
|---|---|
| tartrnswrt acatnadnam rtg | 23 |

```
<210> SEQ ID NO 181
<211> LENGTH: 28
<212> TYPE: DNA
<213> ORGANISM: Artificial
<220> FEATURE:
<223> OTHER INFORMATION: primer

<400> SEQUENCE: 181
```

| | |
|---|---|
| ctgacaaagt ttctcgactg gagcgaca | 28 |

<210> SEQ ID NO 182
<211> LENGTH: 24
<212> TYPE: DNA
<213> ORGANISM: Artificial
<220> FEATURE:
<223> OTHER INFORMATION: primer

<400> SEQUENCE: 182

```
tacgcggcgg tgcccgagcc ccag                                          24
```

<210> SEQ ID NO 183
<211> LENGTH: 28
<212> TYPE: DNA
<213> ORGANISM: Artificial
<220> FEATURE:
<223> OTHER INFORMATION: primer

<400> SEQUENCE: 183

```
tgccgatcgt tgcgtggtgg aacacctg                                      28
```

<210> SEQ ID NO 184
<211> LENGTH: 20
<212> TYPE: DNA
<213> ORGANISM: Artificial
<220> FEATURE:
<223> OTHER INFORMATION: primer

<400> SEQUENCE: 184

```
atggcgacgc gcacctcgaa                                               20
```

<210> SEQ ID NO 185
<211> LENGTH: 22
<212> TYPE: DNA
<213> ORGANISM: Artificial
<220> FEATURE:
<223> OTHER INFORMATION: primer

<400> SEQUENCE: 185

```
ttactcggac ttggtggggg cg                                            22
```

<210> SEQ ID NO 186
<211> LENGTH: 951
<212> TYPE: DNA
<213> ORGANISM: Thraustochytrium aureum
<220> FEATURE:
<223> OTHER INFORMATION: genomic C20 elongase

<400> SEQUENCE: 186

```
atggcgacgc gcacctcgaa gagcgctccg gcggtttcca agtcggccaa ggttgccgcg    60
ccggcgaaga agcggtcggt cgacaggagc gacggtttct tccgcacgtt caacctgtgc   120
gccctgtacg ggtctgccct cgcctatgcg tacaagcacg gccggtggac aatgacggc    180
caggggctgt actttcacaa gtcgcccatg tacgcgttcg ccgtgtcgga cgtcatgacc   240
ttcggcgcgc cgctgatgta cgtgctcggt gtgatgctgc tcagcaggta catggcggac   300
aaaaagcccc tgactggctt catcaagacc tacatccagc ccgtctacaa cgtggtccaa   360
atcgcggtgt gcggctggat ggtgtggggc ctctggccgc aggtcgacct ggccaacggc   420
aacccctttcg gcctcaacaa gtcgcgcgac tcgaacatcg agtttttcgt gttcgtgcac   480
ctcctgacaa agtttctcga ctggagcgac acgttcatga tgatcctcaa gaaaaactac   540
gcccaggtta gctttctgca ggtgttccac cacgcaacga tcggcatggt gtggtcgttc   600
cttcttcagc gtggctgggg ctcgggcacc gccgcgtacg gtgctttcat caactcggtc   660
```

-continued

```
acgcacgtga tcatgtactc gcactacttt gccacctcgc tcaacatcaa caacccgttc     720
aagcggtaca tcacgagctt ccagctcgcc cagtttgcaa gctgcatcgt gcatgcccta     780
ctggtgcttg ccttcgagga ggtgtacccg ctcgagtacg cttacctgca gatcagctac     840
cacatcatca tgctctacct gttcggacgc gcatgaact  ggagcccga  gtggtgcacc    900 ggtgagatcg acggccttga cgccccaagc gccccacca  agtccgagta a             951
```

<210> SEQ ID NO 187
<211> LENGTH: 317
<212> TYPE: PRT
<213> ORGANISM: Thraustochytrium aureum
<220> FEATURE:
<221> NAME/KEY: misc_feature
<222> LOCATION: (317)..(317)
<223> OTHER INFORMATION: Xaa can be any naturally occurring amino acid
<220> FEATURE:
<223> OTHER INFORMATION: C20 elongase
<400> SEQUENCE: 187

```
Met Ala Thr Arg Thr Ser Lys Ser Ala Pro Ala Val Ser Lys Ser Ala
 1               5                  10                  15

Lys Val Ala Ala Pro Ala Lys Lys Arg Ser Val Asp Arg Ser Asp Gly
             20                  25                  30

Phe Phe Arg Thr Phe Asn Leu Cys Ala Leu Tyr Gly Ser Ala Leu Ala
         35                  40                  45

Tyr Ala Tyr Lys His Gly Pro Val Asp Asn Asp Gly Gln Gly Leu Tyr
     50                  55                  60

Phe His Lys Ser Pro Met Tyr Ala Phe Ala Val Ser Asp Val Met Thr
 65                  70                  75                  80

Phe Gly Ala Pro Leu Met Tyr Val Leu Gly Val Met Leu Leu Ser Arg
                 85                  90                  95

Tyr Met Ala Asp Lys Lys Pro Leu Thr Gly Phe Ile Lys Thr Tyr Ile
            100                 105                 110

Gln Pro Val Tyr Asn Val Val Gln Ile Ala Val Cys Gly Trp Met Val
        115                 120                 125

Trp Gly Leu Trp Pro Gln Val Asp Leu Ala Asn Gly Asn Pro Phe Gly
    130                 135                 140

Leu Asn Lys Ser Arg Asp Ser Asn Ile Glu Phe Val Phe Val His
145                 150                 155                 160

Leu Leu Thr Lys Phe Leu Asp Trp Ser Asp Thr Phe Met Met Ile Leu
                165                 170                 175

Lys Lys Asn Tyr Ala Gln Val Ser Phe Leu Gln Val Phe His His Ala
            180                 185                 190

Thr Ile Gly Met Val Trp Ser Phe Leu Leu Gln Arg Gly Trp Gly Ser
        195                 200                 205

Gly Thr Ala Ala Tyr Gly Ala Phe Ile Asn Ser Val Thr His Val Ile
    210                 215                 220

Met Tyr Ser His Tyr Phe Ala Thr Ser Leu Asn Ile Asn Asn Pro Phe
225                 230                 235                 240

Lys Arg Tyr Ile Thr Ser Phe Gln Leu Ala Gln Phe Ala Ser Cys Ile
                245                 250                 255

Val His Ala Leu Leu Val Leu Ala Phe Glu Glu Val Tyr Pro Leu Glu
            260                 265                 270

Tyr Ala Tyr Leu Gln Ile Ser Tyr His Ile Ile Met Leu Tyr Leu Phe
        275                 280                 285

Gly Arg Arg Met Asn Trp Ser Pro Glu Trp Cys Thr Gly Glu Ile Asp
```

```
                290                295                300
Gly Leu Asp Ala Pro Ser Ala Pro Thr Lys Ser Glu Xaa
305                310               315
```

<210> SEQ ID NO 188
<211> LENGTH: 3193
<212> TYPE: DNA
<213> ORGANISM: Artificial
<220> FEATURE:
<223> OTHER INFORMATION: genomic DNA (Thraustochytrium aureum genomic
      DNA contains C20 elongase coding region)

<400> SEQUENCE: 188

```
ggatatcccc cgcgaggcga tggctgctcc gacgacgtgg gctggcgacg tcgctcgcaa       60
aggcgttccg caaccgcgcg ttccgctgta acgagaccgt tttccctgcg ctgctgggtg      120
gacctagcgc gtgtgtcacc tgccggcccc cgttgcgtgc aaccgaattg atcgataata      180
gaattacata acaaacaact tgctggatga gtacaagacc agcgtagtgt ggctgtggga      240
cgttgaacgg agcgggtcct gtgacggcgc agaaaggaac tccgcccgag gtgaaacccc      300
gatgcgcagg actctgcggc cacagcccct ccgccagtat tccactaaaa atccgccccc      360
tttgacaaag atcgcaaccc cgtcccatca actcctcaca ataggctttc cactggcgga      420
aacgtccccg gcacaggagt gcctcccgcg gttctgcgca tacggctgac cactacgcag      480
cgcgatatcc tccatccgcg tatatatccg taaacaacgg aacattctcc ctctcaacga      540
ggcgtggttt tcgaagccat gcctttcttc cttcctactt gccttccttc tttctttctt      600
tctttctttc ttttgcaagc gtgcgcgaac ttgaaggtac tacttacact tgacagagag      660
agatagagac ggcaattcga ccaagtactt tccacgattt ttttttttt gttttggtcg      720
cttttcgttgg tcgtgcatga tggatggccg ggattttttac aattggatgc gccaggctgc      780
cacgcatgcc gtgacgctcg ctcgcggcga ctcatgatgc ttgccagtgg cagtgcatcc      840
agctcttccc tctgctcgtc gtgtactcac tggcgatgct ctcggcgctc gttcaggggc      900
catcgaccga tcgatcgatc gatcgatcga tcaatcacgt tcggtggact cggcagaccc      960
cgaacgtgtt ctcccagga cgtgccgctg tcgctcgctg atccacccga agcgcggtcg     1020
gctggcacgg tcgctcggct ggaagttgag tagtttgctt tctgttgctg cgctgctttg     1080
taaacgcgac catggcgacg cgcacctcga agagcgctcc ggcggtttcc aagtcggcca     1140
aggttgccgc gccggcgaag aagcggtcgg tcgacaggag cgacggtttc ttccgcacgt     1200
tcaacctgtg cgccctgtac gggtctgccc tcgcctatgc gtacaagcac ggcccggtgg     1260
acaatgacgg ccaggggctg tactttcaca gtcgcccat gtacgcgttc gccgtgtcgg     1320
acgtcatgac cttcggcgcg ccgctgatgt acgtgctcgg tgtgatgctg ctcagcaggt     1380
acatggcgga caaaaagccc ctgactggct tcatcaagac ctacatccag cccgtctaca     1440
acgtggtcca aatcgcggtg tgcggctgga tggtgtgggg cctctggccg caggtcgacc     1500
tggccaacgg caaccctttc ggcctcaaca gtcgcgcga ctcgaacatc gagttttcg      1560
tgttcgtgca cctcctgaca aagtttctcg actggagcga cacgttcatg atgatcctca     1620
agaaaaacta cgcccaggtt agctttctgc aggtgttcca ccacgcaacg atcggcatgg     1680
tgtggtcgtt ccttcttcag cgtggctggg gctcgggcac cgccgcgtac ggtgctttca     1740
tcaactcggt cacgcacgtg atcatgtact cgcactactt tgccacctcg ctcaacatca     1800
acaaccgtt caagcggtac atcacgagct tccagctcgc ccagttttgca agctgcatcg     1860
tgcatgccct actggtgctt gccttcgagg aggtgtaccc gctcgagtac gcttacctgc     1920
```

```
agatcagcta ccacatcatc atgctctacc tgttcggacg ccgcatgaac tggagccccg   1980
agtggtgcac cggtgagatc gacggccttg acgccccaag cgcccccacc aagtccgagt   2040
aaacctgttt ccggctggct cccgagccat gcttaccatg aatgaacctg caaacagtct   2100
gaggtccttg tgcaaaccgc tcagtgggac gtcgacgaag aaagaaacaa tgtgtactcg   2160
tcttgctctg ctcccgcgcc gttttttatc gttgttgaga cctctcgcgc agttttggga   2220
atcaaccaaa acaagagccc ggcgtcagcg tttgcttcgc cctcggctgc actcgctcgg   2280
cacgcaggta taactgggtg agtaccaagc cccgcatttg tctgtccgcg atccgcgcac   2340
gctgcgggtc aggacgacat cgcgctgcac gtcacagtgg gtcccttttg acgtggctgc   2400
ggcgatgagg aggcttggct cggcttcatg gcaaggcaac agactcgctt ccaggacgcg   2460
cacgacgagc agcgctgctt tgatcgacct tgcctgcgtc accgcctcgg ctgctttgat   2520
cgatcgttgt caccggccga gtgaccgcga acgcattgcc cgcacggctc ggctcggctc   2580
ggaccggacc ggctcgcctt ggcggcgcgg cgcgatggcg acccagacgc gaccggagcc   2640
gcgcgcggag gacaaggcca tgtacatctt cgggctcggg tacgttggga gcaggctcgc   2700
caaccagctg gcggaacagg ggtggcgcgt cgcggggtcg gtgagggagc tcggcgcga   2760 ggacgacttt gccgagttcg aaaagtccaa gctgagcggc aaggtgcagg tgttccaact   2820
cccgcttgag ggcgaggaca cacgcccgc tcgcgcgcgg gagatactta gcgggtacca   2880
gcgcctgctg ttcacggcgc cagtggaccg cgcccggaac tgtgaccct tcttgggcga   2940 ccccgttctc ggccccgtga tcgtcgagct agcagaggag ggccgcatcg actgggccgg   3000
ctatctctca accacttcgg tctacggcaa ccacgacggc gagtggggtgg acgagaccac   3060 gccgctcatg cccacgctca acgcggcga gcagcgcgtc atggtggagc gcgccttcct   3120
gtacgagtcg ggcctcccgg cccatatctt tcggctgcca ggaatctacg cccagggcg   3180 cggccccgata tca                                                    3193

<210> SEQ ID NO 189
<211> LENGTH: 27
<212> TYPE: DNA
<213> ORGANISM: Artificial
<220> FEATURE:
<223> OTHER INFORMATION: primer

<400> SEQUENCE: 189
gacaaagatc tcgactggag cgaccac                                        27

<210> SEQ ID NO 190
<211> LENGTH: 27
<212> TYPE: DNA
<213> ORGANISM: Artificial
<220> FEATURE:
<223> OTHER INFORMATION: primer

<400> SEQUENCE: 190
gtcgagatct tttgtcagga ggtgcac                                        27

<210> SEQ ID NO 191
<211> LENGTH: 951
<212> TYPE: DNA
<213> ORGANISM: Artificial
<220> FEATURE:
<223> OTHER INFORMATION: BglII inserted C20 elongase

<400> SEQUENCE: 191
```

```
atggcgacgc gcacctcgaa gagcgctccg gcggtttcca agtcggccaa ggttgccgcg      60
ccggcgaaga agcggtcggt cgacaggagc gacggtttct tccgcacgtt caacctgtgc     120
gccctgtacg ggtctgccct cgcctatgcg tacaagcacg gcccggtgga caatgacggc     180
caggggctgt actttcacaa gtcgcccatg tacgcgttcg ccgtgtcgga cgtcatgacc     240
ttcggcgcgc cgctgatgta cgtgctcggt gtgatgctgc tcagcaggta catggcggac     300
aaaaagcccc tgactggctt catcaagacc tacatccagc ccgtctacaa cgtggtccaa     360
atcgcggtgt gcggctggat ggtgtggggc ctctggccgc aggtcgacct ggccaacggc     420
aaccctttcg gcctcaacaa gtcgcgcgac tcgaacatcg agttttttcgt gttcgtgcac     480 ctcctgacaa agatctcgac tggagcgaca cgttcatgat gatcctcaag aaaaactacg     540
cccaggttag ctttctgcag gtgttccacc acgcaacgat cggcatggtg tggtcgttcc     600
ttcttcagcg tggctggggc tcgggcaccg ccgcgtacgg tgctttcatc aactcggtca     660
cgcacgtgat catgtactcg cactactttg ccacctcgct caacatcaac aacccgttca     720
agcggtacat cacgagcttc cagctcgccc agtttgcaag ctgcatcgtg catgccctac     780
tggtgcttgc cttcgaggag gtgtaccccg tcgagtacgc ttacctgcag atcagctacc     840
acatcatcat gctctacctg ttcggacgcc gcatgaactg gagccccgag tggtgcaccg     900
gtgagatcga cggccttgac gccccaagcg ccccccaccaa gtccgagtaa a             951
```

```
<210> SEQ ID NO 192
<211> LENGTH: 23
<212> TYPE: DNA
<213> ORGANISM: Artificial
<220> FEATURE:
<223> OTHER INFORMATION: primer

<400> SEQUENCE: 192
atggcgacgc gcacctcgaa gag                                              23

<210> SEQ ID NO 193
<211> LENGTH: 23
<212> TYPE: DNA
<213> ORGANISM: Artificial
<220> FEATURE:
<223> OTHER INFORMATION: primer

<400> SEQUENCE: 193
ttactcggac ttgctggggg cgc                                              23

<210> SEQ ID NO 194
<211> LENGTH: 2655
<212> TYPE: DNA
<213> ORGANISM: Artificial
<220> FEATURE:
<223> OTHER INFORMATION: fusion DNA(Thraustochytrium aureum C20 elongase
      5' region/SV40 terminator/Neor/ubiquitin promoter/Thraustochytrium
      aureum C20 elongase 3' region)

<400> SEQUENCE: 194
```

```
atggcgacgc gcacctcgaa gagcgctccg gcggtttcca agtcggccaa ggttgccgcg      60
ccggcgaaga agcggtcggt cgacaggagc gacggtttct tccgcacgtt caacctgtgc     120
gccctgtacg ggtctgccct cgcctatgcg tacaagcacg gcccggtgga caatgacggc     180
caggggctgt actttcacaa gtcgcccatg tacgcgttcg ccgtgtcgga cgtcatgacc     240
ttcggcgcgc cgctgatgta cgtgctcggt gtgatgctgc tcagcaggta catggcggac     300
aaaaagcccc tgactggctt catcaagacc tacatccagc ccgtctacaa cgtggtccaa     360
```

| | |
|---|---|
| atcgcggtgt gcggctggat ggtgtggggc ctctggccgc aggtcgacct ggccaacggc | 420 |
| aaccctttcg gcctcaacaa gtcgcgcgac tcgaacatcg agtttttcgt gttcgtgcac | 480 |
| ctcctgacaa agatctagct agaggtcgac ggtatacaga catgataaga tacattgatg | 540 |
| agtttggaca aaccacaact agaatgcagt gaaaaaaatg ctttatttgt gaaatttgtg | 600 |
| atgctattgc tttatttgta accattataa gctgcaataa acaagttggg gtgggcgaag | 660 |
| aactccagca tgagatcccc cgcgctggag atcatccagc cggcgtcccg gaaaacgatt | 720 |
| ccgaagccca acctttcata gaaggcggcg gtggaatcga aatctcgtga tggcaggttg | 780 |
| ggcgtcgctt ggtcggtcat ttcgcggatc tcaaaagaac tcgtccagga ggcggtagaa | 840 |
| cgcaatcctc tggctgtccg gggcggcgat gccgtagagc acgagaaagc ggtcggccca | 900 |
| ctcgccgcca agctcctcgg cgatgtcccg cgtggcgagc gcgatgtctt ggtagcggtc | 960 |
| cgccacgccc aggcgcccgc agtcgataaa gcccgagaag cggccgttct cgaccatgat | 1020 |
| gttggggagg caggcgtcgc cgtgcgtgac cacgaggtcc tcgccgtccg gcatcctagc | 1080 |
| cttaagcctg gcgaacagtt ccgccggcgc gaggccctgg tgctcctcgt cgaggtcgtc | 1140 |
| ttggtcgacg aggccagcct ccatccgcgt gcgggcgcgt tcgatcctgt gcttcgcctg | 1200 |
| gtggtcgaag gggcaggtgg cggggtcgag ggtgtgcagg cggcgcatgg cgtcggccat | 1260 |
| gatggacacc ttctcagcgg gcgcgaggtg gctgctgagg aggtcctggc cgggcacttc | 1320 |
| cccgaggagc agccagtcgc ggccggcttc ggtgacgacg tcgagcacag cggcgcacgg | 1380 |
| aaccccgtc gtggcaagcc agctgaggcg ggcagcttcg tcctggagct cgttgagggc | 1440 |
| gccgctaagg tcggtcttga caaacaggac cggccggccc tgcgcgctaa ggcggaacac | 1500 |
| ggccgcgtcc gagcagccga tcgtctgctg agcccagtcg tagccgaaca gccgttccac | 1560 |
| ccaagcagcg ggcgagccag cgtgaaggcc gtcctgttca atcatgttgg ctagtgttgc | 1620 |
| ttaggtcgct tgctgctgct ggtgttgctt gttctgcttg tcgtttgggg tctgcccgaa | 1680 |
| gtggacgcgt gacacagccc agcgttcgcg acttttccag caaccagctc gctccgcgtc | 1740 |
| agggtcactc tctgctcact cccctgtcta gttcggcaga actggagagg caacccgcgc | 1800 |
| ttccagaggg ttctcctccg gaatcagttc agaattcaga attcagaaga gggaatcgca | 1860 |
| gaaccggccg cttcgggagt tggttcgctg caccatagca ggtgggcgat gaggccaacc | 1920 |
| gccctgctgg ctgattctc tcgggttggc acatcgaacg accgggaccc gcgcgcgagt | 1980 |
| tgtccctgcc agttgctacc agcctgccag cgtcggagag ttatgcgctg cctgccggcc | 2040 |
| ggagagagag cgggcgtgga aagtggcgtg tggggcgaac gcatggccct cccgcgtggc | 2100 |
| ccgatttcct atgcatccgc tccgctctct ctctcggagg caagaagagc acaccaacaa | 2160 |
| cgcccggcg gtgcaccagg cgctgcggca gatccagatc tcgactggag cgacacgttc | 2220 |
| atgatgatcc tcaagaaaaa ctacgcccag gttagctttc tgcaggtgtt ccaccacgca | 2280 |
| acgatcggca tggtgtggtc gttccttctt cagcgtggct ggggctcggg caccgccgcg | 2340 |
| tacggtgctt tcatcaactc ggtcacgcac gtgatcatgt actcgcacta ctttgccacc | 2400 |
| tcgctcaaca tcaacaaccc gttcaagtgg tacatcacga gcttccagct cgcccagttt | 2460 |
| gcaagctgca tcgtgcatgc cctactggtg cttgccttcg aggaggtgta cccgctcgag | 2520 |
| tacgcttacc tgcagatcag ctaccacatc atcatgctct acctgttcgg acgccgcatg | 2580 |
| aactggagcc ccgagtggtg caccggtgag atcgacggcc ttgacgcccc aagcgccccc | 2640 |
| accaagtccg agtaa | 2655 |

<210> SEQ ID NO 195
<211> LENGTH: 2886
<212> TYPE: DNA
<213> ORGANISM: Artificial
<220> FEATURE:
<223> OTHER INFORMATION: fusion DNA(Thraustochytrium aureum C20 elongase 5' region/ubiquitin promoter/Hygr/SV40 terminator/Thraustochytrium aureum C20 elongase 3' region)

<400> SEQUENCE: 195

| | | | | | |
|---|---|---|---|---|---|
| atggcgacgc | gcacctcgaa | gagcgctccg | gcggtttcca | agtcggccaa | ggttgccgcg | 60 |
| ccggcgaaga | agcggtcggt | cgacaggagc | gacggtttct | tccgcacgtt | caacctgtgc | 120 |
| gccctgtacg | ggtctgccct | cgcctatgcg | tacaagcacg | gcccggtgga | caatgacggc | 180 |
| caggggctgt | actttcacaa | gtcgcccatg | tacgcgttcg | ccgtgtcgga | cgtcatgacc | 240 |
| ttcggcgcgc | cgctgatgta | cgtgctcggt | gtgatgctgc | tcagcaggta | catggcggac | 300 |
| aaaaagcccc | tgactggctt | catcaagacc | tacatccagc | ccgtctacaa | cgtggtccaa | 360 |
| atcgcggtgt | gcggctggat | ggtgtggggc | ctctggccgc | aggtcgacct | ggccaacggc | 420 |
| aacccttttcg | gcctcaacaa | gtcgcgcgac | tcgaacatcg | agttttttcgt | gttcgtgcac | 480 |
| ctcctgacaa | agatctggat | ctgccgcagc | gcctggtgca | cccgccgggc | gttgttgtgt | 540 |
| gctcttcttg | cctccgagag | agagagcgga | gcggatgcat | aggaaatcgg | gccacgcggg | 600 |
| agggccatgc | gttcgcccca | cacgccactt | tccacgcccg | ctctctctcc | ggccggcagg | 660 |
| cagcgcataa | ctctccgacg | ctggcaggct | ggtagcaact | ggcagggaca | actcgcgcgc | 720 |
| gggtcccggt | cgttcgatgt | gccaacccga | gagaatccag | ccagcagggc | ggttggcctc | 780 |
| atcgcccacc | tgctatggtg | cagcgaacca | actcccgaag | cggccggttc | tgcgattccc | 840 |
| tcttctgaat | tctgaattct | gaactgattc | cggaggagaa | ccctctggaa | gcgcgggttg | 900 |
| cctctccagt | tctgccgaac | tagacagggg | agtgagcaga | gagtgaccct | gacgcggagc | 960 |
| gagctggttg | ctggaaaagt | cgcgaacgct | gggctgtgtc | acgcgtccac | ttcgggcaga | 1020 |
| ccccaaacga | caagcagaac | aagcaacacc | agcagcagca | agcgacctaa | gcaacactag | 1080 |
| ccaacatgaa | aaagcctgaa | ctcaccgcga | cgtctgtcga | agtttctctg | atcgaaaagt | 1140 |
| tcgacagcgt | ctccgacctg | atgcagctct | cggagggcga | agaatctcgt | gctttcagct | 1200 |
| tcgatgtagg | agggcgtgga | tatgtcctgc | gggtaaatag | ctgcgccgat | ggtttctaca | 1260 |
| aagatcgtta | tgtttatcgg | cactttgcat | cggccgcgct | cccgattccg | gaagtgcttg | 1320 |
| acattgggga | attcagcgag | agcctgacct | attgcatctc | ccgccgtgca | cagggtgtca | 1380 |
| cgttgcaaga | cctgcctgaa | accgaactgc | ccgctgttct | gcagccggtc | gcggaggcca | 1440 |
| tggatgcgat | cgctgcggcc | gatcttagcc | agacgagcgg | gttcggccca | ttcggaccgc | 1500 |
| aaggaatcgg | tcaatacact | acatggcgtg | atttcatatg | cgcgattgct | gatccccatg | 1560 |
| tgtatcactg | gcaaactgtg | atggacgaca | ccgtcagtgc | gtccgtcgcg | caggctctcg | 1620 |
| atgagctgat | gctttgggcc | gaggactgcc | ccgaagtccg | gcacctcgtg | cacgcggatt | 1680 |
| tcggctccaa | caatgtcctg | acggacaatg | gccgcataac | agcggtcatt | gactggagcg | 1740 |
| aggcgatgtt | cggggattcc | caatacgagg | tcgccaacat | cttcttctgg | aggccgtggt | 1800 |
| tggcttgtat | ggagcagcag | acgcgctact | cgagcggag | gcatccggag | cttgcaggat | 1860 |
| cgccgcgget | ccgggcgtat | atgctccgca | ttggtcttga | ccaactctat | cagagcttgg | 1920 |
| ttgacggcaa | tttcgatgat | gcagcttggg | cgcagggtcg | atgcgacgca | atcgtccgat | 1980 |
| ccggagccgg | gactgtcggg | cgtacacaaa | tcgcccgcag | aagcgcggcc | gtctggaccg | 2040 |

```
atggctgtgt agaagtactc gccgatagtg gaaaccgacg ccccagcact cgtccgaggg    2100
caaaggaata gagatccgcg aaatgaccga ccaagcgacg cccaacctgc catcacgaga    2160
tttcgattcc accgccgcct tctatgaaag gttgggcttc ggaatcgttt tccgggacgc    2220
cggctggatg atcctccagc gcggggatct catgctggag ttcttcgccc accccaactt    2280
gtttattgca gcttataatg gttacaaata aagcaatagc atcacaaatt tcacaaataa    2340
agcatttttt tcactgcatt ctagttgtgg tttgtccaaa ctcatcaatg tatcttatca    2400
tgtctgtata ccgtcgacct cyagctagat ctcgactgga gcgacacgtt catgatgatc    2460
ctcaagaaaa actacgccca ggttagcttt ctgcaggtgt tccaccacgc aacgatcggc    2520
atggtgtggt cgttccttct tcagcgtggc tggggctcgg gcaccgccgc gtacggtgct    2580
ttcatcaact cggtcacgca cgtgatcatg tactcgcact actttgccac ctcgctcaac    2640
atcaacaacc cgttcaagtg gtacatcacg agcttccagc tcgcccagtt tgcaagctgc    2700
atcgtgcatg ccctactggt gcttgccttc gaggaggtgt acccgctcga gtacgcttac    2760
ctgcagatca gctaccacat catcatgctc tacctgttcg gacgccgcat gaactggagc    2820
cccgagtggt gcaccggtga gatcgacggc cttgacgccc aagcgcccc caccaagtcc    2880 gagtaa                                                               2886
```

<210> SEQ ID NO 196
<211> LENGTH: 26
<212> TYPE: DNA
<213> ORGANISM: Artificial
<220> FEATURE:
<223> OTHER INFORMATION: primer

<400> SEQUENCE: 196
gctcggctgg aagttgagta gtttgc                                         26

<210> SEQ ID NO 197
<211> LENGTH: 24
<212> TYPE: DNA
<213> ORGANISM: Artificial
<220> FEATURE:
<223> OTHER INFORMATION: primer

<400> SEQUENCE: 197
tctttcttcg tcgacgtccc actg                                           24

<210> SEQ ID NO 198
<211> LENGTH: 24
<212> TYPE: DNA
<213> ORGANISM: Artificial
<220> FEATURE:
<223> OTHER INFORMATION: primer

<400> SEQUENCE: 198
atgattgaac aggacggcct tcac                                           24

<210> SEQ ID NO 199
<211> LENGTH: 24
<212> TYPE: DNA
<213> ORGANISM: Artificial
<220> FEATURE:
<223> OTHER INFORMATION: primer

<400> SEQUENCE: 199
tcaaaagaac tcgtccagga ggcg                                           24

-continued

<210> SEQ ID NO 200
<211> LENGTH: 24
<212> TYPE: DNA
<213> ORGANISM: Artificial
<220> FEATURE:
<223> OTHER INFORMATION: primer

<400> SEQUENCE: 200
atgaaaaagc ctgaactcac cgcg                                          24

<210> SEQ ID NO 201
<211> LENGTH: 25
<212> TYPE: DNA
<213> ORGANISM: Artificial
<220> FEATURE:
<223> OTHER INFORMATION: primer

<400> SEQUENCE: 201
ctattccttt gccctcggac gagtg                                         25

<210> SEQ ID NO 202
<211> LENGTH: 23
<212> TYPE: DNA
<213> ORGANISM: Artificial
<220> FEATURE:
<223> OTHER INFORMATION: primer

<400> SEQUENCE: 202
ggcggagcga agtgtgaaag tta                                           23

<210> SEQ ID NO 203
<211> LENGTH: 24
<212> TYPE: DNA
<213> ORGANISM: Artificial
<220> FEATURE:
<223> OTHER INFORMATION: primer

<400> SEQUENCE: 203
gcgacagcat cttgaaatag gcag                                          24

<210> SEQ ID NO 204
<211> LENGTH: 2571
<212> TYPE: DNA
<213> ORGANISM: Thraustochytrium aureum
<220> FEATURE:
<223> OTHER INFORMATION: Genomic delta 4 desaturase upstream/T. aureum
      delta 4 desaturase

<400> SEQUENCE: 204
ggcggagcga agtgtgaaag ttacaaccca gttactgccc attcccggga aaagttgcgc    60
agctcacgcg gttcgctttt ctggtggcct ggcgacgttc gccgcttgcc ggatactccc   120
tcgtgccccc gcgccaggtt tgcccgctgt cgctcgagga gtggactcgc gagtcgcgac   180
agcagcagca ccaaggggga tggatcctcg ttgacagcac caagatgctc tctgcctttc   240
aggtgaaatc gatcgatcaa ttgatcaatc aagatcattg gaagcaaatg ggaagcaaat   300
gcgaaggggg aagaccctcg gtctctgctc gggaacccga cacgaggctg agggcgcgct   360
tctacaggtt gtgcagcggc cgcactgcga gcttgcgccg ggccaaggcg ctcgccagaa   420
ttgctgcgtc tgccgcctcg ggatcagcca ctcggttttt cgtcatcagg gtccaccttc   480
aacctggaag tggactcggc aagtcggcag atccactccg gaattccaag atccccggtc   540
gatcggtgct ggtgcgaatt aggatggacc caggctatgt gagagtcgga gggtggcggt   600

```
tgtctccacc gtgacagcgc gcgtgtggtg agtaacgcga agcgcgtggt ggagaaatgg    660
ggggagattc gtaggacgcg atgcgctcgt cactgagggt gcgccggtga cgaagcttcg    720
gacccagatt ccgtcggtat ggctcgtgtt cgcacacctt caggaacccg catgacgaga    780
ccactggagt tttcaacgtc acgaagccgc tctgtgtgac gagaattggc ttgcgagtga    840
cgtgaggcgc cgagcatgtc gttggtttgc ctcttcacaa cagaatcaga cgactgggag    900
gctgcacgag gctaaggcca agggcactca ctgactcgga cgtgaagcag aagcagaagc    960
agagcgctcg acggcacgtg gcggcagacc ggcttcggga cgggcaggag acgcaaggcg   1020
cgcaacacta gggggctgga cgtggaccac tggctaagga gcgctggaaa gatgacggtc   1080
gggtttgacg aaacggtgac tatggacacg gtccgcaacc acaacatgcc ggacgacgcc   1140
tggtgcgcga tccacggcac cgtgtacgac atcaccaagt tcagcaaggt gcaccccggc   1200
ggggacatca tcatgctggc cgctggcaag gaggccacca tcctgttcga gacctaccac   1260
atcaagggcg tcccggacgc ggtgctgcgc aagtacaagg tcggcaagct cccccagggc   1320
aagaagggcg aaacgagcca cgtgcccacc gggctcgact cggcctccta ctactcgtgg   1380
gacagcgagt tttacagggt gctccgcgag cgcgtcgcca agaagctggc cgagcccggc   1440
ctcatgcagc gcgcgcgcat ggagctctgg gccaaggcga tcttcctcct ggcaggtttc   1500
tggggctccc tttacgccat gtgcgtgcta gacccgcacg gcggtgccat ggtagccgcc   1560
gttacgctcg gcgtgttcgc tgcctttgtc ggaacttgca tccagcacga cggcagccac   1620
ggcgccttct ccaagtcgcg attcatgaac aaggcggcgg gctggaccct cgacatgatc   1680
ggcgcgagcg cgatgacctg ggagatgcag cacgttcttg gccaccaccc gtacaccaac   1740
ctcatcgaga tggagaacgg tttggccaag gtcaagggcg ccgacgtcga cccgaagaag   1800
gtcgaccagg agagcgaccc ggacgtcttc agtacgtacc cgatgcttcg cctgcacccg   1860
tggcaccgcc agcggtttta ccacaagttc cagcacctgt acgccccgtt tatctttggg   1920
tttatgacga ttaacaaggt gatttcccag gatgtcgggg ttgtgctgcg caagcgcctg   1980
ttccagatcg acgccaactg ccggtatggc agccctggt acgtggcccg cttctggatc   2040
atgaagctcc tcaccacgct ctacatggtg gcgcttccca tgtacatgca ggggcctgct   2100
cagggcttga agcttttctt catggcccac ttcacctgcg gagaggtcct cgccaccatg   2160
tttattgtca accacatcat cgagggcgtc agctacgctt ccaaggacgc ggtcaagggc   2220
gtcatggctc cgccgcgcac tgtgcacggt gtcaccccga tgcaggtgac gcaaaaggcg   2280
ctcagtgcgg ccgagtcgac caagtcggac gccgacaaga cgaccatgat ccccctcaac   2340
gactgggccg ctgtgcagtg ccagacctct gtgaactggg ctgtcgggtc gtggttttgg   2400
aaccactttt cgggcggcct caaccaccag attgagcacc actgcttccc caaaaccccc   2460
acacggtcaa cgtctacatc tcgggcatcg tcaaggagac ctgcgaagaa tacggcgtgc   2520
cgtaccaggc tgagatcagc ctcttctctg cctatttcaa gatgctgtcg c              2571
```

<210> SEQ ID NO 205
<211> LENGTH: 616
<212> TYPE: DNA
<213> ORGANISM: Thraustochytrium aureum
<220> FEATURE:
<223> OTHER INFORMATION: genomic delta 4 desaturase upstream/T. aureum
      delta 4 desaturase

<400> SEQUENCE: 205

```
cgcaaggcgc gcaacactag ggggctggac gtggaccact ggctaaggag cgctggaaag     60
```

| | |
|---|---|
| atgacggtcg ggtttgacga aacggtgact atggacacgg tccgcaacca caacatgccg | 120 |
| gacgacgcct ggtgcgcgat ccacggcacc gtgtacgaca tcaccaagtt cagcaaggtg | 180 |
| caccccggcg gggacatcat catgctggcc gctggcaagg aggccaccat cctgttcgag | 240 |
| acctaccaca tcaagggcgt cccggacgcg gtgctgcgca agtacaaggt cggcaagctc | 300 |
| ccccagggca agaagggcga aacgagccac gtgcccaccg ggctcgactc ggcctcctac | 360 |
| tactcgtggg acagcgagtt ttacaggggtg ctccgcgagc gcgtcgccaa gaagctggcc | 420 |
| gagcccggcc tcatgcagcg cgcgcgcatg gagctctggg ccaaggcgat cttcctcctg | 480 |
| gcaggtttct ggggctccct ttacgccatg tgcgtgctag acccgcacgg cggtgccatg | 540 |
| gtagccgccg ttacgctcgg cgtgttcgct gcctttgtcg gaacttgcat ccagcacgac | 600 |
| ggcagccacg gcgcct | 616 |

<210> SEQ ID NO 206
<211> LENGTH: 25
<212> TYPE: DNA
<213> ORGANISM: Artificial
<220> FEATURE:
<223> OTHER INFORMATION: primer

<400> SEQUENCE: 206

| | |
|---|---|
| caggagatct ccaagtcgcg attca | 25 |

<210> SEQ ID NO 207
<211> LENGTH: 26
<212> TYPE: DNA
<213> ORGANISM: Artificial
<220> FEATURE:
<223> OTHER INFORMATION: primer

<400> SEQUENCE: 207

| | |
|---|---|
| cttggagatc tcctgcccgt cccgaa | 26 |

<210> SEQ ID NO 208
<211> LENGTH: 3264
<212> TYPE: DNA
<213> ORGANISM: Artificial
<220> FEATURE:
<223> OTHER INFORMATION: fusion DNA (T. aureum delta 4 desaturase upstream/SV40 terminator/BlaR/ubiquitin promoter/T. aureum delta 4 desaturase)

<400> SEQUENCE: 208

| | |
|---|---|
| ggcggagcga agtgtgaaag ttacaaccca gttactgccc attcccggga aaagttgcgc | 60 |
| agctcacgcg gttcgctttt ctggtggcct ggcgacgttc gccgcttgcc ggatactccc | 120 |
| tcgtgccccc gcgccaggtt tgcccgctgt cgctcgagga gtggactcgc gagtcgcgac | 180 |
| agcagcagca ccaaggggga tggatcctcg ttgacagcac caagatgctc tctgcctttc | 240 |
| aggtgaaatc gatcgatcaa ttgatcaatc aagatcattg gaagcaaatg ggaagcaaat | 300 |
| gcgaaggggg aagaccctcg gtctctgctc gggaacccga cacgaggctg agggcgcgct | 360 |
| tctacaggtt gtgcagcggc cgcactgcga gcttgcgccg ggccaaggcg ctcgccagaa | 420 |
| ttgctgcgtc tgccgcctcg ggatcagcca ctcggttttt cgtcatcagg gtccaccttc | 480 |
| aacctggaag tggactcggc aagtcggcag atccactccg gaattccaag atccccggtc | 540 |
| gatcggtgct ggtgcgaatt aggatggacc caggctatgt gagagtcgga gggtggcggt | 600 |
| tgtctccacc gtgacagcgc gcgtgtgtg agtaacgcga agcgcgtggt ggagaaatgg | 660 |
| ggggagattc gtaggacgcg atgcgctcgt cactgagggt gcgccggtga cgaagcttcg | 720 |

```
gacccagatt ccgtcggtat ggctcgtgtt cgcacacctt caggaacccg catgacgaga    780
ccactggagt tttcaacgtc acgaagccgc tctgtgtgac gagaattggc ttgcgagtga    840
cgtgaggcgc cgagcatgtc gttggtttgc ctcttcacaa cagaatcaga cgactgggag    900
gctgcacgag gctaaggcca agggcactca ctgactcgga cgtgaagcag aagcagaagc    960
agagcgctcg acggcacgtg gcggcagacc ggcttcggga cgggcaggag atctagctag   1020
aggtcgacgg tatacagaca tgataagata cattgatgag tttggacaaa ccacaactag   1080
aatgcagtga aaaaaatgct ttatttgtga aatttgtgat gctattgctt tatttgtaac   1140
cattataagc tgcaataaac aagttggggt gggcgaagaa ctccagcatg agatccccgc   1200
gctggaggat catccagccg gcgtcccgga aaacgattcc gaagcccaac ctttcataga   1260
aggcggcggt ggaatcgaaa tctcgtgatg gcaggttggg cgtcgcttgg tcggtcattt   1320
cgcggatctt agccctccca cacataacca gagggcagca attcacgaat cccaactgcc   1380
gtcggctgtc catcactgtc cttcactatg gctttgatcc caggatgcag atcgagaagc   1440
acctgtcggc accgtccgca ggggctcaag atgcccctgt tctcatttcc gatcgcgacg   1500
atacaagtca ggttgccagc tgccgcagca gcagcagtgc ccagcaccac gagttctgca   1560
caaggtcccc cagtaaaatg atatacattg acaccagtga agatgcggcc gtcgctagag   1620
agagctgcgc tggcgacgct gtagtcttca gagatgggga tgctgttgat tgtagccgtt   1680 gctcttttcaa tgagggtgga ttcttcttga dacaaaggct tggccatgtt ggctagtgtt   1740
gcttaggtcg cttgctgctg ctggtgttgc ttgttctgct tgtcgtttgg ggactgcccg   1800
aagtggacgc gtgacacagc ccagcgttcg cgactttttcc agcaaccagc tcgctccgcg   1860
tcagggtcac tctctgctca ctcccctgtc tagttcggca gaactggaga ggcaacccgc   1920
gcttccagag ggttctcctc cggaatcagt tcagaattca gaattcagaa gagggaatcg   1980
cagaaccggc cgcttcggga gttggttcgc tgcaccatag caggtgggcg atgaggccaa   2040
ccgccctgct ggctggattc tctcggggttg gcacatcgaa cgaccgggac ccgcgcgcga   2100
gttgtccctg ccagttgcta ccagcctgcc agcgtcggag agttatgcgc tgcctgccgg   2160
ccggagagag agcgggcgtg gaaagtggcg tgtggggcga acgcatggcc ctcccgcgtg   2220
gcccgatttc ctatgcatcc gctccgctct ctctctcgga ggcaagaaga gcacaccaac   2280
aacgcccggc gggtgcacca ggcgctgcgg cagatccaga tctccaagtc gcgattcatg   2340
aacaaggcgg cgggctggac cctcgacatg atcggcgcga gcgcgatgac ctgggagatg   2400
cagcacgttc ttggccacca cccgtacacc aacctcatcg agatggagaa cggtttggcc   2460
aaggtcaagg gcgccgacgt cgacccgaag aaggtcgacc aggagagcga cccggacgtc   2520
ttcagtacgt acccgatgct tcgcctgcac ccgtggcacc gccagcggtt ttaccacaag   2580
ttccagcacc tgtacgcccc gtttatcttt gggtttatga cgattaacaa ggtgatttcc   2640
caggatgtcg gggttgtgct gcgcaagcgc ctgttccaga tcgacgccaa ctgccggtat   2700
ggcagcccct ggtacgtggc ccgcttctgg atcatgaagc tcctcaccac gctctacatg   2760
gtggcgcttc ccatgtacat gcaggggcct gctcagggct tgaagctttt cttcatggcc   2820
cacttcacct gcgagaggt cctcgccacc atgtttattg tcaaccacat catcgagggc   2880
gtcagctacg cttccaagga cgcggtcaag ggcgtcatgg ctccgccgcg cactgtgcac   2940
ggtgtcaccc cgatgcaggt gacgcaaaag gcgctcagtg cggccgagtc gaccaagtcg   3000
gacgccgaca agacgaccat gatcccctc aacgactggg ccgctgtgca gtgccagacc   3060
```

-continued

```
tctgtgaact gggctgtcgg gtcgtggttt tggaaccact tttcgggcgg cctcaaccac    3120
cagattgagc accactgctt ccccaaaacc cccacacggt caacgtctac atctcgggca    3180
tcgtcaagga gacctgcgaa gaatacggcg tgccgtacca ggctgagatc agcctcttct    3240
ctgcctattt caagatgctg tcgc                                           3264
```

<210> SEQ ID NO 209
<211> LENGTH: 3935
<212> TYPE: DNA
<213> ORGANISM: Artificial
<220> FEATURE:
<223> OTHER INFORMATION: fusion DNA (T. aureum delta 4 desaturase upstream/SV40 terminator/ZeoR/Enhanced GFP/ubiquitin promoter/T. aureum delta 4 desaturase)

<400> SEQUENCE: 209

```
ggcggagcga agtgtgaaag ttacaaccca gttactgccc attcccggga aaagttgcgc      60
agctcacgcg gttcgctttt ctggtggcct ggcgacgttc gccgcttgcc ggatactccc     120
tcgtgccccc gcgccaggtt tgcccgctgt cgctcgagga gtggactcgc gagtcgcgac     180
agcagcagca ccaaggggga tggatcctcg ttgacagcac caagatgctc tctgcctttc     240
aggtgaaatc gatcgatcaa ttgatcaatc aagatcattg gaagcaaatg gaagcaaat      300
gcgaaggggg aagaccctcg gtctctgctc gggaacccga cacgaggctg agggcgcgct     360
tctacaggtt gtgcagcggc cgcactgcga gcttgcgccg ggccaaggcg ctcgccagaa     420
ttgctgcgtc tgccgcctcg ggatcagcca ctcggttttt cgtcatcagg gtccaccttc     480
aacctggaag tggactcggc aagtcggcag atccactccg gaattccaag atccccggtc     540
gatcggtgct ggtgcgaatt aggatggacc caggctatgt gagagtcgga gggtggcggt     600
tgtctccacc gtgacagcgc gcgtgtggtg agtaacgcga agcgcgtggt ggagaaatgg     660
ggggagattc gtaggacgcg atgcgctcgt cactgagggt gcgccggtga cgaagcttcg     720
gacccagatt ccgtcggtat ggctcgtgtt cgcacacctt caggaacccg catgacgaga     780
ccactggagt tttcaacgtc acgaagccgc tctgtgtgac gagaattggc ttgcgagtga     840
cgtgaggcgc cgagcatgtc gttggtttgc ctcttcacaa cagaatcaga cgactgggag     900
gctgcacgag gctaaggcca agggcactca ctgactcgga cgtgaagcag aagcagaagc     960
agagcgctcg acggcacgtg gcggcagacc ggcttcggga cgggcaggag atctagctag    1020
aggtcgacgg tatacagaca tgataagata cattgatgag tttggacaaa ccacaactag    1080
aatgcagtga aaaaaatgct ttatttgtga aatttgtgat gctattgctt tatttgtaac    1140
cattataagc tgcaataaac aagttggggt gggcgaagaa ctccagcatg agatccccgc    1200
gctggaggat catccagccg gcgtcccgga aaacgattcc gaagcccaac ctttcataga    1260
aggcggcggt ggaatcgaaa tctcgtgatg gcaggttggg cgtcgcttgg tcggtcattt    1320
cgcggatctc agtcctgctc ctcggccacg aagtgcacgc agttgccggc cgggtcgcgc    1380
agggcgaact cccgccccca cggctgctcg ccgatctcgg tcatggccgg cccggaggcg    1440
tcccggaagt tcgtggacac gacctccgac cactcggcgt acagctcgtc caggccgcgc    1500
acccacaccc aggccaggat gttgtccggc accaccggt cctggaccgc gctgatgaac    1560
agggtcacgt cgtcccggac cacaccggcg aagtcgtcct ccacgaagtc ccgggagaac    1620
ccgagccggt cggtccagaa ctcgaccgct ccggcgacgt cgcgcgcggt gagcaccgga    1680
acggcactgg tcaacttggc gtccatgccg agagtgatcc cggcggcggt cacgaactcc    1740
agcaggacca tgtgatcgcg cttctcgttg gggtctttgc tcagggcgga ctgggtgctc    1800
```

```
aggtagtggt tgtcgggcag cagcacgggg ccgtcgccga tgggggtgtt ctgctggtag    1860
tggtcggcga gctgcacgct gccgtcctcg atgttgtggc ggatcttgaa gttcaccttg    1920
atgccgttct tctgcttgtc ggccatgata tagacgttgt ggctgttgta gttgtactcc    1980
agcttgtgcc ccaggatgtt gccgtcctcc ttgaagtcga tgcccttcag ctcgatgcgg    2040
ttcaccaggg tgtcgccctc gaacttcacc tcggcgcggg tcttgtagtt gccgtcgtcc    2100
ttgaagaaga tggtgcgctc ctggacgtag ccttcgggca tggcggactt gaagaagtcg    2160
tgctgcttca tgtggtcggg gtagcggctg aagcactgca cgccgtaggt cagggtggtc    2220
acgagggtgg gccagggcac gggcagcttg ccggtggtgc agatgaactt cagggtcagc    2280
ttgccgtagg tggcatcgcc ctcgccctcg ccggacacgc tgaacttgtg gccgtttacg    2340
tcgccgtcca gctcgaccag gatgggcacc accccggtga acagctcctc gcccttgctc    2400
accatgttgg ctagtgttgc ttagatcgct tgctgctgct ggtgttgctt gttctgcttg    2460
tcgtttgggg tctgcccgaa gtggacgcgt gacacagccc agcgttcgcg acttttccag    2520
caaccagctc gctccgcgtc agggtcactc tctgctcact cccctgtcta gttcggcaga    2580
actggagagg caacccgcgc ttccagaggg ttctcctccg gaatcagttc agaattcaga    2640
attcagaaga gggaatcgca gaaccggcag cttcgggagt tggttcgctg caccatagca    2700
ggtgggcgat gaggccaacc gccctgctgg ctggattctc tcgggttggc acatcgaacg    2760
accgggaccc gcgcgcgagt tgtccctgcc agttgctacc agcctgccag cgtcggagag    2820
ttatgcgctg cctgccggcc ggagagagag cgggcgtgga aagtggcgtg tggggcaaac    2880
gcatggccct cccgcgtggc ccgatttcct atgcatccgc tccgctctct ctctcggagg    2940
caagaagagc acacaacaac gcccggcggg tgcaccaggc gctgcggcag atctccaagt    3000
cgcgattcat gaacaaggcg gcgggctgga ccctcgacat gatcggcgcg agcgcgatga    3060
cctgggagat gcagcacgtt cttggccacc acccgtacac caacctcatc gagatggaga    3120
acggtttggc caaggtcaag ggcgccgacg tcgacccgaa gaaggtcgac caggagagcg    3180
acccggacgt cttcagtacg tacccgatgc ttcgcctgca cccgtggcac cgccagcggt    3240
tttaccacaa gttccagcac ctgtacgccc cgtttatctt tgggtttatg acgattaaca    3300
aggtgatttc ccaggatgtc ggggttgtgc tgcgcaagcg cctgttccag atcgacgcca    3360
actgccggta tggcagcccc tggtacgtgg cccgcttctg gatcatgaag ctcctcacca    3420
cgctctacat ggtggcgctt cccatgtaca tgcaggggcc tgctcagggc ttgaagcttt    3480
tcttcatggc ccacttcacc tgcggagagg tcctcgccac catgtttatt gtcaaccaca    3540
tcatcgaggg cgtcagctac gcttccaagg acgcggtcaa gggcgtcatg gctccgccgc    3600
gcactgtgca cggtgtcacc ccgatgcagg tgacgcaaaa ggcgctcagt gcggccgagt    3660
cgaccaagtc ggacgccgac aagacgacca tgatcccccct caacgactgg gccgctgtgc    3720
agtgccagac ctctgtgaac tgggctgtcg ggtcgtggtt ttggaaccac ttttcgggcg    3780
gcctcaacca ccagattgag caccactgct tccccaaaac ccccacacgg tcaacgtcta    3840
catctcgggc atcgtcaagg agacctgcga agaatacggc gtgccgtacc aggctgagat    3900
cagcctcttc tctgcctatt tcaagatgct gtcgc                              3935
```

<210> SEQ ID NO 210
<211> LENGTH: 23
<212> TYPE: DNA
<213> ORGANISM: Artificial
<220> FEATURE:

<223> OTHER INFORMATION: primer

<400> SEQUENCE: 210
aaaagaacaa gccctctcct gga                                            23

<210> SEQ ID NO 211
<211> LENGTH: 23
<212> TYPE: DNA
<213> ORGANISM: Artificial
<220> FEATURE:
<223> OTHER INFORMATION: primer

<400> SEQUENCE: 211
gaggtttgta tgttcggcgg ttt                                            23

<210> SEQ ID NO 212
<211> LENGTH: 26
<212> TYPE: DNA
<213> ORGANISM: Artificial
<220> FEATURE:
<223> OTHER INFORMATION: primer

<400> SEQUENCE: 212
tgggggacct tgtgcagaac tcgtgg                                         26

<210> SEQ ID NO 213
<211> LENGTH: 22
<212> TYPE: DNA
<213> ORGANISM: Artificial
<220> FEATURE:
<223> OTHER INFORMATION: primer

<400> SEQUENCE: 213
gacctacggc gtgcagtgct tc                                             22

<210> SEQ ID NO 214
<211> LENGTH: 22
<212> TYPE: DNA
<213> ORGANISM: Artificial
<220> FEATURE:
<223> OTHER INFORMATION: primer

<400> SEQUENCE: 214
atgtgcaagg tcgatgggac aa                                             22

<210> SEQ ID NO 215
<211> LENGTH: 22
<212> TYPE: DNA
<213> ORGANISM: Artificial
<220> FEATURE:
<223> OTHER INFORMATION: primer

<400> SEQUENCE: 215
tcacaaacat cgcagccttc gg                                             22

<210> SEQ ID NO 216
<211> LENGTH: 395
<212> TYPE: PRT
<213> ORGANISM: Thraustochytrium aureum ATCC 34304
<220> FEATURE:
<221> NAME/KEY: misc_feature
<222> LOCATION: (395)..(395)
<223> OTHER INFORMATION: Xaa can be any naturally occurring amino acid

<400> SEQUENCE: 216

Met Cys Lys Val Asp Gly Thr Asn Arg Ala Ser Ser Ala Gln Ala Gln

```
  1               5                   10                  15
Ala Glu Gln Glu Lys Leu Pro Thr Ile Gly Glu Leu Arg Lys Ala Val
                    20                  25                  30

Pro Ala His Cys Phe Glu Lys Ser Thr Leu Lys Ser Leu Phe Phe Val
                35                  40                  45

Ala Arg Asp Leu Ala Phe Cys Ser Ala Ile Gly Tyr Ala Ala Trp Glu
50                  55                  60

Tyr Ile Pro Val Glu Trp Ser Ile Lys Ala Ile Ala Leu Trp Thr Leu
65                  70                  75                  80

Tyr Ala Ile Val Gln Gly Thr Val Ala Thr Gly Val Trp Val Leu Gly
                    85                  90                  95

His Glu Gly Gly His Gly Ile Ser Ser Tyr Ser Ile Val Asn Asp
                100                 105                 110

Thr Val Gly Tyr Val Leu His Ser Ile Leu Leu Val Pro Tyr Phe Ser
                115                 120                 125

Trp Gln Asp Ser His Arg Arg His Ala Arg Cys Asn His Leu Leu
130                 135                 140

Asp Gly Glu Ser His Asn Pro Asp Leu Lys Arg Lys Val Tyr Lys Met
145                 150                 155                 160

Tyr Glu Lys Ile Leu Asp Thr Val Gly Glu Asp Ala Phe Val Ile Met
                    165                 170                 175

Gln Ile Val Leu His Leu Val Leu Gly Trp Pro Met Tyr Leu Leu Met
                180                 185                 190

His Ala Thr Gly Ser Arg Arg Ser Pro Val Thr Gly Gln Lys Tyr Thr
                    195                 200                 205

Lys Lys Pro Asn His Phe Asn Trp Gly Ala Ser Asn Glu Gln Tyr Pro
210                 215                 220

Ala Lys Leu Arg Phe Lys Ile Phe Leu Ser Ser Leu Gly Val Ile Ala
225                 230                 235                 240

Thr Leu Ala Gly Ile Ala Val Leu Ala Asn Lys Leu Gly Ala Ala Lys
                    245                 250                 255

Val Ser Leu Met Tyr Phe Gly Pro Tyr Leu Val Val Asn Ala Trp Leu
                260                 265                 270

Val Gly Tyr Thr Trp Leu Gln His Thr Asp Gln Asp Ala Pro His Tyr
                275                 280                 285

Gly Glu Asp Glu Trp Thr Trp Ile Lys Gly Ala Met Thr Thr Ile Asp
                290                 295                 300

Arg Pro Tyr Pro Trp Ile Val Asp Glu Leu His His Ile Gly Thr
305                 310                 315                 320

Thr His Val Cys His His Leu Phe Ser Asp Met Pro His Tyr Lys Ala
                    325                 330                 335

Gln Glu Ala Thr Glu Ala Leu Lys Pro Val Leu Gly Lys His Tyr Arg
                340                 345                 350

Phe Asp Pro Thr Pro Leu Ala Gln Ala Met Trp Asn Thr Ala Arg Asp
                355                 360                 365

Cys His Tyr Val Glu Gly Leu Asp Gly Val Gln Tyr Pro Gln Ser Ile
                370                 375                 380

Ile Ala Glu Lys Arg Ala Ala Lys Lys Leu Xaa
385                 390                 395

<210> SEQ ID NO 217
<211> LENGTH: 1185
<212> TYPE: DNA
<213> ORGANISM: Artificial
```

```
<220> FEATURE:
<223> OTHER INFORMATION: genomic DNA (T. aureum ATCC34304 delta 4
      desaturase DNA)

<400> SEQUENCE: 217
atgtgcaagg tcgatgggac aaaccgggcg agctcggctc aagcccaggc agagcaggaa     60
aagctgccca ccatcggcga gctgcgcaag gctgtgcccg cgcactgttt cgaaaagtcg    120
acgttgaaga gcctgttctt cgtggctcgt gacctggcgt tttgcagcgc catcgggtac    180
gcggcctggg agtacatccc cgtcgagtgg tcaatcaagg ccatcgccct gtggaccctg    240
tacgccatag tgcagggcac cgtggcgacc ggggtctggg ttctgggcca cgaaggcgga    300
cacggaggga tctcgagcta ctctattgtc aacgatactg tcgggtacgt gctgcactcg    360
atcctgctcg tgccgtactt ttcctggcag gacagccaca ggcgccacca cgcgcggtgc    420
aaccacctcc tggacgggga gtcgcacaac ccggacctca agcgcaaggt ttacaagatg    480
tacgaaaaga tcctcgacac ggtgggcgag gacgcctttg tgatcatgca gatcgtcctt    540
caccttgtct tagggtggcc catgtacctg ctgatgcacg cgaccgggtc tcgccgcagc    600
cccgtgactg ggcaaaagta caccaaaaag cccaatcact tcaactgggg tgcgagcaac    660
gagcagtacc cggccaagtt gcgcttcaag attttctgt cctcgcttgg cgtgatcgcg    720
acgctcgcag ggatcgccgt gctggccaac aagctcggcg ccgccaaggt ctcgctcatg    780
tactttggcc cctacctcgt ggtgaatgcc tggctcgtgg atacacctg gctccagcac    840 accgaccagg acgccccgca ctatggcgag gacgagtgga cctggatcaa gggcgccatg    900
acgacgatcg accgccccta cccctggatt gtggacgagc tccaccacca catcggcacg    960
acgcacgttt gccaccacct gttttccgac atgccgcact acaaggccca ggaagccacc   1020
gaggcgctca gccggtgct cggcaagcac taccgcttcg acccgacccc gctggcgcag   1080
gccatgtgga acaccgctcg cgactgccac tacgtcgagg gcctcgacgg agtgcagtac   1140
ccgcagtcaa tcatcgccga gaagcgtgcg gccaaaaagc tctag                    1185

<210> SEQ ID NO 218
<211> LENGTH: 30
<212> TYPE: DNA
<213> ORGANISM: Artificial
<220> FEATURE:
<223> OTHER INFORMATION: primer

<400> SEQUENCE: 218
ggaagcttat gtgcaaggtc gatgggacaa                                       30

<210> SEQ ID NO 219
<211> LENGTH: 29
<212> TYPE: DNA
<213> ORGANISM: Artificial
<220> FEATURE:
<223> OTHER INFORMATION: primer

<400> SEQUENCE: 219
ttctagacta gagcttttg gccgcacgc                                         29

<210> SEQ ID NO 220
<211> LENGTH: 23
<212> TYPE: DNA
<213> ORGANISM: Artificial
<220> FEATURE:
<223> OTHER INFORMATION: primer

<400> SEQUENCE: 220
```

-continued agtcagccca ggcaccgatg acg                                    23

<210> SEQ ID NO 221
<211> LENGTH: 39
<212> TYPE: DNA
<213> ORGANISM: Artificial
<220> FEATURE:
<223> OTHER INFORMATION: primer

<400> SEQUENCE: 221
agccagagct agatctcttg tgctcctttt caatccttt                   39

<210> SEQ ID NO 222
<211> LENGTH: 39
<212> TYPE: DNA
<213> ORGANISM: Artificial
<220> FEATURE:
<223> OTHER INFORMATION: primer

<400> SEQUENCE: 222
ggagcacaag agatctagct ctggctcaag ggacaccgt                   39

<210> SEQ ID NO 223
<211> LENGTH: 24
<212> TYPE: DNA
<213> ORGANISM: Artificial
<220> FEATURE:
<223> OTHER INFORMATION: primer

<400> SEQUENCE: 223
cacagaaact gccttcacgg gtct                                   24

<210> SEQ ID NO 224
<211> LENGTH: 24
<212> TYPE: DNA
<213> ORGANISM: Artificial
<220> FEATURE:
<223> OTHER INFORMATION: primer

<400> SEQUENCE: 224
tgttatgcgg ccattgtccg tcag                                   24

<210> SEQ ID NO 225
<211> LENGTH: 24
<212> TYPE: DNA
<213> ORGANISM: Artificial
<220> FEATURE:
<223> OTHER INFORMATION: primer

<400> SEQUENCE: 225
tgcgatcgct gcggccgatc ttag                                   24

<210> SEQ ID NO 226
<211> LENGTH: 26
<212> TYPE: DNA
<213> ORGANISM: Artificial
<220> FEATURE:
<223> OTHER INFORMATION: primer

<400> SEQUENCE: 226
atgaaaaagc ctgaactcac cgcgac                                 26

<210> SEQ ID NO 227
<211> LENGTH: 25
<212> TYPE: DNA

```
<213> ORGANISM: Artificial
<220> FEATURE:
<223> OTHER INFORMATION: primer

<400> SEQUENCE: 227
ctattccttt gccctcggac gagtg                                              25

<210> SEQ ID NO 228
<211> LENGTH: 27
<212> TYPE: DNA
<213> ORGANISM: Artificial
<220> FEATURE:
<223> OTHER INFORMATION: primer

<400> SEQUENCE: 228
atggccaagc ctttgtctca agaagaa                                            27

<210> SEQ ID NO 229
<211> LENGTH: 30
<212> TYPE: DNA
<213> ORGANISM: Artificial
<220> FEATURE:
<223> OTHER INFORMATION: primer

<400> SEQUENCE: 229
ttagccctcc cacacataac cagagggcag                                         30

<210> SEQ ID NO 230
<211> LENGTH: 23
<212> TYPE: DNA
<213> ORGANISM: Artificial
<220> FEATURE:
<223> OTHER INFORMATION: primer

<400> SEQUENCE: 230
ggggtcggcc ggtgcagcct tag                                                23

<210> SEQ ID NO 231
<211> LENGTH: 24
<212> TYPE: DNA
<213> ORGANISM: Artificial
<220> FEATURE:
<223> OTHER INFORMATION: primer

<400> SEQUENCE: 231
ggcggtcagc gatcggtcgg actc                                               24

<210> SEQ ID NO 232
<211> LENGTH: 23
<212> TYPE: DNA
<213> ORGANISM: Artificial
<220> FEATURE:
<223> OTHER INFORMATION: primer

<400> SEQUENCE: 232
gcttgcggct cctgttgggt gac                                                23

<210> SEQ ID NO 233
<211> LENGTH: 23
<212> TYPE: DNA
<213> ORGANISM: Artificial
<220> FEATURE:
<223> OTHER INFORMATION: primer

<400> SEQUENCE: 233
acgcctggct gcccaccata aac                                                23
```

<210> SEQ ID NO 234
<211> LENGTH: 28
<212> TYPE: DNA
<213> ORGANISM: Artificial
<220> FEATURE:
<223> OTHER INFORMATION: primer

<400> SEQUENCE: 234
ttagcgggat cccaattcgc cctatagt                                  28

<210> SEQ ID NO 235
<211> LENGTH: 27
<212> TYPE: DNA
<213> ORGANISM: Artificial
<220> FEATURE:
<223> OTHER INFORMATION: primer

<400> SEQUENCE: 235
aattgggatc ccgctaagta tctcccg                                   27

<210> SEQ ID NO 236
<211> LENGTH: 28
<212> TYPE: DNA
<213> ORGANISM: Artificial
<220> FEATURE:
<223> OTHER INFORMATION: primer

<400> SEQUENCE: 236
agatctggta ccgcagcgcc tggtgcac                                  28

<210> SEQ ID NO 237
<211> LENGTH: 27
<212> TYPE: DNA
<213> ORGANISM: Artificial
<220> FEATURE:
<223> OTHER INFORMATION: primer

<400> SEQUENCE: 237
gctgcggtac cagatctggt cgcgttt                                   27

<210> SEQ ID NO 238
<211> LENGTH: 5611
<212> TYPE: DNA
<213> ORGANISM: Artificial
<220> FEATURE:
<223> OTHER INFORMATION: fusion DNA (Thraustochytrium aureum C20
      elongase upstream/ubiquitin promoter/3 desaturase/ubiquitin
      terminator/ubiquitin promoter/BlaR/SV40 terminator/T.aureum C20
      elongase downstream)

<400> SEQUENCE: 238
tcccccgggc tgcaggaatt cactagtgat tctcccgggt ggacctagcg cgtgtgtcac    60
ctgccggccc ccgttgcgtg caaccgaatt gatcgataat agaattacat aacaaacaac   120
ttgctggatg agtacaagac cagcgtagtg tggctgtggg acgttgaacg gagcgggtcc   180
tgtgatggcg cagaaaggaa ctccgcccga ggtgaaaccc cgatgcgcag gactctgcgg   240
ccacagcccc tccgccagta ttccactaaa atccgccccc ttttgacaaa gatcgcaacc   300
ccgtcccatc aactcctcac aataggcttt ccactggcgg aaacgtcccc ggcacaggag   360
tgcctcccgc ggttctgcgc atgcggctga ccactacgca gcgcgatatc ctccatccgc   420
gtatatatcc gtaaacaacg gaacattctc cctctcaacg aggcgtggtt ttcgaagtca   480
tgcctttctt ccttcctact ttccttcctt ctttctttct ttctttcctt cttttgcaag   540

```
cgtgcgcgaa cttgaaggta ctacttacac ttgacagaga gagatagaga cggcaattcg    600
accaagtact ttccacgatt ttttttttt ttgttttggt cgctttcgtt ggtcgtgcat    660
gatggatggc cgggatttt acaattggat gcgccaggct gccacgcatg ccgtgacgct    720
tgctcgcggc gactcatgat gcttgccagt ggcagtgcat ccagctcttc cctctgctcg    780
tcgtgtactc actggcgatg ctctcggcgc tcgttcaagg gccatcgatc gatcgatcga    840
tcgatcgatc gatcaatcac gtttggtgga ctcggcagac cccgaacgtg tttctcccag    900
gacgcgccgc tgtcgctcgc taatccaccc gaagcgcggt cggctggcac ggtcgctcgg    960
ctggaagttg agtagtttgc tttctgttgc tgcgctgctt tgtaaacgcg accagatctg   1020
gtacccgtta aacgcgtaa tacgactcac tatagggaga gtcgactgag cacaactctg   1080
ctgcgagcgg gcctcgagag cgtttgcttc gagccgcgga gcaaggggga tggatcgctc   1140
atgcggtcgt gcggccctcg gtcacccggt gggtcctgca ctgacgcatc tgttctgatc   1200
agacacacga acgaacaaac cgaggagccg cagcgcctgg tgcacccgcc gggcgttgtt   1260
gtgtgctctt cttgcctccg agagagagag cggagcggat gcataggaaa tcgggccacg   1320
cgggagggcc atgcgttcgc cccacacgcc actttccacg cccgctctct ctccggccgg   1380
caggcagcgc ataactctcc gacgctggca ggctggtagc aactggcagg acaactcgc    1440 gcgcgggtcc cggtcgttcg atgtgccaac ccgagagaat ccagccagca gggcggttgg   1500
cctcatcgcc cacctgctat ggtgcagcga accaactccc gaagcggccg ttctgcgat    1560 tccctcttct gaattctgaa ttctgaactg attccggagg agaaccctct ggaagcgcgg   1620
gttgcctctc cagttctgcc gaactagaca ggggagtgag cagagagtga ccctgacgcg   1680
gagcgagctg gttgctggaa aagtcgcgaa cgctgggctg tgtcacgcgt ccacttcggg   1740
cagaccccaa acgacaagca gaacaagcaa caccagcagc agcaagcgac ctaagcaaca   1800
ctagccaaca tgactgagga taagacgaag gtcgagttcc cgacgctcac ggagctcaag   1860
cactcgatcc cgaacgcgtg ctttgagtcg aacctcggcc tctcgctcta ctacacggcc   1920
cgcgcgatct tcaacgcgtc ggcctcggcc gcgctgctct acgcggcgcg ctcgacgccg   1980
ttcattgccg ataacgttct gctccacgcg ctcgtttgcg ccacctacat ctacgtgcag   2040
ggcgtcatct tctggggctt cttcacggtc ggccacgact gcggccactc ggccttctcg   2100
cgctaccaca gcgtcaactt tatcatcggc tgcatcatgc actctgcgat tttgacgccg   2160
ttcgagagct ggcgcgtgac gcaccgccac caccacaaga acacgggcaa cattgataag   2220
gacgagatct tttacccgca ccggtcggtc aaggacctcc aggacgtgcg ccaatgggtc   2280
tacacgctcg gcggtgcgtg gtttgtctac ttgaaggtcg ggtatgcccc gcgcacgatg   2340
agccactttg acccgtggga cccgctcctc cttcgccgcg cgtcggccgt catcgtgtcg   2400
ctcggcgtct gggccgcctt cttcgccgcg tacgcgtacc tcacatactc gctcggcttt   2460
gccgtcatgg gcctctacta ctatgcgccg ctctttgtct ttgcttcgtt cctcgtcatt   2520
acgaccttct tgcaccacaa cgacgaagcg acgccgtggt acggcgactc ggagtggacg   2580
tacgtcaagg gcaacctctc gagcgtcgac cgctcgtacg gcgcgttcgt ggacaacctg   2640
agccaccaca ttggcacgca ccaggtccac cacttgttcc cgatcattcc gcactacaag   2700
ctcaacgaag ccaccaagca ctttgcggcc gcgtacccgc acctcgtgcg caagaacgac   2760
gagcccatca tctcggcctt cttcaagacc gcgcacctct ttgtcaacta cggcgctgtg   2820
cccgagacgg cgcagatctt cacgctcaaa gagtcggccg cggccgccaa ggccaagtcg   2880
```

```
gactaaacta agctatctgt agtatgtgct atactcgaat catgctgccc tgtacgtacc    2940
tacctatatc tgattgagcg tgctgcgtcg accatagacg cgggaacgcg ggccagccta    3000
ccacgttgcc gccgccggta tccacgggca cgccaaagca ttggtcgata acgctctgcc    3060
cagggcttcc tggcgaggac ccgaggccaa catgcatgca tgtgctatca gcggtcatca    3120
tcgccctcat cagcgcgcat cggcgagctc gcgcacgaac ggcaagcgcc caactcaact    3180
cacttactca cactatggtc ttgccgttgg cggttgctta gctaatgcgt gacgtcactc    3240
tgcctccaac atcgcgaggc agagtcgcga gcagtgcaga ggccacggcg gacgccaaca    3300
aagcgccaac cagcgcaacg caccagcggg tctgtgggcg tagctcgagc gggcgtcttc    3360
aagagccgcc gtggagccga cgcccctgcg aagggctcga gtgcaagcgg ggccgttgag    3420
ccgcgtggta ggaacaactg cagtctccct atagtgagtc gtattacgcg gtggtaccgc    3480
agcgcctggt gcaccgccg gcgttgttg tgtgctcttc ttgcctccga gagagagagc    3540
ggagcggatg cataggaaat cgggccacgc gggagggcca tgcgttcgcc ccacacgcca    3600
cttcacgc ccgctctctc tccggccggc aggcagcgca taactctccg acgctggcag    3660
gctggtagca actggcaggg acaactcgcg cgcgggtccc ggtcgttcga tgtgccaacc    3720
cgagagaatc cagccagcag ggcggttggc ctcatcgccc acctgctatg gtgcagcgaa    3780
ccaactcccg aagcggccgg ttctgcgatt ccctcttctg aattctgaat tctgaactga    3840
ttccggagga gaaccctctg gaagcgcggg ttgcctctcc agttctgccg aactagacag    3900
gggagtgagc agagagtgac cctgacgcgg agcgagctgg ttgctggaaa agtcgcgaac    3960
gctgggctgt gtcacgcgtc cacttcgggc agtcccaaa cgacaagcag aacaagcaac    4020
accagcagca gcaagcgacc taagcaacac tagccaacat ggccaagcct tgtctcaag    4080
aagaatccac cctcattgaa agagcaacgg ctacaatcaa cagcatcccc atctctgaag    4140
actacagcgt cgccagcgca gctctctcta gcgacggccg catcttcact ggtgtcaatg    4200
tatatcattt tactggggga ccttgtgcag aactcgtggt gctgggcact gctgctgctg    4260
cggcagctgg caacctgact tgtatcgtcg cgatcggaaa tgagaacagg ggcatcttga    4320
gcccctgcgg acgtgccga caggtgcttc tcgatctgca tcctgggatc aaagccatag    4380
tgaaggacag tgatggacag ccgacggcag ttgggattcg tgaattgctg ccctctggtt    4440
atgtgtggga gggctaagat ccgcgaaatg accgaccaag cgacgcccaa cctgccatca    4500
cgagatttcg attccaccgc cgccttctat gaaaggttgg gcttcggaat cgttttccgg    4560
gacgccggct ggatgatcct ccagcgcggg gatctcatgc tggagttctt cgcccacccc    4620
aacttgttta ttgcagctta taatggttac aaataaagca atagcatcac aaatttcaca    4680
aataaagcat ttttttcact gcattctagt tgtggtttgt ccaaactcat caatgtatct    4740
tatcatgtct gtataccgtc gacctctagc tagatctacc tgtttccggc tggctcccga    4800
gccatgctta ccatgaatgg acctgcaaac agtctgaggt ccttgtgcaa accgctcagt    4860
gggacgtcga cgaagaaaga acaatgtgt actcgtcttg ctctgctccc gcgccgtttt    4920
ttatcgttgt tgagacctct cgcgcagttt tgggaatcaa ccaaaacaag agcccggcgt    4980
cagcgtttgc ttcgccctcg gctgcactcg ctcggcacgc aggtataact gggtgagtac    5040
caagccccgc atttgtctgt ccgcgatccg cgcacgctgc gggtcaggac gacatcgcgc    5100
tgcacgtcac agtgggtccc ttttgacgtg gctgcggcga tgaggaggct tggctcgggt    5160
tcatggcaag gcaacagact cgcttccggg acgcgcacga cgagcagcgc tgctttgatc    5220
gaccttgcct gcgtcaccgc ctcggctgct ttgatcgatc gttgtcaccg gccgagtgac    5280
```

```
cgcgaacgca ttgcccgcac ggctcggctc ggcccggacc ggaccggctc gccttggcgg    5340
cgcggcgcga tggcgaccca gacgcggccg gagccgcgcg cggaggacaa ggccatgttc    5400
atcttcgggc tcgggtacgt tgggagcagg ctcgccaacc agctggcgga acaggggtgg    5460
cgcgtcgcgg ggtcggtgag ggagctcggg cgcgaggacg actttgccga gttcgaaaag    5520
tccaagctga gcggcaaggt gcaggtgttc caactcccgc ttgagggcga ggacaacacg    5580
cccgctcgcg cgcgggagat acttagcggg a                                   5611

<210> SEQ ID NO 239
<211> LENGTH: 904
<212> TYPE: DNA
<213> ORGANISM: Artificial
<220> FEATURE:
<223> OTHER INFORMATION: Genomic DNA (Parietichytrium C20 elongase
      upstream)

<400> SEQUENCE: 239
gacgtcgatt cccggaagag agaggacttg taaggaactt ttgtgtaaaa agatgtaaaa      60
agatggaaag tattcaacgc gttggcgtga cgcctcactc acggttgcac gggcagagtc     120
aggcgtggtg agtggtgact ccaaaagaaa gaaagaaaga aggagggctt tcgtttcttg     180
cttgagatca agattgaaag ttttttctgaa ttttgaattc tttttttttg gcggtctgac    240
tcgtgtgttt gtgccaagtt cgaaaagcat tgcagtcttg ccacgtgaac acgagaacca    300
gcattctttg atttctttgg actggaaaag acgagactca tgcgctaaag gagagaagct    360
gtctcggggg gtccaatcat gtggaaatgt gtgagtgtgt aattggcggt tccatgcctc    420
gcctagagag tcgggtagac ggctttgcca gtctgcagcg gagtcatcgg accacgtatc    480
cggaaactcg tgtgtctccg atgtctcagc ctctctctct cgacaacttt gtttctaata    540
ttttctaatt gtcgtgatcg tcgtgacagg tgagcatagg tgagcccgca tcatcatcga    600
tcggtgggtg tctctgacgg ggggttgggac tccgatgaac tttgaaaaga gacgtggtag   660
tacaagtatg taataaacac cggtacatat catgaaggtt acgcttgcta ggctactgga    720
agaggaaagt ggagcttaga ctttacgaga tgaagggtgt agcgccttga gtgtggcgct    780
gacgggtctg caaatcctga aacgccggat tggttgcgtg gtcgagctga aaacgacaga    840
acggtggtcc agtgcagtag tccccgattt ggtagttgac caaaagttga gagaaacgga    900
gagg                                                                 904

<210> SEQ ID NO 240
<211> LENGTH: 721
<212> TYPE: DNA
<213> ORGANISM: Artificial
<220> FEATURE:
<223> OTHER INFORMATION: Genomic DNA (Parietichytrium C20 elongase
      downstream)

<400> SEQUENCE: 240
taccgacctt gtactcgagg agttgttgtg cgcgcggatc cgagcgcaaa agtggacgtc     60
ggtgagagac aggacaatgt ttggtagcag agcagcagtt cgcgctttgc aaagcagcgg    120
cttgcgactt gggagcacag cgcggagggc ctctcaccat gggctgtttt cgctggaagg    180
cacggcgccc agagtgcacc cggaggcgtg gattgcgcat aacgcagttg tcgtgggcga    240
tgtagaaatc ggggccaggt cgagcgtgtg gtttgggggcc tgcattcgcg gtgaccgcga    300
cttgatatcg atcggggaag agacaaacat tcaggacggg agtgtgctgc acacggatgc    360
```

```
aggcgtccct atgaagatac atgatcgcgt caccatcgga cacatggtca tgctgcacgg      420
ctgcacggtg cattctgggt ctctgatcgg cattggggcg acaatactaa acaagtaggt      480
ttctatgaag tgaggaaggg ggaaggaatt cggttgtgtg tttcctgact gtgcaccgct      540
tctctgcagg gccgtcatcg ggaagaattg cctgattggt gcgaacgctc taatcacgga      600
agggaaagtc atcccggacg gaagtctagt gatgggccgc aaccaggtgg ttcgacagct      660
caccgagaag gagatcgagg gaattcagcg cactgcggct ggctatgtgc agaaccaagg      720
g                                                                     721
```

<210> SEQ ID NO 241
<211> LENGTH: 4592
<212> TYPE: DNA
<213> ORGANISM: Artificial
<220> FEATURE:
<223> OTHER INFORMATION: fusion DNA (pGEM-T easy vector/Parietichytrium
      C20 elongase upstream/Parietichytrium C20 elongase
      downstream/pGEM-T easy vector)

<400> SEQUENCE: 241

```
gggcgaattg ggcccgacgt cgcatgctcc cggccgccat ggcggccgcg ggaattcgat       60
tgacgtcgat tcccggaaga gagggacttg taaggaactt tttgtgtaaa aagatgtaaa      120
aagatggaaa gtattcaacg cgttggcgtg acgcctcact cacggttgca cgggcagagt      180
caggcgtggt gagtggtgac tccaaaagaa agaaagaaag aaggagggct ttcgtttctt      240
gcttgagatc aagattgaaa gttttctga attttgaatt ctttttttt ggcggtctga       300 ctcgtgtgtt tgtgccaagt cgaaaagca ttgcagtctt gccacgtgaa cacgagaacc      360
agcattcttt gatttcttg gactggaaaa gacgagactc atgcgctaaa ggagagaagc      420
tgtctcgggg ggtccaatca tgtggaaatg tgtgagtgtg taattggcgg ttccatgcct      480
cgcctagaga gtcgggtaga cggctttgcc agtctgcagc ggagtcatcg gaccacgtat      540
ccggaaactc gtgtgtctcc gatgtctcag cctctctctc tcgacaactt tgtttctaat      600
attttctaat tgtcgtgatc gtcgtgacag gtgagcatag gtgagcccgc atcatcatcg      660
atcggtgggt gtctctgacg ggggttggga ctccgatgaa cttgaaaag agacgtggta      720 gtacaagtat gtaataaaca ccggtacata tcatgaaggt tacgcttgct aggctactgg      780
aagaggaaag tggagcttag actttacgag atgaagggtg tagcgccttg agtgtggcgc      840
tgacgggtct gcaaatcctg aaacgccgga ttggttgcgt ggtcgagctg aaaacgacag      900
aacggtggtc cagtgcagta gtccccgatt tggtagttga ccaaaagttg agagaaacgg      960
agaggtaccg accttgtact cgaggagttg ttgtgcgcgc ggatccgagc gcaaaagtgg     1020
acgtcggtga gagacaggac aatgtttggt agcagagcag cagttcgcgc tttgcaaagc     1080
agcggcttgc gacttgggag cacagcgcgg agggcctctc accatgggct gttttcgctg     1140
gaaggcacgg cgcccagagt gcacccggag gcgtggattg cgcataacgc agttgtcgtg     1200
ggcgatgtag aaatcggggc caggtcgagc gtgtggtttg gggcctgcat tcgcggtgac     1260
cgcgacttga tatcgatcgg ggaagagaca acattcagg acgggagtgt gctgcacacg     1320
gatgcaggcg tccctatgaa gatacatgat cgcgtcacca tcggacacat ggtcatgctg     1380
cacggctgca cggtgcattc tgggtctctg atcggcattg ggcgacaat actaaacaag     1440 taggtttcta tgaagtgagg aaggggaag gaattcggtt gtgtgtttcc tgactgtgca     1500
ccgcttctct gcagggccgt catcgggaag aattgcctga ttggtgcgaa cgctctaatc     1560
acggaaggga agtcatccc ggacggaagt ctagtgatgg gccgcaacca ggtggttcga     1620
```

```
cagctcaccg agaaggagat cgagggaatt cagcgcactg cggctggcta tgtgcagaac    1680
caagggccca acgcgttgga tgcatagctt gagtattcta tagtgtcacc taaatagctt    1740
ggcgtaatca tggtcatagc tgtttcctgt gtgaaattgt tatccgctca caattccaca    1800
caacatacga gccggaagca taaagtgtaa agcctgggt gcctaatgag tgagctaact     1860
cacattaatt gcgttgcgct cactgcccgc tttccagtcg ggaaacctgt cgtgccagct    1920
gcattaatga atcggccaac gcgcggggag aggcggtttg cgtattgggc gctcttccgc    1980
ttcctcgctc actgactcgc tgcgctcggt cgttcggctg cggcgagcgg tatcagctca    2040
ctcaaaggcg gtaatacggt tatccacaga atcaggggat aacgcaggaa agaacatgtg    2100
agcaaaaggc cagcaaaagg ccaggaaccg taaaaaggcc gcgttgctgg cgttttttcca   2160 taggctccgc ccccctgacg agcatcacaa aaatcgacgc tcaagtcaga ggtggcgaaa    2220
cccgacagga ctataaagat accaggcgtt tcccctgga agctccctcg tgcgctctcc     2280
tgttccgacc ctgccgctta ccggatacct gtccgccttt ctcccttcgg aagcgtggc    2340 gctttctcat agctcacgct gtaggtatct cagttcggtg taggtcgttc gctccaagct    2400
gggctgtgtg cacgaacccc ccgttcagcc cgaccgctgc gccttatccg gtaactatcg    2460
tcttgagtcc aacccggtaa gacacgactt atcgccactg gcagcagcca ctggtaacag    2520
gattagcaga gcgaggtatg taggcggtgc tacagagttc ttgaagtggt ggcctaacta    2580
cggctacact agaagaacag tatttggtat ctgcgctctg ctgaagccag ttaccttcgg    2640
aaaaagagtt ggtagctctt gatccggcaa acaaaccacc gctggtagcg gtggtttttt    2700
tgtttgcaag cagcagatta cgcgcagaaa aaaaggatct caagaagatc ctttgatctt    2760
ttctacgggg tctgacgctc agtggaacga aaactcacgt taagggattt tggtcatgag    2820
attatcaaaa aggatcttca cctagatcct tttaaattaa aaatgaagtt ttaaatcaat    2880
ctaaagtata tatgagtaaa cttggtctga cagttaccaa tgcttaatca gtgaggcacc    2940
tatctcagcg atctgtctat ttcgttcatc catagttgcc tgactccccg tcgtgtagat    3000
aactacgata cgggagggct taccatctgg ccccagtgct gcaatgatac cgcgagaccc    3060
acgctcaccg gctccagatt tatcagcaat aaaccagcca gccggaaggg ccgagcgcag    3120
aagtggtcct gcaactttat ccgcctccat ccagtctatt aattgttgcc gggaagctag    3180
agtaagtagt tcgccagtta atagtttgcg caacgttgtt gccattgcta caggcatcgt    3240
ggtgtcacgc tcgtcgtttg gtatggcttc attcagctcc ggttcccaac gatcaaggcg    3300
agttacatga tcccccatgt tgtgcaaaaa agcggttagc tccttcggtc ctccgatcgt    3360
tgtcagaagt aagttggccg cagtgttatc actcatggtt atggcagcac tgcataattc    3420
tcttactgtc atgccatccg taagatgctt ttctgtgact ggtgagtact caaccaagtc    3480
attctgagaa tagtgtatgc ggcgaccgag ttgctcttgc ccggcgtcaa tacgggataa    3540
taccgcgcca catagcagaa ctttaaaagt gctcatcatt ggaaaacgtt cttcggggcg    3600
aaaactctca aggatcttac cgctgttgag atccagttcg atgtaaccca ctcgtgcacc    3660
caactgatct tcagcatctt ttactttcac cagcgtttct gggtgagcaa aaacaggaag    3720
gcaaaatgcc gcaaaaaagg gaataagggc gacacggaaa tgttgaatac tcatactctt    3780
cctttttcaa tattattgaa gcatttatca gggttattgt ctcatgagcg gatacatatt    3840
tgaatgtatt tagaaaaata aacaaatagg ggttccgcgc acatttcccc gaaaagtgcc    3900
acctgatgcg gtgtgaaata ccgcacagat gcgtaaggag aaaataccgc atcaggaaat    3960
```

```
tgtaagcgtt aatattttgt taaaattcgc gttaaatttt tgttaaatca gctcattttt    4020
taaccaatag gccgaaatcg gcaaaatccc ttataaatca aaagaataga ccgagatagg    4080
gttgagtgtt gttccagttt ggaacaagag tccactatta agaacgtgg actccaacgt     4140 caaagggcga aaaccgtct atcagggcga tggcccacta cgtgaaccat caccctaatc     4200
aagttttttg gggtcgaggt gccgtaaagc actaaatcgg aaccctaaag ggagccccg     4260 atttagagct tgacggggaa agccggcgaa cgtggcgaga aaggaaggga agaaagcgaa    4320
aggagcgggc gctagggcgc tggcaagtgt agcggtcacg ctgcgcgtaa ccaccacacc    4380
cgccgcgctt aatgcgccgc tacagggcgc gtccattcgc cattcaggct gcgcaactgt    4440
tgggaagggc gatcggtgcg ggcctcttcg ctattacgcc agctggcgaa aggggatgt    4500 gctgcaaggc gattaagttg gtaacgcca gggttttccc agtcacgacg ttgtaaaacg    4560
acggccagtg aattgtaata cgactcacta ta                                 4592

<210> SEQ ID NO 242
<211> LENGTH: 37
<212> TYPE: DNA
<213> ORGANISM: Artificial
<220> FEATURE:
<223> OTHER INFORMATION: Genomic DNA (Parietichytrium C20 elongase
      downstream)

<400> SEQUENCE: 242
accgaccttg tactcgagga gttgttgtgc gcgcgga                             37

<210> SEQ ID NO 243
<211> LENGTH: 4448
<212> TYPE: DNA
<213> ORGANISM: Artificial
<220> FEATURE:
<223> OTHER INFORMATION: fusion DNA fusion DNA (ubiquitin promoter/omega
      3 desaturase/ubiquitin terminator/ubiquitin promoter/HygR/SV40
      terminator)

<400> SEQUENCE: 243
tcggtacccg ttagaacgcg taatacgact cactataggg agagtcgact gagcacaact    60
ctgctgcgag cgggcctcga gagcgttttgc ttcgagccgc ggagcaaggg ggatggatcg   120
ctcatgcggt cgtgcggccc tcggtcaccc ggtgggtcct gcactgacgc atctgttctg   180
atcagacaca cgaacgaaca aaccgaggag ccgcagcgcc tggtgcaccc gccgggcgtt   240
gttgtgtgct cttcttgcct ccgagagaga gagcggagcg gatgcatagg aaatcgggcc   300
acgcgggagg gccatgcgtt cgccccacac gccactttcc acgcccgctc tctctccggc   360
cggcaggcag cgcataactc tccgacgctg gcaggctggt agcaactggc agggacaact   420
cgcgcgcggg tccggtcgt tcgatgtgcc aacccgagag aatccagcca gcagggcggt    480
tggcctcatc gcccacctgc tatggtgcag cgaaccaact cccgaagcgg ccggttctgc   540
gattccctct tctgaattct gaattctgaa ctgattccgg aggagaaccc tctggaagcg   600
cgggttgcct ctccagttct gccgaactag acaggggagt gagcagagag tgaccctgac   660
gcggagcgag ctggttgctg gaaagtcgcg gaacgctggg ctgtgtcacg cgtccacttc   720
gggcagaccc caaacgacaa gcagaacaag caacaccagc agcagcaagc gacctaagca   780
acactagcca acatgactga ggataagacg aaggtcgagt tcccgacgct cacggagctc   840
aagcactcga tcccgaacgc gtgctttgag tcgaacctcg gcctctcgct ctactacacg   900
gcccgcgcga tcttcaacgc gtcggcctcg gcggcgctgc tctacgcggc gcgctcgacg   960
```

```
ccgttcattg ccgataacgt tctgctccac gcgctcgttt gcgccaccta catctacgtg    1020
cagggcgtca tcttctgggg cttcttcacg gtcggccacg actgcggcca ctcggccttc    1080
tcgcgctacc acagcgtcaa ctttatcatc ggctgcatca tgcactctgc gattttgacg    1140
ccgttcgaga gctggcgcgt gacgcaccgc caccaccaca agaacacggg caacattgat    1200
aaggacgaga tcttttaccc gcaccggtcg gtcaaggacc tccaggacgt gcgccaatgg    1260
gtctacacgc tcggcggtgc gtggtttgtc tacttgaagg tcgggtatgc cccgcgcacg    1320
atgagccact ttgacccgtg ggacccgctc ctccttcgcc gcgcgtcggc cgtcatcgtg    1380
tcgctcggcg tctgggccgc cttcttcgcc gcgtacgcgt acctcacata ctcgctcggc    1440
tttgccgtca tgggcctcta ctactatgcg ccgctctttg tctttgcttc gttcctcgtc    1500
attacgacct tcttgcacca caacgacgaa gcgacgccgt ggtacggcga ctcggagtgg    1560
acgtacgtca agggcaacct ctcgagcgtc gaccgctcgt acggcgcgtt cgtggacaac    1620
ctgagccacc acattggcac gcaccaggtc caccacttgt tcccgatcat tccgcactac    1680
aagctcaacg aagccaccaa gcactttgcg gccgcgtacc cgcacctcgt gcgcaagaac    1740
gacgagccca tcatctcggc cttcttcaag accgcgcacc tctttgtcaa ctacggcgct    1800 gtgccccgaga cggcgcagat cttcacgctc aaagagtcgg ccgcggccgc caaggccaag    1860
tcggactaaa ctaagctatc tgtagtatgt gctatactcg aatcatgctg ccctgtacgt    1920
acctacctat atctgattga gcgtgctgcg tcgaccatag acgcgggaac gcgggccagc    1980
ctaccacgtt gccgccgccg gtatccacgg gcacgccaaa gcattggtcg ataacgctct    2040
gcccagggct tcctggcgag gacccgaggc caacatgcat gcatgtgcta tcagcggtca    2100
tcatcgccct catcagcgcg catcggcgag ctcgcgcacg aacggcaagc gcccaactca    2160
actcacttac tcacactatg gtcttgccgt tggcggttgc ttagctaatg cgtgacgtca    2220
ctctgcctcc aacatcgcga ggcagagtcg cgagcagtgc agaggccacg gcggacgcca    2280
acaaagcgcc aaccagcgca acgcaccagc gggtctgtgg gcgtagctcg agcgggcgtc    2340
ttcaagagcc gccgtggagc cgacgcccct gcgaagggct cgagtgcaag cggggccgtt    2400
gagccgcgtg gtaggaacaa ctgcagtctc cctatagtga gtcgtattac gcggtggtac    2460
cgaccttgta ctcgaggagt tgttgtgcgc gcggatctgg atctgccgca gcgcctggtg    2520
cacccgccgg gcgttgttgt gtgctcttct tgcctccgag agagagagcg gagcggatgc    2580
ataggaaatc gggccacgcg ggagggccat gcgttcgccc cacacgccac tttccacgcc    2640
cgctctctct ccggccggca ggcagcgcat aactctccga cgctggcagg ctggtagcaa    2700
ctggcaggga caactcgcgc gcgggtcccg gtcgttcgat gtgccaaccc gagagaatcc    2760
agccagcagg gcgttggcc tcatcgccca cctgctatgg tgcagcgaac caactcccga    2820
agcggccggt tctgcgattc cctcttctga attctgaatt ctgaactgat tccggaggag    2880
aaccctctgg aagcgcgggt tgcctctcca gttctgccga actagacagg ggagtgagca    2940
gagagtgacc ctgacgcgga gcgagctggt tgctggaaaa gtcgcgaacg ctgggctgtg    3000
tcacgcgtcc acttcgggca gaccccaaac gacaagcaga acaagcaaca ccagcagcag    3060
caagcgacct aagcaacact agccaacatg aaaaagcctg aactcaccgc gacgtctgtc    3120
gagaagtttc tgatcgaaaa gttcgacagc gtctccgacc tgatgcagct ctcggagggc    3180
gaagaatctc gtgctttcag cttcgatgta ggagggcgtg gatatgtcct gcgggtaaat    3240
agctgcgccg atggtttcta caaagatcgt tatgtttatc ggcactttgc atcggccgcg    3300
ctcccgattc cggaagtgct tgacattggg gaattcagcg agagcctgac ctattgcatc    3360
```

```
tcccgccgtg cacagggtgt cacgttgcaa gacctgcctg aaaccgaact gcccgctgtt    3420
ctgcagccgg tcgcggaggc catggatgcg atcgctgcgg ccgatcttag ccagacgagc    3480
gggttcggcc cattcggacc gcaaggaatc ggtcaataca ctacatggcg tgatttcata    3540
tgcgcgattg ctgatcccca tgtgtatcac tggcaaactg tgatggacga caccgtcagt    3600
gcgtccgtcg cgcaggctct cgatgagctg atgctttggg ccgaggactg ccccgaagtc    3660
cggcacctcg tgcacgcgga tttcggctcc aacaatgtcc tgacggacaa tggccgcata    3720
acagcggtca ttgactggag cgaggcgatg ttcggggatt cccaatacga ggtcgccaac    3780
atcttcttct ggaggccgtg gttggcttgt atggagcagc agacgcgcta cttcgagcgg    3840
aggcatccgg agcttgcagg atcgccgcgg ctccgggcgt atatgctccg cattggtctt    3900
gaccaactct atcagagctt ggttgacggc aatttcgatg atgcagcttg ggcgcagggt    3960
cgatgcgacg caatcgtccg atccggagcc gggactgtcg ggcgtacaca aatcgcccgc    4020
agaagcgcgg ccgtctggac cgatggctgt gtagaagtac tcgccgatag tggaaaccga    4080
cgccccagca ctcgtccgag ggcaaaggaa tagagatccg cgaaatgacc gaccaagcga    4140
cgcccaacct gccatcacga gatttcgatt ccaccgccgc cttctatgaa aggttgggct    4200
tcggaatcgt tttccgggac gccggctgga tgatcctcca gcgcggggat ctcatgctgg    4260
agttcttcgc ccacccccaac ttgtttattg cagcttataa tggttacaaa taaagcaata    4320
gcatcacaaa tttcacaaat aaagcatttt tttcactgca ttctagttgt ggtttgtcca    4380
aactcatcaa tgtatcttat catgtctgta taccgtcgac ctctagctag atctgagatt    4440
aattgcgt                                                             4448

<210> SEQ ID NO 244
<211> LENGTH: 27
<212> TYPE: DNA
<213> ORGANISM: Artificial
<220> FEATURE:
<223> OTHER INFORMATION: primer

<400> SEQUENCE: 244
cgttagaacg cgtaatacga ctcacta                                          27

<210> SEQ ID NO 245
<211> LENGTH: 32
<212> TYPE: DNA
<213> ORGANISM: Artificial
<220> FEATURE:
<223> OTHER INFORMATION: primer

<400> SEQUENCE: 245
cccggatcca tggtggccag cgaggtgctc ag                                    32

<210> SEQ ID NO 246
<211> LENGTH: 34
<212> TYPE: DNA
<213> ORGANISM: Artificial
<220> FEATURE:
<223> OTHER INFORMATION: primer

<400> SEQUENCE: 246
cccggatcct tagtcgcgct tgagctcagc atcc                                  34

<210> SEQ ID NO 247
<211> LENGTH: 314
<212> TYPE: PRT
```

<213> ORGANISM: Schizochytrium

<400> SEQUENCE: 247

| | | | | | | | | | | | | | | | |
|---|---|---|---|---|---|---|---|---|---|---|---|---|---|---|---|
|Met|Val|Ala|Ser|Glu|Val|Leu|Ser|Ala|Pro|Lys|Ala|Ala|Asp|Ala|
|1| | | |5| | | |10| | | |15| | |
|Ala|Ala|Lys|Pro|Lys|Gln|Ala|Arg|Arg|Pro|Val|Lys|Val|Asp|Arg|Asp|
| | | |20| | | | |25| | | | |30| | |
|Asp|Ala|Phe|Phe|Arg|Thr|Phe|Asn|Leu|Gly|Ala|Leu|Tyr|Cys|Ser|Ala|
| | | | |35| | | | |40| | | | |45| |
|Leu|Tyr|Tyr|Ala|Ile|Gln|Val|Gly|Pro|Val|Asp|Asn|Asp|Gly|Lys|Gly|
| | |50| | | | |55| | | | |60| | | |
|Leu|Tyr|Phe|Ala|Lys|Asn|Lys|Phe|Tyr|Gln|Ile|Met|Leu|Ser|Asp|Ala|
|65| | | | |70| | | | |75| | | | |80|
|Val|Val|Phe|Gly|Ala|Pro|Val|Leu|Tyr|Val|Leu|Ala|Val|Met|Gly|Leu|
| | | | |85| | | | |90| | | | |95| |
|Ser|Arg|Phe|Met|Val|Asn|Lys|Lys|Pro|Leu|Thr|Ala|Phe|Leu|Arg|Ala|
| | | |100| | | | |105| | | | |110| | |
|Tyr|Val|Gln|Pro|Leu|Tyr|Asn|Val|Val|Gln|Ile|Val|Val|Cys|Ala|Trp|
| | | |115| | | | |120| | | | |125| | |
|Met|Val|Tyr|Gly|Ile|Met|Pro|Gln|Val|Asp|Ile|Leu|Asn|Gly|Asn|Pro|
| | |130| | | | |135| | | | |140| | | |
|Phe|Gly|Leu|Asn|Thr|Lys|Arg|Asp|Ala|Arg|Ile|Glu|Phe|Val|Phe|
|145| | | | |150| | | | |155| | | | |160|
|Val|His|Tyr|Leu|Thr|Lys|Phe|Leu|Asp|Trp|Thr|Asp|Thr|Phe|Ile|Met|
| | | | |165| | | | |170| | | | |175| |
|Ile|Leu|Ser|Lys|Ser|Tyr|His|Gln|Val|Ser|Phe|Leu|Gln|Val|Phe|His|
| | | |180| | | | |185| | | | |190| | |
|His|Ala|Thr|Ile|Gly|Met|Val|Trp|Gly|Phe|Leu|Leu|Gln|Arg|Gly|Trp|
| | |195| | | | |200| | | | |205| | | |
|Gly|Ser|Gly|Thr|Cys|Ala|Tyr|Gly|Ala|Phe|Ile|Asn|Ser|Val|Thr|His|
| | |210| | | | |215| | | | |220| | | |
|Val|Leu|Met|Tyr|Ser|His|Tyr|Leu|Trp|Thr|Ser|Phe|Gly|Phe|Lys|Asn|
|225| | | | |230| | | | |235| | | | |240|
|Pro|Leu|Lys|Lys|Trp|Leu|Thr|Lys|Phe|Gln|Leu|Ala|Gln|Phe|Ala|Ser|
| | | | |245| | | | |250| | | | |255| |
|Cys|Ile|Val|His|Ala|Leu|Leu|Val|Leu|Ala|Phe|Glu|Glu|Ala|Tyr|Pro|
| | | |260| | | | |265| | | | |270| | |
|Leu|Glu|Phe|Ala|Phe|Met|Gln|Ile|Ser|Tyr|His|Ile|Ile|Met|Leu|Tyr|
| | |275| | | | |280| | | | |285| | | |
|Leu|Phe|Gly|Lys|Arg|Met|Ser|Trp|Ala|Pro|Leu|Trp|Cys|Thr|Gly|Met|
| | |290| | | | |295| | | | |300| | | |
|Thr|Asp|Met|Asp|Ala|Glu|Leu|Lys|Arg|Asp|
|305| | | |310| | | | | |

<210> SEQ ID NO 248
<211> LENGTH: 945
<212> TYPE: DNA
<213> ORGANISM: Schizochytrium
<220> FEATURE:
<223> OTHER INFORMATION: cDNA (genomic DNA contains C20 elongase coding region)

<400> SEQUENCE: 248

```
atggtggcca gcgaggtgct cagcgccccc aaggccgcgg ccgacgccgc ggccaagccc      60
aagcaggcgc gtcgcccggt caaggtggac cgcgacgatg cattcttccg cacctttaac    120
```

```
ctgggggcac tctactgcag cgcactctac tacgccatcc aggttggccc cgtcgacaat    180
gacggcaagg gcctctactt tgccaagaac aagttctacc agatcatgct ctccgacgcg    240
gtcgtctttg gcgcccccgt cctctacgtc ctcgccgtca tgggtctctc ccgcttcatg    300
gtcaacaaga agcccctcac cgccttcctc cgcgcctacg tgcagccgct ctacaacgtc    360
gtgcagatcg tcgtgtgcgc ctggatggtc tacggcatca tgccccaggt cgatatcctc    420
aacgggaacc ccttcggcct caacaccaag cgggacgccc gcatcgagtt cttcgtgttt    480
gtccactacc tcaccaagtt tcttgactgg accgacacct tcatcatgat cctctccaag    540
agctaccacc aggtctcctt cctgcaggtc ttccaccacg ccaccatcgg catggtctgg    600
ggctttcttc tgcagcgcgg ctggggatcg ggcacctgtg cttacggcgc cttcatcaac    660
tcggtcaccc acgtcctcat gtactcgcac tacctctgga cctcctttgg cttcaagaac    720
ccgctcaaga agtggctcac caagttccag ctcgcgcagt ttgcctcgtg cattgtccac    780
gccctcctgg tccttgcctt cgaggaggcc tacccgctcg agtttgcttt catgcagatc    840
agctaccaca ttatcatgct ctaccttttt ggcaagcgca tgagctgggc ccgctttgg    900
tgcacgggga tgactgatat ggatgctgag ctcaagcgcg actaa                    945

<210> SEQ ID NO 249
<211> LENGTH: 24
<212> TYPE: DNA
<213> ORGANISM: Artificial
<220> FEATURE:
<223> OTHER INFORMATION: primer

<400> SEQUENCE: 249
catcgagatc ttcgtgtttg tcca                                             24

<210> SEQ ID NO 250
<211> LENGTH: 25
<212> TYPE: DNA
<213> ORGANISM: Artificial
<220> FEATURE:
<223> OTHER INFORMATION: primer

<400> SEQUENCE: 250
acgaagatct cgatgcgggc gtccc                                            25

<210> SEQ ID NO 251
<211> LENGTH: 945
<212> TYPE: DNA
<213> ORGANISM: Artificial
<220> FEATURE:
<223> OTHER INFORMATION: Schizochytrium derived BglII inserted C20
      elongase

<400> SEQUENCE: 251
atggtggccg gcgaggtgct cagcgccccc aaggccgcgg ccgacgccgc ggccaagccc     60
aagcaggcgc gccgcccggt caaggtggac cgtgacgatg cattcttccg cacctttaac    120
ctgggggcac tctactgcag cgcactctac tacgccatcc aggttggtcc cgtcgacaat    180
gacggcaagg gcctctactt tgccaagaac aagttctacc agatcatgct ctccgacgcg    240
gtcgtctttg gcgcccccgt cctctacgtc ctcgccgtca tgggcctctc ccgcttcatg    300
gtcaacaaga agcccctcac cgccttcctc cgcgcctacg tgcagccgct ctacaacgtc    360
gtgcagatcg tcgtgtgcgc ctggatggtc tacggcatca tgccccaggt cgatatcctc    420
aacgggaacc ccttcggcct caacaccaag cgggacgccc gcatcgagat cttcgtgttt    480
```

```
gtccactacc tcaccaagtt tcttgactgg accgacacct tcatcatgat cctctccaag      540
agctaccacc aggtctcctt cctgcaggtc ttccaccacg ccaccatcgg catggtctgg      600
ggctttcttc tgcagcgcgg ctggggatcg ggcacctgtg cttacggcgc cttcatcaac      660
tcggtcaccc acgtcctcat gtactcgcac tacctctgga cctcctttgg cttcaagaac      720
ccgctcaaga agtggctcac caagttccag ctcgcgcagt ttgcctcgtg cattgtccac      780
gccctcctgg tccttgcctt cgaggaggcc tacccgctcg agtttgcttt catgcagatc      840
agctaccaca ttatcatgct ctacctttt ggcaagcgca tgagctgggc ccgctttgg       900 tgcacgggga tgactgatat ggatgctgag ctcaagcgcg actaa                     945

<210> SEQ ID NO 252
<211> LENGTH: 20
<212> TYPE: DNA
<213> ORGANISM: Artificial
<220> FEATURE:
<223> OTHER INFORMATION: primer

<400> SEQUENCE: 252
agatggtggc cagcgaggtg                                                   20

<210> SEQ ID NO 253
<211> LENGTH: 25
<212> TYPE: DNA
<213> ORGANISM: Artificial
<220> FEATURE:
<223> OTHER INFORMATION: primer

<400> SEQUENCE: 253
ttagtcgcgc ttgagctcag catcc                                             25

<210> SEQ ID NO 254
<211> LENGTH: 2644
<212> TYPE: DNA
<213> ORGANISM: Artificial
<220> FEATURE:
<223> OTHER INFORMATION: fusion DNA (Schizochytrium C20 elongase 5'
      region/SV40 terminator/Neor/ubiquitin promoter/Schizochytrium C20
      elongase 3' region)

<400> SEQUENCE: 254
atggtggccg gcgaggtgct cagcgccccc aaggccgcgg ccgacgccgc ggccaagccc       60
aagcaggcgc gccgcccggt caaggtggac cgtgacgatg cattcttccg caccttaac      120 ctgggggcac tctactgcag cgcactctac tacgccatcc aggttggtcc cgtcgacaat      180
gacggcaagg gcctctactt tgccaagaac aagttctacc agatcatgct ctccgacgcg      240
gtcgtctttg gcgcccccgt cctctacgtc ctcgccgtca tgggcctctc ccgcttcatg      300
gtcaacaaga agcccctcac cgccttcctc cgcgcctacg tgcagccgct ctacaacgtc      360
gtgcagatcg tcgtgtgcgc ctggatggtc tacggcatca tgcccaggt cgatatcctc      420 aacgggaacc ccttcggcct caacaccaag cgggacgccc gcatcgagat ctgccgcagc      480
gcctggtgca cccgccgggc gttgttggtg tgctcttctt gcctccgaga gagagagcgg      540
agcggatgca taggaaatcg ggccacgcgg gagggccatg cgttcgcccc acacgccact      600
ttccacgccc gctctctctc cggccggcag gcagcgcata actctccgac gctggcaggc      660
tggtagcaac tggcagggac aactcgcgcg cgggtcccgg tcgttcgatg tgccaacccg      720
agagaatcca gccagcaggg cggttggcct catcgcccac tgctatggt gcagcgaacc       780 aactcccgaa gcggccggtt ctgcgattcc ctcttctgaa ttctgaattc tgaactgatt      840
```

```
ccggaggaga acoctctgga agcgcgggtt gcctctccag ttctgccgaa ctagacaggg    900
gagtgagcag agagtgaccc tgacgcggag cgagctggtt gctggaaaag tcgcgaacgc    960
tgggctgtgt cacgcgtcca cttcgggcag accccaaacg acaagcagaa caagcaacac   1020
cagcagcagc aagcgaccta agcaacacta gccaacatga ttgaacagga cggccttcac   1080
gctggctcgc ccgctgcttg ggtggaacgg ctgttcggct acgactgggc tcagcagacg   1140
atcggctgct cggacgcggc cgtgttccgc cttagcgcgc agggccggcc ggtcctgttt   1200
gtcaagaccg accttagcgg cgccctcaac gagctccagg acgaagctgc ccgcctcagc   1260
tggcttgcca cgacggggt tccgtgcgcc gctgtgctcg acgtcgtcac cgaagccggc   1320
cgcgactggc tgctcctcgg ggaagtgccc ggccaggacc tcctcagcag ccacctcgcg   1380
cccgctgaga aggtgtccat catggccgac gccatgcgcc gcctgcacac cctcgacccc   1440
gccacctgcc ccttcgacca ccaggcgaag cacaggatcg aacgcgcccg cacgcggatg   1500
gaggctggcc tcgtcgacca agacgacctc gacgaggagc accagggcct cgcgccggcg   1560
gaactgttcg ccaggcttaa ggctaggatg ccggacggcg aggacctcgt ggtcacgcac   1620
ggcgacgcct gcctcccaa catcatggtc gagaacggcc gcttctcggg ctttatcgac   1680
tgcgggcgcc tgggcgtggc ggaccgctac caagacatcg cgctcgccac gcgggacatc   1740
gccgaggagc ttggcggcga gtgggccgac cgctttctcg tgctctacgg catcgccgcc   1800
ccggacagcc agaggattgc gttctaccgc ctcctggacg agttcttttg agatccgcga   1860
aatgaccgac caagcgacgc ccaacctgcc atcacgagat ttcgattcca ccgccgcctt   1920
ctatgaaagg ttgggcttcg gaatcgtttt ccgggacgcc ggctggatga tcctccagcg   1980
cggggatctc atgctggagt tcttcgccca ccccaacttg tttattgcag cttataatgg   2040
ttacaaataa agcaatagca tcacaaattt cacaaataaa gcatttttt cactgcattc   2100 tagttgtggt ttgtccaaac tcatcaatgt atcttatcat gtctgtatac cgtcgacctc   2160
tagctagatc ttcgtgtttg tccactacct caccaagttt cttgactgga ccgacaccttt   2220 catcatgatc ctctccaaga gctaccacca ggtctccttc ctgcaggtct tccaccacgc   2280
caccatcggc atggtctggg gctttcttct gcagcgcggc tggggatcgg gcacctgtgc   2340
ttacggcgcc ttcatcaact cggtcaccca cgtcctcatg tactcgcact acctctggac   2400
ctcctttggc ttcaagaacc cgctcaagaa gtggctcacc aagttccagc tcgcgcagtt   2460
tgcctcgtgc attgtccacg ccctcctggt ccttgccttc gaggaggcct acccgctcga   2520
gtttgctttc atgcagatca gctaccacat tatcatgctc tacctttttg gcaagcgcat   2580
gagctgggcc ccgctttggt gcacggggat gactgatatg gatgctgagc tcaagcgcga   2640
ctaa                                                                2644
```

<210> SEQ ID NO 255
<211> LENGTH: 2881
<212> TYPE: DNA
<213> ORGANISM: Artificial
<220> FEATURE:
<223> OTHER INFORMATION: fusion DNA (Schizochytrium C20 elongase 5'
      region/ubiquitin promoter/Hygr/SV40 terminator/Schizochytrium C20
      elongase 3' region)

<400> SEQUENCE: 255

```
atggtggccg gcgaggtgct cagcgccccc aaggccgcgg ccgacgccgc ggccaagccc     60
aagcaggcgc gccgcccggt caaggtggac cgtgacgatg cattcttccg caccttaac    120
```

```
ctgggggcac tctactgcag cgcactctac tacgccatcc aggttggtcc cgtcgacaat    180
gacggcaagg gcctctactt tgccaagaac aagttctacc agatcatgct ctccgacgcg    240
gtcgtctttg gcgcccccgt cctctacgtc ctcgccgtca tgggcctctc ccgcttcatg    300
gtcaacaaga agcccctcac cgccttcctc cgcgcctacg tgcagccgct ctacaacgtc    360
gtgcagatcg tcgtgtgcgc ctggatggtc tacggcatca tgccccaggt cgatatcctc    420
aacgggaacc ccttcggcct caacaccaag cgggacgccc gcatcgagat ctagctrgag    480
gtcgacggta tacagacatg ataagataca ttgatgagtt tggacaaacc acaactagaa    540
tgcagtgaaa aaaatgcttt atttgtgaaa tttgtgatgc tattgcttta tttgtaacca    600
ttataagctg caataaacaa gttggggtgg gcgaagaact ccagcatgag atccccgcgc    660
tggaggatca tccagccggc gtcccggaaa acgattccga agcccaacct ttcatagaag    720
gcggcggtgg aatcgaaatc tcgtgatggc aggttgggcg tcgcttggtc ggtcatttcg    780
cggatctcta ttccttttgcc ctcggacgag tgctggggcg tcggtttcca ctatcggcga    840
gtacttctac acagccatcg gtccagacgg ccgcgcttct gcgggcgatt tgtgtacgcc    900
cgacagtccc ggctccggat cggacgattg cgtcgcatcg accctgcgcc caagctgcat    960
catcgaaatt gccgtcaacc aagctctgat agagttggtc aagaccaatg cggagcatat   1020
acgcccggag ccgcggcgat cctgcaagct ccggatgcct ccgctcgaag tagcgcgtct   1080
gctgctccat acaagccaac cacggcctcc agaagaagat gttggcgacc tcgtattggg   1140
aatccccgaa catcgcctcg ctccagtcaa tgaccgctgt tatgcggcca ttgtccgtca   1200
ggacattgtt ggagccgaaa tccgcgtgca cgaggtgccg gacttcgggg cagtcctcgg   1260
cccaaagcat cagctcatcg agagcctgcg cgacggacgc actgacggtg tcgtccatca   1320
cagtttgcca gtgatacaca tggggatcag caatcgcgca tatgaaatca cgccatgtag   1380
tgtattgacc gattccttgc ggtccgaatg ggccgaaccc gctcgtctgg ctaagatcgg   1440
ccgcagcgat cgcatccatg gcctccgcga ccggctgcag aacagcgggc agttcggttt   1500
caggcaggtc ttgcaacgtg acaccctgtg cacggcggga gatgcaatag gtcaggctct   1560
cgctgaattc cccaatgtca agcacttccg gaatcgggag cgcggccgat gcaaagtgcc   1620
gataaacata acgatctttg tagaaaccat cggcgcagct atttacccgc aggacatatc   1680
cacgccctcc tacatcgaag ctgaaagcac gagattcttc gccctccgag agctgcatca   1740
ggtcggagac gctgtcgaac ttttcgatca gaaacttctc gacagacgtc gcggtgagtt   1800
caggcttttt catgttggct agtgttgctt aggtcgcttg ctgctgctgg tgttgcttgt   1860
tctgcttgtc gtttggggtc tgcccgaagt ggacgcgtga cacagcccag cgttcgcgac   1920
ttttccagca accagctcgc tccgcgtcag ggtcactctc tgctcactcc cctgtctagt   1980
tcggcagaac tggagaggca acccgcgctt ccagagggtt ctcctccgga atcagttcag   2040
aattcagaat tcagaagagg gaatcgcaga accggccgct tcgggagttg gttcgctgca   2100
ccatagcagg tgggcgatga ggccaaccgc cctgctggct ggattctctc gggttggcac   2160
atcgaacgac cgggacccgc gcgcgagttg tccctgccag ttgctaccag cctgccagcg   2220
tcggagagtt atgcgctgcc tgccggccgg agagagagcg ggcgtggaaa gtggcgtgtg   2280
gggcgaacgc atggccctcc cgcgtggccc gatttcctat gcatccgctc cgctctctct   2340
ctcggaggca agaagagcac acaacaacgc ccggcgggtg caccaggcgc tgcggcagat   2400
ccagatcttc gtgtttgtcc actacctcac caagttctct gactggaccg acaccttcat   2460
catgatcctc tccaagagct accaccaggt ctccttcctg caggtcttcc accacgccac   2520
```

```
catcggcatg gtctggggct ttcttctgca gcgcggctgg ggatcgggca cctgtgctta    2580
cggcgccttc atcaactcgg tcacccacgt cctcatgtac tcgcactacc tctggacctc    2640
ctttggcttc aagaacccgc tcaagaagtg gctcaccaag ttccagctcg cgcagtttgc    2700
ctcgtgcatt gtccacgccc tcctggtcct tgccttcgag gaggcctacc cgctcgagtt    2760
tgctttcatg cagatcagct accacattat catgctctac cttttggca agcgcatgag    2820 ctgggccccg ctttggtgca cggggatgac tgatatggat gctgagctca agcgcgacta    2880
a                                                                    2881
```